US011712481B2

(12) United States Patent
Hope et al.

(10) Patent No.: US 11,712,481 B2
(45) Date of Patent: Aug. 1, 2023

(54) LIPID NANOPARTICLE FORMULATIONS

(71) Applicant: Acuitas Therapeutics, Inc., Vancouver (CA)

(72) Inventors: Michael J. Hope, Vancouver (CA); Barbara Mui, Vancouver (CA); Paulo Jia Ching Lin, Vancouver (CA); Christopher J. Barbosa, Coquitlam (CA); Thomas D. Madden, Vancouver (CA); Steven M. Ansell, Vancouver (CA); Xinyao Du, Richmond (CA)

(73) Assignee: Acuitas Therapeutics, Inc., Vancouver (CA)

(*) Notice: Subject to any disclaimer, the term of this patent is extended or adjusted under 35 U.S.C. 154(b) by 0 days.

(21) Appl. No.: 16/345,592

(22) PCT Filed: Oct. 26, 2017

(86) PCT No.: PCT/US2017/058619
§ 371 (c)(1),
(2) Date: Apr. 26, 2019

(87) PCT Pub. No.: WO2018/081480
PCT Pub. Date: May 3, 2018

(65) Prior Publication Data
US 2020/0121809 A1   Apr. 23, 2020

Related U.S. Application Data

(63) Continuation-in-part of application No. 15/337,434, filed on Oct. 28, 2016, now Pat. No. 10,166,298.

(60) Provisional application No. 62/485,833, filed on Apr. 14, 2017, provisional application No. 62/485,836, filed on Apr. 14, 2017, provisional application No. 62/413,319, filed on Oct. 26, 2016.

(51) Int. Cl.
| | |
|---|---|
| *A61K 48/00* | (2006.01) |
| *A61K 9/127* | (2006.01) |
| *C07C 219/06* | (2006.01) |
| *C07C 229/16* | (2006.01) |
| *C07C 233/18* | (2006.01) |
| *C07C 255/24* | (2006.01) |
| *C12N 9/02* | (2006.01) |
| *A61K 47/18* | (2017.01) |
| *C07C 229/12* | (2006.01) |

(52) U.S. Cl.
CPC .......... *A61K 48/0033* (2013.01); *A61K 9/127* (2013.01); *A61K 47/18* (2013.01); *C07C 219/06* (2013.01); *C07C 229/12* (2013.01); *C07C 229/16* (2013.01); *C07C 233/18* (2013.01); *C07C 255/24* (2013.01); *C12N 9/0069* (2013.01); *C12Y 113/12007* (2013.01)

(58) Field of Classification Search
CPC ............................ A61K 47/18; C07C 219/06
See application file for complete search history.

(56) References Cited

U.S. PATENT DOCUMENTS

| | | | |
|---|---|---|---|
| 2,856,420 | A | 10/1958 | Crawford, Jr. |
| 3,340,299 | A | 9/1967 | Weintraub et al. |
| 3,729,564 | A | 4/1973 | Chang et al. |
| 3,931,430 | A | 1/1976 | Tada et al. |
| 4,121,898 | A | 10/1978 | Kirschnek et al. |
| 4,491,583 | A | 1/1985 | Cronin et al. |
| 4,639,468 | A | 1/1987 | Roncucci et al. |
| 5,705,385 | A | 1/1998 | Bally et al. |
| 5,756,785 | A | 5/1998 | O'Lenick, Jr. |
| 5,919,743 | A | 7/1999 | O'Lenick, Jr. |
| 5,965,542 | A | 10/1999 | Wasan et al. |
| 5,976,567 | A | 11/1999 | Wheeler et al. |
| 5,981,501 | A | 11/1999 | Wheeler et al. |
| 6,013,813 | A | 1/2000 | O'Lenick, Jr. |
| 6,034,137 | A | 3/2000 | Belloni et al. |
| 6,077,509 | A | 6/2000 | Weiner et al. |
| 6,107,286 | A | 8/2000 | Byk et al. |
| 6,300,321 | B1 | 10/2001 | Scherman et al. |
| 6,333,433 | B1 | 12/2001 | Banerjee et al. |
| 6,410,328 | B1 | 6/2002 | Maclachlan et al. |
| 6,458,381 | B1 | 10/2002 | Sourovoi et al. |
| 6,534,484 | B1 | 3/2003 | Wheeler et al. |
| 6,586,410 | B1 | 7/2003 | Wheeler et al. |
| 6,620,794 | B1 | 9/2003 | O'Lenick, Jr. et al. |
| 6,815,432 | B2 | 11/2004 | Wheeler et al. |
| 6,858,224 | B2 | 2/2005 | Wheeler et al. |
| 6,986,902 | B1 | 1/2006 | Chen et al. |
| 7,112,337 | B2 | 9/2006 | Huang et al. |
| 7,470,781 | B2 | 12/2008 | Crouzet et al. |
| 7,745,651 | B2 | 6/2010 | Heyes et al. |

(Continued)

FOREIGN PATENT DOCUMENTS

| | | |
|---|---|---|
| CN | 104876831 A | 9/2015 |
| EP | 1 083 232 B1 | 2/2005 |

(Continued)

OTHER PUBLICATIONS

Akinc et al., "Targeted delivery of RNAi therapeutics with endogenous and exogenous ligand-based mechanisms," *Mol. Ther.* 18(7):1357-1364, 2010.
Ansell et al., "Application of Oligo-(14-amino-3,6,9,12-tetraoxatetradecanoic acid) Lipid Conjugates as Steric Barrier Molecules in Liposomal Formulations," *Bioconjugate Chem.* 10:653-666, 1999.
Basha et al., "Influence of cationic lipid composition on gene silencing properties of lipid nanoparticle formulations of siRNA in antigen-presenting cells," *Mol. Ther.* 19(12):2186-2200, 2011.
Belliveau et al., "Microfluidic Synthesis of Highly Potent Limit-size Lipid Nanoparticles for In Vivo Delivery of siRNA," *Mol. Ther. Nucleic Acids* 1:e37, 2012.
Bhattacharya et al., "Synthesis, Thermotropic Behavior, and Permeability Properties of Vesicular Membranes Composed of Cationic Mixed-Chain Surfactants," *Langmuir* 11:4748-4757, 1995.

(Continued)

*Primary Examiner* — Andrew S Rosenthal
(74) *Attorney, Agent, or Firm* — Seed IP Law Group LLP

(57) ABSTRACT

Improved formulations of lipid nanoparticles are provided. Use of the lipid nanoparticles for delivery of a therapeutic agent and methods for their preparation are also provided.

35 Claims, 1 Drawing Sheet

(56) References Cited

U.S. PATENT DOCUMENTS

| | | | |
|---|---|---|---|
| 7,799,565 B2 | 9/2010 | MacLachlan et al. | |
| 7,803,397 B2 | 9/2010 | Heyes et al. | |
| 7,811,602 B2 | 10/2010 | Cullis et al. | |
| 7,901,708 B2 | 3/2011 | MacLachlan et al. | |
| 7,982,027 B2 | 7/2011 | MacLachlan et al. | |
| 8,034,376 B2 | 10/2011 | Manoharan et al. | |
| 8,158,601 B2 | 4/2012 | Chen et al. | |
| 8,278,036 B2 | 10/2012 | Kariko et al. | |
| 8,283,333 B2 | 10/2012 | Yaworski et al. | |
| 8,329,070 B2 | 12/2012 | MacLachlan et al. | |
| 8,466,122 B2 | 6/2013 | Heyes et al. | |
| 8,569,256 B2 | 10/2013 | Heyes et al. | |
| 8,575,123 B2 | 11/2013 | Manoharan et al. | |
| 8,642,076 B2 | 2/2014 | Manoharan et al. | |
| 8,691,750 B2 | 4/2014 | Constien et al. | |
| 8,722,082 B2 | 5/2014 | Manoharan et al. | |
| 8,748,089 B2 | 6/2014 | Kariko et al. | |
| 8,754,062 B2 | 6/2014 | De Fougerolles et al. | |
| 8,802,644 B2 | 8/2014 | Chen et al. | |
| 8,822,668 B2 | 9/2014 | Yaworski et al. | |
| 8,835,108 B2 | 9/2014 | Kariko et al. | |
| 9,012,498 B2 | 4/2015 | Manoharan et al. | |
| 9,139,554 B2 | 9/2015 | Hope et al. | |
| 9,352,042 B2 | 5/2016 | Heyes et al. | |
| 9,604,908 B2 | 3/2017 | Stanton et al. | |
| 9,682,922 B2 | 6/2017 | Manoharan et al. | |
| 9,737,619 B2 | 8/2017 | Ansell et al. | |
| 9,738,593 B2 | 8/2017 | Ansell et al. | |
| 9,750,824 B2 | 9/2017 | Kariko et al. | |
| 9,795,566 B2 | 10/2017 | Oya et al. | |
| 10,106,490 B2 | 10/2018 | Du et al. | |
| 10,144,725 B2 | 12/2018 | Brown | |
| 10,166,298 B2 | 1/2019 | Ansell et al. | |
| 10,221,127 B2 | 3/2019 | Du et al. | |
| 10,723,692 B2 | 7/2020 | Ansell et al. | |
| 11,040,112 B2 | 6/2021 | Ansell et al. | |
| 11,168,051 B2 | 11/2021 | Du et al. | |
| 2003/0031704 A1 | 2/2003 | Huang et al. | |
| 2003/0153081 A1 | 8/2003 | Tagawa et al. | |
| 2004/0142025 A1 | 7/2004 | MacLachlan et al. | |
| 2004/0142474 A1 | 7/2004 | Mahato et al. | |
| 2005/0064595 A1 | 3/2005 | MacLachlan et al. | |
| 2006/0100177 A1 | 5/2006 | Nishimura et al. | |
| 2007/0042031 A1 | 2/2007 | MacLachlan et al. | |
| 2009/0209037 A1 | 8/2009 | Tagawa et al. | |
| 2009/0247608 A1 | 10/2009 | Manoharan et al. | |
| 2010/0203076 A1 | 8/2010 | Fotin-Mleczek et al. | |
| 2010/0285112 A1 | 11/2010 | Novobrantseva et al. | |
| 2011/0045473 A1 | 2/2011 | De Fougerolles et al. | |
| 2011/0091525 A1 | 4/2011 | Heyes et al. | |
| 2011/0097720 A1 | 4/2011 | Ciufolini et al. | |
| 2011/0256175 A1 | 10/2011 | Hope et al. | |
| 2011/0262527 A1 | 10/2011 | Heyes et al. | |
| 2011/0300205 A1 | 12/2011 | Geall et al. | |
| 2011/0305770 A1 | 12/2011 | Zhao et al. | |
| 2011/0311582 A1 | 12/2011 | Manoharan et al. | |
| 2011/0311583 A1 | 12/2011 | Manoharan et al. | |
| 2012/0027796 A1 | 2/2012 | Manoharan et al. | |
| 2012/0027803 A1 | 2/2012 | Manoharan et al. | |
| 2012/0046478 A1 | 2/2012 | Manoharan et al. | |
| 2012/0058144 A1 | 3/2012 | Manoharan et al. | |
| 2012/0058188 A1 | 3/2012 | Manoharan et al. | |
| 2012/0095075 A1 | 4/2012 | Manoharan et al. | |
| 2012/0101148 A1 | 4/2012 | Aking et al. | |
| 2012/0128760 A1 | 5/2012 | Manoharan et al. | |
| 2012/0172411 A1 | 7/2012 | Heyes et al. | |
| 2012/0183602 A1 | 7/2012 | Chen et al. | |
| 2012/0225434 A1 | 9/2012 | Ciufolini et al. | |
| 2012/0244207 A1 | 9/2012 | Fitzgerald et al. | |
| 2012/0251618 A1 | 10/2012 | Schrum et al. | |
| 2012/0264810 A1* | 10/2012 | Lin | A61K 9/1271 514/44 A |
| 2012/0276209 A1 | 11/2012 | Cullis et al. | |
| 2012/0295832 A1 | 11/2012 | Constien et al. | |
| 2013/0017223 A1 | 1/2013 | Hope et al. | |
| 2013/0022649 A1 | 1/2013 | Yaworski et al. | |
| 2013/0064894 A1* | 3/2013 | Martin | C12N 15/88 977/773 |
| 2013/0108685 A1 | 5/2013 | Kuboyama et al. | |
| 2013/0122104 A1 | 5/2013 | Yaworski et al. | |
| 2013/0123338 A1 | 5/2013 | Heyes et al. | |
| 2013/0129754 A1 | 5/2013 | Thess et al. | |
| 2013/0129811 A1 | 5/2013 | Kuboyama et al. | |
| 2013/0261172 A1 | 10/2013 | Kariko et al. | |
| 2013/0266640 A1 | 10/2013 | de Fougerolles et al. | |
| 2013/0280305 A1 | 10/2013 | Kuboyama et al. | |
| 2013/0323269 A1 | 12/2013 | Manoharan et al. | |
| 2013/0338210 A1 | 12/2013 | Manoharan et al. | |
| 2014/0044772 A1 | 2/2014 | MacLachlan et al. | |
| 2014/0121393 A1 | 5/2014 | Manoharan et al. | |
| 2014/0134260 A1 | 5/2014 | Heyes et al. | |
| 2014/0179761 A1 | 6/2014 | Manoharan et al. | |
| 2014/0256785 A1 | 9/2014 | Manoharan et al. | |
| 2014/0294937 A1 | 10/2014 | MacLachlan et al. | |
| 2014/0295449 A1 | 10/2014 | Ciufolini et al. | |
| 2014/0308304 A1 | 10/2014 | Manoharan et al. | |
| 2014/0323548 A1 | 10/2014 | Budzik et al. | |
| 2015/0203446 A1 | 6/2015 | Manoharan et al. | |
| 2016/0009637 A1 | 1/2016 | Manoharan et al. | |
| 2016/0095924 A1 | 4/2016 | Hope et al. | |
| 2016/0166710 A1 | 6/2016 | Baumhof | |
| 2016/0361411 A1 | 12/2016 | Gindy et al. | |
| 2017/0266292 A1 | 9/2017 | Luo et al. | |
| 2018/0044687 A1 | 2/2018 | Thess et al. | |
| 2018/0148727 A1 | 5/2018 | Grund et al. | |
| 2018/0185516 A1 | 7/2018 | Ansell et al. | |
| 2018/0214537 A1 | 8/2018 | Mutzke et al. | |
| 2018/0237786 A1 | 8/2018 | Schlake et al. | |
| 2018/0303925 A1 | 10/2018 | Weissman et al. | |
| 2019/0022247 A1 | 1/2019 | Ansell et al. | |
| 2019/0270697 A1 | 9/2019 | Ansell et al. | |
| 2019/0274968 A1 | 9/2019 | Weissman et al. | |
| 2019/0314524 A1 | 10/2019 | Ansell et al. | |
| 2019/0359556 A1 | 11/2019 | Du et al. | |
| 2020/0046838 A1 | 2/2020 | Ansell et al. | |
| 2020/0163878 A1 | 5/2020 | Baumhof et al. | |
| 2020/0172472 A1 | 6/2020 | Du | |
| 2020/0283372 A1 | 9/2020 | Du | |
| 2021/0107861 A1 | 4/2021 | Ansell et al. | |
| 2021/0122702 A1 | 4/2021 | Du | |
| 2021/0122703 A1 | 4/2021 | Du | |
| 2021/0128488 A1 | 5/2021 | Du | |
| 2021/0251898 A1 | 8/2021 | Baumhof et al. | |
| 2021/0395188 A1 | 12/2021 | Ansell | |
| 2022/0040285 A1 | 2/2022 | Weissman et al. | |
| 2022/0072155 A1 | 3/2022 | Ansell et al. | |
| 2022/0081392 A1 | 3/2022 | Du et al. | |

FOREIGN PATENT DOCUMENTS

| | | |
|---|---|---|
| GB | 1 277 947 A | 6/1972 |
| JP | 5-331118 A | 12/1993 |
| JP | H10-3643 A | 1/1998 |
| JP | 2001-338416 A | 12/2001 |
| JP | 4681425 B2 | 2/2011 |
| WO | 87/07183 A1 | 12/1987 |
| WO | 97/03939 A1 | 2/1997 |
| WO | 97/30024 A2 | 8/1997 |
| WO | 98/16599 A1 | 4/1998 |
| WO | 99/05094 A1 | 2/1999 |
| WO | 99/33493 A1 | 7/1999 |
| WO | 00/30444 A1 | 6/2000 |
| WO | 01/07548 A1 | 2/2001 |
| WO | 01/48233 A1 | 7/2001 |
| WO | 03/053409 A1 | 7/2003 |
| WO | 2005/060934 A1 | 7/2005 |
| WO | 2006/138380 A2 | 12/2006 |
| WO | 2007/024708 A2 | 3/2007 |
| WO | 2009/132131 A1 | 10/2009 |
| WO | 2010/042877 A1 | 4/2010 |
| WO | 2010/048536 A2 | 4/2010 |
| WO | 2010/054405 A1 | 5/2010 |
| WO | 2010/054406 A1 | 5/2010 |
| WO | 2010/057150 A1 | 5/2010 |

(56) References Cited

FOREIGN PATENT DOCUMENTS

| | | | |
|---|---|---|---|
| WO | 2010/062322 A2 | 6/2010 | |
| WO | 2010/088537 A2 | 8/2010 | |
| WO | 2011/075656 A1 | 6/2011 | |
| WO | 2011/141703 A1 | 11/2011 | |
| WO | 2011/141705 A1 | 11/2011 | |
| WO | 2011/143230 A1 | 11/2011 | |
| WO | 2011/153493 A2 | 12/2011 | |
| WO | 2012/000104 A1 | 1/2012 | |
| WO | 2012/016184 A2 | 2/2012 | |
| WO | 2012/019630 A1 | 2/2012 | |
| WO | 2012/068176 A1 | 5/2012 | |
| WO | 2013/014073 A1 | 1/2013 | |
| WO | 2013/016058 A1 | 1/2013 | |
| WO | 2013/044008 A2 | 3/2013 | |
| WO | 2013/059496 A1 | 4/2013 | |
| WO | 2013/086322 A1 | 6/2013 | |
| WO | 2013/086354 A1 | 6/2013 | |
| WO | 2013/086373 A1 | 6/2013 | |
| WO | 2013/143555 A1 | 10/2013 | |
| WO | 2014/008334 A1 | 1/2014 | |
| WO | 2014/028487 A1 | 2/2014 | |
| WO | 2014/089239 A1 | 6/2014 | |
| WO | 2014/153163 A1 | 9/2014 | |
| WO | 2014/160243 A1 | 10/2014 | |
| WO | 2014/160284 A1 | 10/2014 | |
| WO | 2015/074085 A1 | 5/2015 | |
| WO | 2015/123576 A2 | 8/2015 | |
| WO | 2015/130584 A2 | 9/2015 | |
| WO | 2015/164674 A1 | 10/2015 | |
| WO | 2015/177752 A1 | 11/2015 | |
| WO | 2015/199952 A1 | 12/2015 | |
| WO | 2016/010840 A1 | 1/2016 | |
| WO | 2016/014794 A1 | 1/2016 | |
| WO | 2016/176330 A1 | 11/2016 | |
| WO | WO-2016176330 A1 * | 11/2016 | ............. A61K 39/12 |
| WO | 2017/004143 A1 | 1/2017 | |
| WO | 2017/048770 A1 | 3/2017 | |
| WO | 2017/049245 A2 | 3/2017 | |
| WO | 2017/075531 A1 | 5/2017 | |
| WO | 2017/112865 A1 | 6/2017 | |
| WO | 2017/117528 A1 | 7/2017 | |
| WO | 2017/173054 A1 | 10/2017 | |
| WO | 2017/194454 A1 | 11/2017 | |
| WO | 2017/201332 A1 | 11/2017 | |
| WO | 2018/078053 A1 | 5/2018 | |
| WO | 2018/081480 A1 | 5/2018 | |
| WO | 2018/081638 A1 | 5/2018 | |
| WO | 2018/191657 A1 | 10/2018 | |
| WO | 2018/191719 A1 | 10/2018 | |
| WO | 2018/200943 A1 | 11/2018 | |

OTHER PUBLICATIONS

Cattanach et al., "Studies in the Indole Series. Part IV. Tetrahydro-1H-pyrido[4,3-b]-indoles as Serotonin Antagonists," *J. Chem Soc.* (C): 1235-1243, 1968.

Chen et al., "Influence of particle size on the in vivo potency of lipid nanoparticle formulations of siRNA," *Journal of Controlled Release* 235:236-244, 2016.

Cook et al., "Synthesis and Characterization of cis-Dioxomolybdenum(VI) Complexes with Sterically Bulky Tripodal Tetradentate Ligands," *Inorganica Chimica Acta* 144:81-87, 1988.

Ernsting et al., "Factors controlling the pharmacokinetics, biodistribution and intratumoral penetration of nanoparticles," *Journal of Controlled Release* 172:782-794, 2013.

Jayaraman et al., "Maximizing the Potency of siRNA Lipid Nanoparticles for Hepatic Gene Silencing In Vivo," *Angewandte Chemie* 51(34):8529-8533, XP055063645, 2012.

Lee et al., "Lipid nanoparticle siRNA systems for silencing the androgen receptor in human prostate cancer in vivo," *Int. J. Cancer* 131(5):E781-790, 2012.

Leroueil et al., "Wide Varieties of Cationic Nanoparticles Induce Defects in Supported Lipid Bilayers," *Nano Letters* 8(2):420-424, 2008.

Leung et al., "Lipid Nanoparticles Containing siRNA Synthesized by Microfluidic Mixing Exhibit an Electron-Dense Nanostructured Core," *J. Phys. Chem. C. Nanomater. Interfaces* 116(34):18440-18450, 2012.

Leung et al., "Microfluidic Mixing: A General Method for Encapsulating Macromolecules in Lipid Nanoparticle Systems," *J. Phys. Chem. B* 119:8698-8706, 2015.

Maier et al., "Biodegradable lipids enabling rapidly eliminated lipid nanoparticles for systemic delivery of RNAi therapeutics," *Mol. Ther.* 21(8):1570-1578, 2013.

Marchi-Artzner et al., "Adhesion of Arg-Gly-Asp (RGD) Peptide Vesicles onto an Integrin Surface: Visualization of the Segregation of RGD Ligands into the Adhesion Plaques by Fluorescence," *Langmuir* 19:835-841, 2003.

Masuda et al., "Envelope-type lipid nanoparticles incorporating a short PEG-lipid conjugate for improved control of intracellular trafficking and transgene transcription," *Biomaterials* 30:4806-4814, 2009.

Mui et al., "Influence of Polyethylene Glycol Lipid Desorption Rates on Pharmacokinetics and Pharmacodynamics of siRNA Lipid Nanoparticles," *Mol. Ther. Nucleic Acids* 2:e139, 2013 (8 pages).

Nishida, "Disk-shaped magnetic recording medium," CAPLUS Database, Accession No. 2001:881906, 2001 (1 page).

Pardi et al., "Expression kinetics of nucleoside-modified mRNA delivered in lipid nanoparticles to mice by various routes," *Journal of Controlled Release* 217:345-351, 2015.

Szebeni et al., "Activation of complement by therapeutic liposomes and other lipid excipient-based therapeutic products: Prediction and prevention," *Advanced Drug Delivery Reviews* 63:1020-1030, 2011.

Szebeni et al., "Complement activation as a bioequivalence issue relevant to the development of generic liposomes and other nanoparticulate drugs," *Biochemical and Biophysical Research Communications* 468:490-497, 2015.

Szebeni, "Complement activation-related pseudoallergy: A stress reaction in blood triggered by nanomedicines and biologicals" *Molecular Immunology* 61:163-173, 2014.

Tam et al., "Small molecule ligands for enhanced intracellular delivery of lipid nanoparticle formulations of siRNA," *Nanomedicine* 9(5):665-674, 2013.

Xue et al., "Lipid-Based Nanocarriers for RNA Delivery," *Current Pharmaceutical Design* 21:3140-3147, 2015.

Akinc et al., "A combinatorial library of lipid-like materials for delivery of RNAi therapeutics," Nature Biotechnology 26(5):561-569, May 2008.

Alabi et al., "Multiparametric approach for the evaluation of lipid nanoparticles for siRNA delivery," PNAS 110(32):12881-12886, Aug. 6, 2013.

Alexidis et al., "Novel 1,4 Substituted Piperidine Derivatives. Synthesis and Correlation of Antioxidant Activity with Structure and Lipophilicity," J. Pharm. Pharmacol. 47:131-137, 1995.

Brito et al., "A Cationic Nanoemulsion for the Delivery of Next-generation RNA Vaccines," Molecular Therapy 22(12):2118-2129, 2014.

Chen et al., "Rapid Discovery of Potent siRNA-Containing Lipid Nanoparticles Enabled by Controlled Microfluidic Formulation," J. Am. Chem. Soc. 134:6948-6951, 2012.

Chevalier et al., "Design, Activity, and Structure of a Highly Specific Artificial Endonuclease," Molecular Cell 70:895-905, 2002.

Choo et al., "Advances in Zinc Finger Engineering," Current Opinion in Structural Biology 10:411-416, 2000.

Fagerlund et al., "The Cpf1 CRISPR-Cas Protein Expands Genome-Editing Tools," Genom Bio 16:251, 2015 (3 pages).

Frisch et al. "A New Triantennary Galactose-Targeted PEGylated Gene Carrier, Characterization of Its Complex with DNA, and Transfection of Hepatoma Cells," Bioconjugate Chem. 15: 754-764, 2004.

Haft et al., "A Guild of 45 CRISPR-Associated (Cas) Protein Families and Multiple CRISPR/Cas Subtypes Exist in Prokaryotic Genomes," PLoS Computational Biology 1(6):e60, 2005.

Han et al., "Synthesis and Properties of Di-Chain Esterquat Surfactants," J. Surfact Deterg. 18: 91-95, 2015.

(56) References Cited

OTHER PUBLICATIONS

Heuer et al., "Repeat Domain Diversity of avrBs3-Like Genes in *Ralstonia Solancearum* Strains and Association with Host Preferences in the Field," *Applied and Environmental Microbiology* 73(13):4379-4384, 2007.
Jasin, "Genetic Manipulation of Genomes with Rare-Cutting Endonucleases," *Trends Genet* 12:224-228, 1996.
Kay et al., "A Bacterial Effector Acts as a Plant Transcription Factor and Induces a Cell Size Regulator," *Science* 318:648-651, 2007.
Kim et al., "Highly Efficient RNA-Guided Genome Editing in Human Cells via Delivery of Purified Cas9 Ribonucleoproteins," *Genome Research* 24(6):1012-1019, 2014.
Kim et al., "Hybrid restriction enzymes: zinc finger fusions to Fok I cleavage domain," *PNAS USA* 93(3):1156-1160, 1996.
Makarova et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," *Biology Direct* 1:7, 2006.
Nguyen et al., "Lipid-derived nanoparticles for immunostimulatory RNA adjuvant delivery", Proceedings of the National Academy of Sciences 109(14):E797-E803, 2012.
Pabo et al., "Design and Selection of Novel $Cys_2His_2$ Zinc Finger Proteins," *Ann. Rev. Biochem.* 70:313-340, 2001.
Perler et al., "Protein splicing elements: inteins and exteins—a definition of terms and recommended nomenclature," *Nucleic Acids Research* 22:1125-1127, 1994.
Rajesh et al., "Dramatic Influence of the Orientation of Linker between Hydrophilic and Hydrophobic Lipid Moiety in Liposomal Gene Delivery," *Journal of the American Chemical Society* 129(37):11408-11420, 2007.
Ran et al., "In Vivo Genome Editing Using *Staphylococcus Aureus* Cas9," *Nature* 520:186-194, 2015.
Russell et al., "The Stability of Human β-Globin mRNA is Dependent on Structural Determinants Positioned Within Its 3' Untranslated Region," *Blood* 87:5314-5323, 1996.
Schar et al., "Long Chain Linear Fatty Alcohols from ZIEGLER-Synthesis, their Mixtures, Derivatives and Use," IP.com Prior Art Database Technical Disclosure, Jan. 17, 2011, 39 pages.
Schornack et al., "Gene-for-Gene-Mediated Recognition of Nuclear-Targeted AvrBs3-Like Bacterial Effector Proteins," *Journal of Plant Physiology* 163(3):256-272, 2006.
Semple et al., "Interactions of liposomes and lipid-based carrier systems with blood proteins: Relation to clearance behaviour in vivo," *Advanced Drug Delivery Reviews* 32:3-17, 1998.
Semple et al., "Rational design of cationic lipids for siRNA delivery," *Nature Biotechnology* 28(2):172-176, Feb. 2010, 26 pages.
Szolcsányi et al., "Short racemic syntheses of calvine and epicalvine," *Tetrahedron Letters* 49:1357-1360, 2008.
Tam et al., "Advances in Lipid Nanoparticles for siRNA Delivery," *Pharmaceutics* 5:498-507, 2013.
Tekmira Pharmaceuticals Corp, Form 20-F, EDGAR Online, filed Mar. 27, 2013, 298 pages.
Tekmira, "Tekmira and Alnylam Restructure Relationship and Settle All Litigation," Tekmira Pharmaceuticals Corporation, Nov. 12, 2012, 3 pages.
Torrecilla et al., "Lipid Nanoparticles as Carriers for RNAi against Viral Infections: Current Status and Future Perspectives," BioMed Research International 2014:Article ID 161794, 17 pages.
Vogel et al., "A Bacterial Seek-and-Destroy System for Foreign DNA," *Science* 344(6187):972-73, 2014.
Wah et al., "Structure of the Multimodular Endonuclease FokI Bound to DNA," *Nature* 388:97-100, 1997.
Wang et al., "Composite Nanoparticles for Gene Delivery," *Adv. Genet.* 88:111-137, 2014.
Whitehead et al., "Synergistic Silencing: Combinations of Lipid-like Materials for Efficacious siRNA Delivery," *Molecular Therapy* 19(9):1688-1694, 2011.
Wilson et al., "The Combination of Stabilized Plasmid Lipid Particles and Lipid Nanoparticle Encapsulated CpG Containing Oligodeoxynucleotides as Systemic Genetic Vaccine," *The Journal of Gene Medicine* 11(1):14-25, 2009.
Yoshimura et al., "Solution Properties of Tadpole-type Cationic Amphiphilic Dendrimers Consisting of an Alkyl Chain, a Quaternary Ammonium, and a Poly(amidoamine) Dendron," Journal of Oleo Science 62(4):213-221, 2013.
Zhang et al., "Biodegradable Amino-Ester Nanomaterials for Cas9 mRNA Delivery in Vitro and in Vivo," *ACS Appl. Mater. Interfaces* 9(30):25481-25487, 2017. (15 pages).
U.S. Appl. No. 17/371,261, filed Jul. 9, 2021.
U.S. Appl. No. 17/378,083, filed Jul. 16, 2021.
Van Doren et al., "Structure-Property Relationships in D-Glucitol Derivatives with Two Geminal Hydrocarbon Chains," *J. Mater. Chem.* 5(12):2153-2160, 1995.

* cited by examiner

LIPID NANOPARTICLE FORMULATIONS

BACKGROUND

Technical Field

Embodiments of the present invention generally relate to optimized formulations of lipid nanoparticles useful for facilitating the intracellular delivery of therapeutic agents, such as nucleic acids (e.g., oligonucleotides, messenger RNA) both in vitro and in vivo.

Description of the Related Art

There are many challenges associated with the delivery of nucleic acids to affect a desired response in a biological system. Nucleic acid based therapeutics have enormous potential but there remains a need for more effective delivery of nucleic acids to appropriate sites within a cell or organism in order to realize this potential. Therapeutic nucleic acids include, e.g., messenger RNA (mRNA), antisense oligonucleotides, ribozymes, DNAzymes, plasmids, immune stimulating nucleic acids, antagomir, antimir, mimic, supermir, and aptamers. Some nucleic acids, such as mRNA or plasmids, can be used to effect expression of specific cellular products as would be useful in the treatment of, for example, diseases related to a deficiency of a protein or enzyme. The therapeutic applications of translatable nucleotide delivery are extremely broad as constructs can be synthesized to produce any chosen protein sequence, whether or not indigenous to the system. The expression products of the nucleic acid can augment existing levels of protein, replace missing or non-functional versions of a protein, or introduce new protein and associated functionality in a cell or organism.

Some nucleic acids, such as miRNA inhibitors, can be used to effect expression of specific cellular products that are regulated by miRNA as would be useful in the treatment of, for example, diseases related to deficiency of protein or enzyme. The therapeutic applications of miRNA inhibition are extremely broad as constructs can be synthesized to inhibit one or more miRNA that would in turn regulate the expression of mRNA products. The inhibition of endogenous miRNA can augment its downstream target endogenous protein expression and restore proper function in a cell or organism as a means to treat disease associated to a specific miRNA or a group of miRNA.

Other nucleic acids can down-regulate intracellular levels of specific mRNA and, as a result, down-regulate the synthesis of the corresponding proteins through processes such as RNA interference (RNAi) or complementary binding of antisense RNA. The therapeutic applications of antisense oligonucleotide and RNAi are also extremely broad, since oligonucleotide constructs can be synthesized with any nucleotide sequence directed against a target mRNA. Targets may include mRNAs from normal cells, mRNAs associated with disease-states, such as cancer, and mRNAs of infectious agents, such as viruses. To date, antisense oligonucleotide constructs have shown the ability to specifically down-regulate target proteins through degradation of the cognate mRNA in both in vitro and in vivo models. In addition, antisense oligonucleotide constructs are currently being evaluated in clinical studies.

However, two problems currently face the use of oligonucleotides in therapeutic contexts. First, free RNAs are susceptible to nuclease digestion in plasma. Second, free RNAs have limited ability to gain access to the intracellular compartment where the relevant translation machinery resides. Lipid nanoparticles formed from cationic lipids with other lipid components, such as neutral lipids, cholesterol, PEG, PEGylated lipids, and oligonucleotides have been used to block degradation of the RNAs in plasma and facilitate the cellular uptake of the oligonucleotides.

There remains a need for improved cationic lipid formulations and lipid nanoparticles for the delivery of oligonucleotides. Preferably, these lipid nanoparticle formulations would provide optimal drug:lipid ratios, protect the nucleic acid from degradation and clearance in serum, be suitable for systemic or local delivery, and provide intracellular delivery of the nucleic acid. In addition, these lipid-nucleic acid particles should be well-tolerated and provide an adequate therapeutic index, such that patient treatment at an effective dose of the nucleic acid is not associated with unacceptable toxicity and/or risk to the patient. The present invention provides these and related advantages.

BRIEF SUMMARY

In brief, embodiments of the present invention provide optimized lipid nanoparticle (LNP) formulation. Exemplary LNPs comprise cationic lipid(s), a neutral lipid, a steroid, a polymer conjugated lipid, and a therapeutic agent, or a pharmaceutically acceptable salt thereof, encapsulated within or associated with the LNP. LNPs known in the art typically comprise higher concentrations of cationic lipids (e.g., >50 mol percent), a single cationic lipid or cationic lipids with a different pKa than embodiments of the present disclosure. In contrast to such prior art LNPs, the present Applicant has unexpectedly discovered that characteristics of the optimized formulations of the present disclosure provide important improvements for LNP properties related to delivery of the therapeutic agent (e.g., increased stability and enhanced delivery).

In some instances, the lipid nanoparticles are used to deliver nucleic acids such as antisense and/or messenger RNA.

Accordingly, in one embodiment is provided a lipid nanoparticle comprising:
  i) between 40 and 50 mol percent of a cationic lipid;
  ii) a neutral lipid;
  iii) a steroid;
  iv) a polymer conjugated lipid; and
  v) a therapeutic agent, or a pharmaceutically acceptable salt thereof, encapsulated within or associated with the lipid nanoparticle.

Another embodiment provides a lipid nanoparticle comprising:
  i) a cationic lipid having an effective pKa greater than 6.0;
  ii) from 5 to 15 mol percent of a neutral lipid;
  iii) from 1 to 15 mol percent of an anionic lipid;
  iv) from 30 to 45 mol percent of a steroid;
  v) a polymer conjugated lipid; and
  vi) a therapeutic agent, or a pharmaceutically acceptable salt thereof, encapsulated within or associated with the lipid nanoparticle,
wherein the mol percent is determined based on total mol of lipid present in the lipid nanoparticle.

One other embodiment provides a lipid nanoparticle comprising:
  i) a first cationic lipid having a first effective pKa;
  ii) a second cationic lipid having a second effective pKa, the second effective pKa being greater than the first effective pKa;
  iii) a neutral lipid;
  iv) a steroid;
  v) a polymer conjugated lipid; and vi) a therapeutic agent, or a pharmaceutically acceptable salt or prodrug thereof, encapsulated within or associated with the lipid nanoparticle, wherein the lipid nanoparticle has an effective pKa between the first and second effective pKa's.

Pharmaceutical compositions comprising the disclosed lipid nanoparticles and methods for use of the same for treatment of various diseases or conditions, such as those caused by infectious entities and/or insufficiency of a protein, are also provided.

In other embodiments, the present invention provides a method for administering a therapeutic agent to a patient in need thereof, the method comprising administering the disclosed lipid nanoparticles, or pharmaceutical composition comprising the same, to the patient.

These and other aspects of embodiments of the invention will be apparent upon reference to the following detailed description.

BRIEF DESCRIPTION OF THE SEVERAL VIEWS OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1A:
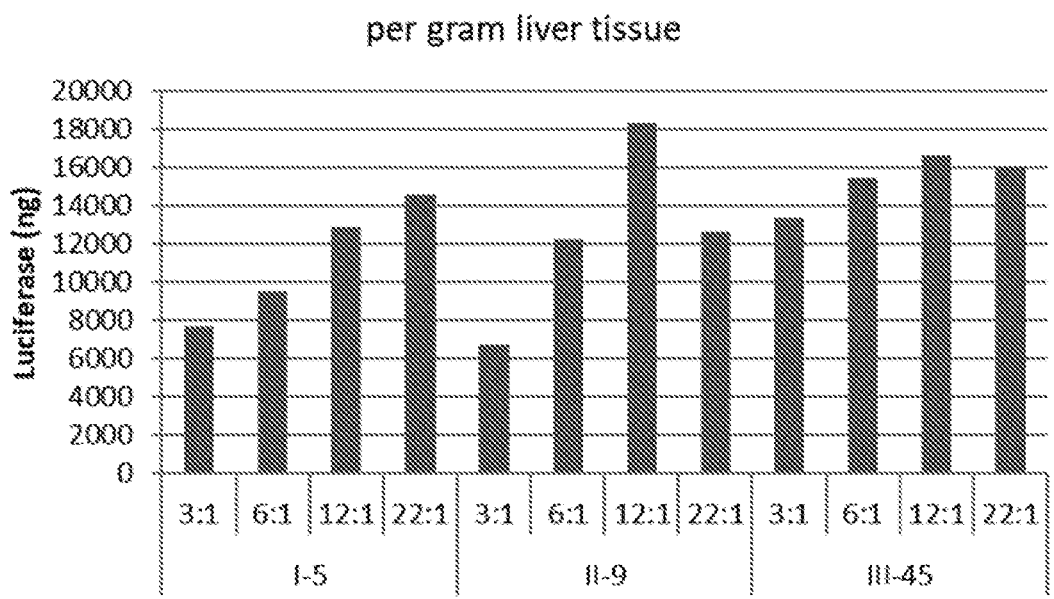
FIGS. 1A and 1B provide luciferase activity data as a function of N/P Ratio for representative lipids in liver and spleen tissue, respectively.

In the following description, certain specific details are set forth in order to provide a thorough understanding of various embodiments of the invention. However, one skilled in the art will understand that the invention may be practiced without these details.

Embodiments of the present invention are based, in part, upon the discovery that modulating aspects of the cationic lipid content and/or effective pKa of a lipid nanoparticle provides surprisingly superior characteristics. Namely, certain unpredicted modifications (e.g., concentration of cationic lipid, including an additional distinct cationic lipid and/or including an anionic lipid) surprisingly result in improved properties of a lipid nanoparticle as a delivery vehicle for therapeutic agents (e.g., nucleic acids).

Accordingly, in some embodiments, lipid nanoparticles (LNPs) comprising, inter alia, between 40 and 50 mol percent of a cationic lipid provide unexpected advantages over previously known LNPs when used for delivery of an active or therapeutic agent, such as a nucleic acid, into a cell of a mammal. In particular, one embodiment provides a lipid nanoparticle comprising between 40 and 50 mol percent of a cationic lipid, a neutral lipid, a steroid, a polymer conjugated lipid, and a therapeutic agent encapsulated within or associated with the lipid nanoparticle.

In some embodiments, the LNPs comprise, inter alia, first and second cationic lipids, each of the first and second cationic lipids having a different effective pKa. Other known LNPs comprise only one type of cationic lipid and the effective pKa of the LNP is thus highly dependent on use of cationic lipids having an optimized effective pKa. However, the data provided herein demonstrate the surprising result that cationic lipids which would have previously been excluded from use in LNPs due to an undesirable effective pKa can be admixed with other cationic lipids having a different effective pKa to form an LNP having an optimized effective pKa. Specifically, the present inventors have discovered that LNPs comprising, inter alia, first and second cationic lipids, each of the first and second cationic lipids having a different effective pKa, have surprisingly better properties for use as a delivery vehicle for therapeutic agents, such as nucleic acids, relative to LNPs comprising only the first or the second cationic lipid.

In addition, the present inventors have discovered that LNPs comprising, inter alia, a cationic lipid having an effective pKa greater than 6.0 and from 1 to 15 mol percent of an anionic lipid, have surprisingly improved properties for use as a delivery vehicle. Embodiments of the LNPs described herein provide increased encapsulation efficiency and/or increased in vivo activity, resulting in a significant increase in the therapeutic index as compared to LNPs previously described.

In particular embodiments, the present invention provides lipid nanoparticles for the in vitro and in vivo delivery of mRNA and/or other oligonucleotides. In some embodiments, these improved lipid nanoparticle compositions are useful for expression of protein encoded by mRNA. In other embodiments, these improved lipid nanoparticles are useful for upregulation of endogenous protein expression by delivering miRNA inhibitors targeting one specific miRNA or a group of miRNA regulating one target mRNA or several mRNA. In other embodiments, these improved lipid nanoparticle compositions are useful for down-regulating (e.g., silencing) the protein levels and/or mRNA levels of target genes. In some other embodiments, the lipid nanoparticles are also useful for delivery of mRNA and plasmids for expression of transgenes. In yet other embodiments, the lipid nanoparticles are useful for inducing a pharmacological effect resulting from expression of a protein, e.g., increased production of red blood cells through the delivery of a suitable erythropoietin mRNA, or protection against infection through delivery of mRNA encoding for a suitable antigen or antibody.

The lipid nanoparticles of embodiments of the present invention may be used for a variety of purposes, including the delivery of encapsulated or associated (e.g., complexed) therapeutic agents such as nucleic acids to cells, both in vitro and in vivo. Accordingly, embodiments of the present invention provide a method for administering a therapeutic agent to a patient in need thereof, the method comprising administering a lipid nanoparticle as described herein to the patient.

As described herein, embodiments of the lipid nanoparticles of the present invention are particularly useful for the delivery of nucleic acids, including, e.g., mRNA, antisense oligonucleotide, plasmid DNA, microRNA (miRNA), miRNA inhibitors (antagomirs/antimirs), messenger-RNA-interfering complementary RNA (micRNA), DNA, multivalent RNA, dicer substrate RNA, complementary DNA (cDNA), etc. Therefore, the lipid nanoparticles of embodiments of the present invention may be used to induce expression of a desired protein both in vitro and in vivo by contacting cells with a lipid nanoparticle. The expressed protein may have a biological effect, such as inducing an immune response. Alternatively, the lipid nanoparticles and compositions of embodiments of the present invention may be used to decrease the expression of target genes and proteins both in vitro and in vivo by contacting cells with a lipid nanoparticle. The lipid nanoparticles and compositions of embodiments of the present invention may also be used for co-delivery of different nucleic acids (e.g., mRNA and plasmid DNA) separately or in combination, such as may be useful to provide an effect requiring colocalization of different nucleic acids (e.g. mRNA encoding for a suitable gene modifying enzyme and DNA segment(s) for incorporation into the host genome).

Nucleic acids for use with embodiments of this invention may be prepared according to any available technique. For mRNA, the primary methodology of preparation is, but not limited to, enzymatic synthesis (also termed in vitro transcription) which currently represents the most efficient method to produce long sequence-specific mRNA. In vitro transcription describes a process of template-directed synthesis of RNA molecules from an engineered DNA template comprised of an upstream bacteriophage promoter sequence (e.g. including but not limited to that from the T7, T3 and SP6 coliphage) linked to a downstream sequence encoding the gene of interest. Template DNA can be prepared for in vitro transcription from a number of sources with appropriate techniques which are well known in the art including, but not limited to, plasmid DNA and polymerase chain reaction amplification (see Linpinsel, J. L. and Conn, G. L., General protocols for preparation of plasmid DNA template and Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012).

Transcription of the RNA occurs in vitro using the linearized DNA template in the presence of the corresponding RNA polymerase and adenosine, guanosine, uridine and cytidine ribonucleoside triphosphates (rNTPs) under conditions that support polymerase activity while minimizing potential degradation of the resultant mRNA transcripts. In vitro transcription can be performed using a variety of commercially available kits including, but not limited to RiboMax Large Scale RNA Production System (Promega), MegaScript Transcription kits (Life Technologies) as well as with commercially available reagents including RNA polymerases and rNTPs. The methodology for in vitro transcription of mRNA is well known in the art. (see, e.g. Losick, R., 1972, In vitro transcription, Ann Rev Biochem v. 41 409-46; Kamakaka, R. T. and Kraus, W. L. 2001. In Vitro Transcription. Current Protocols in Cell Biology. 2:11.6:11.6.1-11.6.17; Beckert, B. And Masquida, B., (2010) Synthesis of RNA by In Vitro Transcription in RNA in Methods in Molecular Biology v. 703 (Neilson, H. Ed), New York, N.Y. Humana Press, 2010; Brunelle, J. L. and Green, R., 2013, Chapter Five—In vitro transcription from plasmid or PCR-amplified DNA, Methods in Enzymology v. 530, 101-114; all of which are incorporated herein by reference).

The desired in vitro transcribed mRNA is then purified from the undesired components of the transcription or associated reactions (including unincorporated rNTPs, protein enzyme, salts, short RNA oligos, etc.). Techniques for the isolation of the mRNA transcripts are well known in the art. Well known procedures include phenol/chloroform extraction or precipitation with either alcohol (e.g., ethanol, isopropanol) in the presence of monovalent cations or lithium chloride. Additional, non-limiting examples of purification procedures which can be used include size exclusion chromatography (Lukaysky, P. J. and Puglisi, J. D., 2004, Large-scale preparation and purification of polyacrylamide-free RNA oligonucleotides, RNA v. 10, 889-893), silica-based affinity chromatography and polyacrylamide gel electrophoresis (Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012). Purification can be performed using a variety of commercially available kits including, but not limited to SV Total Isolation System (Promega) and In Vitro Transcription Cleanup and Concentration Kit (Norgen Biotek).

Furthermore, while reverse transcription can yield large quantities of mRNA, the products can contain a number of aberrant RNA impurities associated with undesired polymerase activity which may need to be removed from the full-length mRNA preparation. These include short RNAs that result from abortive transcription initiation as well as double-stranded RNA (dsRNA) generated by RNA-dependent RNA polymerase activity, RNA-primed transcription from RNA templates and self-complementary 3' extension. It has been demonstrated that these contaminants with dsRNA structures can lead to undesired immunostimulatory activity through interaction with various innate immune sensors in eukaryotic cells that function to recognize specific nucleic acid structures and induce potent immune responses. This in turn, can dramatically reduce mRNA translation since protein synthesis is reduced during the innate cellular immune response. Therefore, additional techniques to remove these dsRNA contaminants have been developed and are known in the art including but not limited to scaleable HPLC purification (see, e.g., Kariko, K., Muramatsu, H., Ludwig, J. And Weissman, D., 2011, Generating the optimal mRNA for therapy: HPLC purification eliminates immune activation and improves translation of nucleoside-modified, protein-encoding mRNA, Nucl Acid Res, v. 39 e142; Weissman, D., Pardi, N., Muramatsu, H., and Kariko, K., HPLC Purification of in vitro transcribed long RNA in Synthetic Messenger RNA and Cell Metabolism Modulation in Methods in Molecular Biology v. 969 (Rabinovich, P. H. Ed), 2013). HPLC purified mRNA has been reported to be translated at much greater levels, particularly in primary cells and in vivo.

A significant variety of modifications have been described in the art which are used to alter specific properties of in vitro transcribed mRNA, and improve its utility. These include, but are not limited to modifications to the 5' and 3' termini of the mRNA. Endogenous eukaryotic mRNA typically contain a cap structure on the 5'-end of a mature molecule which plays an important role in mediating binding of the mRNA Cap Binding Protein (CBP), which is in turn responsible for enhancing mRNA stability in the cell and efficiency of mRNA translation. Therefore, highest levels of protein expression are achieved with capped mRNA transcripts. The 5'-cap contains a 5'-5'-triphosphate linkage between the 5'-most nucleotide and guanine nucleotide. The conjugated guanine nucleotide is methylated at the N7 position. Additional modifications include methylation of the ultimate and penultimate most 5'-nucleotides on the 2'-hydroxyl group.

Multiple distinct cap structures can be used to generate the 5'-cap of in vitro transcribed synthetic mRNA. 5'-capping of synthetic mRNA can be performed co-transcriptionally with chemical cap analogs (i.e., capping during in vitro transcription). For example, the Anti-Reverse Cap Analog (ARCA) cap contains a 5'-5'-triphosphate guanine-guanine linkage where one guanine contains an N7 methyl group as well as a 3'-O-methyl group. However, up to 20% of transcripts remain uncapped during this co-transcriptional process and the synthetic cap analog is not identical to the 5'-cap structure of an authentic cellular mRNA, potentially reducing translatability and cellular stability. Alternatively, synthetic mRNA molecules may also be enzymatically capped post-transcriptionally. These may generate a more authentic 5'-cap structure that more closely mimics, either structurally or functionally, the endogenous 5'-cap which have enhanced binding of cap binding proteins, increased half-life, reduced susceptibility to 5' endonucleases and/or reduced 5' decapping. Numerous synthetic 5'-cap analogs have been developed and are known in the art to enhance mRNA stability and translatability (see, e.g., Grudzien-Nogalska, E., Kowalska, J., Su, W., Kuhn, A. N., Slepenkov, S. V., Darynkiewicz, E., Sahin, U., Jemiely, J., and Rhoads, R. E., Synthetic mRNAs with superior translation and stability properties in Synthetic Messenger RNA and Cell Metabolism Modulation in Methods in Molecular Biology v. 969 (Rabinovich, P. H. Ed), 2013).

On the 3'-terminus, a long chain of adenine nucleotides (poly-A tail) is normally added to mRNA molecules during RNA processing. Immediately after transcription, the 3' end of the transcript is cleaved to free a 3' hydroxyl to which poly-A polymerase adds a chain of adenine nucleotides to the RNA in a process called polyadenylation. The poly-A tail has been extensively shown to enhance both translational efficiency and stability of mRNA (see Bernstein, P. and Ross, J., 1989, Poly (A), poly (A) binding protein and the regulation of mRNA stability, Trends Bio Sci v. 14 373-377; Guhaniyogi, J. And Brewer, G., 2001, Regulation of mRNA stability in mammalian cells, Gene, v. 265, 11-23; Dreyfus, M. And Regnier, P., 2002, The poly (A) tail of mRNAs: Bodyguard in eukaryotes, scavenger in bacteria, Cell, v. 111, 611-613).

Poly (A) tailing of in vitro transcribed mRNA can be achieved using various approaches including, but not limited to, cloning of a poly (T) tract into the DNA template or by post-transcriptional addition using Poly (A) polymerase. The first case allows in vitro transcription of mRNA with poly (A) tails of defined length, depending on the size of the poly (T) tract, but requires additional manipulation of the template. The latter case involves the enzymatic addition of a poly (A) tail to in vitro transcribed mRNA using poly (A) polymerase which catalyzes the incorporation of adenine residues onto the 3'termini of RNA, requiring no additional manipulation of the DNA template, but results in mRNA with poly(A) tails of heterogeneous length. 5'-capping and 3'-poly (A) tailing can be performed using a variety of commercially available kits including, but not limited to Poly (A) Polymerase Tailing kit (EpiCenter), mMESSAGE mMACHINE T7 Ultra kit and Poly (A) Tailing kit (Life Technologies) as well as with commercially available reagents, various ARCA caps, Poly (A) polymerase, etc.

In addition to 5' cap and 3' poly adenylation, other modifications of the in vitro transcripts have been reported to provide benefits as related to efficiency of translation and stability. It is well known in the art that pathogenic DNA and RNA can be recognized by a variety of sensors within eukaryotes and trigger potent innate immune responses. The ability to discriminate between pathogenic and self DNA and RNA has been shown to be based, at least in part, on structure and nucleoside modifications since most nucleic acids from natural sources contain modified nucleosides In contrast, in vitro synthesized RNA lacks these modifications, thus rendering it immunostimulatory which in turn can inhibit effective mRNA translation as outlined above. The introduction of modified nucleosides into in vitro transcribed mRNA can be used to prevent recognition and activation of RNA sensors, thus mitigating this undesired immunostimulatory activity and enhancing translation capacity (see e.g. Kariko, K. And Weissman, D. 2007, Naturally occurring nucleoside modifications suppress the immunostimulatory activity of RNA: implication for therapeutic RNA development, Curr Opin Drug Discov Devel, v.10 523-532; Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013); Kariko, K., Muramatsu, H., Welsh, F. A., Ludwig, J., Kato, H., Akira, S., Weissman, D., 2008, Incorporation of Pseudouridine Into mRNA Yields Superior Nonimmunogenic Vector With Increased Translational Capacity and Biological Stability, Mol Ther v. 16, 1833-1840. The modified nucleosides and nucleotides used in the synthesis of modified RNAs can be prepared monitored and utilized using general methods and procedures known in the art. A large variety of nucleoside modifications are available that may be incorporated alone or in combination with other modified nucleosides to some extent into the in vitro transcribed mRNA (see, e.g., U.S. Pub. No. 2012/0251618). In vitro synthesis of nucleoside-modified mRNA have been reported to have reduced ability to activate immune sensors with a concomitant enhanced translational capacity.

Other components of mRNA which can be modified to provide benefit in terms of translatability and stability include the 5' and 3' untranslated regions (UTR). Optimization of the UTRs (favorable 5' and 3' UTRs can be obtained from cellular or viral RNAs), either both or independently, have been shown to increase mRNA stability and translational efficiency of in vitro transcribed mRNA (see, e.g., Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v. 969 (Rabinovich, P. H. Ed), 2013).

In addition to mRNA, other nucleic acid payloads may be used for this invention. For oligonucleotides, methods of preparation include but are not limited to chemical synthesis and enzymatic, chemical cleavage of a longer precursor, in vitro transcription as described above, etc. Methods of synthesizing DNA and RNA nucleotides are widely used and well known in the art (see, e.g., Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

For plasmid DNA, preparation for use with this invention commonly utilizes but is not limited to expansion and isolation of the plasmid DNA in vitro in a liquid culture of bacteria containing the plasmid of interest. The presence of a gene in the plasmid of interest that encodes resistance to a particular antibiotic (penicillin, kanamycin, etc.) allows those bacteria containing the plasmid of interest to selectively grow in antibiotic-containing cultures. Methods of isolating plasmid DNA are widely used and well known in the art (see, e.g., Heilig, J., Elbing, K. L. and Brent, R (2001) Large-Scale Preparation of Plasmid DNA. Current Protocols in Molecular Biology. 41:11:1.7:1.7.1-1.7.16; Rozkov, A., Larsson, B., Gillstrom, S., Bjornestedt, R. and Schmidt, S. R. (2008), Large-scale production of endotoxin-free plasmids for transient expression in mammalian cell culture. Biotechnol. Bioeng., 99: 557-566; and U.S. Pat. No. 6,197,553 B1). Plasmid isolation can be performed using a variety of commercially available kits including, but not limited to Plasmid Plus (Qiagen), GenJET plasmid MaxiPrep (Thermo) and PureYield MaxiPrep (Promega) kits as well as with commercially available reagents.

As used herein, the following terms have the meanings ascribed to them unless specified otherwise.

Unless the context requires otherwise, throughout the present specification and claims, the word "comprise" and variations thereof, such as, "comprises" and "comprising" are to be construed in an open and inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

The phrase "induce expression of a desired protein" refers to the ability of a nucleic acid to increase expression of the desired protein. To examine the extent of protein expression, a test sample (e.g., a sample of cells in culture expressing the desired protein) or a test mammal (e.g., a mammal such as a human or an animal model such as a rodent (e.g. mouse) or a non-human primate (e.g., monkey) model) is contacted with a nucleic acid (e.g., nucleic acid in combination with a lipid of the present invention). Expression of the desired protein in the test sample or test animal is compared to expression of the desired protein in a control sample (e.g. a sample of cells in culture expressing the desired protein) or a control mammal (e.g., a mammal such as a human or an animal model such as a rodent (e.g., mouse) or non-human primate (e.g., monkey) model) that is not contacted with or administered the nucleic acid. When the desired protein is present in a control sample or a control mammal, the expression of a desired protein in a control sample or a control mammal may be assigned a value of 1.0. In particular embodiments, inducing expression of a desired protein is achieved when the ratio of desired protein expression in the test sample or the test mammal to the level of desired protein expression in the control sample or the control mammal is greater than 1, for example, about 1.1, 1.5, 2.0. 5.0 or 10.0. When a desired protein is not present in a control sample or a control mammal, inducing expression of a desired protein is achieved when any measurable level of the desired protein in the test sample or the test mammal is detected. One of ordinary skill in the art will understand appropriate assays to determine the level of protein expression in a sample, for example dot blots, northern blots, in situ hybridization, ELISA, immunoprecipitation, enzyme function, and phenotypic assays, or assays based on reporter proteins that can produce fluorescence or luminescence under appropriate conditions.

The phrase "inhibiting expression of a target gene" refers to the ability of a nucleic acid to silence, reduce, or inhibit the expression of a target gene. To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with a nucleic acid that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the nucleic acid. The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the nucleic acids are capable of silencing, reducing, or inhibiting the expression of a target gene by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the nucleic acid. Suitable assays for determining the level of target gene expression include, without limitation, examination of protein or mRNA levels using techniques known to those of skill in the art, such as, e.g., dot blots, northern blots, in situ hybridization, ELISA, immunoprecipitation, enzyme function, as well as phenotypic assays known to those of skill in the art.

An "effective amount" or "therapeutically effective amount" of an active agent or therapeutic agent such as a therapeutic nucleic acid is an amount sufficient to produce the desired effect, e.g. an increase or inhibition of expression of a target sequence in comparison to the normal expression level detected in the absence of the nucleic acid. An increase in expression of a target sequence is achieved when any measurable level is detected in the case of an expression product that is not present in the absence of the nucleic acid. In the case where the expression product is present at some level prior to contact with the nucleic acid, an in increase in expression is achieved when the fold increase in value obtained with a nucleic acid such as mRNA relative to control is about 1.05, 1.1, 1.2, 1.3, 1.4, 1.5, 1.75, 2, 2.5, 3, 4, 5, 6, 7, 8, 9, 10, 15, 20, 25, 30, 40, 50, 75, 100, 250, 500, 750, 1000, 5000, 10000 or greater. Inhibition of expression of a target gene or target sequence is achieved when the value obtained with a nucleic acid such as antisense oligonucleotide relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, fluorescence or luminescence of suitable reporter proteins, as well as phenotypic assays known to those of skill in the art.

The term "nucleic acid" as used herein refers to a polymer containing at least two deoxyribonucleotides or ribonucleotides in either single- or double-stranded form and includes DNA, RNA, and hybrids thereof. DNA may be in the form of antisense molecules, plasmid DNA, cDNA, PCR products, or vectors. RNA may be in the form of small hairpin RNA (shRNA), messenger RNA (mRNA), antisense RNA, miRNA, micRNA, multivalent RNA, dicer substrate RNA or viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, single nucleotide polymorphisms, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are generally characterized by being poorly soluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "steroid" is a compound comprising the following carbon skeleton:

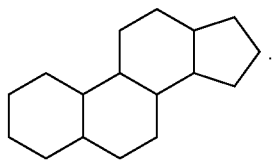 [SMILES: C1CCC2C(C1)CCC1C3CCCC3CCC21]

Non-limiting examples of steroids include cholesterol, and the like.

A "cationic lipid" refers to a lipid capable of being positively charged. Exemplary cationic lipids include one or more amine group(s) which bear the positive charge. Preferred cationic lipids are ionizable such that they can exist in a positively charged or neutral form depending on pH. The ionization of the cationic lipid affects the surface charge of the lipid nanoparticle under different pH conditions. This charge state can influence plasma protein absorption, blood clearance and tissue distribution (Semple, S. C., et al., Adv. Drug Deliv Rev 32:3-17 (1998)) as well as the ability to form endosomolytic non-bilayer structures (Hafez, I. M., et al., Gene Ther 8:1188-1196 (2001)) critical to the intracellular delivery of nucleic acids.

An "anionic lipid" refers to a lipid capable of being negatively charged. Exemplary anionic lipids include one or more phosphate group(s) which bear a negative charge, for example at physiological pHs. In some embodiments, the anionic lipid does not include a serine moiety, including phosphatidylserine lipids.

"Phosphatidylglycerol lipid" refers to a lipid with a structure that generally comprises a glycerol 3-phosphate backbone which is attached to saturated or unsaturated fatty acids via and ester linkage. Exemplary phosphatidylglycerol lipids have the following structure:

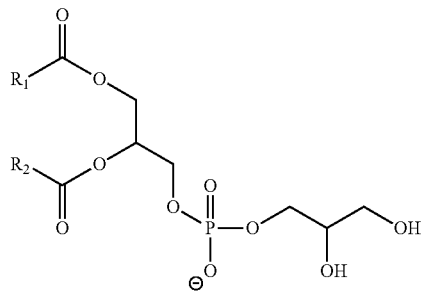

wherein $R_1$ and $R_2$ are each independently a branched or straight, saturated or unsaturated carbon chain (e.g., alkyl, alkenyl, alkynyl).

The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-DMG) and the like.

The term "neutral lipid" refers to any of a number of lipid species that exist either in an uncharged or neutral zwitterionic form at a selected pH. At physiological pH, such lipids include, but are not limited to, phosphotidylcholines such as 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), phophatidylethanolamines such as 1,2-Dioleoyl-sn-glycero-3-phosphoethanolamine (DOPE), sphingomyelins (SM), ceramides, steroids such as sterols and their derivatives. Neutral lipids may be synthetic or naturally derived.

The term "charged lipid" refers to any of a number of lipid species that exist in either a positively charged or negatively charged form independent of the pH within a useful physiological range, e.g., pH ~3 to pH ~9. Charged lipids may be synthetic or naturally derived. Examples of charged lipids include phosphatidylserines, phosphatidic acids, phosphatidylglycerols, phosphatidylinositols, sterol hemi succinates, dialkyl trimethylammonium-propanes, (e.g., DOTAP, DOTMA), dialkyl dimethylaminopropanes, ethyl phosphocholines, dimethylaminoethane carbamoyl sterols (e.g., DC-Chol).

The term "lipid nanoparticle" refers to particles having at least one dimension on the order of nanometers (e.g., 1-1,000 nm) which include one or more of the compounds of Formula I, II, III, IV or V or other specified cationic lipids. In some embodiments, lipid nanoparticles are included in a formulation that can be used to deliver an active agent or therapeutic agent, such as a nucleic acid (e.g., mRNA) to a target site of interest (e.g., cell, tissue, organ, tumor, and the like). In some embodiments, the lipid nanoparticles of the invention comprise a nucleic acid. Such lipid nanoparticles typically comprise a compound of Formula III, III, IV or V and one or more excipient selected from neutral lipids, charged lipids, steroids and polymer conjugated lipids. In some embodiments, the active agent or therapeutic agent, such as a nucleic acid, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells, e.g., an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, nucleic acids, when present in the lipid nanoparticles, are resistant in aqueous solution to degradation with a nuclease. Lipids and lipid nanoparticles comprising nucleic acids and their method of preparation are disclosed in, e.g., U.S. Pat. Nos. 8,569,256, 5,965,542 and U.S. Patent Publication Nos. 2016/0199485, 2016/0009637, 2015/0273068, 2015/0265708, 2015/0203446, 2015/0005363, 2014/0308304, 2014/0200257, 2013/086373, 2013/0338210, 2013/0323269, 2013/0245107, 2013/0195920, 2013/0123338, 2013/0022649, 2013/0017223, 2012/0295832, 2012/0183581, 2012/0172411, 2012/0027803, 2012/0058188, 2011/0311583, 2011/0311582, 2011/0262527, 2011/0216622, 2011/0117125, 2011/0091525, 2011/0076335, 2011/0060032, 2010/0130588, 2007/0042031, 2006/0240093, 2006/0083780, 2006/0008910, 2005/0175682, 2005/017054, 2005/0118253, 2005/0064595, 2004/0142025, 2007/0042031, 1999/009076 and PCT Pub. Nos. WO 99/39741, WO 2017/004143, WO 2017/075531, WO 2015/199952, WO 2014/008334, WO 2013/086373, WO 2013/086322, WO 2013/016058, WO 2013/086373, WO2011/141705, and WO 2001/07548, the full disclosures of which are herein incorporated by reference in their entirety for all purposes.

Other exemplary lipids and lipid nanoparticles and their manufacture are described in the art, for example in U.S. Patent Application Publication No. U.S. 2012/0276209, Semple et al., 2010, Nat Biotechnol., 28(2):172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids. 2, e139; Maier et al., 2013, Mol Ther., 21(8): 1570-1578; and Tam et al., 2013, Nanomedicine, 9(5): 665-74, each of which are incorporated by reference in their entirety. Lipids and their manufacture can be found, for example, in U.S. Pub. No. 2015/0376115 and 2016/0376224, both of which are incorporated herein by reference.

As used herein, "lipid encapsulated" refers to a lipid nanoparticle that provides an active agent or therapeutic agent, such as a nucleic acid (e.g., mRNA), with full encapsulation, partial encapsulation, or both. In an embodiment, the nucleic acid (e.g., mRNA) is fully encapsulated in the lipid nanoparticle.

As used herein, the term "aqueous solution" refers to a composition comprising water.

"Serum-stable" in relation to nucleic acid-lipid nanoparticles means that the nucleotide is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of a therapeutic product that can result in a broad exposure of an active agent within an organism. Some techniques of administration can lead to the systemic delivery of certain agents, but not others. Systemic delivery means that a useful, preferably therapeutic, amount of an agent is exposed to most parts of the body. Systemic delivery of lipid nanoparticles can be by any means known in the art including, for example, intravenous, intraarterial, subcutaneous, and intraperitoneal delivery. In some embodiments, systemic delivery of lipid nanoparticles is by intravenous delivery.

"Local delivery," as used herein, refers to delivery of an active agent directly to a target site within an organism. For example, an agent can be locally delivered by direct injection into a disease site such as a tumor, other target site such as a site of inflammation, or a target organ such as the liver, heart, pancreas, kidney, and the like. Local delivery can also include topical applications or localized injection techniques such as intramuscular, subcutaneous or intradermal injection. Local delivery does not preclude a systemic pharmacological effect.

"Amino acid" refers to naturally-occurring and non-naturally occurring amino acids. An amino acid lipid can be made from a genetically encoded amino acid, a naturally occurring non-genetically encoded amino acid, or a synthetic amino acid. Examples of amino acids include Ala, Arg, Asn, Asp, Cys, Gln, Glu, Gly, His, Ile, Leu, Lys, Met, Phe, Pro, Ser, Thr, Trp, Tyr, and Val. Examples of amino acids also include azetidine, 2-aminooctadecanoic acid, 2-aminoadipic acid, 3-aminoadipic acid, 2,3-diaminopropionic acid, 2-aminobutyric acid, 4-aminobutyric acid, 2,3-diaminobutyric acid, 2,4-diaminobutyric acid, 2-aminoisobutyric acid, 4-aminoisobutyric acid, 2-aminopimelic acid, 2,2'-diaminopimelic acid, 6-aminohexanoic acid, 6-aminocaproic acid, 2-aminoheptanoic acid, desmosine, ornithine, citrulline, N-methylisoleucine, norleucine, tert-leucine, phenylglycine, t-butylglycine, N-methylglycine, sacrosine, N-ethylglycine, cyclohexylglycine, 4-oxo-cyclohexylglycine, N-ethylasparagine, cyclohexylalanine, t-butylalanine, naphthylalanine, pyridylalanine, 3-chloroalanine, 3-benzothienylalanine, 4-halophenylalanine, 4-chlorophenylalanine, 2-fluorophenylalanine, 3-fluorophenylalanine, 4-fluorophenylalanine, penicillamine, 2-thienylalanine, methionine, methionine sulfoxide, homoarginine, norarginine, nor-norarginine, N-acetyllysine, 4-aminophenylalanine, N-methylvaline, homocysteine, homoserine, hydroxylysine, allo-hydroxylysine, 3-hydroxyproline, 4-hydroxyproline, isodesmosine, allo-isoleucine, 6-N-methyllysine, norvaline, 0-allyl-serine, 0-allyl-threonine, alpha-aminohexanoic acid, alpha-aminovaleric acid, pyroglutamic acid, and derivatives thereof. "Amino acid" includes alpha- and beta-amino acids. Examples of amino acid residues can be found in Fasman, CRC Practical Handbook of Biochemistry and Molecular Biology, CRC Press, Inc. (1989).

"Alkyl" refers to a straight or branched hydrocarbon chain radical consisting solely of carbon and hydrogen atoms, which is saturated or unsaturated (i.e., contains one or more double (alkenyl) and/or triple bonds (alkynyl)), having, for example, from one to twenty-four carbon atoms ($C_1$-$C_{24}$ alkyl), four to twenty carbon atoms ($C_4$-$C_{20}$ alkyl), six to sixteen carbon atoms ($C_6$-$C_{16}$ alkyl), six to nine carbon atoms ($C_6$-$C_9$ alkyl), one to fifteen carbon atoms ($C_1$-$C_{15}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond, e.g., methyl, ethyl, n propyl, 1 methylethyl (iso propyl), n butyl, n pentyl, 1,1-dimethylethyl (t butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double (alkenylene) and/or triple bonds (alkynylene)), and having, for example, from one to twenty-four carbon atoms ($C_1$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene), e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

The term "alkenyl" refers to an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkoxy" refers to an alkyl, cycloalkyl, alkenyl, or alkynyl group covalently bonded to an oxygen atom.

"Alkanoyloxy" refers to —O—C(=O)-alkyl groups.

"Alkylamino" refers to the group —NRR', where R and R' are each either hydrogen or alkyl, and at least one of R and R' is alkyl. Alkylamino includes groups such as piperidino wherein R and R' form a ring. The term "alkylaminoalkyl" refers to -alkyl-NRR'.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The terms "acyl," "carbonyl," and "alkanoyl" refer to any alkyl, alkenyl, or alkynyl wherein the carbon at the point of attachment is substituted with an oxo group, as defined below. The following are non-limiting examples of acyl, carbonyl or alkanoyl groups: —C(=O)alkyl, —C(=O)alkenyl, and —C(=O)alkynyl.

"Aryl" refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

"Carboxyl" refers to a functional group of the formula —C(=O)OH.

"Cyano" refers to a functional group of the formula —CN.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylene" is a divalent cycloalkyl group. Unless otherwise stated specifically in the specification, a cycloalkylene group may be optionally substituted.

The term "diacylglycerol" or "DAG" includes a compound having 2 fatty acyl chains, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl (C12), myristoyl (C14), palmitoyl (C16), stearoyl (C18), and icosoyl (C20). In preferred embodiments, the fatty acid acyl chains of one compound are the same, i.e., both myristoyl (i.e., dimyristoyl), both stearoyl (i.e., distearoyl), etc.

The term "heterocycle" or "heterocyclyl" refers to an aromatic or nonaromatic ring system of from five to twenty-two atoms, wherein from 1 to 4 of the ring atoms are heteroatoms selected from oxygen, nitrogen, and sulfur. Thus, a heterocycle may be a heteroaryl or a dihydro or tetrathydro version thereof. Heterocycles include, but are not limited to, pyrrolidine, tetryhydrofuran, thiolane, azetidine, oxetane, thietane, diazetidine, dioxetane, dithietane, piperidine, tetrahydrofuran, pyran, tetrahydropyran, thiacyclohexane, tetrahydrothiophene, pyridine, pyrimidine and the like.

"Heteroaryl" refers to any stable monocyclic, bicyclic, or polycyclic carbon ring system of from 4 to 12 atoms in each ring, wherein at least one ring is aromatic and contains from 1 to 4 heteroatoms selected from oxygen, nitrogen and sulfur. Some examples of a heteroaryl include acridinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, and tetrahydroquinolinyl. A heteroaryl includes the N-oxide derivative of a nitrogen-containing heteroaryl.

The terms "alkylamine" and "dialkylamine" refer to —NH(alkyl) and —N(alkyl)$_2$ radicals respectively.

The term "alkylphosphate" refers to —O—P(Q')(Q'')—O—R, wherein Q' and Q'' are each independently O, S, N(R)$_2$, optionally substituted alkyl or alkoxy; and R is optionally substituted alkyl, ω-aminoalkyl or ω-(substituted)aminoalkyl.

The term "alkylphosphorothioate" refers to an alkylphosphate wherein at least one of Q' or Q'' is S.

The term "alkylphosphonate" refers to an alkylphosphate wherein at least one of Q' or Q'' is alkyl.

"Hydroxyalkyl" refers to an —O-alkyl radical.

The term "alkylheterocycle" refers to an alkyl where at least one methylene has been replaced by a heterocycle.

The term "ω-aminoalkyl" refers to -alkyl-NH$_2$ radical. And the term "ω-(substituted)aminoalkyl refers to an ω-aminoalkyl wherein at least one of the H on N has been replaced with alkyl.

The term "ω-phosphoalkyl" refers to -alkyl-O—P(Q')(Q'')—O—R, wherein Q' and Q'' are each independently O or S and R optionally substituted alkyl.

The term "ω-thiophosphoalkyl" refers to ω-phosphoalkyl wherein at least one of Q' or Q'' is S.

The term "substituted" used herein means any of the above groups (e.g., alkyl, alkylene, cycloalkyl or cycloalkylene) wherein at least one hydrogen atom is replaced by a bond to a non-hydrogen atom such as, but not limited to: a halogen atom such as F, Cl, Br, or I; oxo groups (=O); hydroxyl groups (—OH); $C_1$-$C_{12}$ alkyl groups; cycloalkyl groups; —(C=O)OR'; —O(C=O)R'; —C(=O)R'; —OR'; —S(O)$_x$R'; —C(=O)SR'; —SC(=O)R'; —NR'R'; —NR'C(=O)R'; —C(=O)NR'R'; —NR'C(=O)NR'R'; —OC(=O)NR'R'; —NR'C(=O)OR'; —NR'S(O)$_x$NR'R'; —NR'S(O)$_x$R'; and —S(O)$_x$NR'R', wherein: R' is, at each occurrence, independently H, $C_1$-$C_{15}$ alkyl or cycloalkyl, and x is 0, 1 or 2. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is an oxo group. In other embodiments, the substituent is a hydroxyl group. In other embodiments, the substituent is an alkoxy group (—OR'). In other embodiments, the substituent is a carboxyl group. In other embodiments, the substituent is an amine group (—NR'R').

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Prodrug" is meant to indicate a compound, such as a therapeutic agent, that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs (e.g., a prodrug of a therapeutic agent) may be prepared by modifying functional groups present in the compound of the invention in such a way that the modifications are cleaved, either in routine manipulation or in vivo, to the parent compound of the invention. Prodrugs include compounds wherein a hydroxy, amino or mercapto group is bonded to any group such that, when the prodrug is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the therapeutic agents of the invention and the like.

Embodiments of the invention disclosed herein are also meant to encompass all pharmaceutically acceptable lipid nanoparticles and components thereof (e.g., cationic lipid, therapeutic agent, etc.) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled LNPs could be useful to help determine or measure the effectiveness of the compounds, by characterizing, for example, the site or mode of action, or binding affinity to pharmacologically important site of action. Certain isotopically-labelled LNPs, for example, those incorporating a radioactive isotope, are useful in drug and/or substrate tissue distribution studies. The radioactive isotopes tritium, i.e., $^3$H, and carbon-14, that is, $^{14}$C, are particularly useful for this purpose in view of their ease of incorporation and ready means of detection.

Substitution with heavier isotopes such as deuterium, that is, $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula I, II, III, IV or V can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethane-sulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of an LNP of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment in the mammal, preferably a human. The amount of a lipid nanoparticle of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

Lipid Nanoparticles

In certain embodiments, the present invention provides lipid nanoparticles comprising a therapeutic agent encapsulated within or associated with the lipid nanoparticle. The conventional knowledge in the art is that the most effective LNP formulation is one where the cationic lipid concentration is maximized with respect to the other LNP components. For example, prior art LNPs typically comprise a cationic lipid at molar ratios of 50% or more since maximal cationic lipid concentration was thought to be essential to obtaining desirable encapsulation efficiency, in vivo activity and other characteristics of LNPs. However, the data provided herein demonstrate the surprising result that the most effective cationic lipid proportion is not necessarily the maximum concentration accommodated and the performance of LNPs can be improved with other unpredicted combinations with charged lipid species (e.g., cationic lipids with lower pKa, an additional cationic lipid or an anionic lipid).

Accordingly, in one embodiment ("Embodiment 1") is provided a lipid nanoparticle comprising:

i) between 40 and 50 mol percent of a cationic lipid;
ii) a neutral lipid;
iii) a steroid;
iv) a polymer conjugated lipid; and
v) a therapeutic agent encapsulated within or associated with the lipid nanoparticle.

As used herein, "mol percent" refers to a component's molar percentage relative to total mols of all lipid components in the LNP (i.e., total mols of cationic lipid(s), the neutral lipid, the steroid and the polymer conjugated lipid).

In certain aspects of Embodiment 1, the lipid nanoparticle comprises from 41 to 49 mol percent, from 41 to 48 mol percent, from 42 to 48 mol percent, from 43 to 48 mol percent, from 44 to 48 mol percent, from 45 to 48 mol percent, from 46 to 48 mol percent, or from 47.2 to 47.8 mol percent of the cationic lipid. In certain specific embodiments, the lipid nanoparticle comprises about 47.0, 47.1, 47.2, 47.3, 47.4, 47.5, 47.6, 47.7, 47.8, 47.9 or 48.0 mol percent of the cationic lipid.

In certain other embodiments of Embodiment 1, the neutral lipid is present in a concentration ranging from 5 to 15 mol percent, 7 to 13 mol percent, or 9 to 11 mol percent. In certain specific embodiments, the neutral lipid is present in a concentration of about 9.5, 10 or 10.5 mol percent. In some embodiments, the molar ratio of the cationic lipid to the neutral lipid ranges from about 4.1:1.0 to about 4.9:1.0, from about 4.5:1.0 to about 4.8:1.0, or from about 4.7:1.0 to 4.8:1.0.

In different embodiments of Embodiment 1, the steroid is cholesterol. In some embodiments, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In certain specific embodiments, the steroid is present in a concentration of 40, 41, 42, 43, 44, 45, or 46 molar percent. In certain embodiments, the molar ratio of cationic lipid to the steroid ranges from 1.0:0.9 to 1.0:1.2, or from 1.0:1.0 to 1.0:1.2. In different embodiments, the steroid is cholesterol.

In other embodiments of Embodiment 1, the mRNA to lipid ratio in the LNP (i.e., N/P, were N represents the moles of cationic lipid and P represents the moles of phosphate present as part of the nucleic acid backbone) range from 2:1 to 30:1, for example 3:1 to 22:1. In other embodiments, N/P ranges from 6:1 to 20:1 or 2:1 to 12:1. Exemplary N/P ranges include about 3:1. About 6:1, about 12:1 and about 22:1.

Another embodiment ("Embodiment 2") provides a lipid nanoparticle comprising:
  i) a cationic lipid having an effective pKa greater than 6.0;
  ii) from 5 to 15 mol percent of a neutral lipid;
  iii) from 1 to 15 mol percent of an anionic lipid;
  iv) from 30 to 45 mol percent of a steroid;
  v) a polymer conjugated lipid; and
  vi) a therapeutic agent, or a pharmaceutically acceptable salt or prodrug thereof, encapsulated within or associated with the lipid nanoparticle,
wherein the mol percent is determined based on total mol of lipid present in the lipid nanoparticle.

In certain embodiments of Embodiment 2, the cationic lipid can be any of a number of lipid species which carry a net positive charge at a selected pH, such as physiological pH. Exemplary cationic lipids are described herein below. In some embodiments, the cationic lipid has a pKa greater than 6.25. In other embodiments, the cationic lipid has a pKa greater than 6.5. In certain embodiments, the cationic lipid has a pKa greater than 6.1, greater than 6.2, greater than 6.3, greater than 6.35, greater than 6.4, greater than 6.45, greater than 6.55, greater than 6.6, greater than 6.65, or greater than 6.7.

In other embodiments of Embodiment 2, the lipid nanoparticle comprises from 40 to 45 mol percent of the cationic lipid. In some embodiments, the lipid nanoparticle comprises from 45 to 50 mole percent of the cationic lipid.

In various embodiments, the molar ratio of the cationic lipid to the neutral lipid ranges from about 2:1 to about 8:1.

In some embodiments, the lipid nanoparticle comprises from 5 to 10 mol percent of the neutral lipid.

Exemplary anionic lipids for use in Embodiment 2 include, but are not limited to, phosphatidylglycerol, dioleoylphosphatidylglycerol (DOPG), dipalmitoylphosphatidylglycerol (DPPG) or 1,2-distearoyl-sn-glycero-3-phospho-(1'-rac-glycerol) (DSPG).

In some embodiments of Embodiment 2, the lipid nanoparticle comprises from 1 to 10 mole percent of the anionic lipid. In certain embodiments, the lipid nanoparticle comprises from 1 to 5 mole percent of the anionic lipid. In some embodiments, the lipid nanoparticle comprises from 1 to 9 mole percent, from 1 to 8 mole percent, from 1 to 7 mole percent, or from 1 to 6 mole percent of the anionic lipid. In certain embodiments, the mol ratio of anionic lipid to neutral lipid ranges from 1:1 to 1:10.

In certain embodiments of Embodiment 2, the steroid cholesterol. In some of these embodiments, the molar ratio of the cationic lipid to cholesterol ranges from about 5:1 to 1:1. In certain embodiments, the lipid nanoparticle comprises from 32 to 40 mol percent of the steroid.

In certain other embodiments of Embodiment 2, the sum of the mol percent of neutral lipid and mol percent of anionic lipid ranges from 5 to 15 mol percent. In certain embodiments, wherein the sum of the mol percent of neutral lipid and mol percent of anionic lipid ranges from 7 to 12 mol percent.

In different embodiments of Embodiment 2, the mol ratio of anionic lipid to neutral lipid ranges from 1:1 to 1:10. In some embodiments, the sum of the mol percent of neutral lipid and mol percent steroid ranges from 35 to 45 mol percent.

In some more specific examples of Embodiment 2, the lipid nanoparticle comprises:
  i) from 45 to 55 mol percent of the cationic lipid;
  ii) from 5 to 10 mol percent of the neutral lipid;
  iii) from 1 to 5 mol percent of the anionic lipid; and
  iv) from 32 to 40 mol percent of the steroid.

In certain other embodiments of Embodiment 2, the lipid nanoparticle comprises from 1.0 to 2.5 mol percent of the conjugated lipid. In some embodiments, the polymer conjugated lipid is present in a concentration of about 1.5 mol percent.

Still another embodiment ("Embodiment 3") provides a lipid nanoparticle comprising:
  i) a first cationic lipid having a effective pKa;
  ii) a second cationic lipid having a second effective pKa, the second effective pKa being greater than the first effective pKa;
  iii) a neutral lipid;
  iv) a steroid;
  v) a polymer conjugated lipid; and
  vi) a therapeutic agent, or a pharmaceutically acceptable salt thereof, encapsulated within or associated with the lipid nanoparticle,
wherein the lipid nanoparticle has an effective pKa between the first and second effective pKa's.

In embodiments of Embodiment 3, the first effective pKa is less than 5.50, less than 5.60, less than 5.70, less than 5.80, less than 5.90 or less than 6.0. In other embodiments, the first effective pKa is less than 5.55, less than 5.65, less than 5.75, less than 5.85 or less than 5.95. In some embodiments, the first effective pKa ranges from about 5.5 to about 6.3.

In other embodiments of Embodiment 3, the second effective pKa ranges from about 6.3 to about 7. In different embodiments, the second effective pKa is greater than 6.25, greater than 6.35, greater than 6.45, greater than 6.55, greater than 6.65 or greater than 6.75. In other embodiments, the second effective pKa is greater than 6.30, greater than 6.40, greater than 6.50, greater than 6.60 or greater than 6.70.

The lipid nanoparticle of various embodiments of Embodiment 3 has an optimized effective pKa. For example, in some embodiments the lipid nanoparticle has an effective pKa ranging from 5.5 to 6.5, from 5.9 to 6.4, from 5.9 to 6.35 or from 6.0 to 6.2.

In certain embodiments of Embodiment 3, the total mol percent of cationic lipid in the lipid nanoparticle ranges from 40 to 55 mol percent or from 45 to 55 mol percent based on total lipid present in the lipid nanoparticle. As used herein, "mol percent" refers to a component's molar percentage relative to total mols of all lipid components in the LNP (i.e., total mols of cationic lipid, the neutral lipid, the steroid and the polymer conjugated lipid).

In other embodiments of Embodiment 3, the mol ratio of the first cationic lipid to the second cationic lipid ranges from 1:9 to 1:2 or from 1:20 to 1:2.

The first and second cationic lipids of Embodiment 3 can independently be any of a number of lipid species which carry a net positive charge at a selected pH, such as physiological pH. Such lipids include, but are not limited to the lipids disclosed herein below.

In certain embodiments of Embodiment 3, the neutral lipid is present in a concentration ranging from 5 to 15 mol percent, 7 to 13 mol percent, or 9 to 11 mol percent. In certain specific embodiments, the neutral lipid is present in a concentration of about 9.5, 10 or 10.5 mol percent. In some embodiments, the molar ratio of the cationic lipid to the neutral lipid ranges from about 4.1:1.0 to about 4.9:1.0, from about 4.5:1.0 to about 4.8:1.0, or from about 4.7:1.0 to 4.8:1.0.

In certain other embodiments of Embodiment 3, the steroid is cholesterol. In some embodiments, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In certain specific embodiments, the steroid is present in a concentration of 40, 41, 42, 43, 44, 45, or 46 molar percent. In certain embodiments, the molar ratio of cationic lipid to the steroid ranges from 1.0:0.9 to 1.0:1.2, or from 1.0:1.0 to 1.0:1.2.

In some embodiments of Embodiment 3, the molar ratio of total cationic lipid (i.e., the sum of the first and second cationic lipid) to steroid ranges from 5:1 to 1:1.

In any of Embodiment 1, 2 or 3, the lipid nanoparticle comprises from 1.0 to 2.5 mol percent of the conjugated lipid. In some embodiments, the polymer conjugated lipid is present in a concentration of about 1.5 mol percent.

In various embodiments of Embodiments 1, 2 or 3, the molar ratio of cationic lipid to polymer conjugated lipid ranges from about 100:1 to about 20:1. In some embodiments, the molar ratio of cationic lipid to the polymer conjugated lipid ranges from about 35:1 to about 25:1.

In other of any of Embodiments 1, 2 or 3, the molar ratio of total cationic lipid to polymer conjugated lipid ranges from about 100:1 to about 20:1. In some embodiments, the molar ratio of total cationic lipid to the polymer conjugated lipid ranges from about 35:1 to about 25:1.

In some of Embodiments 1, 2 or 3, the lipid nanoparticle has a mean diameter ranging from 50 nm to 100 nm, or from 60 nm to 85 nm.

The cationic lipid(s) for use in any of Embodiments 1, 2 or 3 can be any of a number of lipid species which carry a net positive charge at a selected pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3dioleoyloxy)propyl)-N,N,N-trimethylammonium chloride (DOTAP); 3-(N—(N',N'dimethylaminoethane)-carbamoyl)cholesterol (DC-Chol), N-(1-(2,3-dioleoyloxy)propyl)N-2-(sperminecarboxamido)ethyl)-N,N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE).

Additionally, a number of commercial preparations of cationic lipids are available which can be used in Embodiments 1, 2 or 3. These include, for example, LIPOFECTIN® (commercially available cationic liposomes comprising DOTMA and 1,2-dioleoyl-sn-3phosphoethanolamine (DOPE), from GIBCO/BRL, Grand Island, N.Y.); LIPOFECTAMINE® (commercially available cationic liposomes comprising N-(1-(2,3dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In one specific embodiment, the cationic lipid for use in Embodiments 1, 2 or 3 is independently an amino lipid. Suitable amino lipids include those described in WO 2012/016184, incorporated herein by reference in its entirety. Representative amino lipids include, but are not limited to, 1,2-dilinoleyoxy-3-(dimethylamino)acetoxypropane (DLinDAC), 1,2-dilinoleyoxy-3morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N, Ndilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

In some of Embodiments 1, 2 or 3, a cationic lipid (e.g., the cationic lipid, the first cationic lipid, the second cationic lipid) has the following formula:

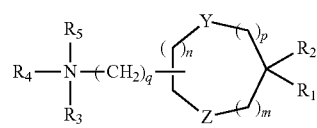

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl; m, n, and p are either the same or different and independently either 0 or 1 with the proviso that m, n, and p are not simultaneously 0; q is 0, 1, 2, 3, or 4; and Y and Z are either the same or different and independently O, S, or NH. In one embodiment, $R_1$ and $R_2$ are each linoleyl, and the amino lipid is a dilinoleyl amino lipid. In one embodiment, the amino lipid is a dilinoleyl amino lipid.

In various other embodiments, a cationic lipid of Embodiments 1, 2 or 3 (e.g., the cationic lipid, the first cationic lipid, the second cationic lipid) has the following structure:

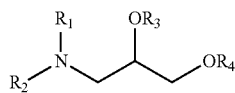

or a pharmaceutically acceptable salt, tautomer, prodrug or stereoisomer thereof, wherein:

$R_1$ and $R_2$ are independently selected from the group consisting of H, and $C_1$-$C_3$ alkyls;

$R_3$ and $R_4$ are independently selected from the group consisting of alkyl groups having from about 10 to about 20 carbon atoms, wherein at least one of $R_3$ and $R_4$ comprises at least two sites of unsaturation. (e.g., $R_3$ and $R_4$ may be, for example, dodecadienyl, tetradecadienyl, hexadecadienyl, linoleyl, and icosadienyl. In a preferred embodiment, $R_3$ and $R_4$ are both linoleyl. $R_3$ and $R_4$ may comprise at least three sites of unsaturation (e.g., $R_3$ and $R_4$ may be, for example, dodecatrienyl, tetradectrienyl, hexadecatrienyl, linolenyl, and icosatrienyl).

In some embodiments, a cationic lipid of Embodiments 1, 2 or 3 (e.g., the cationic lipid, the first cationic lipid, the second cationic lipid) has the following structure:

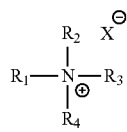

or a pharmaceutically acceptable salt, tautomer, prodrug or stereoisomer thereof, wherein:

$R_1$ and $R_2$ are independently selected and are H or $C_1$-$C_3$ alkyls. $R_3$ and $R_4$ are independently selected and are alkyl groups having from about 10 to about 20 carbon atoms, wherein at least one of $R_4$ and $R_4$ comprises at least two sites of unsaturation. In one embodiment, $R_3$ and $R_4$ are both the same, for example, in some embodiments $R_3$ and $R_4$ are both linoleyl (i.e., C18), etc. In another embodiment, $R_3$ and $R_4$ are different, for example, in some embodiments $R_3$ is tetradectrienyl (C14) and $R_4$ is linoleyl (C18). In a preferred embodiment, the cationic lipids) of the present invention are symmetrical, i.e., $R_3$ and $R_4$ are the same. In another preferred embodiment, both $R_3$ and $R_4$ comprise at least two sites of unsaturation. In some embodiments, $R_3$ and $R_4$ are independently selected from dodecadienyl, tetradecadienyl, hexadecadienyl, linoleyl, and icosadienyl. In a preferred embodiment, $R_3$ and $R_4$ are both linoleyl. In some embodiments, $R_4$ and $R_4$ comprise at least three sites of unsaturation and are independently selected from, e.g., dodecatrienyl, tetradectrienyl, hexadecatrienyl, linolenyl, and icosatrienyl.

In various embodiments, a cationic lipid of Embodiments 1, 2 or 3 (e.g., the cationic lipid, the first cationic lipid, the second cationic lipid) has the formula:

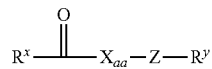

or a pharmaceutically acceptable salt, tautomer, prodrug or stereoisomer thereof, wherein:

$X_{aa}$ is a D- or L-amino acid residue having the formula $-NR^N-CR^1R^2-C(C=O)-$, or a peptide or a peptide of amino acid residues having the formula $-\{NR^N-CR^1R^2-(C=O)\}_n-$, wherein n is 2 to 20;

$R^1$ is independently, for each occurrence, a non-hydrogen, substituted or unsubstituted side chain of an amino acid;

$R^2$ and $R^N$ are independently, for each occurrence, hydrogen, an organic group consisting of carbon, oxygen, nitrogen, sulfur, and hydrogen atoms, or any combination of the foregoing, and having from 1 to 20 carbon atoms, $C_{(1-5)}$alkyl, cycloalkyl, cycloalkylalkyl, $C_{(3-5)}$alkenyl, $C_{(3-5)}$alkynyl, $C_{(1-5)}$alkanoyl, $C_{(1-5)}$alkanoyloxy, $C_{(1-5)}$alkoxy, $C_{(1-5)}$alkoxy-$C_{(1-5)}$alkyl, $C_{(1-5)}$alkoxy-$C_{(1-5)}$alkoxy, $C_{(1-5)}$alkyl-amino-$C_{(1-5)}$alkyl-, $C_{(1-5)}$dialkyl-amino-$C_{(1-5)}$alkyl-, nitro-$C_{(1-5)}$alkyl, cyano-$C_{(1-5)}$alkyl, aryl-$C_{(1-5)}$alkyl, 4-biphenyl-$C_{(1-5)}$alkyl, carboxyl, or hydroxyl;

Z is NH, O, S, $-CH_2S-$, $-CH_2S(O)-$, or an organic linker consisting of 1-40 atoms selected from hydrogen, carbon, oxygen, nitrogen, and sulfur atoms (preferably, Z is NH or O);

$R^x$ and $R^y$ are, independently, (i) a lipophilic tail derived from a lipid (which can be naturally-occurring or synthetic), phospholipid, glycolipid, triacylglycerol, glycerophospholipid, sphingolipid, ceramide, sphingomyelin, cerebroside, or ganglioside, wherein the tail optionally includes a steroid; (ii) an amino acid terminal group selected from hydrogen, hydroxyl, amino, and an organic protecting group; or (iii) a substituted or unsubstituted $C_{(3-22)}$alkyl, $C_{(6-12)}$cycloalkyl, $C_{(6-12)}$cycloalkyl-$C_{(3-22)}$alkyl, $C_{(3-22)}$alkenyl, $C_{(3-22)}$alkynyl, $C_{(1-22)}$alkoxy, or $C_{(6-12)}$-alkoxy-$C_{(3-22)}$alkyl;

one of $R^x$ and $R^y$ is a lipophilic tail as defined above and the other is an amino acid terminal group, or both $R^x$ and $R^y$ are lipophilic tails;

at least one of $R^x$ and $R^y$ is interrupted by one or more biodegradable groups (e.g., $-OC(O)-$, $-C(O)O-$, $-SC(O)-$, $-C(O)S-$, $-OC(S)-$, $-C(S)O-$, $-S-S-$, $-C(R^5)=N-$, $-N=C(R^5)-$, $-C(R^5)=N-O-$, $-O-N=C(R^5)-$, $-C(O)(NR^5)-$, $-N(R^5)C(O)-$, $-C(S)(NR^5)-$, $-N(R^5)C(O)-$, $-N(R^5)C(O)N(R^5)-$, $-OC(O)O-$, $-OSi(R^5)_2O-$, $-C(O)(CR^3R^4)C(O)O-$, $-OC(O)(CR^3R^4)C(O)-$ or

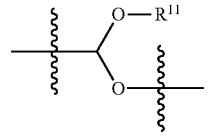

wherein $R^{11}$ is a $C_2$-$C_8$ alkyl or alkenyl and each occurrence of $R^5$ is, independently, H or alkyl; and each occurrence of $R^3$ and $R^4$ are, independently H, halogen, OH, alkyl, alkoxy, $-NH_2$, alkylamino, or dialkylamino; or $R^3$ and $R^4$, together with the carbon atom to which they are directly attached, form a cycloalkyl group (in one preferred embodiment, each occurrence of $R^3$ and $R^4$ are, independently H or $C_1$-$C_4$ alkyl)); and $R^x$ and $R^y$ each, independently, optionally have one or more carbon-carbon double bonds.

In some embodiments, a cationic lipid of Embodiments 1, 2 or 3 (e.g., the cationic lipid, the first cationic lipid, the second cationic lipid) is one of the following:

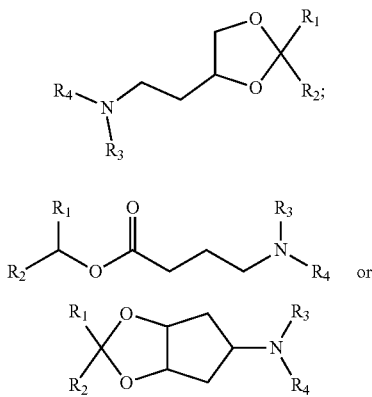

or a pharmaceutically acceptable salt, tautomer, prodrug or stereoisomer thereof, wherein:

$R_1$ and $R_2$ are independently alkyl, alkenyl or alkynyl, and each can be optionally substituted;

$R_3$ and $R_4$ are independently a $C_1$-$C_6$ alkyl, or $R_3$ and $R_4$ can be taken together to form an optionally substituted heterocyclic ring.

A representative useful dilinoleyl amino lipid has the formula:

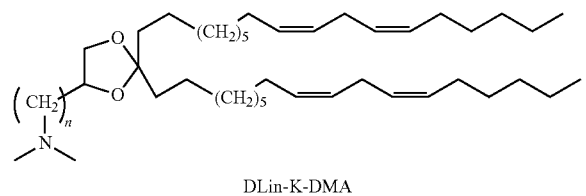

DLin-K-DMA wherein n is 0, 1, 2, 3, or 4.

In one embodiment, a cationic lipid of Embodiments 1, 2 or 3 (e.g., the cationic lipid, the first cationic lipid, the second cationic lipid) is DLin-K-DMA. In one embodiment, a cationic lipid of any one of the disclosed embodiments (e.g., the cationic lipid, the first cationic lipid, the second cationic lipid) is DLin-KC2-DMA (DLin-K-DMA above, wherein n is 2).

In one embodiment, a cationic lipid of Embodiments 1, 2 or 3 (e.g., the cationic lipid, the first cationic lipid, the second cationic lipid) has the following structure:

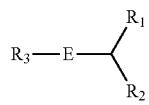

or a pharmaceutically acceptable salt, tautomer, prodrug or stereoisomer thereof, wherein:

$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl or optionally substituted $C_{10}$-$C_{30}$ acyl;

$R_3$ is H, optionally substituted $C_{10}$-$C_{10}$ alkyl, optionally substituted alkenyl, optionally substituted $C_2$-$C_{10}$ alkynyl, alkylhetrocycle, alkylphosphate, alkylphosphorothioate, alkylphosphorodithioate, alkylphosphonate, alkylamine, hydroxyalkyl, ω-aminoalkyl, ω-(substituted)aminoalkyl, ω-phosphoalkyl, ω-thiophosphoalkyl, optionally substituted polyethylene glycol (PEG, mw 100-40K), optionally substituted mPEG (mw 120-40K) heteroaryl, or heterocycle, or linker-ligand, for example in some embodiments $R_3$ is $(CH_3)_2\bar{N}(CH_2)_n$—, wherein n is 1, 2, 3 or 4;

E is O, S, N(Q), C(O), OC(O), C(O)O, N(Q)C(O), C(O)N(Q), (Q)N(CO)O, O(CO)N(Q), S(O), NS(O)$_2$N(Q), S(O)$_2$, N(Q)S(O)$_2$, SS, O=N, aryl, heteroaryl, cyclic or heterocycle, for example —C(O)O, wherein - is a point of connection to $R_3$; and Q is H, alkyl, ω-aminoalkyl, ω-(substituted)aminoalkyl, ω-phosphoalkyl or ω-thiophosphoalkyl.

In one specific embodiment, a cationic lipid of Embodiments 1, 2 or 3 (e.g., the cationic lipid, the first cationic lipid, the second cationic lipid) has the following structure:

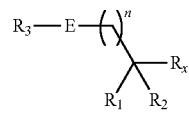

or a pharmaceutically acceptable salt, tautomer, prodrug or stereoisomer thereof, wherein:

E is O, S, N(Q), C(O), N(Q)C(O), C(O)N(Q), (Q)N(CO)O, O(CO)N(Q), S(O), NS(O)$_2$N(Q), S(O)$_2$, N(Q)S(O)$_2$, SS, O=N, aryl, heteroaryl, cyclic or heterocycle;

Q is H, alkyl, ω-amninoalkyl, ω-(substituted)amninoalky, ω-phosphoalkyl or ω-thiophosphoalkyl;

$R_1$ and $R_2$ and $R_x$ are each independently for each occurrence H, optionally substituted $C_1$-$C_{10}$ alkyl, optionally substituted $C_{10}$-$C_{30}$alkyl, optionally substituted $C_{10}$-$C_{30}$ alkenyl, optionally substituted $C_{10}$-$C_{30}$ alkynyl, optionally substituted $C_{10}$-$C_{30}$ acyl, or linker-ligand, provided that at least one of $R_1$, $R_2$ and $R_x$ is not H;

$R_3$ is H, optionally substituted $C_1$-$C_{10}$ alkyl, optionally substituted $C_2$-$C_{10}$ alkenyl, optionally substituted $C_2$-$C_{10}$ alkynyl, alkylhetrocycle, alkylphosphate, alkylphosphorothioate, alkylphosphorodithioate, alkylphosphonate, alkylamine, hydroxyalkyl, ω-aminoalkyl, ω-(substituted)aminoalkyl, ω-phosphoalkyl, ω-thiophosphoalkyl, optionally substituted polyethylene glycol (PEG, mw 100-40K), optionally substituted mPEG (mw 120-40K) heteroaryl, or heterocycle, or linker-ligand; and n is 0, 1, 2, or 3.

In certain embodiments, a cationic lipid of Embodiments 1, 2 or 3 (e.g., the cationic lipid, the first cationic lipid, the second cationic lipid) has one of the following structures:

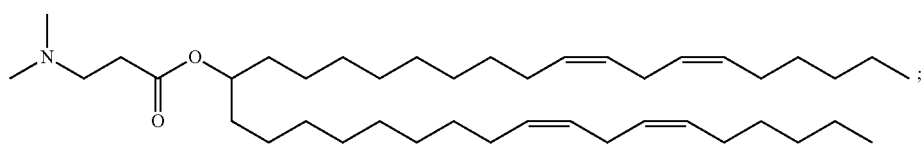

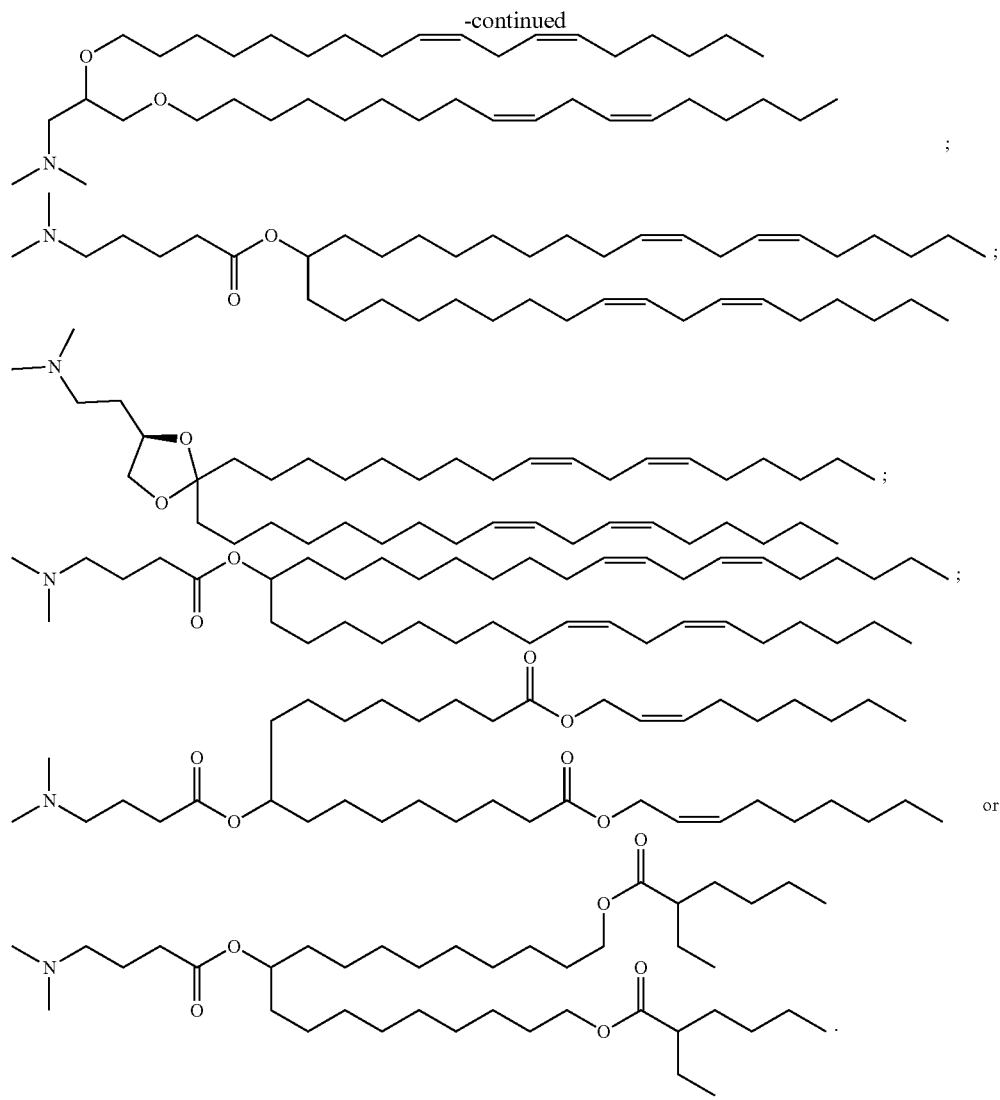

In one embodiment, a cationic lipid of Embodiments 1, 2 or 3 (e.g., the cationic lipid, the first cationic lipid, the second cationic lipid) has the structure of Formula I:

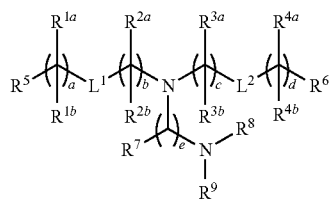

or a pharmaceutically acceptable salt, tautomer, prodrug or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$, —NR$^a$C(=O)NR$^a$—, —OC(=O)NR$^a$— or —NR$^a$C(=O)O— or a direct bond;

$R^a$ is H or $C_1$-$C_{12}$ alkyl;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;
b and c are each independently an integer from 1 to 24;
e is 1 or 2; and
x is 0, 1 or 2.

In some embodiments of Formula I, $L^1$ and $L^2$ are independently —O(C=O)— or —(C=O)O—.

In certain embodiments of Formula I, at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—. In other embodiments, $R^{1a}$ and $R^{1b}$ are not isopropyl when a is 6 or n-butyl when a is 8.

In still further embodiments of Formula I, at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—; and $R^{1a}$ and $R^{1b}$ are not isopropyl when a is 6 or n-butyl when a is 8.

In other embodiments of Formula I, $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

In certain embodiments of Formula I, any one of $L^1$ or $L^2$ may be —O(C=O)— or a carbon-carbon double bond. $L^1$ and $L^2$ may each be —O(C=O)— or may each be a carbon-carbon double bond.

In some embodiments of Formula I, one of $L^1$ or $L^2$ is —O(C=O)—. In other embodiments, both $L^1$ and $L^2$ are —O(C=O)—.

In some embodiments of Formula I, one of $L^1$ or $L^2$ is —(C=O)O—. In other embodiments, both $L^1$ and $L^2$ are —(C=O)O—.

In some other embodiments of Formula I, one of $L^1$ or $L^2$ is a carbon-carbon double bond. In other embodiments, both $L^1$ and $L^2$ are a carbon-carbon double bond.

In still other embodiments of Formula I, one of $L^1$ or $L^2$ is —O(C=O)— and the other of $L^1$ or $L^2$ is —(C=O)O—. In more embodiments, one of $L^1$ or $L^2$ is —O(C=O)— and the other of $L^1$ or $L^2$ is a carbon-carbon double bond. In yet more embodiments, one of $L^1$ or $L^2$ is —(C=O)O— and the other of $L^1$ or $L^2$ is a carbon-carbon double bond.

It is understood that "carbon-carbon" double bond, as used throughout the specification, refers to one of the following structures:

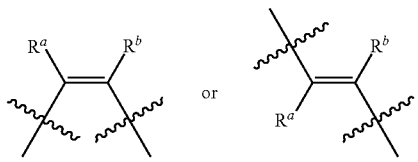

wherein $R^a$ and $R^b$ are, at each occurrence, independently H or a substituent. For example, in some embodiments $R^a$ and $R^b$ are, at each occurrence, independently H, $C_1$-$C_{12}$ alkyl or cycloalkyl, for example H or $C_1$-$C_{12}$ alkyl.

In other embodiments, the lipid compounds of Formula I have the following Formula (Ia):

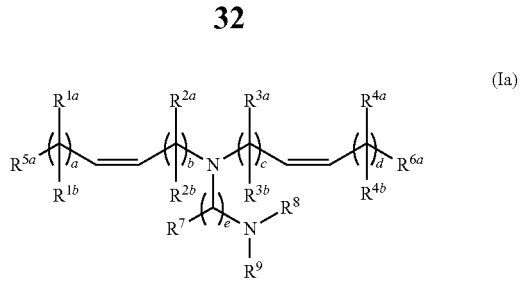

In other embodiments, the lipid compounds of Formula I have the following Formula (Ib):

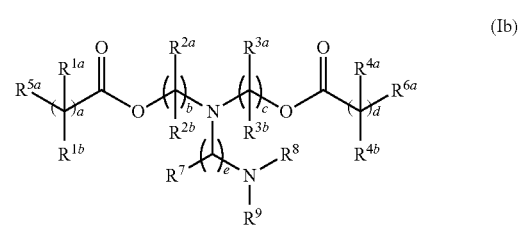

In yet other embodiments, the lipid compounds of Formula I have the following Formula (Ic):

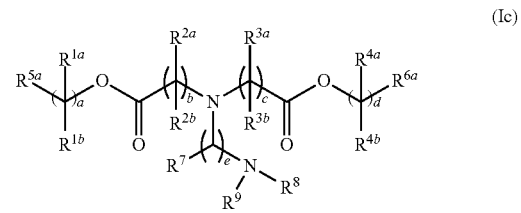

In certain embodiments of the lipid compound of Formula I, a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some other embodiments of Formula I, b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some more embodiments of Formula I, c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11.

In yet other embodiments, c is 12. In some embodiments, c is 13. In other embodiments, c is 14. In more embodiments, c is 15. In yet other embodiments, c is 16.

In some certain other embodiments of Formula I, d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments of Formula I, a and d are the same. In some other embodiments, b and c are the same. In some other specific embodiments, a and d are the same and b and c are the same.

The sum of a and b and the sum of c and d in Formula I are factors which may be varied to obtain a lipid of formula I having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a, b, c and d are selected such the sum of a and b and the sum of c and d is 12 or greater.

In some embodiments of Formula I, e is 1. In other embodiments, e is 2.

The substituents at $R^{1a}$, $R^{2a}$, $R^{3a}$ and $R^{4a}$ of Formula I are not particularly limited. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula I, $R^{1a}$, $R^{1b}$, $R^{4a}$ and $R^{4b}$ are $C_1$-$C_{12}$ alkyl at each occurrence.

In further embodiments of Formula I, at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula I, $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula I are not particularly limited in the foregoing embodiments. In certain embodiments one or both of $R^5$ or $R^6$ is methyl. In certain other embodiments one or both of $R^5$ or $R^6$ is cycloalkyl for example cyclohexyl. In these embodiments the cycloalkyl may be substituted or not substituted. In certain other embodiments the cycloalkyl is substituted with $C_1$-$C_{12}$ alkyl, for example tert-butyl.

The substituents at $R^7$ are not particularly limited in the foregoing embodiments of Formula I. In certain embodiments at least one $R^7$ is H. In some other embodiments, $R^7$ is H at each occurrence. In certain other embodiments $R^7$ is $C_1$-$C_{12}$ alkyl.

In certain other of the foregoing embodiments of Formula I, one of $R^8$ or $R^9$ is methyl. In other embodiments, both $R^8$ and $R^9$ are methyl.

In some different embodiments of Formula I, $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In some embodiments of Embodiment 3, the first and second cationic lipids are each, independently selected from a lipid of Formula I.

In various different embodiments, the lipid of Formula I has one of the structures set forth in Table 1 below.

TABLE 1

Representative Lipids of Formula I

| No. | Structure | Prep. Method | pKa |
|---|---|---|---|
| I-1 | 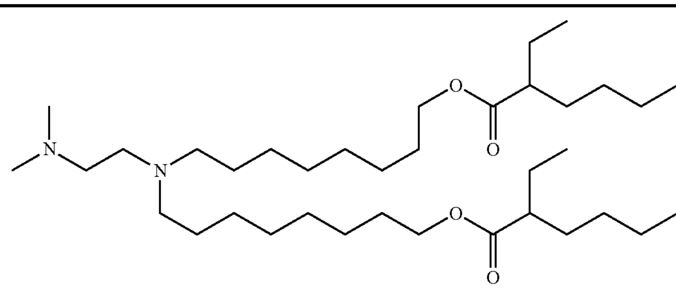 | B | — |

TABLE 1-continued

Representative Lipids of Formula I

| No. | Structure | Prep. Method | pKa |
|---|---|---|---|
| I-2 | 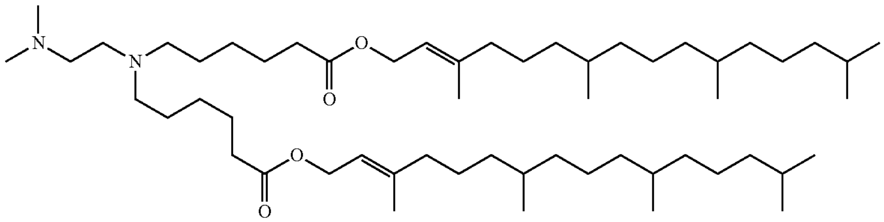 [SMILES: C/C(=C\COC(=O)CCCCCN(CCCCCC(=O)OC/C=C(\C)CCCC(C)CCCC(C)CCCC(C)C)CCN(C)C)CCCC(C)CCCC(C)CCCC(C)C] | A | 5.64 |
| I-3 | 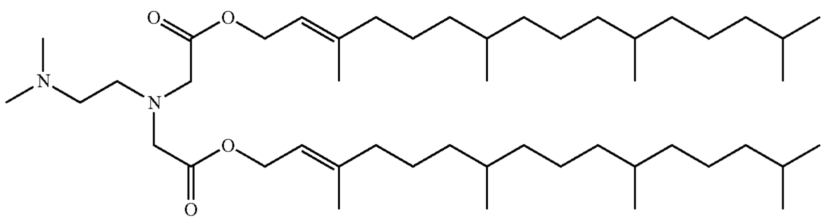 [SMILES: C/C(=C\COC(=O)CN(CCN(C)C)CC(=O)OC/C=C(\C)CCCC(C)CCCC(C)CCCC(C)C)CCCC(C)CCCC(C)CCCC(C)C] | A | 7.15 |
| I-4 | 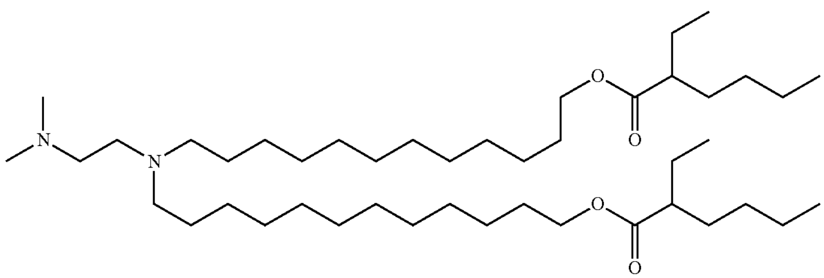 [SMILES: CCCCC(CC)C(=O)OCCCCCCCCCCCCN(CCCCCCCCCCCCOC(=O)C(CC)CCCC)CCN(C)C] | B | 6.43 |
| I-5 | 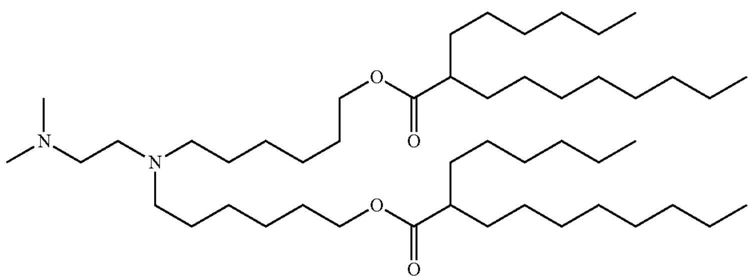 [SMILES: CCCCCCCCC(CCCCCC)C(=O)OCCCCCCN(CCCCCCOC(=O)C(CCCCCC)CCCCCCCC)CCN(C)C] | B | 6.28 |
| I-6 | 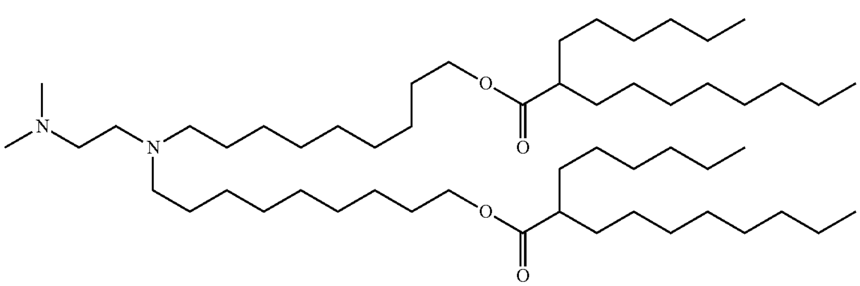 [SMILES: CCCCCCCCC(CCCCCC)C(=O)OCCCCCCCCCN(CCCCCCCCCOC(=O)C(CCCCCC)CCCCCCCC)CCN(C)C] | B | 6.12 |
| I-7 | 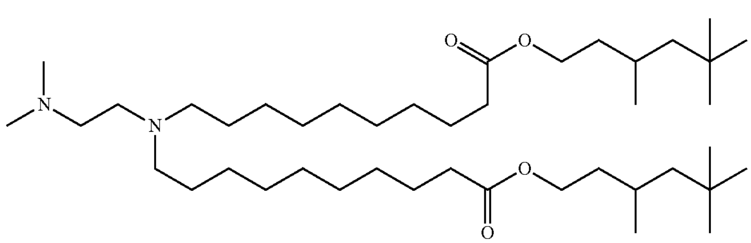 [SMILES: CC(CCOC(=O)CCCCCCCCCN(CCCCCCCCCC(=O)OCCC(C)CC(C)(C)C)CCN(C)C)CC(C)(C)C] | A | — |

TABLE 1-continued

Representative Lipids of Formula I

| No. | Structure | Prep. Method | pKa |
|---|---|---|---|
| I-8 | 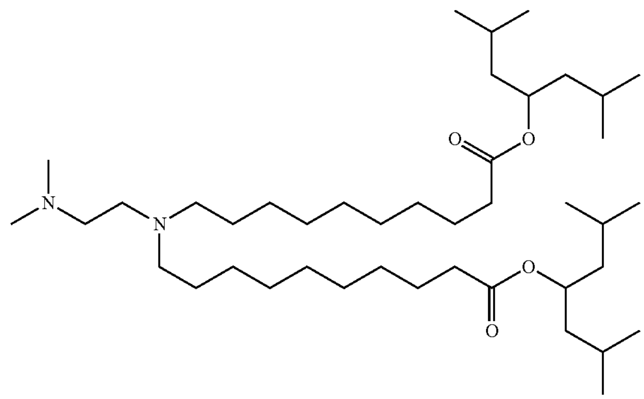 [SMILES: CC(C)CC(CC(C)C)OC(=O)CCCCCCCCCN(CCCCCCCCCC(=O)OC(CC(C)C)CC(C)C)CCN(C)C] | A | — |
| I-9 | 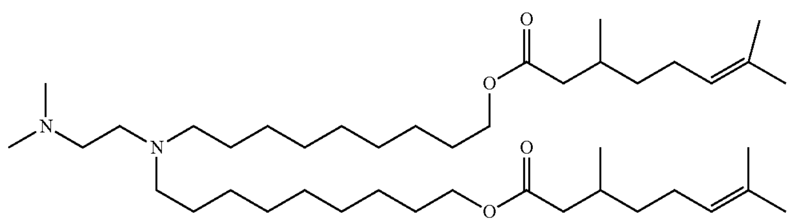 [SMILES: CC(C)=CCCC(C)CC(=O)OCCCCCCCCCN(CCCCCCCCCOC(=O)CC(C)CCC=C(C)C)CCN(C)C] | B | — |
| I-10 | 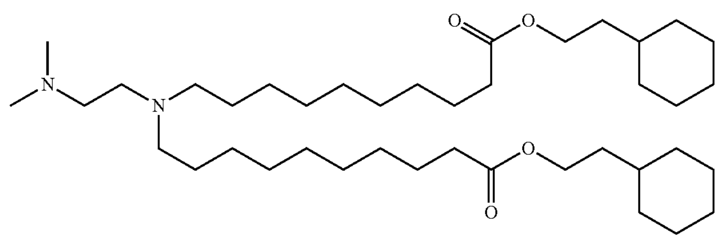 [SMILES: CN(C)CCN(CCCCCCCCCC(=O)OCCC1CCCCC1)CCCCCCCCCC(=O)OCCC1CCCCC1] | A | — |
| I-11 | 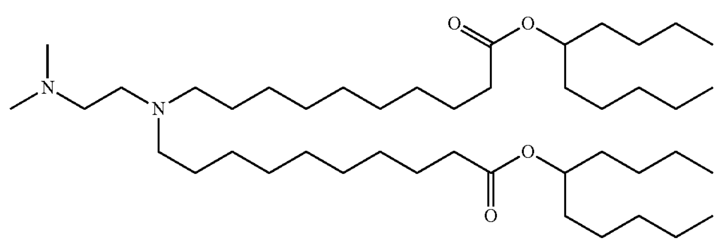 [SMILES: CCCCCC(CCCC)OC(=O)CCCCCCCCCN(CCCCCCCCCC(=O)OC(CCCC)CCCCC)CCN(C)C] | A | 6.36 |
| I-12 | 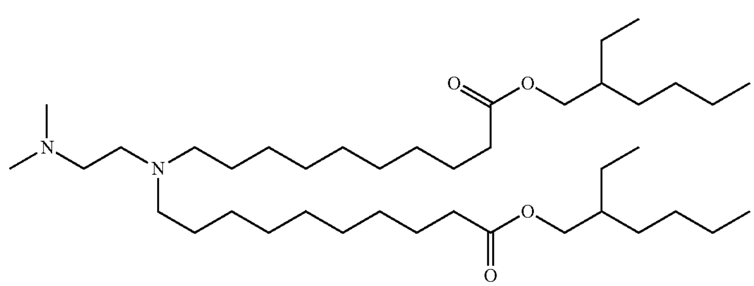 [SMILES: CCCCC(CC)COC(=O)CCCCCCCCCN(CCCCCCCCCC(=O)OCC(CC)CCCC)CCN(C)C] | A | — |

TABLE 1-continued

Representative Lipids of Formula I

| No. | Structure | Prep. Method | pKa |
|---|---|---|---|
| I-13 | 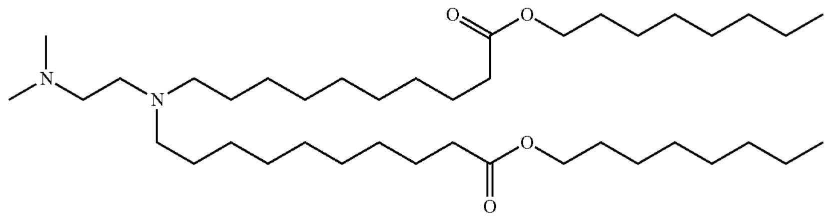 [SMILES: CCCCCCCCOC(=O)CCCCCCCCCN(CCCCCCCCCC(=O)OCCCCCCCC)CCN(C)C] | A | 6.51 |
| I-14 | 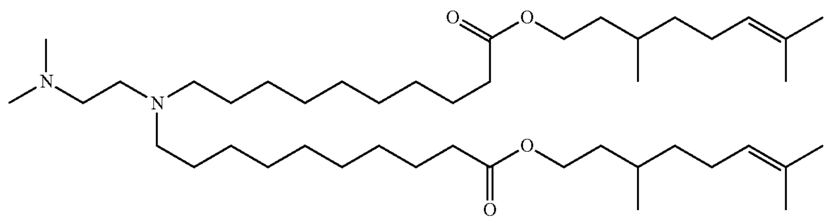 [SMILES: CC(C)=CCCC(C)CCOC(=O)CCCCCCCCCN(CCCCCCCCCC(=O)OCCC(C)CCC=C(C)C)CCN(C)C] | A | — |
| I-15 | 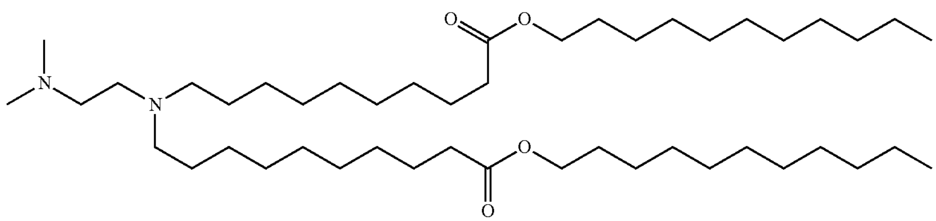 [SMILES: CCCCCCCCCCCOC(=O)CCCCCCCCCN(CCCCCCCCCC(=O)OCCCCCCCCCCC)CCN(C)C] | A | 6.30 |
| I-16 | 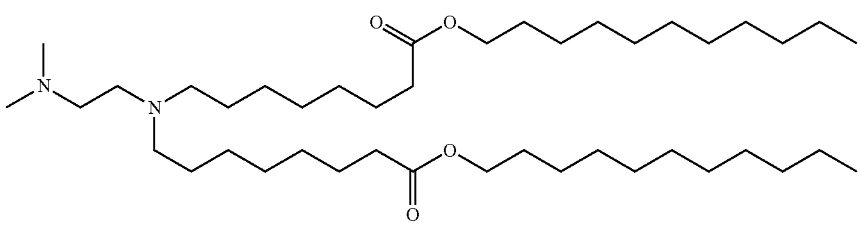 [SMILES: CCCCCCCCCCCOC(=O)CCCCCCCN(CCCCCCCC(=O)OCCCCCCCCCCC)CCN(C)C] | A | 6.63 |
| I-17 | 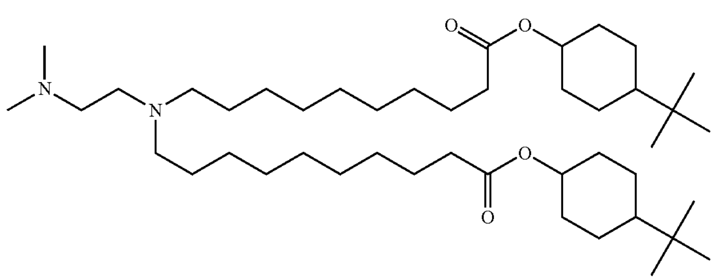 [SMILES: CN(C)CCN(CCCCCCCCCC(=O)OC1CCC(C(C)(C)C)CC1)CCCCCCCCCC(=O)OC1CCC(C(C)(C)C)CC1] | A | — |
| I-18 | 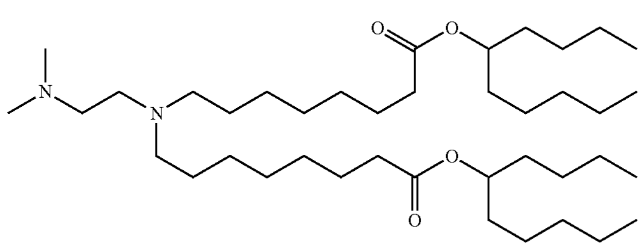 [SMILES: CCCCCC(CCCC)OC(=O)CCCCCCCN(CCCCCCCC(=O)OC(CCCC)CCCCC)CCN(C)C] | A | — |

TABLE 1-continued

Representative Lipids of Formula I

| No. | Structure | Prep. Method | pKa |
|---|---|---|---|
| I-19 | 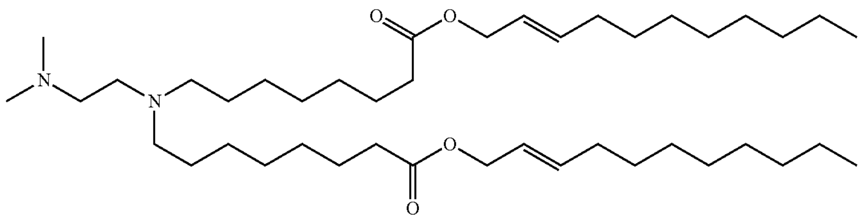 [SMILES: CCCCCCCC/C=C/COC(=O)CCCCCCCN(CCCCCCCC(=O)OC/C=C/CCCCCCCC)CCN(C)C] | A | 6.72 |
| I-20 | 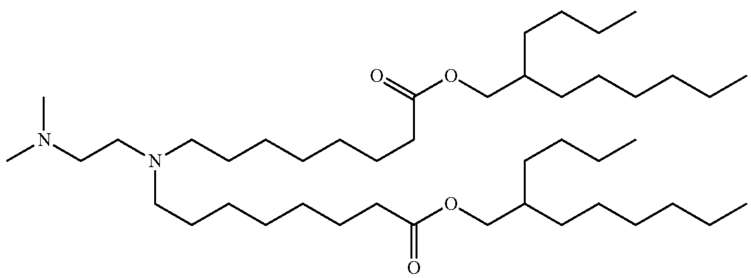 [SMILES: CCCCCCC(CCCC)COC(=O)CCCCCCCN(CCCCCCCC(=O)OCC(CCCC)CCCCCC)CCN(C)C] | A | 6.44 |
| I-21 | 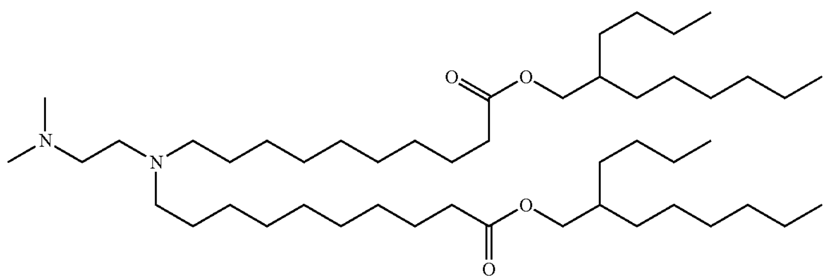 [SMILES: CCCCCCC(CCCC)COC(=O)CCCCCCCCCN(CCCCCCCCCC(=O)OCC(CCCC)CCCCCC)CCN(C)C] | A | 6.28 |
| I-22 | 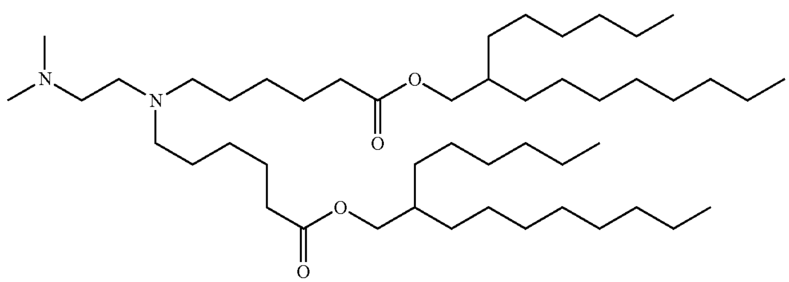 [SMILES: CCCCCCCCC(CCCCCC)COC(=O)CCCCCN(CCCCCC(=O)OCC(CCCCCC)CCCCCCCC)CCN(C)C] | A | 6.53 |
| I-23 | 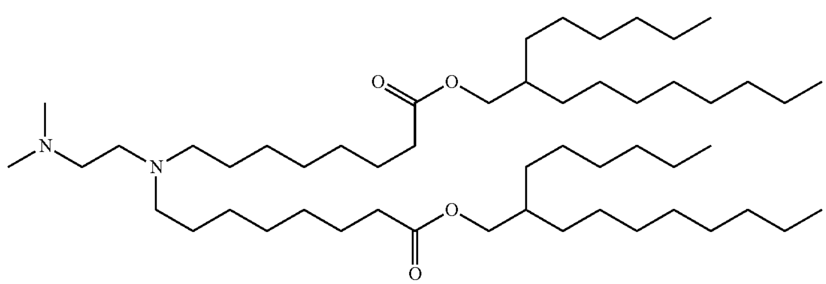 [SMILES: CCCCCCCCC(CCCCCC)COC(=O)CCCCCCCN(CCCCCCCC(=O)OCC(CCCCCC)CCCCCCCC)CCN(C)C] | A | 6.24 |
| I-24 | 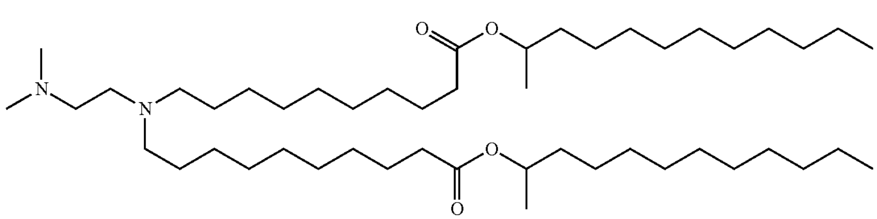 [SMILES: CCCCCCCCCCC(C)OC(=O)CCCCCCCCCN(CCCCCCCCCC(=O)OC(C)CCCCCCCCCC)CCN(C)C] | A | 6.28 |

TABLE 1-continued
Representative Lipids of Formula I
| No. | Structure | Prep. Method | pKa |
|---|---|---|---|
| I-25 | 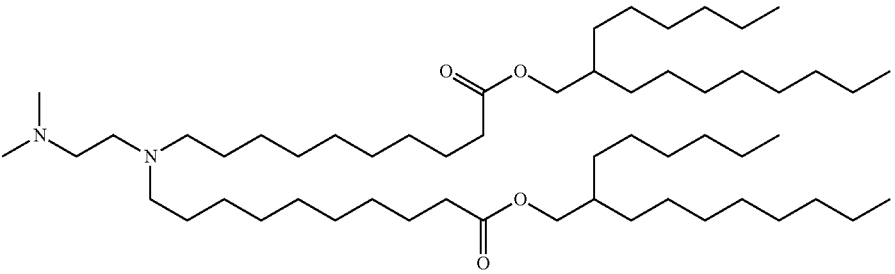 [SMILES: CCCCCCCCC(CCCCCC)COC(=O)CCCCCCCCCN(CCCCCCCCCC(=O)OCC(CCCCCC)CCCCCCCC)CCN(C)C] | A | 6.20 |
| I-26 | 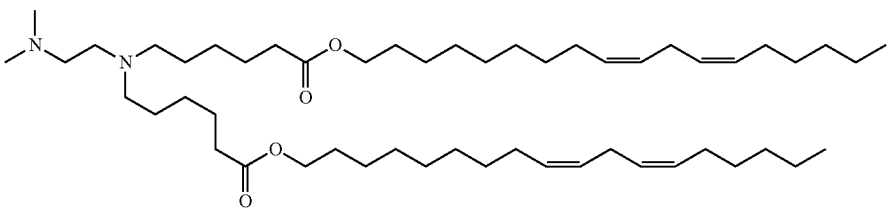 [SMILES: CCCCC/C=C\C/C=C\CCCCCCCCOC(=O)CCCCCN(CCCCCC(=O)OCCCCCCCC/C=C\C/C=C\CCCCC)CCN(C)C] | A | 6.89 |
| I-27 | 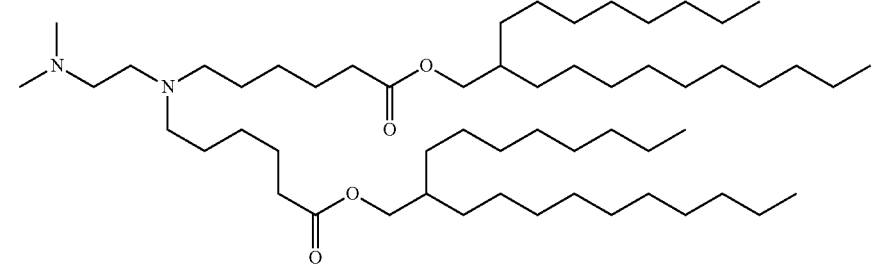 [SMILES: CCCCCCCCCCC(CCCCCCCC)COC(=O)CCCCCN(CCCCCC(=O)OCC(CCCCCCCC)CCCCCCCCCC)CCN(C)C] | A | 6.30 |
| I-28 | 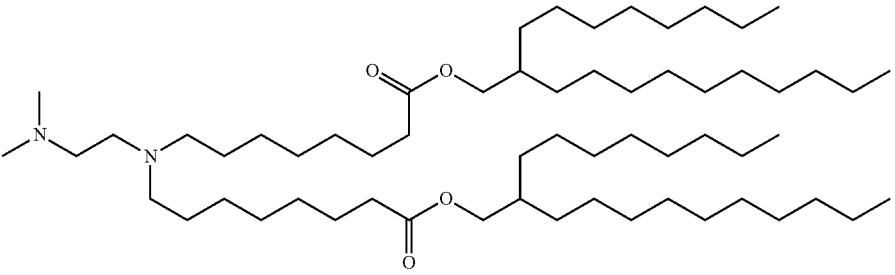 [SMILES: CCCCCCCCCCC(CCCCCCCC)COC(=O)CCCCCCCN(CCCCCCCC(=O)OCC(CCCCCCCC)CCCCCCCCCC)CCN(C)C] | A | 6.20 |
| I-29 | 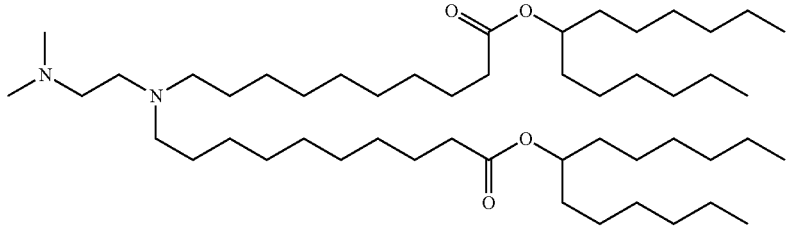 [SMILES: CCCCCCC(CCCCCC)OC(=O)CCCCCCCCCN(CCCCCCCCCC(=O)OC(CCCCCC)CCCCCC)CCN(C)C] | A | 6.22 |

TABLE 1-continued

Representative Lipids of Formula I

| No. | Structure | Prep. Method | pKa |
|---|---|---|---|
| I-30 | 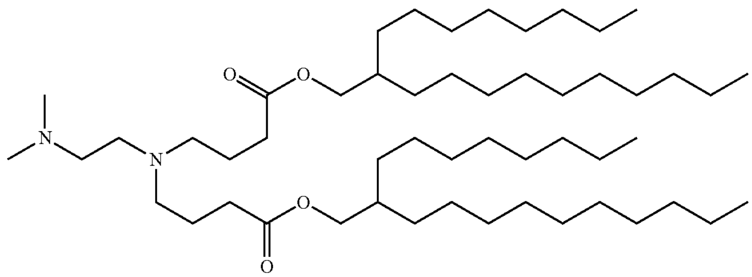 [SMILES: CCCCCCCCCCC(CCCCCCCC)COC(=O)CCCN(CCCC(=O)OCC(CCCCCCCC)CCCCCCCCCC)CCN(C)C] | A | — |
| I-31 | 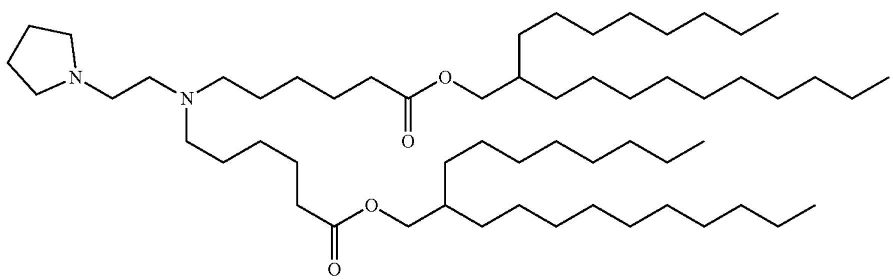 [SMILES: CCCCCCCCCCC(CCCCCCCC)COC(=O)CCCCCN(CCCCCC(=O)OCC(CCCCCCCC)CCCCCCCCCC)CCN1CCCC1] | C | 6.33 |
| I-32 | 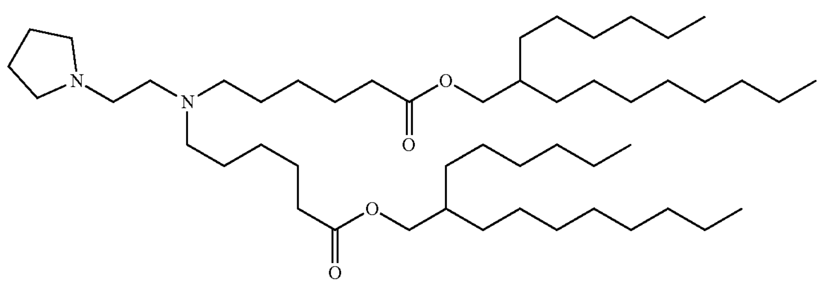 [SMILES: CCCCCCCCC(CCCCCC)COC(=O)CCCCCN(CCCCCC(=O)OCC(CCCCCC)CCCCCCCC)CCN1CCCC1] | C | 6.47 |
| I-33 | 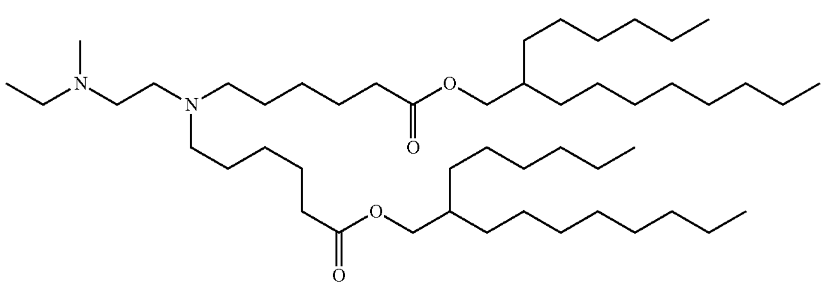 [SMILES: CCCCCCCCC(CCCCCC)COC(=O)CCCCCN(CCCCCC(=O)OCC(CCCCCC)CCCCCCCC)CCN(C)CC] | C | 6.27 |
| I-34 | 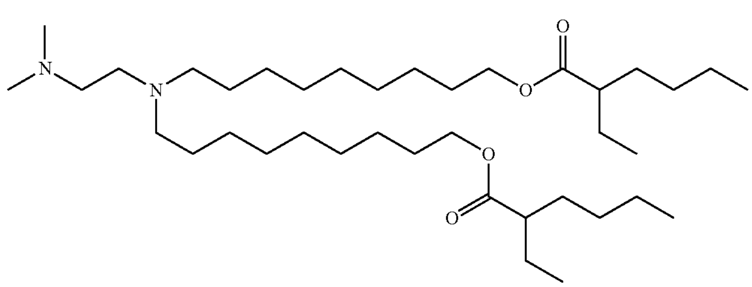 [SMILES: CCCCC(CC)C(=O)OCCCCCCCCCN(CCCCCCCCCOC(=O)C(CC)CCCC)CCN(C)C] | B | — |

TABLE 1-continued

Representative Lipids of Formula I

| No. | Structure | Prep. Method | pKa |
|---|---|---|---|
| I-35 | 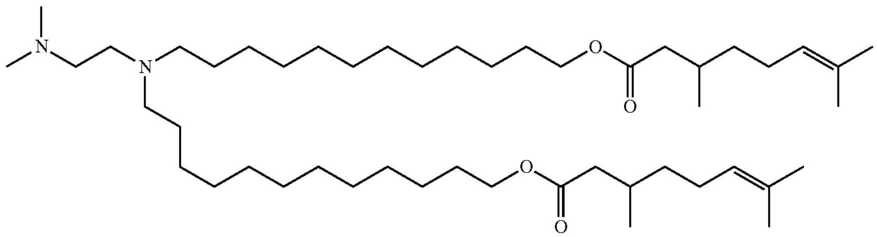 [SMILES: CC(C)=CCCC(C)CC(=O)OCCCCCCCCCCCCN(CCCCCCCCCCCCOC(=O)CC(C)CCC=C(C)C)CCN(C)C] | B | 6.21 |
| I-36 | 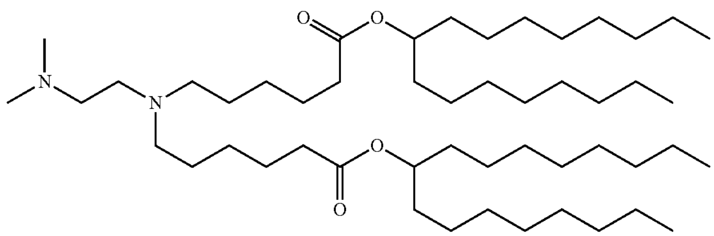 [SMILES: CCCCCCCCC(CCCCCCCC)OC(=O)CCCCCN(CCCCCC(=O)OC(CCCCCCCC)CCCCCCCC)CCN(C)C] | C | — |
| I-37 | 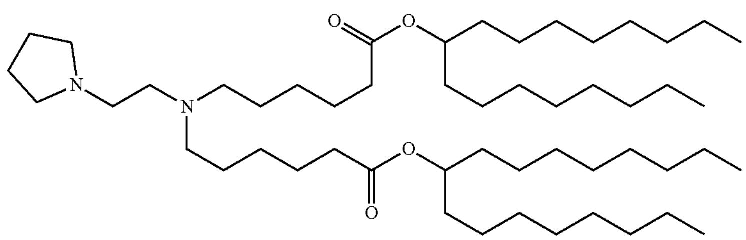 [SMILES: CCCCCCCCC(CCCCCCCC)OC(=O)CCCCCN(CCCCCC(=O)OC(CCCCCCCC)CCCCCCCC)CCN1CCCC1] | C | — |
| I-38 | 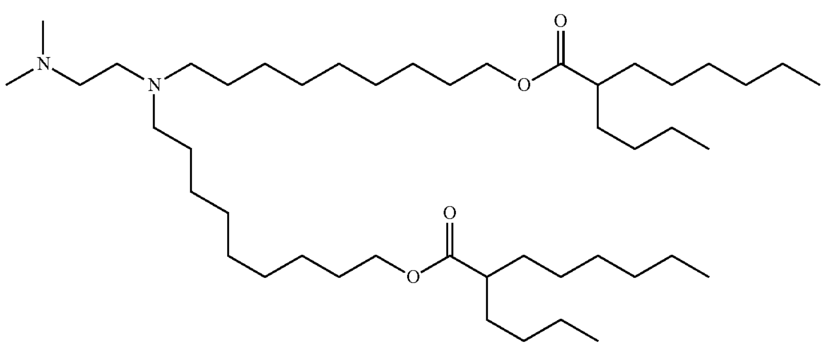 [SMILES: CCCCCCC(CCCC)C(=O)OCCCCCCCCCN(CCCCCCCCCOC(=O)C(CCCC)CCCCCC)CCN(C)C] | B | 6.24 |
| I-39 | 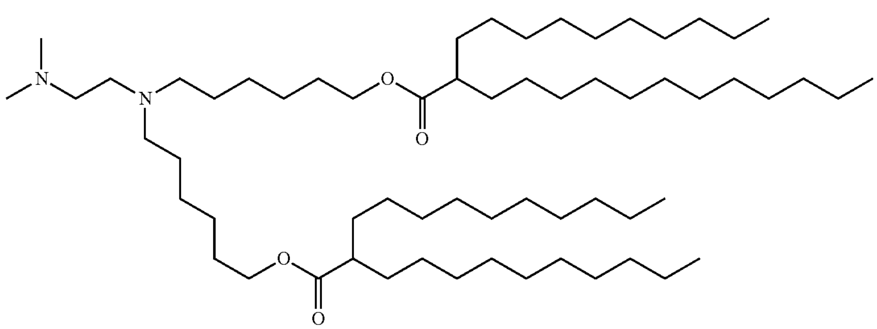 [SMILES: CCCCCCCCCCCCC(CCCCCCCCCC)C(=O)OCCCCCCN(CCCCCCOC(=O)C(CCCCCCCCCC)CCCCCCCCCC)CCN(C)C] | B | 5.82 |

TABLE 1-continued

Representative Lipids of Formula I

| No. | Structure | Prep. Method | pKa |
|---|---|---|---|
| I-40 | 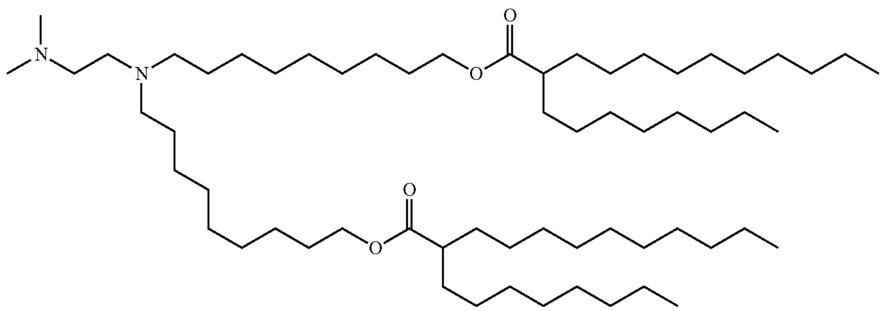 [SMILES: CCCCCCCCCCC(CCCCCCCC)C(=O)OCCCCCCCCCN(CCCCCCCCCOC(=O)C(CCCCCCCC)CCCCCCCCCC)CCN(C)C] | B | 6.38 |
| I-41 | 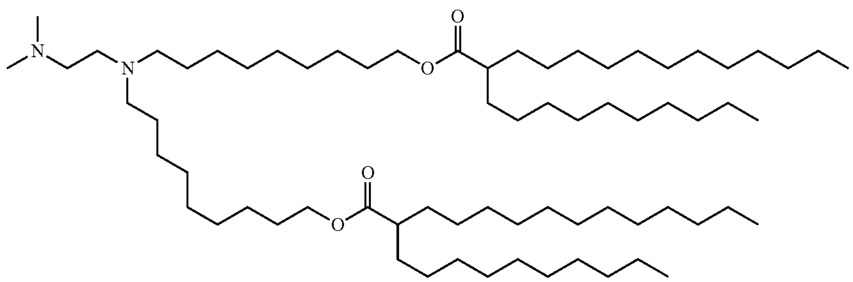 [SMILES: CCCCCCCCCCCCC(CCCCCCCCCC)C(=O)OCCCCCCCCCN(CCCCCCCCCOC(=O)C(CCCCCCCCCC)CCCCCCCCCCCC)CCN(C)C] | B | 5.91 |

In some embodiments the lipid of Formula I is compound I-5. In some embodiments the lipid of Formula I is compound I-6.

In some embodiments, a cationic lipid of Embodiments 1, 2 or 3 (e.g., the cationic lipid, the first cationic lipid, the second cationic lipid) has a structure of Formula II:

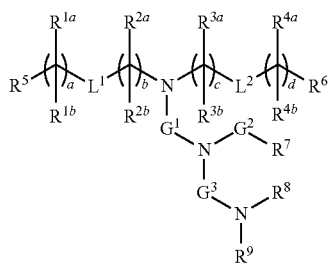

II or a pharmaceutically acceptable salt, tautomer, prodrug or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond;

$G^1$ is $C_1$-$C_2$ alkylene, —(C=O)—, —O(C=O)—, —SC(=O)—, —NR$^a$C(=O)— or a direct bond;

$G^2$ is —C(=O)—, —(C=O)O—, —C(=O)S—, —C(=O)NR$^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments of Formula (II), $L^1$ and $L^2$ are each independently —O(C=O)—, —(C=O)O— or a direct bond. In other embodiments, $G^1$ and $G^2$ are each independently —(C=O)— or a direct bond. In some different embodiments, $L^1$ and $L^2$ are each independently —O(C=O)—, —(C=O)O— or a direct bond; and $G^1$ and $G^2$ are each independently —(C=O)— or a direct bond.

In some different embodiments of Formula (II), $L^1$ and $L^2$ are each independently —C(=O)—, —O—, —S(O)$_x$—, —S—S—, —C(=O)S—, —SC(=O)—, —NR$^a$C(=O)—, —C(=O)NR$^a$—, —NR$^a$C(=O)NR$^a$—, —OC(=O)NR$^a$—, —NR$^a$C(=O)O—, —NR$^a$S(O)$_x$NR$^a$—, —NR$^a$S(O)$_x$— or —S(O)$_x$NR$^a$—.

In other of the foregoing embodiments of Formula (II), the lipid compound has one of the following Formulae (IIA) or (IIB):

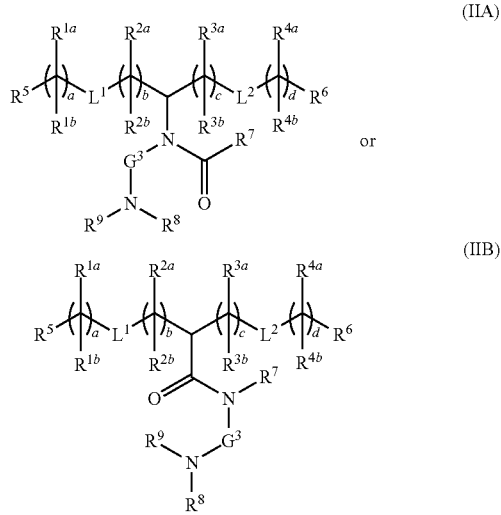

In some embodiments of Formula (II), the lipid compound has Formula (IIA). In other embodiments, the lipid compound has Formula (IIB).

In any of the foregoing embodiments of Formula (II), one of $L^1$ or $L^2$ is —O(C=O)—. For example, in some embodiments each of $L^1$ and $L^2$ are —O(C=O)—.

In some different embodiments of Formula (II), one of $L^1$ or $L^2$ is —(C=O)O—. For example, in some embodiments each of $L^1$ and $L^2$ is —(C=O)O—.

In different embodiments of Formula (II), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of Formula (II), for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of Formula (II), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of Formula (II), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of Formula (II), for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

In various other embodiments of Formula (II), the lipid compound has one of the following Formulae (IIC) or (IID):

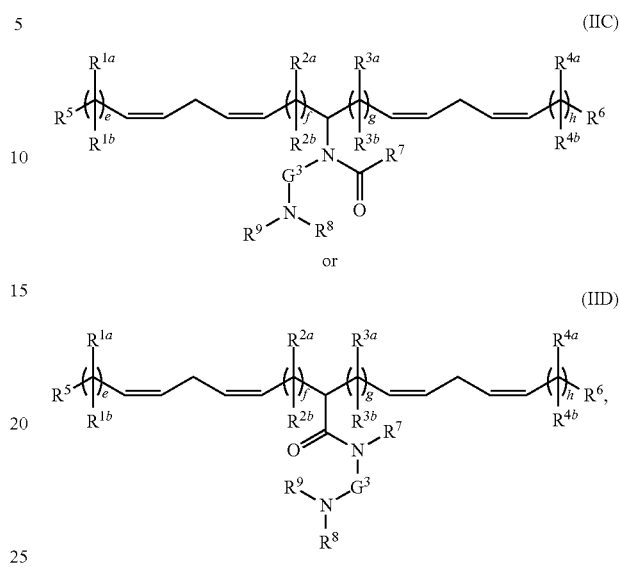

wherein e, f, g and h are each independently an integer from 1 to 12.

In some embodiments of Formula (II), the lipid compound has Formula (IIC). In other embodiments, the lipid compound has Formula (IID).

In various embodiments of Formulae (IIC) or (IID), e, f, g and h are each independently an integer from 4 to 10.

In certain embodiments of Formula (II), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of Formula (II), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of Formula (II), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of Formula (II), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of Formula (II), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of Formula (II), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of Formula (II), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of Formula (II), his 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of Formula (II), a and d are the same. In some other embodiments, b and c are the same. In some other specific embodiments and a and d are the same and b and c are the same.

The sum of a and b and the sum of c and d of Formula (II) are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a, b, c and d are selected such that the sum of a and b and the sum of c and d is 12 or greater.

The substituents at $R^{1a}$, $R^{2a}$, $R^{3a}$ and $R^{4a}$ of Formula (II) are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (II), $R^{1a}$, $R^{1b}$, $R^{4a}$ and $R^{4b}$ are $C_1$-$C_{12}$ alkyl at each occurrence.

In further embodiments of Formula (II), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (II), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (II) are not particularly limited in the foregoing embodiments. In certain embodiments one of $R^5$ or $R^6$ is methyl. In other embodiments each of $R^5$ or $R^6$ is methyl.

The substituents at $R^7$ of Formula (II) are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with —(C=O)OR$^b$, —O(C=O)R$^b$, —C(=O)R$^b$, —OR$^b$, —S(O)$_x$R$^b$, —S—SR$^b$, —C(=O)SR$^b$, —SC(=O)R$^b$, —NR$^a$R$^b$, —NR$^a$C(=O)R$^b$, —C(=O)NR$^a$R$^b$, —NR$^a$C(=O)NR$^a$R$^b$, —OC(=O)NR$^a$R$^b$, —NR$^a$C(=O)OR$^b$, —NR$^a$S(O)$_x$NR$^a$R$^b$, —NR$^a$S(O)$_x$R$^b$ or —S(O)$_x$NR$^a$R$^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with —(C=O)OR$^b$ or —O(C=O)R$^b$.

In some of the foregoing embodiments of Formula (II), $R^b$ is branched $C_1$-$C_{16}$ alkyl. For example, in some embodiments $R^b$ has one of the following structures:

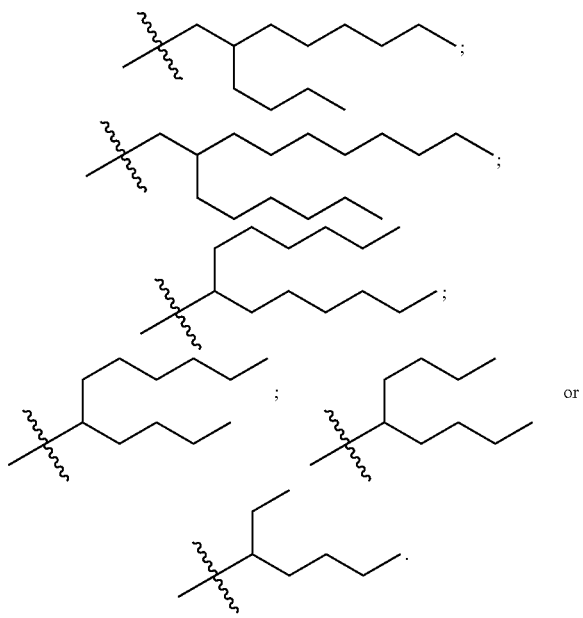

In certain other of the foregoing embodiments of Formula (II), one of $R^8$ or $R^9$ is methyl. In other embodiments, both $R^8$ and $R^9$ are methyl.

In some different embodiments of Formula (II), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring. In some different embodiments of the foregoing, $R^8$ and $R^9$, together with the nitrogen atom to which they are attached, form a 6-membered heterocyclic ring, for example a piperazinyl ring.

In certain embodiments of Embodiment 3, the first and second cationic lipids are each, independently selected from a lipid of Formula II.

In still other embodiments of the foregoing lipids of Formula (II), $G^3$ is $C_2$-$C_4$ alkylene, for example $C_3$ alkylene. In various different embodiments, the lipid compound has one of the structures set forth in Table 2 below

TABLE 2

Representative Lipids of Formula (II)

| No. | Structure | Prep. Method | pKa |
|---|---|---|---|
| II-1 | 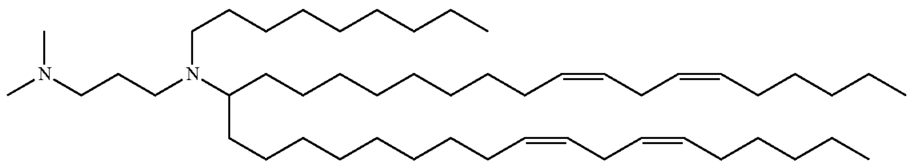 [SMILES: CCCCC/C=C\C/C=C\CCCCCCCCC(CCCCCCCC/C=C\C/C=C\CCCCC)N(CCCCCCCCC)CCCN(C)C] | D | 5.64 |
| II-2 | 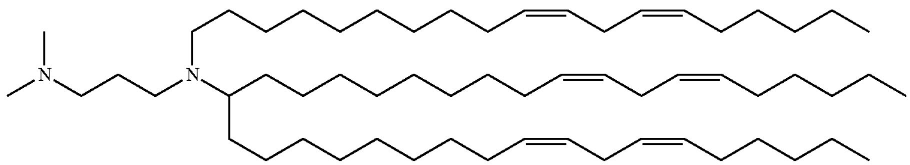 [SMILES: CCCCC/C=C\C/C=C\CCCCCCCCCN(CCCN(C)C)C(CCCCCCCC/C=C\C/C=C\CCCCC)CCCCCCCC/C=C\C/C=C\CCCCC] | D | — |
| II-3 | 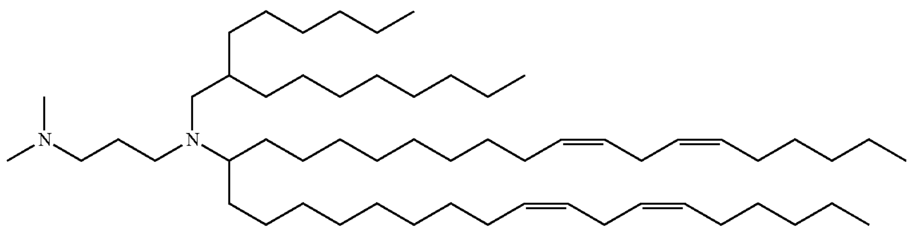 [SMILES: CCCCC/C=C\C/C=C\CCCCCCCCC(CCCCCCCC/C=C\C/C=C\CCCCC)N(CCCN(C)C)CC(CCCCCC)CCCCCCCC] | D | — |
| II-4 | 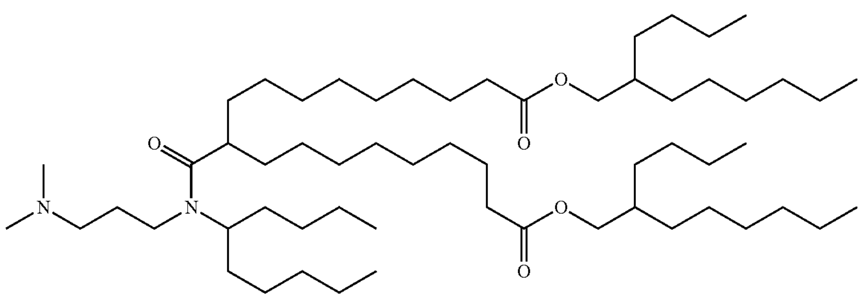 [SMILES: CCCCCCC(CCCC)COC(=O)CCCCCCCCC(CCCCCCCCC(=O)OCC(CCCC)CCCCCC)C(=O)N(CCCN(C)C)C(CCCC)CCCCC] | E | — |
| II-5 | 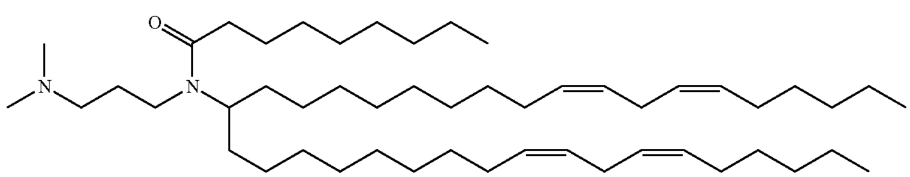 [SMILES: CCCCC/C=C\C/C=C\CCCCCCCCC(CCCCCCCC/C=C\C/C=C\CCCCC)N(CCCN(C)C)C(=O)CCCCCCCC] | D | 6.27 |
| II-6 | 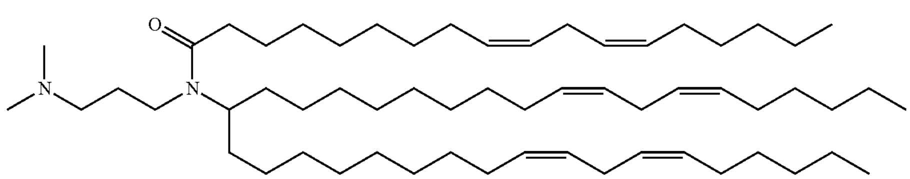 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC] | D | 6.14 |
| II-7 | 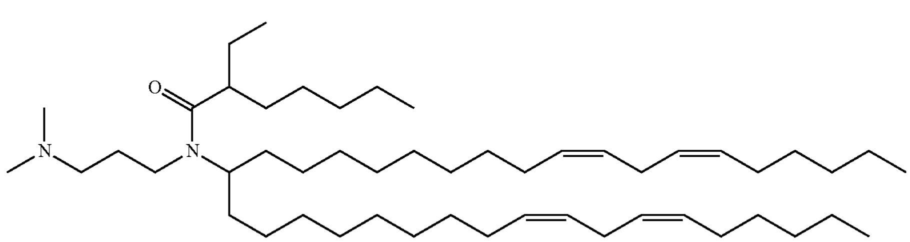 [SMILES: CCCCC/C=C\C/C=C\CCCCCCCCC(CCCCCCCC/C=C\C/C=C\CCCCC)N(CCCN(C)C)C(=O)C(CC)CCCCC] | D | 5.93 |

TABLE 2-continued

Representative Lipids of Formula (II)

| No. | Structure | Prep. Method | pKa |
|---|---|---|---|
| II-8 | 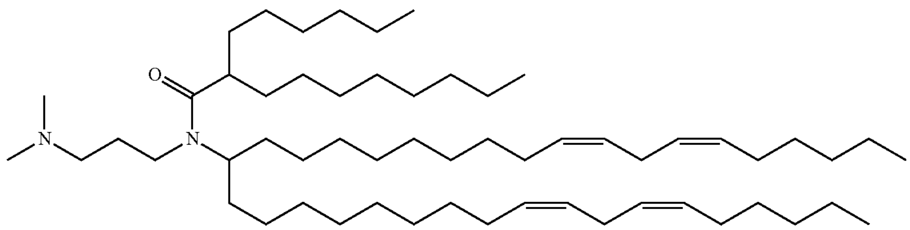 [SMILES: CCCCC/C=C\C/C=C\CCCCCCCCC(CCCCCCCC/C=C\C/C=C\CCCCC)N(CCCN(C)C)C(=O)C(CCCCCC)CCCCCCCC] | D | 5.35 |
| II-9 | 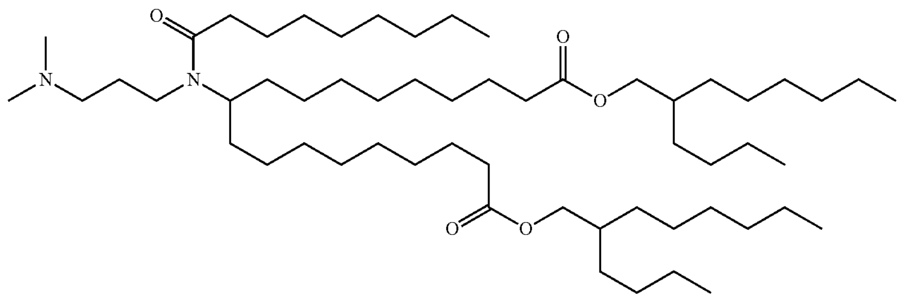 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] | D | 6.27 |
| II-10 | 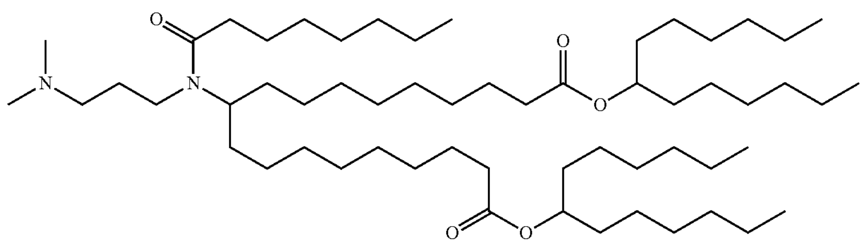 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC] | D | 6.16 |
| II-11 | 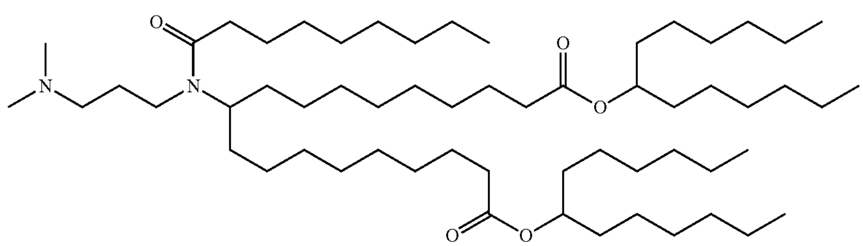 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] | D | 6.13 |
| II-12 | 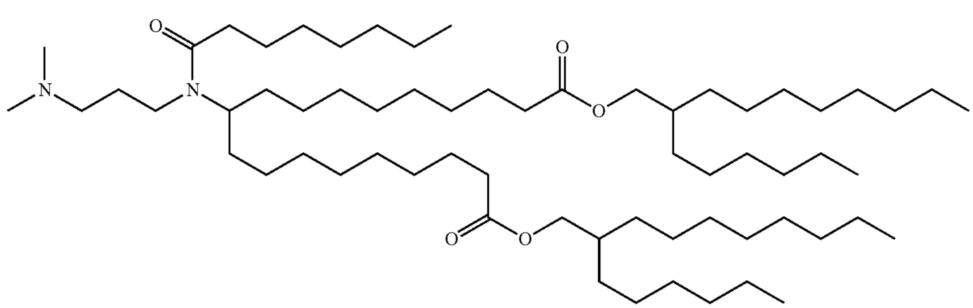 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] | D | 6.21 |

TABLE 2-continued

Representative Lipids of Formula (II)

| No. | Structure | Prep. Method | pKa |
|---|---|---|---|
| II-13 | 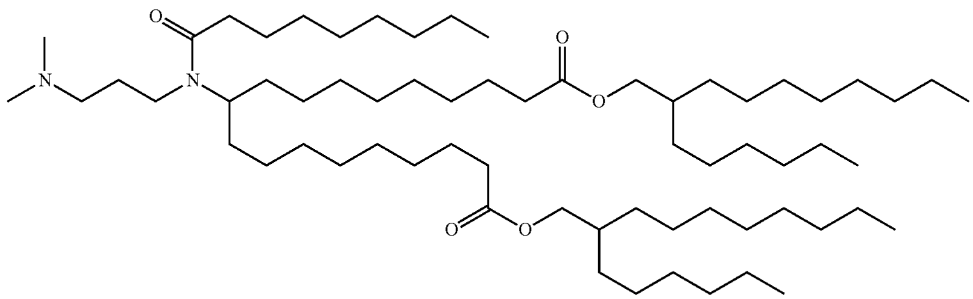 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC] | D | 6.22 |
| II-14 | 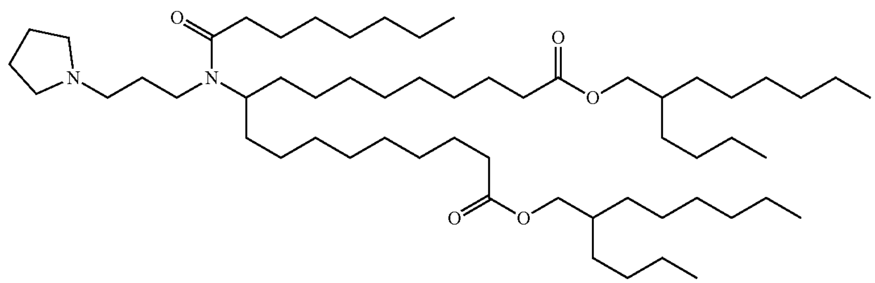 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC] | D | 6.33 |
| II-15 | 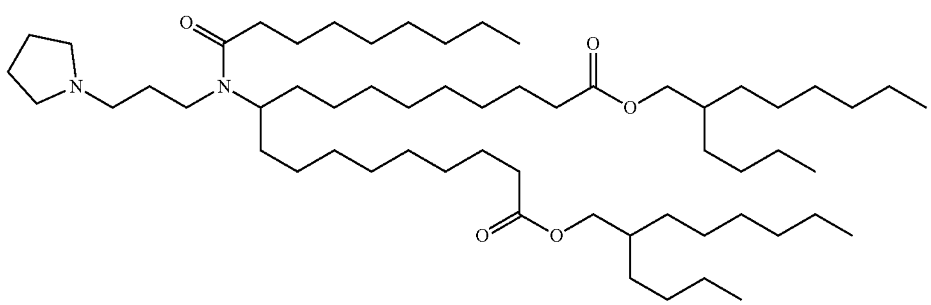 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC] | D | 6.32 |
| II-16 | 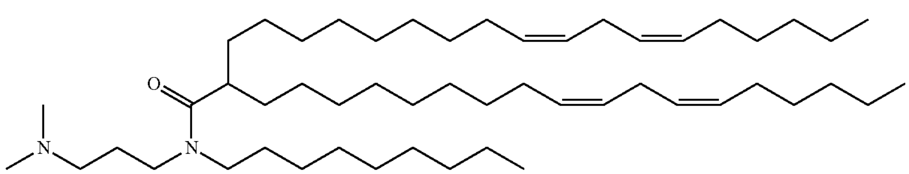 [SMILES: CCCCC/C=C\C/C=C\CCCCCCCCC(CCCCCCCC/C=C\C/C=C\CCCCC)C(=O)N(CCCCCCCCC)CCCN(C)C] | E | 6.37 |
| II-17 | 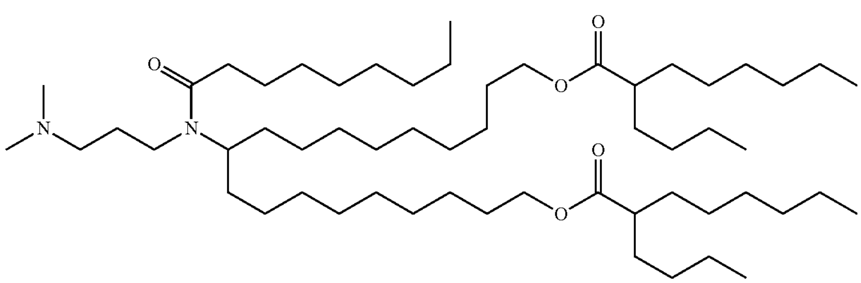 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC] | F | 6.27 |

TABLE 2-continued

Representative Lipids of Formula (II)

| No. | Structure | Prep. Method | pKa |
|---|---|---|---|
| II-18 | 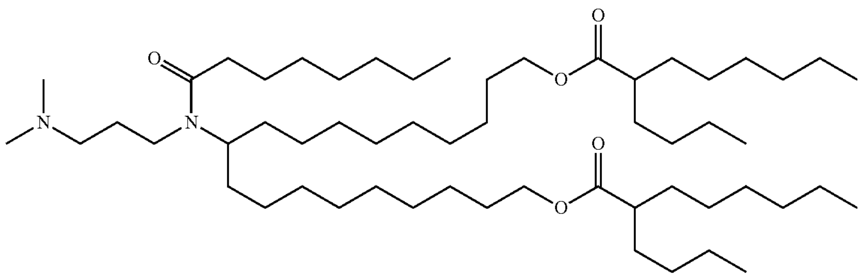 [SMILES: CCCCCCCC(=O)N(CCCN(C)C)C(CCCCCCCCCOC(=O)C(CCCC)CCCCCC)CCCCCCCCCOC(=O)C(CCCC)CCCCCC] | D | — |
| II-19 | 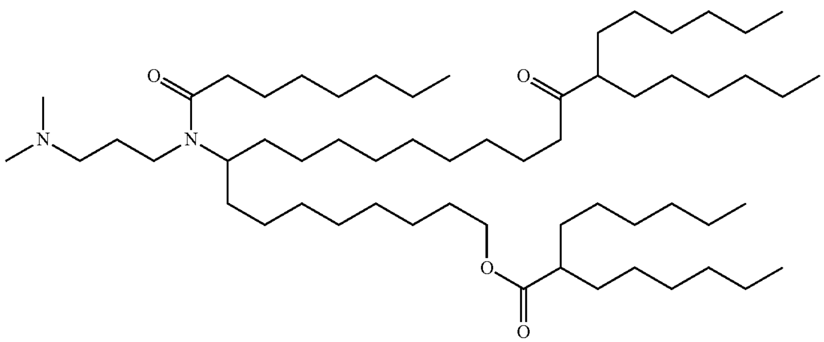 [SMILES: CCCCCCCC(=O)N(CCCN(C)C)C(CCCCCCCCCC(=O)C(CCCCCC)CCCCCC)CCCCCCCCOC(=O)C(CCCCCC)CCCCCC] | D | — |
| II-20 | 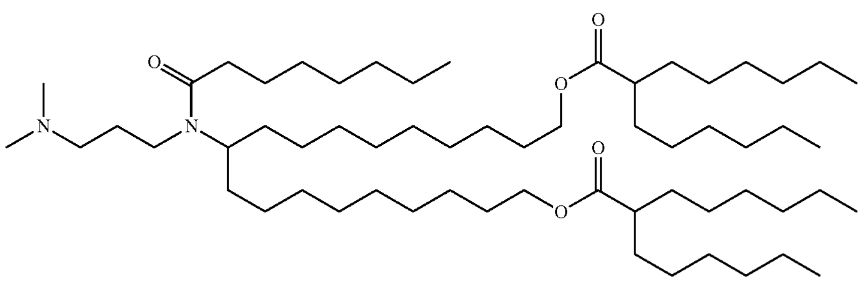 [SMILES: CCCCCCCC(=O)N(CCCN(C)C)C(CCCCCCCCCOC(=O)C(CCCCCC)CCCCCC)CCCCCCCCCOC(=O)C(CCCCCC)CCCCCC] | D | — |
| II-21 | 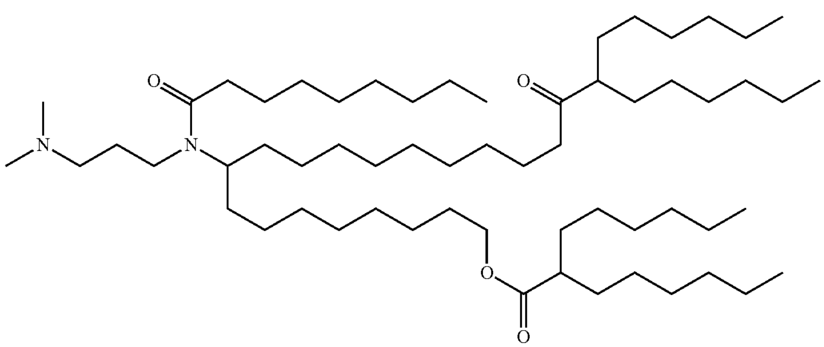 [SMILES: CCCCCCCCC(=O)N(CCCN(C)C)C(CCCCCCCCCC(=O)C(CCCCCC)CCCCCC)CCCCCCCCOC(=O)C(CCCCCC)CCCCCC] | D | — |
| II-22 | 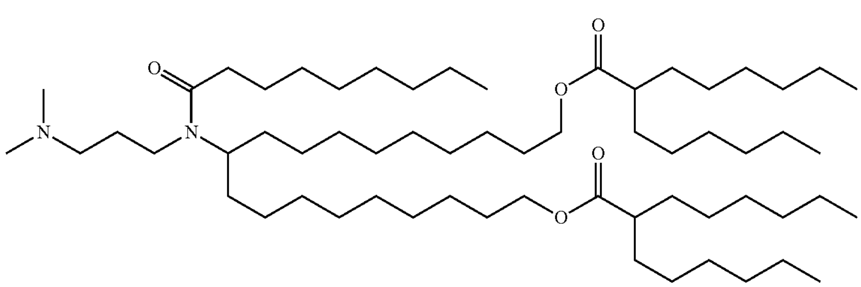 [SMILES: CCCCCCCCC(=O)N(CCCN(C)C)C(CCCCCCCCCOC(=O)C(CCCCCC)CCCCCC)CCCCCCCCCOC(=O)C(CCCCCC)CCCCCC] | D | — |

TABLE 2-continued

Representative Lipids of Formula (II)

| No. | Structure | Prep. Method | pKa |
|---|---|---|---|
| II-23 | 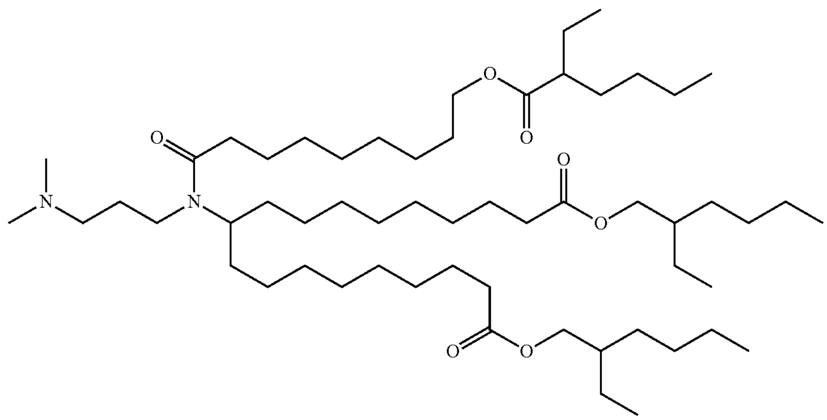 [SMILES: CCCCC(CC)COC(=O)CCCCCCCCC(CCCCCCCCC(=O)OCC(CC)CCCC)N(CCCN(C)C)C(=O)CCCCCCCCOC(=O)C(CC)CCCC] | D | — |
| II-24 | 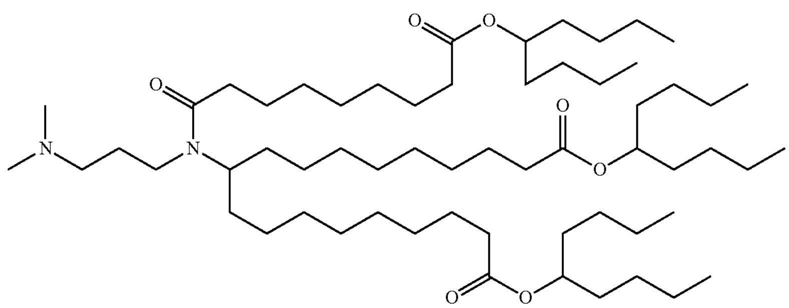 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] | D | 6.14 |
| II-25 | 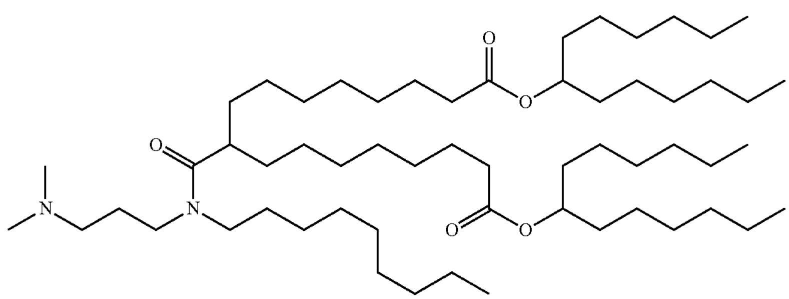 [SMILES: CCCCCCCCCN(CCCN(C)C)C(=O)C(CCCCCCCC(=O)OC(CCCCCC)CCCCCC)CCCCCCCC(=O)OC(CCCCCC)CCCCCC] | E | — |
| II-26 | 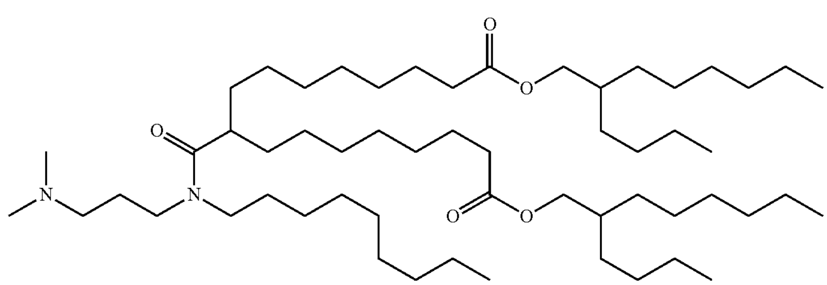 [SMILES: CCCCCCCCCN(CCCN(C)C)C(=O)C(CCCCCCCC(=O)OCC(CCCC)CCCCCC)CCCCCCCC(=O)OCC(CCCC)CCCCCC] | E | — |

TABLE 2-continued
Representative Lipids of Formula (II)
| No. | Structure | Prep. Method | pKa |
|---|---|---|---|
| II-27 | 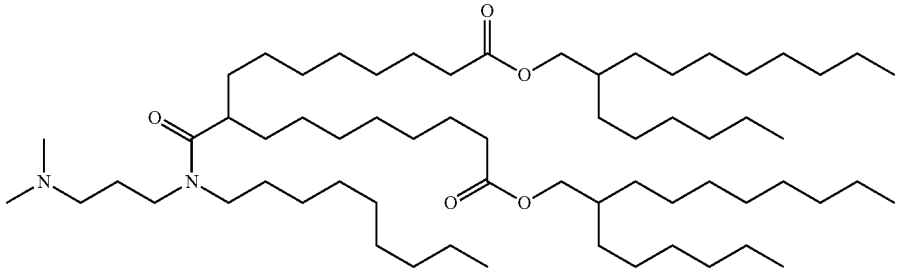 [SMILES: CCCCCCCCCN(CCCN(C)C)C(=O)C(CCCCCCCC(=O)OCC(CCCCCC)CCCCCCCC)CCCCCCCC(=O)OCC(CCCCCC)CCCCCCCC] | E | — |
| II-28 | 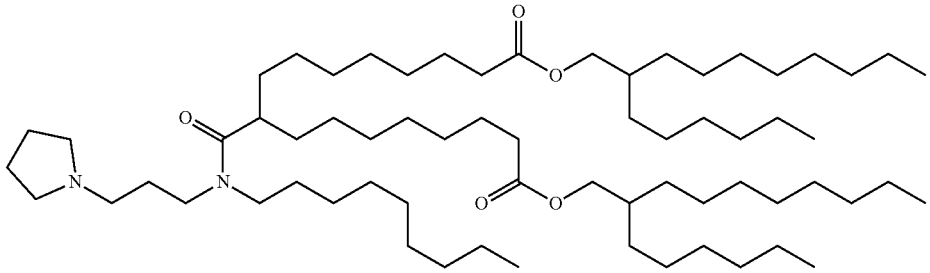 [SMILES: CCCCCCCCCN(CCCN1CCCC1)C(=O)C(CCCCCCCC(=O)OCC(CCCCCC)CCCCCCCC)CCCCCCCC(=O)OCC(CCCCCC)CCCCCCCC] | E | — |
| II-29 | 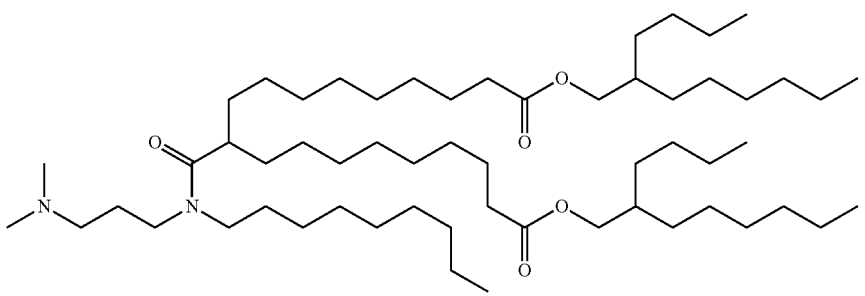 [SMILES: CCCCCCCCCN(CCCN(C)C)C(=O)C(CCCCCCCCC(=O)OCC(CCCC)CCCCCC)CCCCCCCCC(=O)OCC(CCCC)CCCCCC] | E | — |
| II-30 | 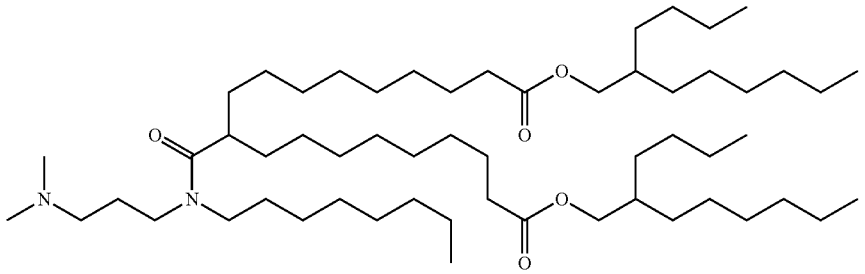 [SMILES: CCCCCCCCN(CCCN(C)C)C(=O)C(CCCCCCCCC(=O)OCC(CCCC)CCCCCC)CCCCCCCCC(=O)OCC(CCCC)CCCCCC] | E | — |
| II-31 | 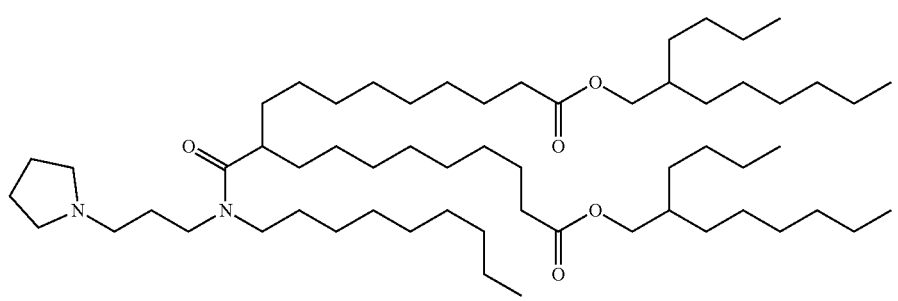 [SMILES: CCCCCCCCCN(CCCN1CCCC1)C(=O)C(CCCCCCCCC(=O)OCC(CCCC)CCCCCC)CCCCCCCCC(=O)OCC(CCCC)CCCCCC] | E | — |

TABLE 2-continued

Representative Lipids of Formula (II)

| No. | Structure | Prep. Method | pKa |
|---|---|---|---|
| II-32 | 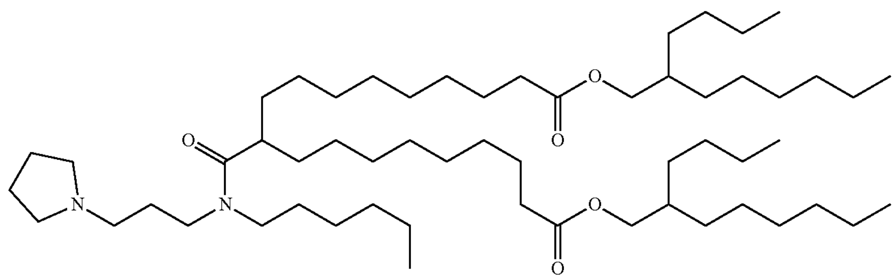 [SMILES: CCCCCCC(CCCC)COC(=O)CCCCCCCCC(CCCCCCCCC(=O)OCC(CCCC)CCCCCC)C(=O)N(CCCCCC)CCCN1CCCC1] | E | — |
| II-33 | 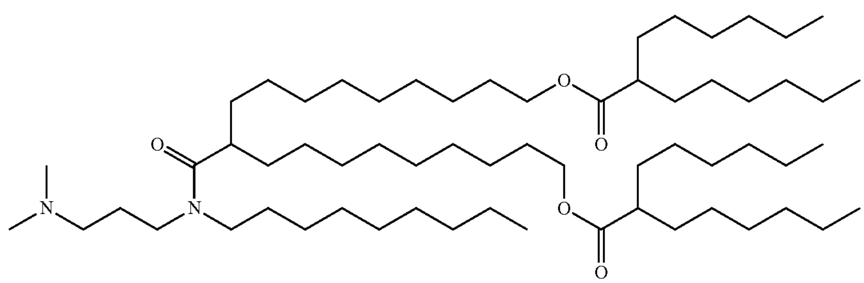 [SMILES: CCCCCCCCCN(CCCN(C)C)C(=O)C(CCCCCCCCCOC(=O)C(CCCCCC)CCCCCC)CCCCCCCCCOC(=O)C(CCCCCC)CCCCCC] | E | — |
| II-34 | 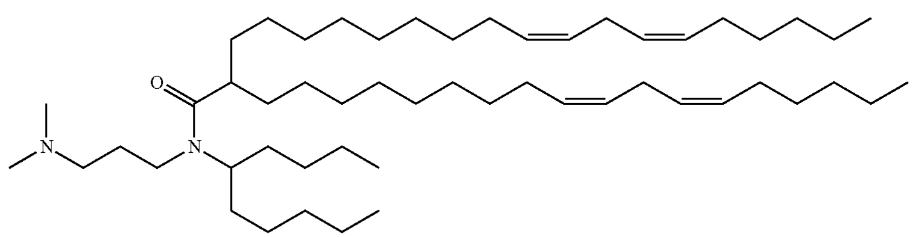 [SMILES: CCCCC/C=C\C/C=C\CCCCCCCCC(CCCCCCCC/C=C\C/C=C\CCCCC)C(=O)N(CCCN(C)C)C(CCCC)CCCCC] | E | — |
| II-35 | 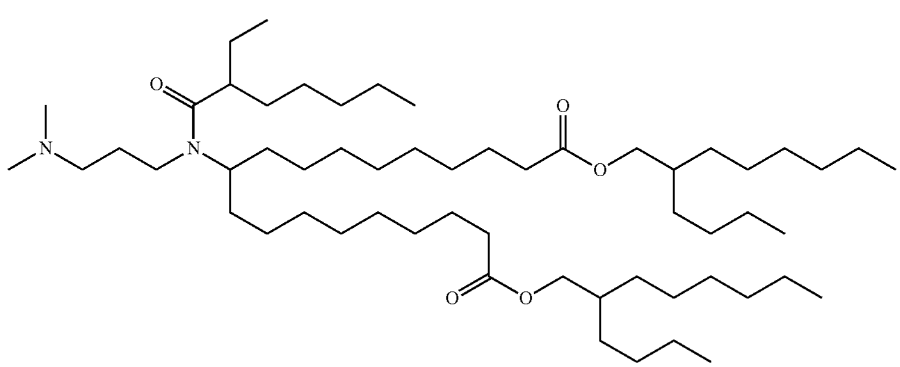 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC] | D | 5.97 |
| II-36 | 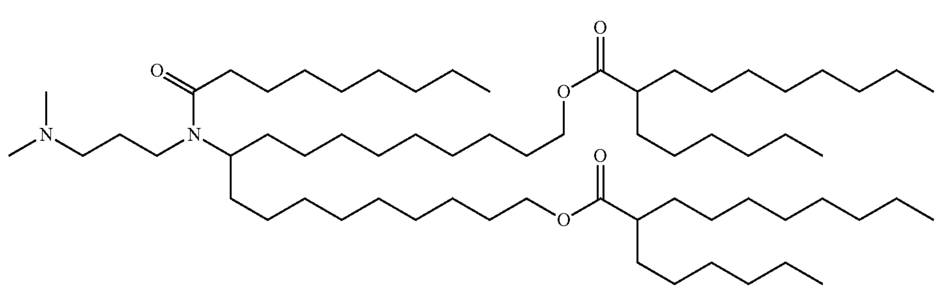 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC] | F | 6.13 |

TABLE 2-continued

Representative Lipids of Formula (II)

| No. | Structure | Prep. Method | pKa |
|---|---|---|---|
| II-37 | 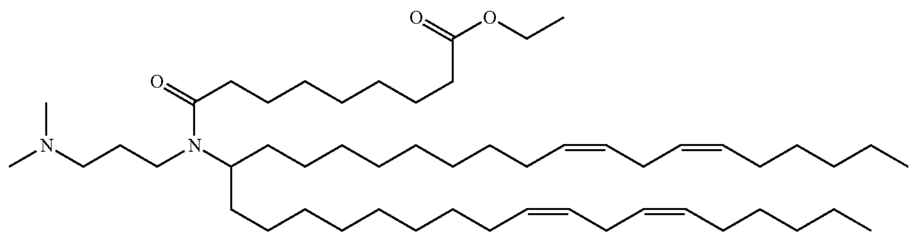 [SMILES: CCCCC/C=C\C/C=C\CCCCCCCCC(CCCCCCCC/C=C\C/C=C\CCCCC)N(CCCN(C)C)C(=O)CCCCCCCC(=O)OCC] | D | 5.61 |
| II-38 | 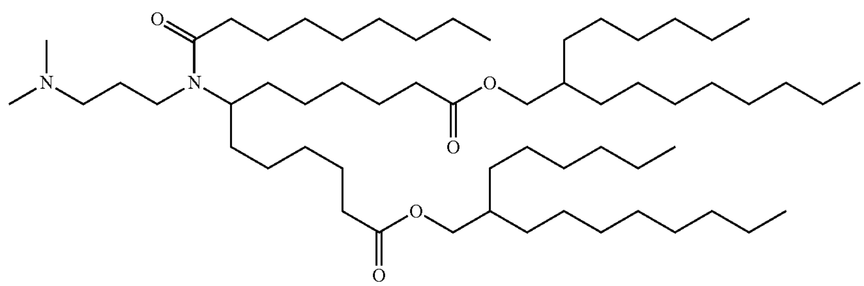 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC] | D | 6.45 |
| II-39 | 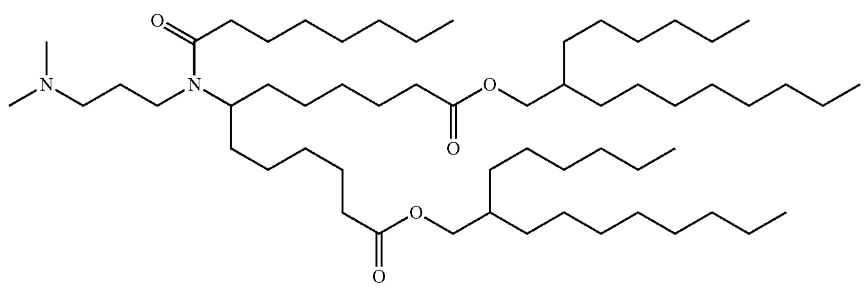 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC] | D | 6.45 |
| II-40 | 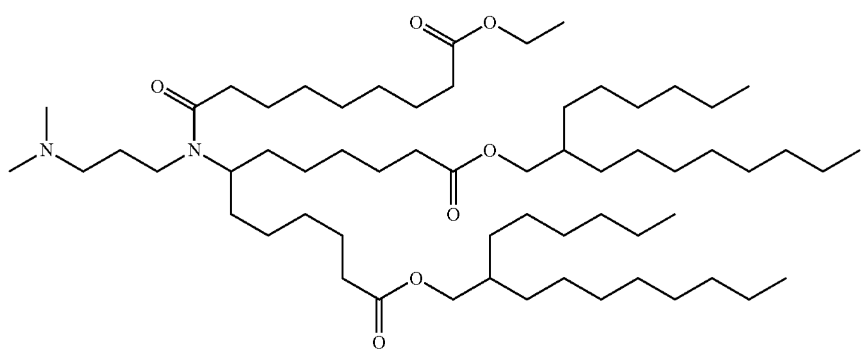 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC] | D | 6.57 |
| II-41 | 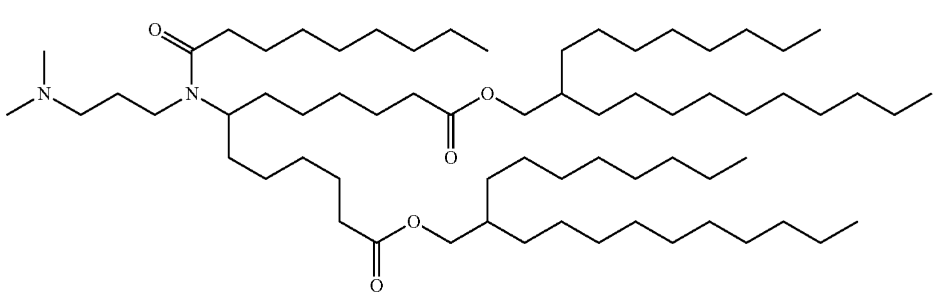 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC] | D | — |

TABLE 2-continued

Representative Lipids of Formula (II)

| No. | Structure | Prep. Method | pKa |
|---|---|---|---|
| II-42 | 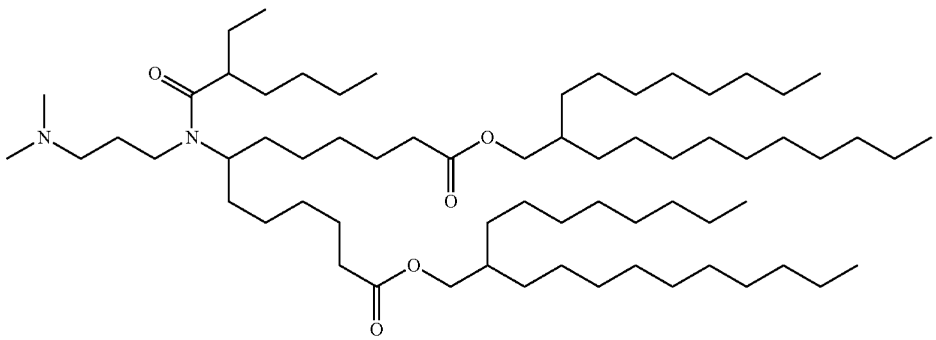 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)C(CC)CCCC] | D | — |
| II-43 | 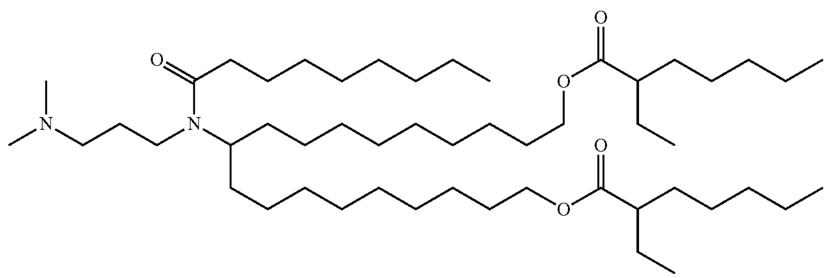 [SMILES: CCCCCCCCC(=O)N(CCCN(C)C)C(CCCCCCCCCOC(=O)C(CC)CCCCC)CCCCCCCCCOC(=O)C(CC)CCCCC] | F | — |
| II-44 | 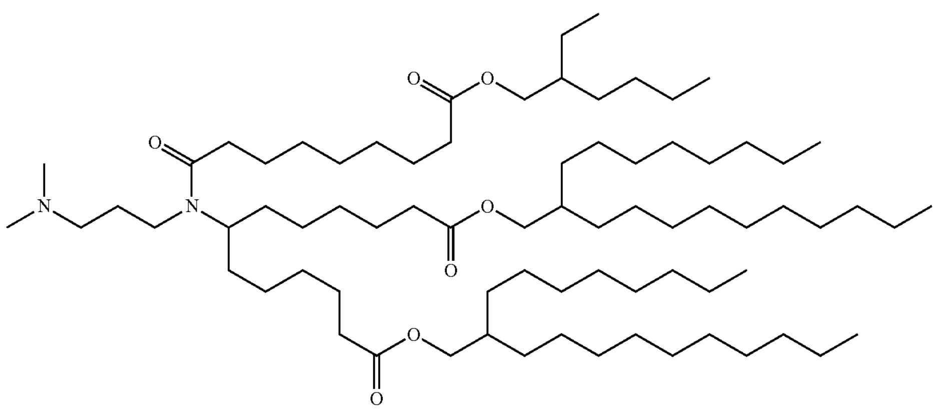 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC(=O)OCC(CC)CCCC] | D | — |
| II-45 | 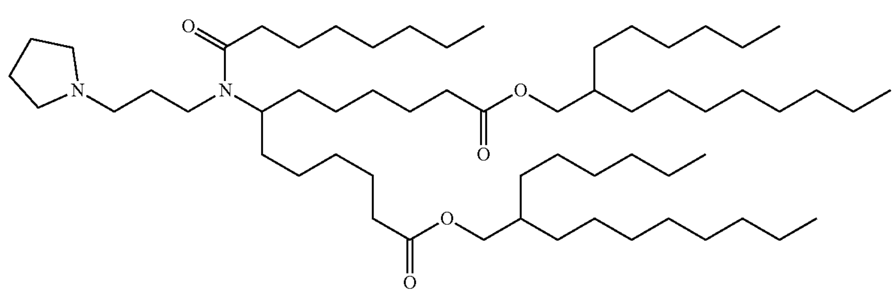 [SMILES: CCCCCCCCC(CCCCCC)COC(=O)CCCCCC(CCCCCC(=O)OCC(CCCCCC)CCCCCCCC)N(CCCN1CCCC1)C(=O)CCCCCCC] | D | — |

TABLE 2-continued

Representative Lipids of Formula (II)

| No. | Structure | Prep. Method | pKa |
|---|---|---|---|
| II-46 | 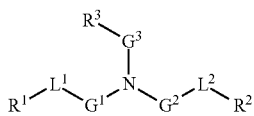 | D | — |

In some embodiments the lipid of Formula (II) is compound II-9. In some embodiments the lipid of Formula (II) is compound II-10. In some embodiments the lipid of Formula (II) is compound II-11. In some embodiments the lipid of Formula (II) is compound II-12. In some embodiments the lipid of Formula (II) is compound II-14. In some embodiments the lipid of Formula (II) is compound II-15.

In some other embodiments, a cationic lipid of Embodiments 1, 2 or 3 (e.g., the cationic lipid, the first cationic lipid, the second cationic lipid) has a structure of Formula III:

III or a pharmaceutically acceptable salt, prodrug or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, OR$^S$, CN, —C(=O)OR$^4$, —OC(=O)R$^4$ or —NR$^5$C(=O)R$^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the lipid has one of the following Formulae (IIIA) or (IIIB):

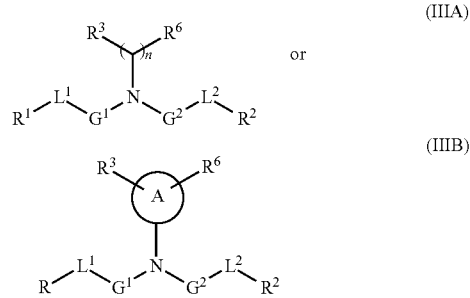

wherein:

A is a 3 to 8-membered cycloalkyl or cycloalkylene ring;
$R^6$ is, at each occurrence, independently H, OH or $C_1$-$C_{24}$ alkyl;
n is an integer ranging from 1 to 15.

In some of the foregoing embodiments of Formula (III), the lipid has Formula (IIIA), and in other embodiments, the lipid has Formula (IIIB).

In other embodiments of Formula (III), the lipid has one of the following Formulae (IIIC) or (IIID):

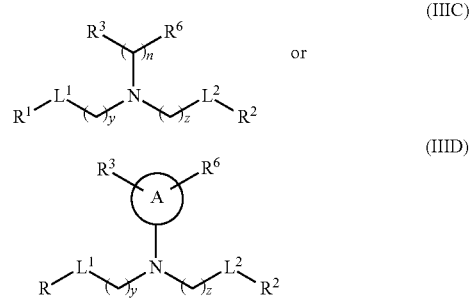

wherein y and z are each independently integers ranging from 1 to 12.

In any of the foregoing embodiments of Formula (III), one of $L^1$ or $L^2$ is —O(C=O)—. For example, in some embodiments each of $L^1$ and $L^2$ are —O(C=O)—. In some different embodiments of any of the foregoing, $L^1$ and $L^2$ are each independently —(C=O)O— or —O(C=O)—. For example, in some embodiments each of $L^1$ and $L^2$ is —(C=O)O—.

In some different embodiments of Formula (III), the lipid has one of the following Formulae (IIIE) or (IIIF):

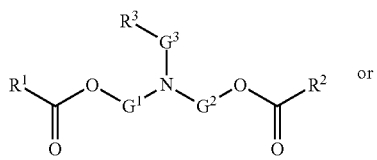 (IIIE)

or

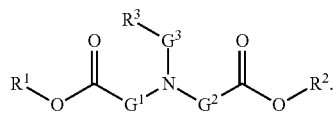 (IIIF)

In some of the foregoing embodiments of Formula (III), the lipid has one of the following Formulae (IIIG), (IIIH), (IIII), or (IIIJ):

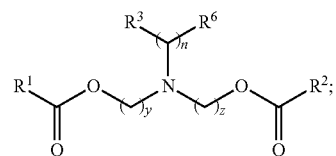 (IIIG)

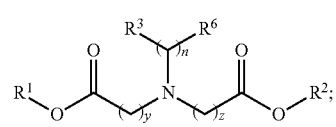 (IIIH)

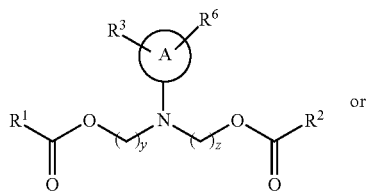 (IIII)

or

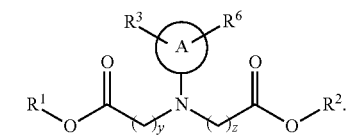 (IIIJ)

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R^2$ each, independently have the following structure:

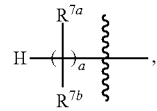

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures:

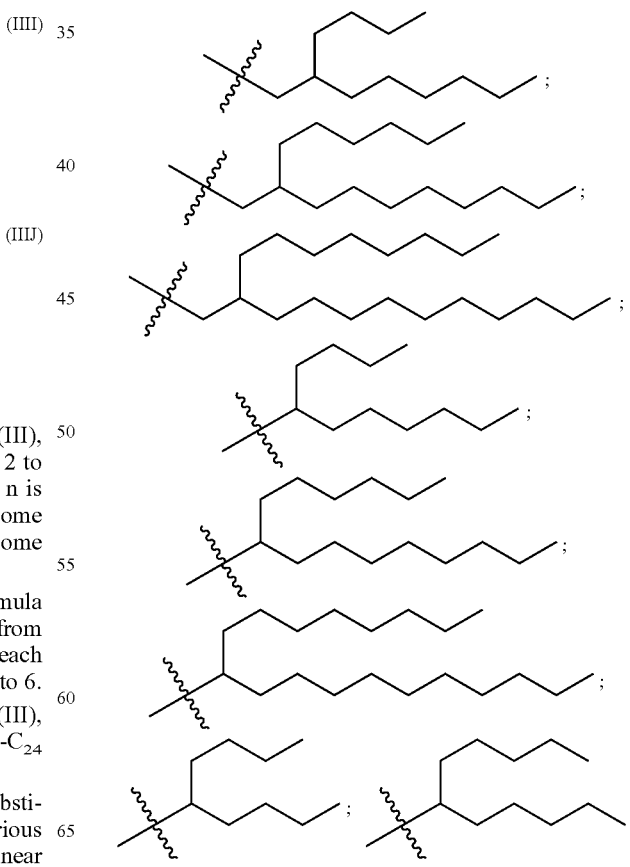

-continued

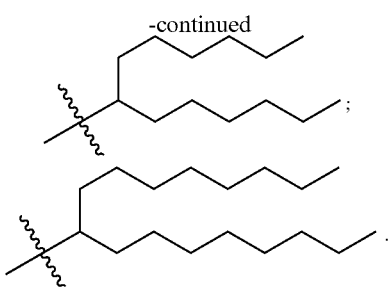

In some of the foregoing embodiments of Formula (III), $R^3$ is OH, CN, —C(=O)OR$^4$, —OC(=O)R$^4$ or —NHC(=O)R$^4$. In some embodiments, $R^4$ is methyl or ethyl.

In some specific embodiments of Embodiment 3, the first and second cationic lipids are each, independently selected from a lipid of Formula III.

In various different embodiments, a cationic lipid of any one of the disclosed embodiments (e.g., the cationic lipid, the first cationic lipid, the second cationic lipid) of Formula (III) has one of the structures set forth in Table 3 below.

TABLE 3

Representative Compounds of Formula (III)

| No. | Structure | Prep. Method | pKa |
|---|---|---|---|
| III-1 | 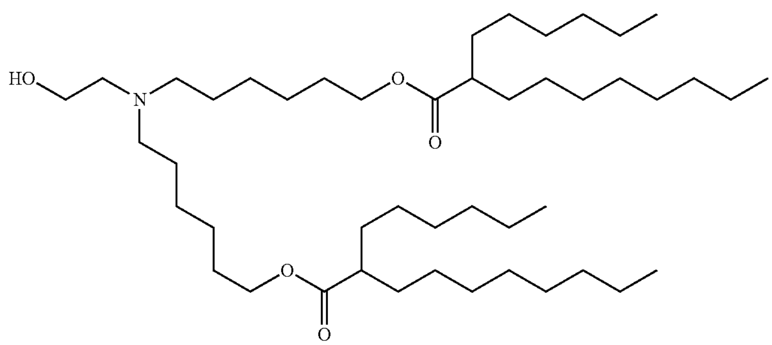 [SMILES: CCCCCCCCC(CCCCCC)C(=O)OCCCCCCN(CCO)CCCCCCOC(=O)C(CCCCCC)CCCCCCCC] | G | 5.89 |
| III-2 | 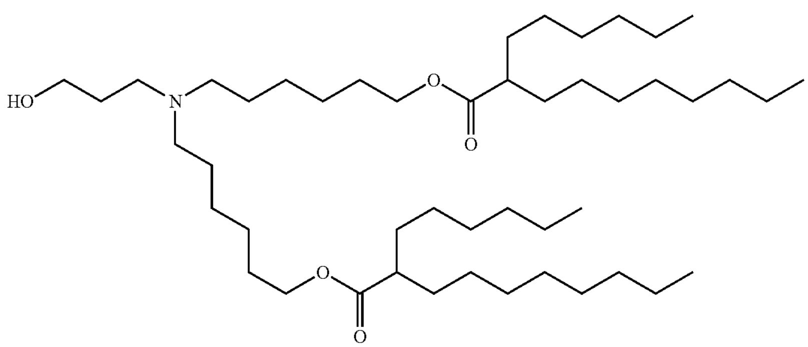 [SMILES: CCCCCCCCC(CCCCCC)C(=O)OCCCCCCN(CCCO)CCCCCCOC(=O)C(CCCCCC)CCCCCCCC] | G | 6.05 |
| III-3 | 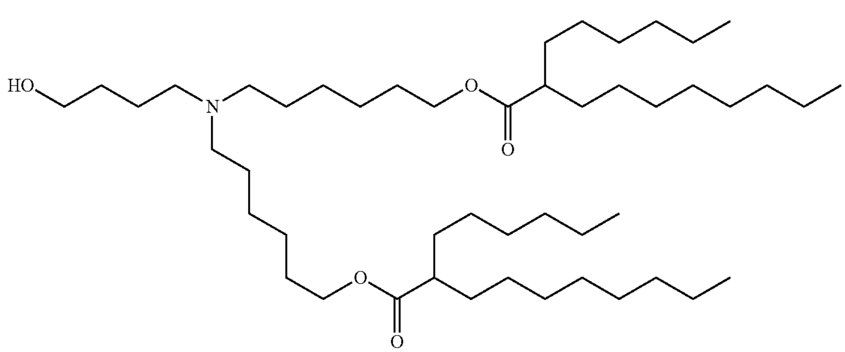 [SMILES: CCCCCCCCC(CCCCCC)C(=O)OCCCCCCN(CCCCO)CCCCCCOC(=O)C(CCCCCC)CCCCCCCC] | G | 6.09 |

TABLE 3-continued
Representative Compounds of Formula (III)
| No. | Structure | Prep. Method | pKa |
|---|---|---|---|
| III-4 | 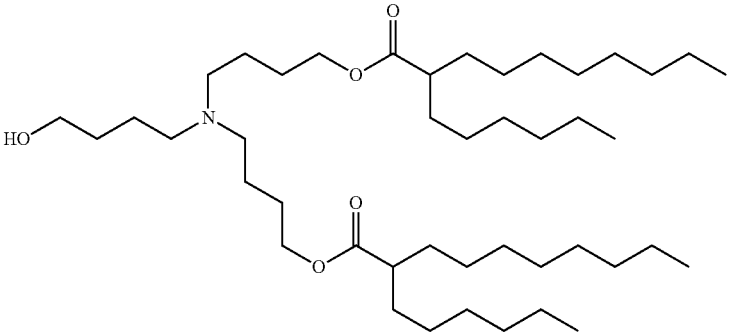 [SMILES: CCCCCCCCC(CCCCCC)C(=O)OCCCCN(CCCCO)CCCCOC(=O)C(CCCCCC)CCCCCCCC] | G | 5.60 |
| III-5 | 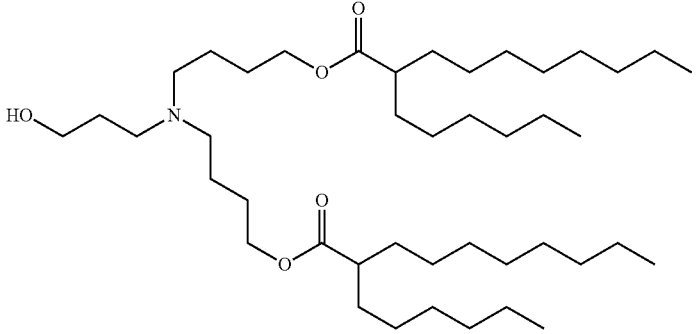 [SMILES: CCCCCCCCC(CCCCCC)C(=O)OCCCCN(CCCO)CCCCOC(=O)C(CCCCCC)CCCCCCCC] | G | 5.59 |
| III-6 | 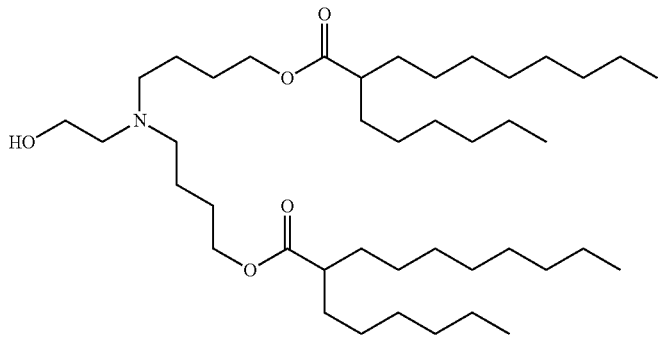 [SMILES: CCCCCCCCC(CCCCCC)C(=O)OCCCCN(CCO)CCCCOC(=O)C(CCCCCC)CCCCCCCC] | G | 5.42 |
| III-7 | 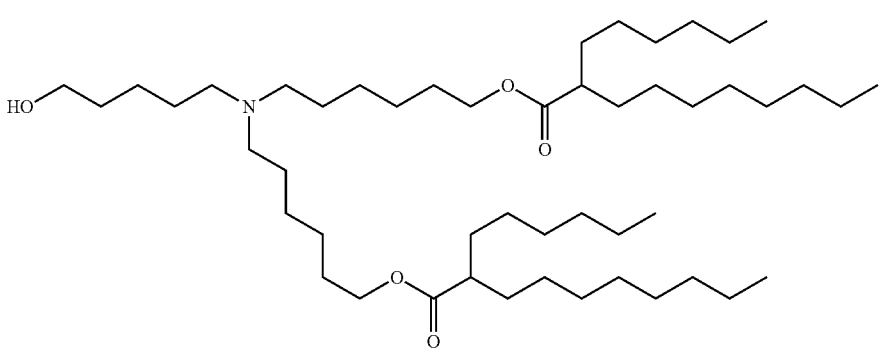 [SMILES: CCCCCCCCC(CCCCCC)C(=O)OCCCCCCN(CCCCCO)CCCCCCOC(=O)C(CCCCCC)CCCCCCCC] | G | 6.11 |

TABLE 3-continued

Representative Compounds of Formula (III)

| No. | Structure | Prep. Method | pKa |
|---|---|---|---|
| III-8 | 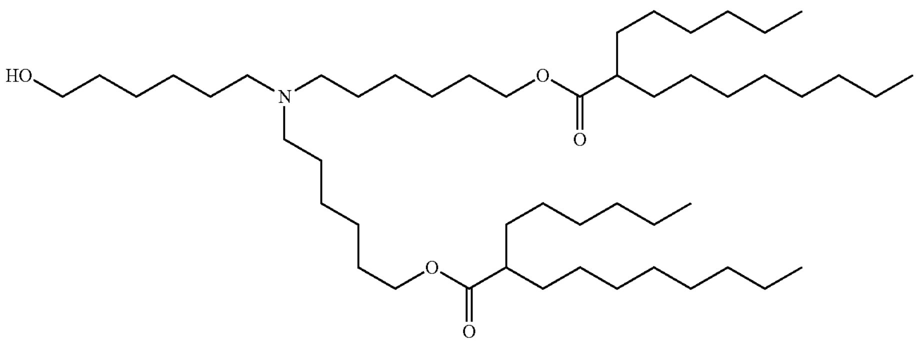 [SMILES: CCCCCCCCC(CCCCCC)C(=O)OCCCCCCN(CCCCCCO)CCCCCCOC(=O)C(CCCCCC)CCCCCCCC] | G | 5.84 |
| III-9 | 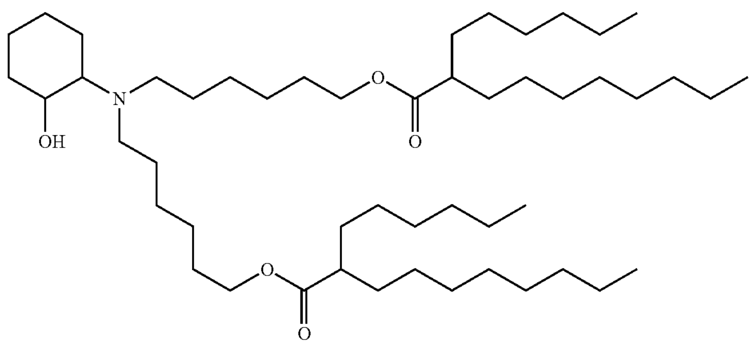 [SMILES: CCCCCCCCC(CCCCCC)C(=O)OCCCCCCN(CCCCCCOC(=O)C(CCCCCC)CCCCCCCC)C1CCCCC1O] | G | — |
| III-10 | 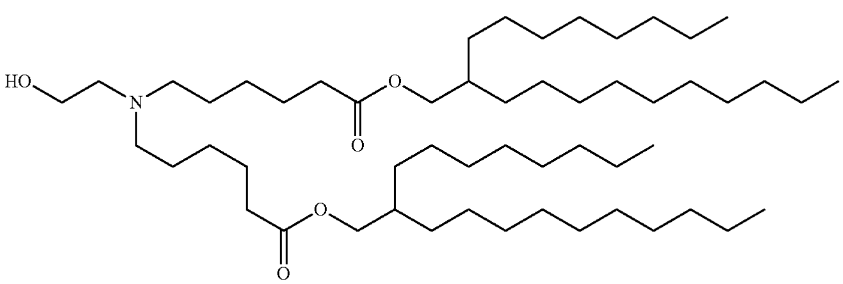 [SMILES: CCCCCCCCCCC(CCCCCCCC)COC(=O)CCCCCN(CCO)CCCCCC(=O)OCC(CCCCCCCC)CCCCCCCCCC] | G | — |
| III-11 | 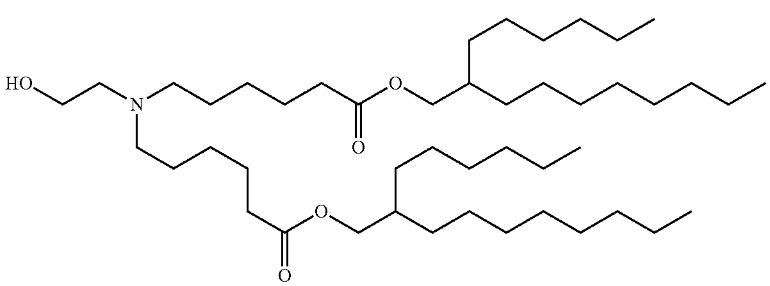 [SMILES: CCCCCCCCC(CCCCCC)COC(=O)CCCCCN(CCO)CCCCCC(=O)OCC(CCCCCC)CCCCCCCC] | G | — |
| III-12 | 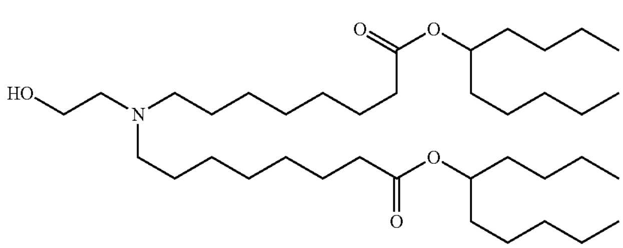 [SMILES: CCCCCC(CCCC)OC(=O)CCCCCCCN(CCO)CCCCCCCC(=O)OC(CCCC)CCCCC] | G | — |

TABLE 3-continued
Representative Compounds of Formula (III)
| No. | Structure | Prep. Method | pKa |
|---|---|---|---|
| III-13 | 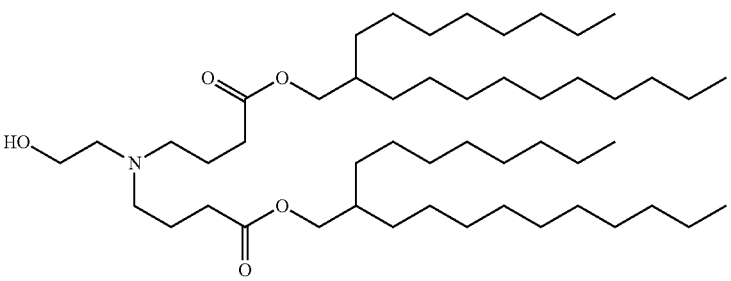 [SMILES: CCCCCCCCCCC(CCCCCCCC)COC(=O)CCCN(CCO)CCCC(=O)OCC(CCCCCCCC)CCCCCCCCCC] | G | — |
| III-14 | 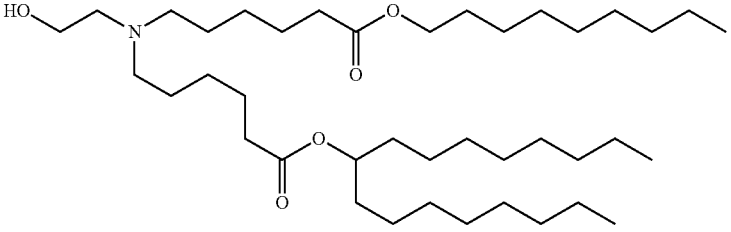 [SMILES: CCCCCCCCCOC(=O)CCCCCN(CCO)CCCCCC(=O)OC(CCCCCCCC)CCCCCCCC] | G | — |
| III-15 | 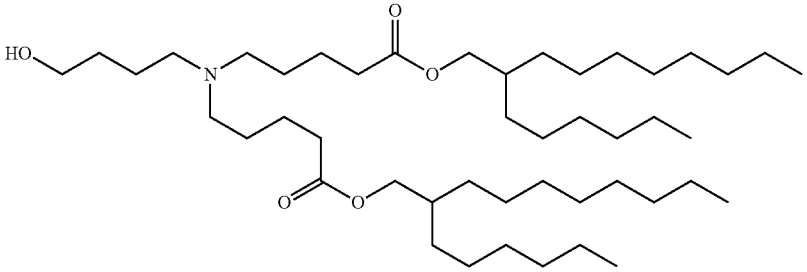 [SMILES: CCCCCCCCC(CCCCCC)COC(=O)CCCCN(CCCCO)CCCCC(=O)OCC(CCCCCC)CCCCCCCC] | G | 6.14 |
| III-16 | 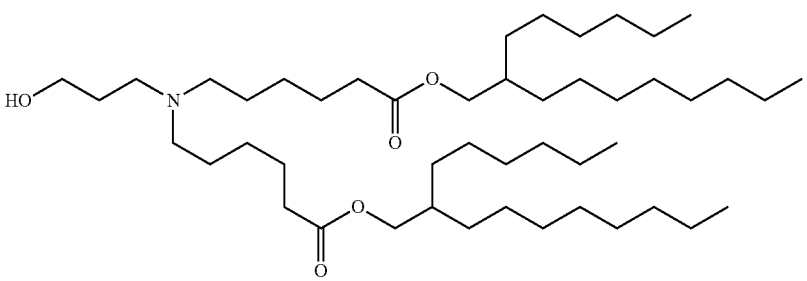 [SMILES: CCCCCCCCC(CCCCCC)COC(=O)CCCCCN(CCCO)CCCCCC(=O)OCC(CCCCCC)CCCCCCCC] | G | 6.31 |
| III-17 | 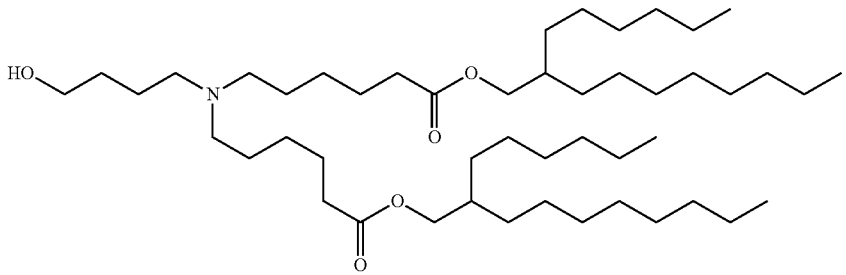 [SMILES: CCCCCCCCC(CCCCCC)COC(=O)CCCCCN(CCCCO)CCCCCC(=O)OCC(CCCCCC)CCCCCCCC] | G | 6.28 |

TABLE 3-continued

Representative Compounds of Formula (III)

| No. | Structure | Prep. Method | pKa |
|---|---|---|---|
| III-18 | 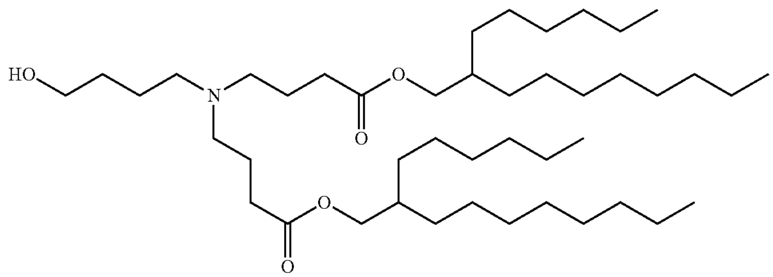 [SMILES: CCCCCCCCC(CCCCCC)COC(=O)CCCN(CCCCO)CCCC(=O)OCC(CCCCCC)CCCCCCCC] | G | — |
| III-19 | 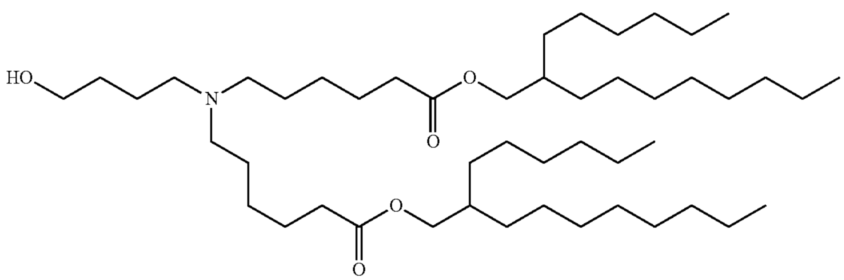 [SMILES: CCCCCCCCC(CCCCCC)COC(=O)CCCCCN(CCCCO)CCCCCC(=O)OCC(CCCCCC)CCCCCCCC] | G | — |
| III-20 | 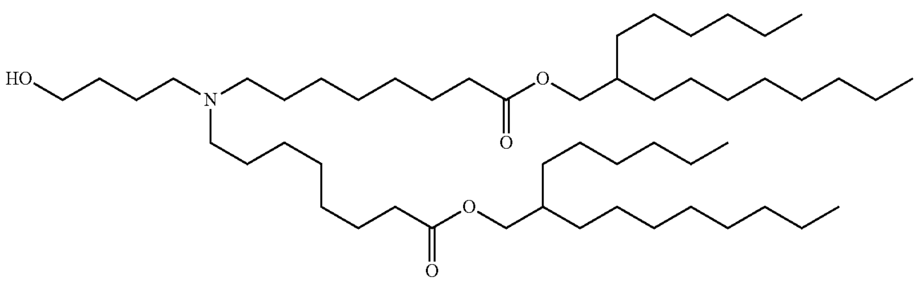 [SMILES: CCCCCCCCC(CCCCCC)COC(=O)CCCCCCCN(CCCCO)CCCCCCCC(=O)OCC(CCCCCC)CCCCCCCC] | G | 6.36 |
| III-21 | 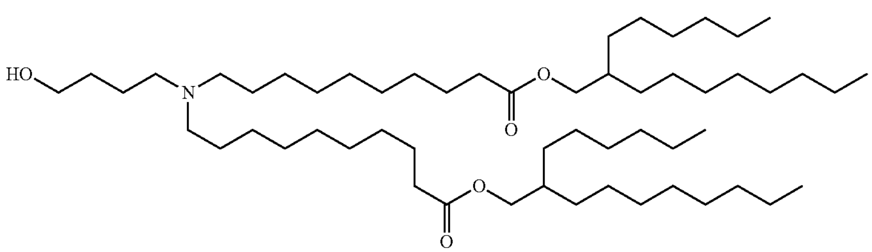 [SMILES: CCCCCCCCC(CCCCCC)COC(=O)CCCCCCCCCN(CCCCO)CCCCCCCCCC(=O)OCC(CCCCCC)CCCCCCCC] | G | — |
| III-22 | 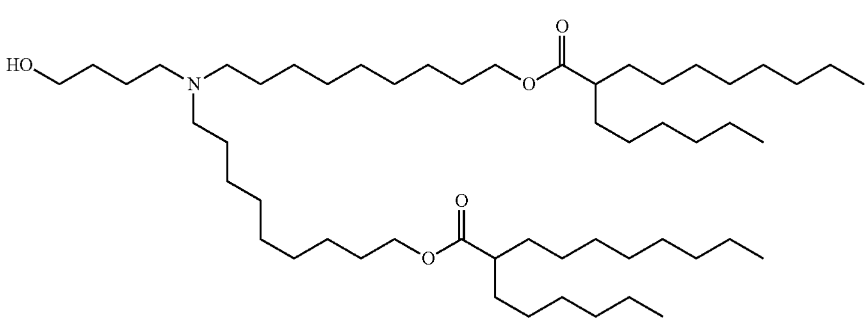 [SMILES: CCCCCCCCC(CCCCCC)C(=O)OCCCCCCCCCN(CCCCO)CCCCCCCCCOC(=O)C(CCCCCC)CCCCCCCC] | G | 6.10 |

TABLE 3-continued

Representative Compounds of Formula (III)

| No. | Structure | Prep. Method | pKa |
|---|---|---|---|
| III-23 | 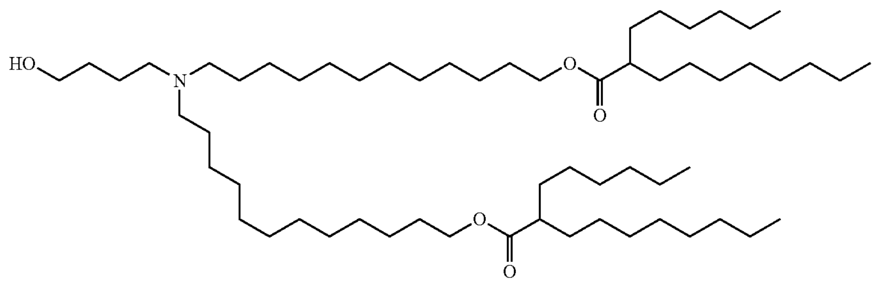 [SMILES: CCCCCCCCC(CCCCCC)C(=O)OCCCCCCCCCCCCN(CCCCO)CCCCCCCCCCCCOC(=O)C(CCCCCC)CCCCCCCC] | G | 5.98 |
| III-24 | 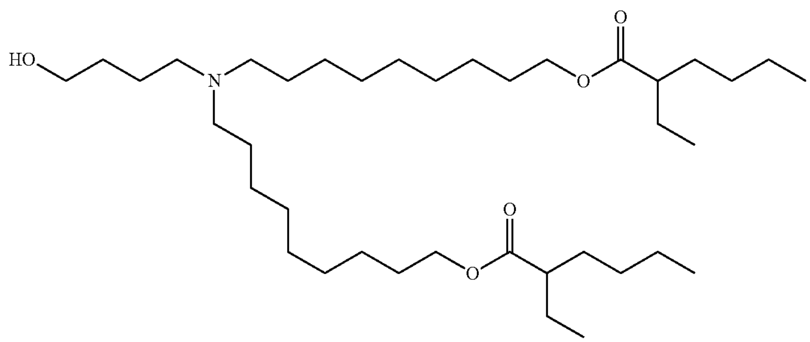 [SMILES: CCCCC(CC)C(=O)OCCCCCCCCCN(CCCCO)CCCCCCCCCOC(=O)C(CC)CCCC] | G | — |
| III-25 | 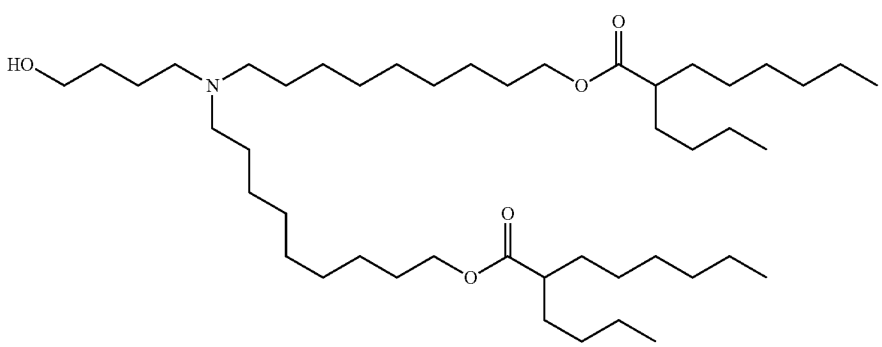 [SMILES: CCCCCCC(CCCC)C(=O)OCCCCCCCCCN(CCCCO)CCCCCCCCCOC(=O)C(CCCC)CCCCCC] | G | 6.22 |
| III-26 | 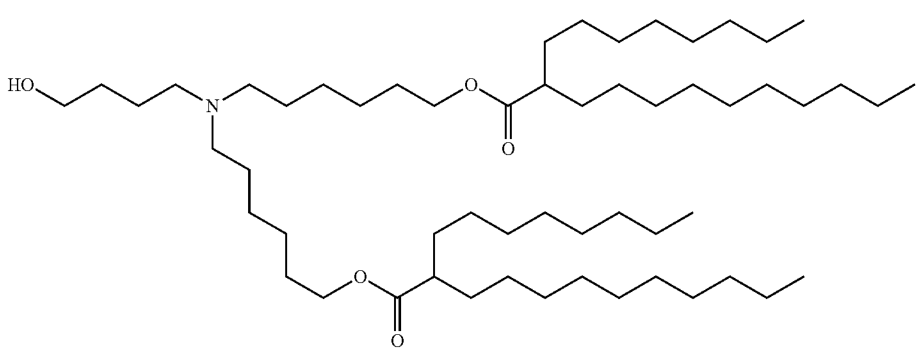 [SMILES: CCCCCCCCCCC(CCCCCCCC)C(=O)OCCCCCCN(CCCCO)CCCCCCOC(=O)C(CCCCCCCC)CCCCCCCCCC] | G | 5.84 |

TABLE 3-continued

Representative Compounds of Formula (III)

| No. | Structure | Prep. Method | pKa |
|---|---|---|---|
| III-27 | 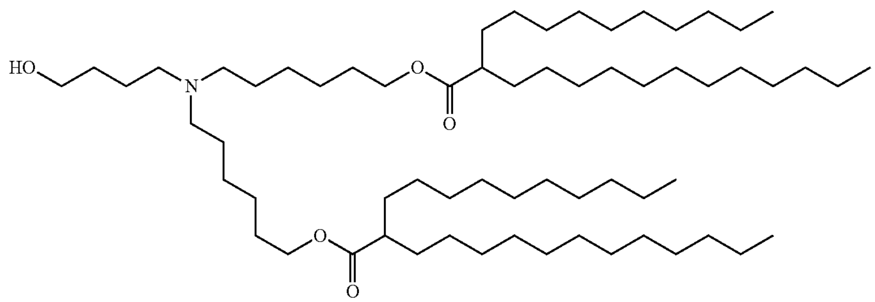 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] | G | 5.77 |
| III-28 | 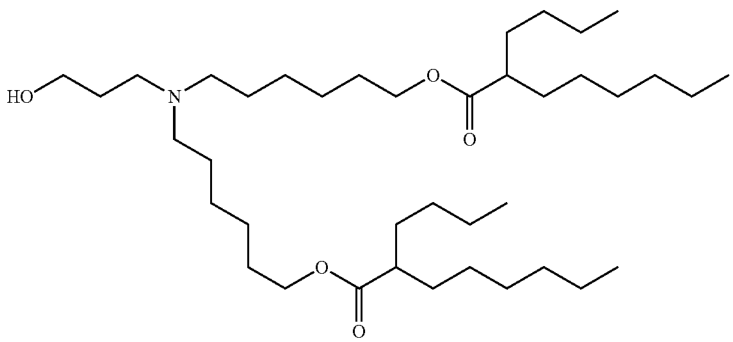 [SMILES: CCCCCCC(CCCC)C(=O)OCCCCCCN(CCCO)CCCCCCOC(=O)C(CCCC)CCCCCC] | G | — |
| III-29 | 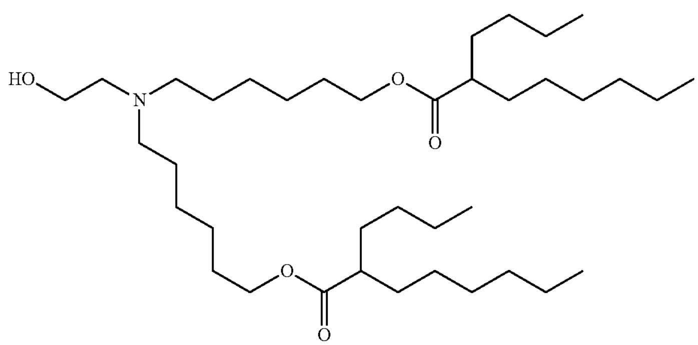 [SMILES: CCCCCCC(CCCC)C(=O)OCCCCCCN(CCO)CCCCCCOC(=O)C(CCCC)CCCCCC] | G | — |
| III-30 | 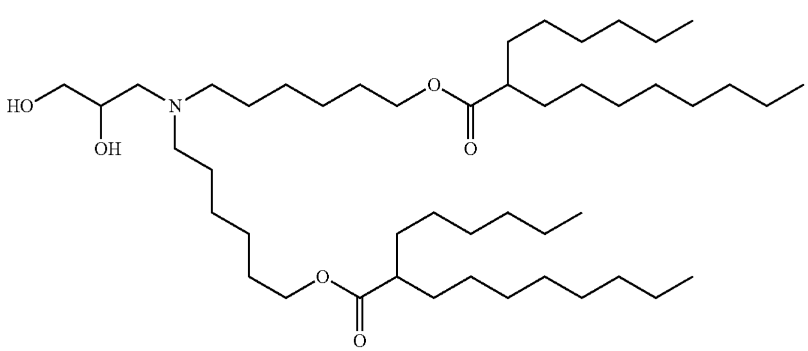 [SMILES: CCCCCCCCC(CCCCCC)C(=O)OCCCCCCN(CCCCCCOC(=O)C(CCCCCC)CCCCCCCC)CC(O)CO] | G | 6.09 |

TABLE 3-continued

Representative Compounds of Formula (III)

| No. | Structure | Prep. Method | pKa |
|---|---|---|---|
| III-31 | 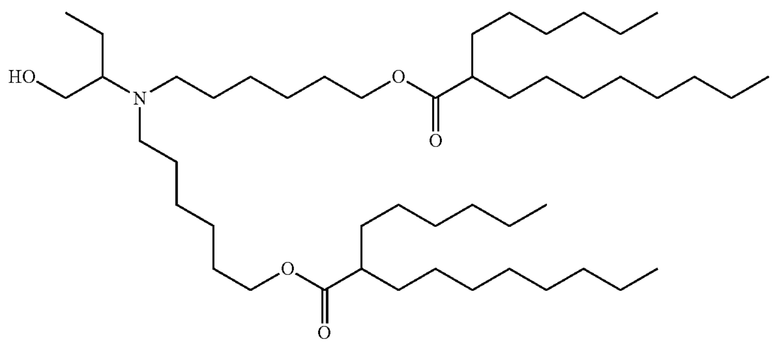 [SMILES: CCCCCCCCC(CCCCCC)C(=O)OCCCCCCN(CCCCCCOC(=O)C(CCCCCC)CCCCCCCC)C(CC)CO] | G | — |
| III-32 | 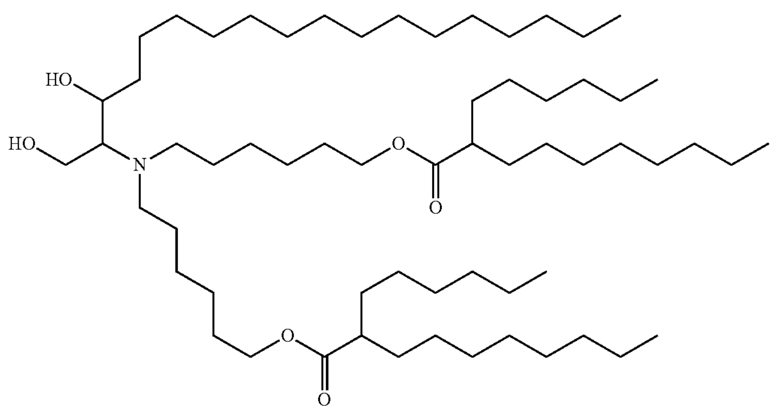 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] | G | — |
| III-33 | 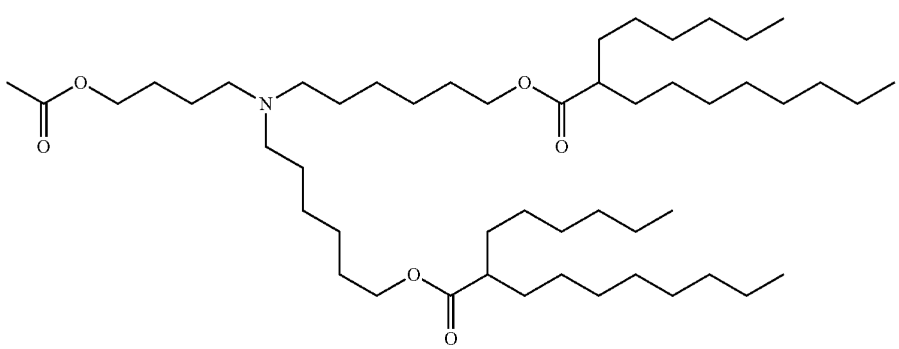 [SMILES: CCCCCCCCC(CCCCCC)C(=O)OCCCCCCN(CCCCCCOC(=O)C(CCCCCC)CCCCCCCC)CCCCOC(C)=O] | G | — |
| III-34 | 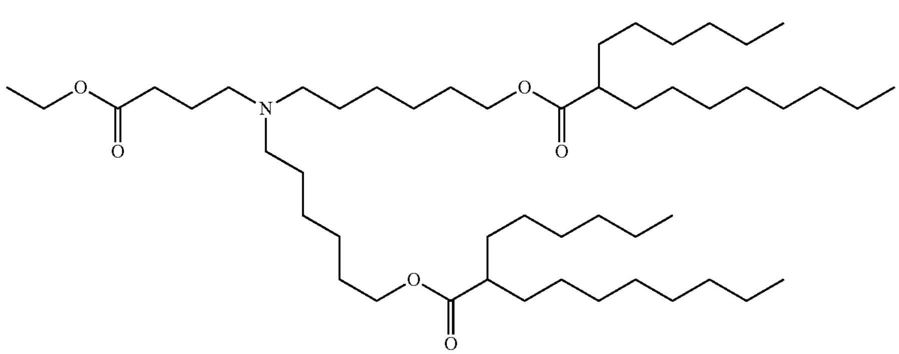 [SMILES: CCCCCCCCC(CCCCCC)C(=O)OCCCCCCN(CCCCCCOC(=O)C(CCCCCC)CCCCCCCC)CCCC(=O)OCC] | G | — |

TABLE 3-continued

Representative Compounds of Formula (III)

| No. | Structure | Prep. Method | pKa |
|---|---|---|---|
| III-35 | 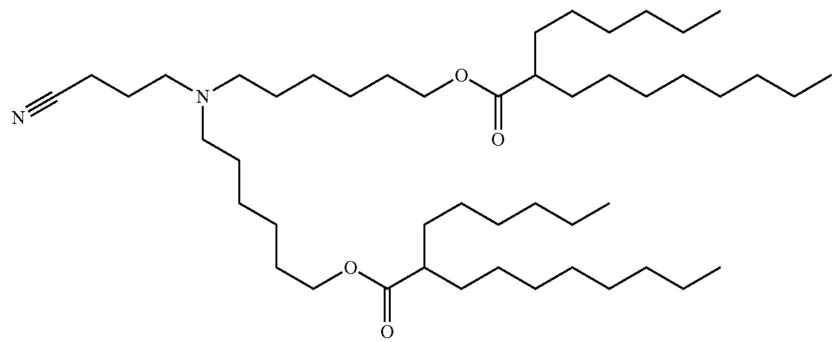 [SMILES: CCCCCCCCC(CCCCCC)C(=O)OCCCCCCN(CCCC#N)CCCCCCOC(=O)C(CCCCCC)CCCCCCCC] | G | — |
| III-36 | 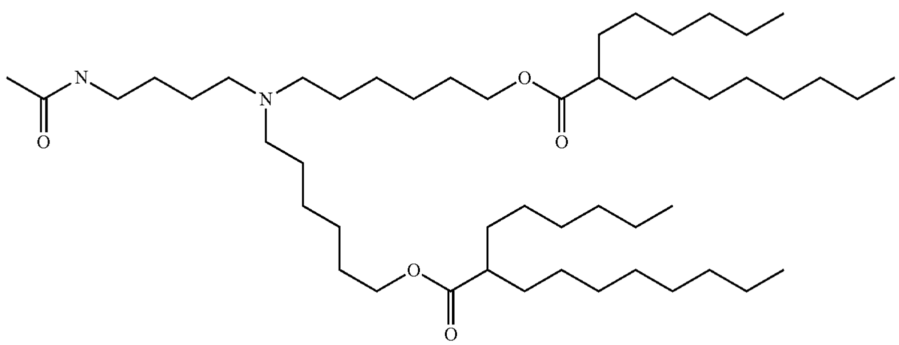 | G | — |
| III-37 | 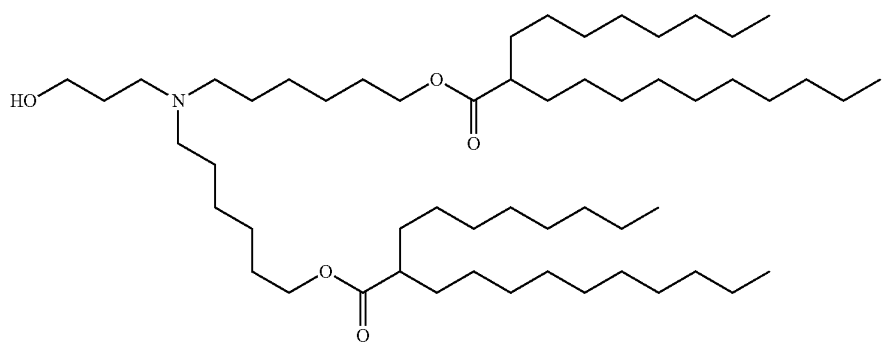 [SMILES: CCCCCCCCCCC(CCCCCCCC)C(=O)OCCCCCCN(CCCO)CCCCCCOC(=O)C(CCCCCCCC)CCCCCCCCCC] | G | — |
| III-38 | 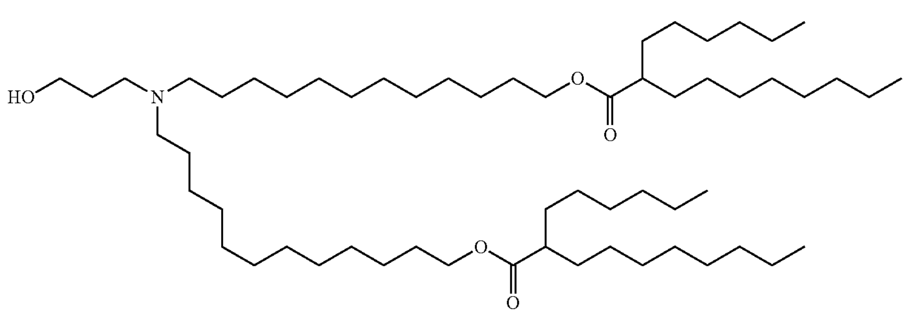 [SMILES: CCCCCCCCC(CCCCCC)C(=O)OCCCCCCCCCCCCN(CCCO)CCCCCCCCCCCCOC(=O)C(CCCCCC)CCCCCCCC] | G | — |

TABLE 3-continued

Representative Compounds of Formula (III)

| No. | Structure | Prep. Method | pKa |
|---|---|---|---|
| III-39 | 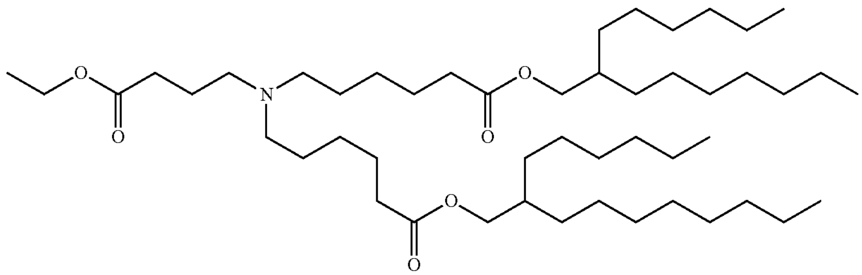 [SMILES: CCCCCCCCC(CCCCCC)COC(=O)CCCCCN(CCCCCC(=O)OCC(CCCCCC)CCCCCCC)CCCC(=O)OCC] | G | — |
| III-40 | 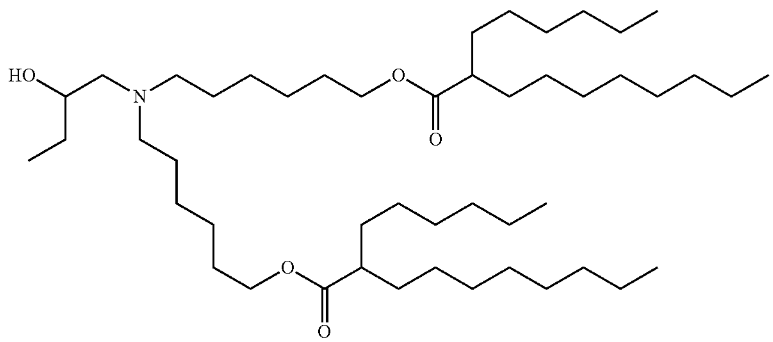 [SMILES: CCCCCCCCC(CCCCCC)C(=O)OCCCCCCN(CCCCCCOC(=O)C(CCCCCC)CCCCCCCC)CC(O)CC] | G | — |
| III-41 | 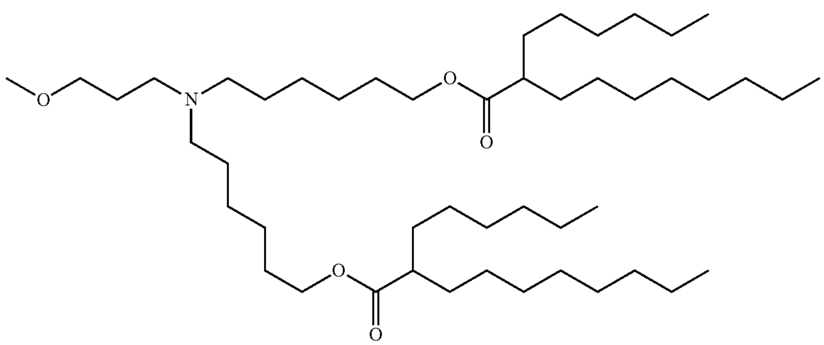 [SMILES: CCCCCCCCC(CCCCCC)C(=O)OCCCCCCN(CCCCCCOC(=O)C(CCCCCC)CCCCCCCC)CCCOC] | G | — |
| III-42 | 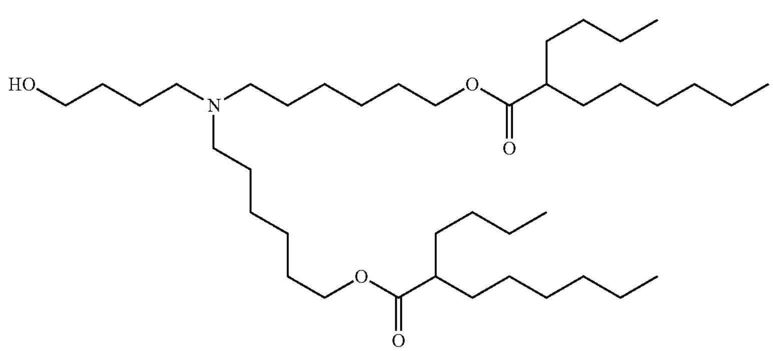 [SMILES: CCCCCCC(CCCC)C(=O)OCCCCCCN(CCCCO)CCCCCCOC(=O)C(CCCC)CCCCCC] | G | — |

TABLE 3-continued
Representative Compounds of Formula (III)
| No. | Structure | Prep. Method | pKa |
|---|---|---|---|
| III-43 | 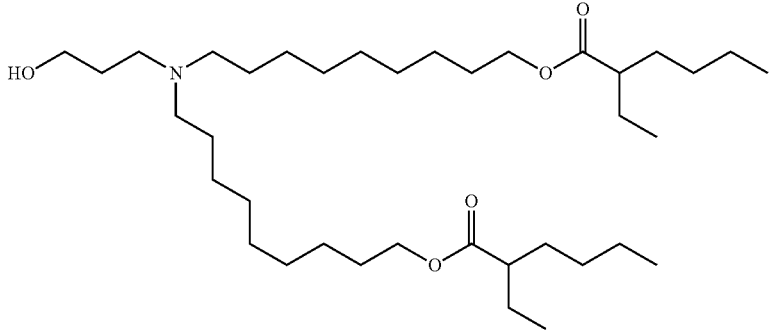 [SMILES: CCCCC(CC)C(=O)OCCCCCCCCCN(CCCO)CCCCCCCCCOC(=O)C(CC)CCCC] | G | — |
| III-44 | 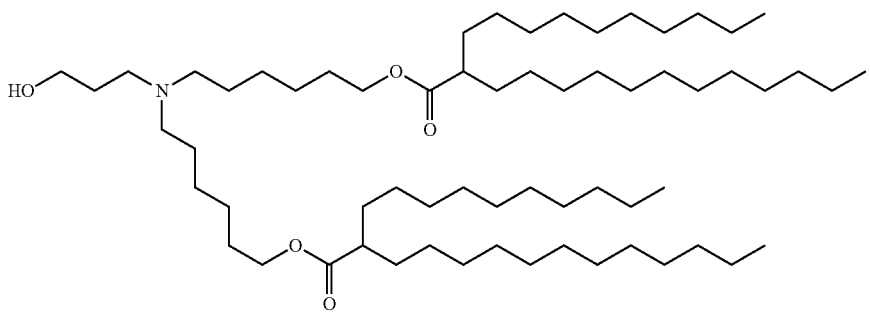 [SMILES: CCCCCCCCCCCCC(CCCCCCCCCC)C(=O)OCCCCCCN(CCCO)CCCCCCOC(=O)C(CCCCCCCCCC)CCCCCCCCCCCC] | G | — |
| III-45 | 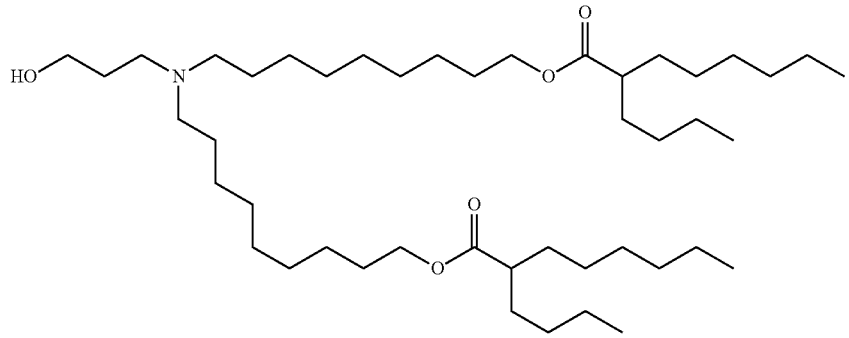 [SMILES: CCCCCCC(CCCC)C(=O)OCCCCCCCCCN(CCCO)CCCCCCCCCOC(=O)C(CCCC)CCCCCC] | G | — |
| III-46 | 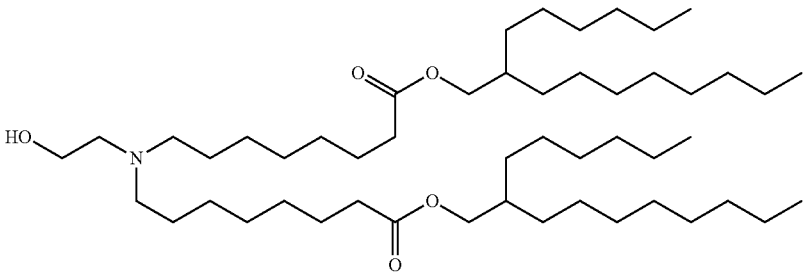 [SMILES: CCCCCCCCC(CCCCCC)COC(=O)CCCCCCCN(CCO)CCCCCCCC(=O)OCC(CCCCCC)CCCCCCCC] | G | — |

TABLE 3-continued

Representative Compounds of Formula (III)

| No. | Structure | Prep. Method | pKa |
|---|---|---|---|
| III-47 | 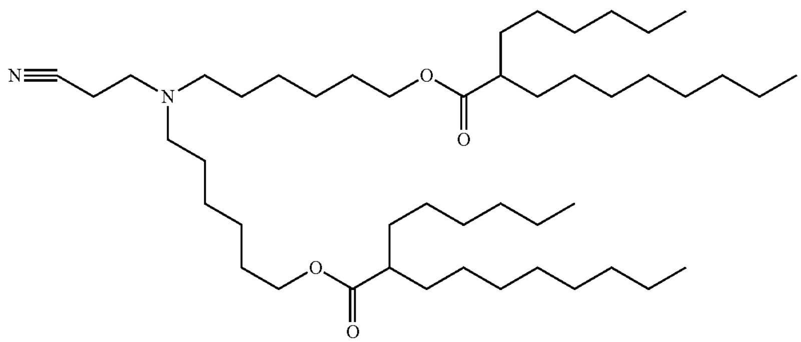 [SMILES: CCCCCCCCC(CCCCCC)C(=O)OCCCCCCN(CCC#N)CCCCCCOC(=O)C(CCCCCC)CCCCCCCC] | G | — |
| III-48 | 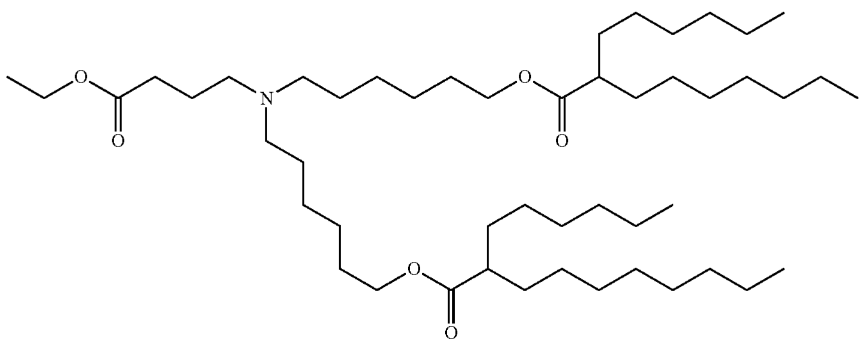 [SMILES: CCCCCCCCC(CCCCCC)C(=O)OCCCCCCN(CCCCCCOC(=O)C(CCCCCC)CCCCCCC)CCCC(=O)OCC] | G | — |
| III-49 | 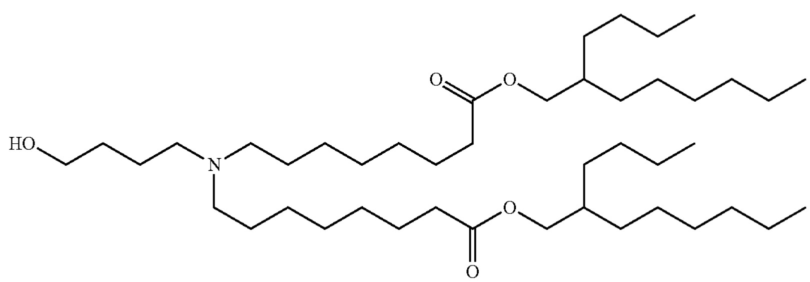 [SMILES: CCCCCCC(CCCC)COC(=O)CCCCCCCN(CCCCO)CCCCCCCC(=O)OCC(CCCC)CCCCCC] | G | — |

In some embodiments the lipid of Formula (III) is compound III-3. In some embodiments the lipid of Formula (III) is compound III-25.

In one embodiment, the first cationic lipid, or the second cationic lipid, or both, independently has a structure of Formula (IV):

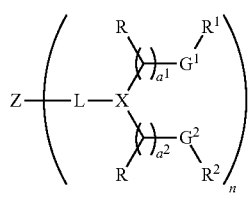

(IV)

or a pharmaceutically acceptable salt, prodrug or stereoisomer thereof, wherein:

one of $G^1$ or $G^2$ is, at each occurrence, —O(C=O)—, —(C=O)O—, —C(=O)—, —O—, —S(O)$_y$—, —S—S—, —C(=O)S—, SC(=O)—, —N($R^a$)C(=O)—, —C(=O)N($R^a$)—, —N($R^a$)C(=O)N($R^a$)—, —OC(=O)N($R^a$)— or —N($R^a$)C(=O)O—, and the other of $G^1$ or $G^2$ is, at each occurrence, —O(C=O)—, —(C=O)O—, —C(=O)—, —O—, —S(O)$_y$—, —S—S—, —C(=O)S—, —SC(=O)—, —N($R^a$)C(=O)—, —C(=O)N($R^a$)—, —N($R^a$)C(=O)N($R^a$)—, —OC(=O)N($R^a$)— or —N($R^a$)C(=O)O— or a direct bond;

L is, at each occurrence, —O(C=O)—, wherein - represents a covalent bond to X;

X is $CR^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

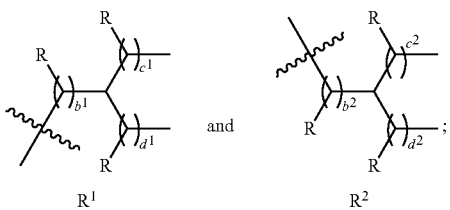

$a^1$ and $a^2$ are, at each occurrence, independently an integer from 3 to 12;

$b^1$ and $b^2$ are, at each occurrence, independently 0 or 1;

$c^1$ and $c^2$ are, at each occurrence, independently an integer from 5 to 10;

$d^1$ and $d^2$ are, at each occurrence, independently an integer from 5 to 10;

y is, at each occurrence, independently an integer from 0 to 2; and n is an integer from 1 to 6, wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In some embodiments of Formula (IV), $G^1$ and $G^2$ are each independently —O(C═O)— or —(C═O)O—.

In other embodiments of Formula (IV), X is CH.

In different embodiments of Formula (IV), the sum of $a^1+b^1+c^1$ or the sum of $a^2+b^2+c^2$ is an integer from 12 to 26.

In still other embodiments of Formula (IV), $a^1$ and $a^2$ are independently an integer from 3 to 10. For example, in some embodiments $a^1$ and $a^2$ are independently an integer from 4 to 9.

In various embodiments of Formula (IV), $b^1$ and $b^2$ are 0. In different embodiments, $b^1$ and $b^2$ are 1.

In more embodiments of Formula (IV), $c^1$, $c^2$, $d^1$ and $d^2$ are independently an integer from 6 to 8.

In other embodiments of Formula (IV), $c^1$ and $c^2$ are, at each occurrence, independently an integer from 6 to 10, and $d^1$ and $d^2$ are, at each occurrence, independently an integer from 6 to 10.

In other embodiments of Formula (IV), $c^1$ and $c^2$ are, at each occurrence, independently an integer from 5 to 9, and $d^1$ and $d^2$ are, at each occurrence, independently an integer from 5 to 9.

In more embodiments of Formula (IV), Z is alkyl, cycloalkyl or a monovalent moiety comprising at least one polar functional group when n is 1. In other embodiments, Z is alkyl.

In various embodiments of the foregoing Formula (IV), R is, at each occurrence, independently either: (a) H or methyl; or (b) R together with the carbon atom to which it is bound is taken together with an adjacent R and the carbon atom to which it is bound to form a carbon-carbon double bond. In certain embodiments, each R is H. In other embodiments at least one R together with the carbon atom to which it is bound is taken together with an adjacent R and the carbon atom to which it is bound to form a carbon-carbon double bond.

In other embodiments of the compound of Formula (IV), $R^1$ and $R^2$ independently have one of the following structures:

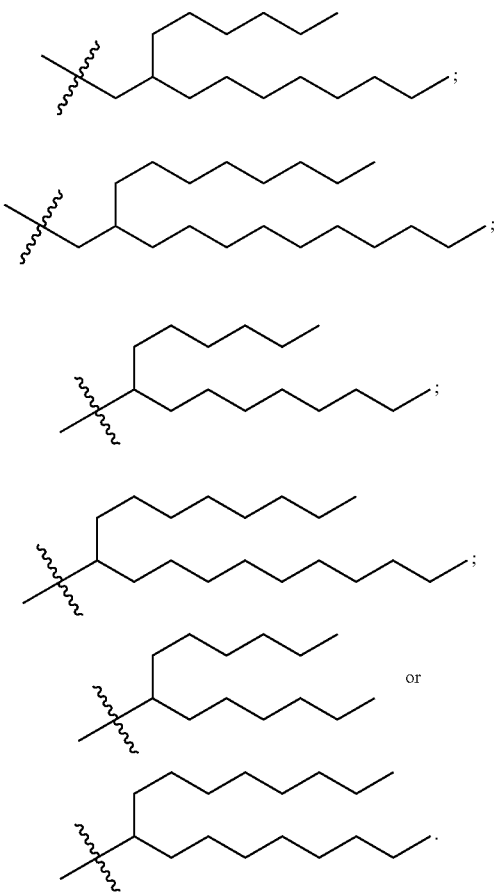

In certain embodiments of Formula (IV), the compound has one of the following structures:

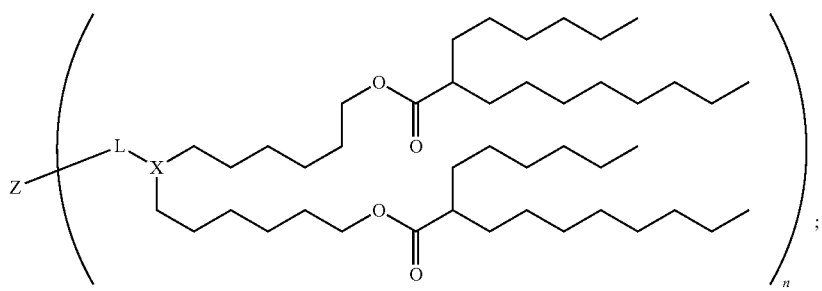

-continued
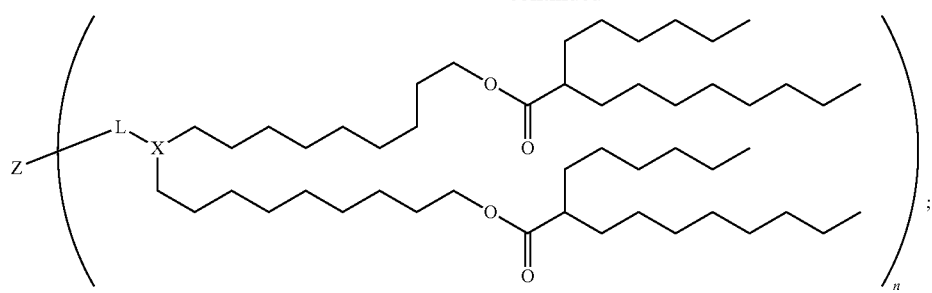
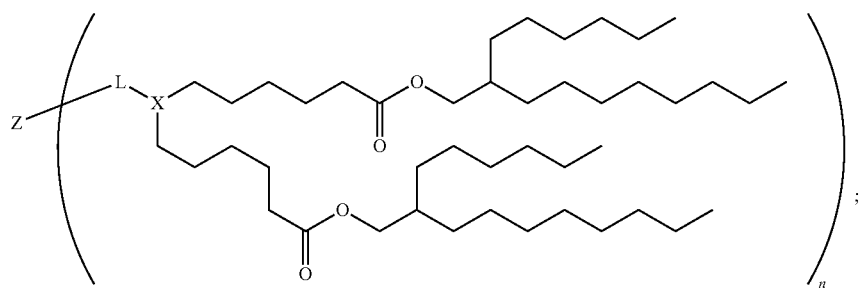
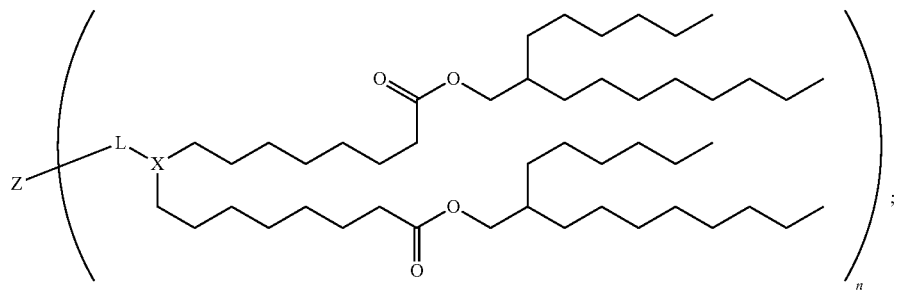
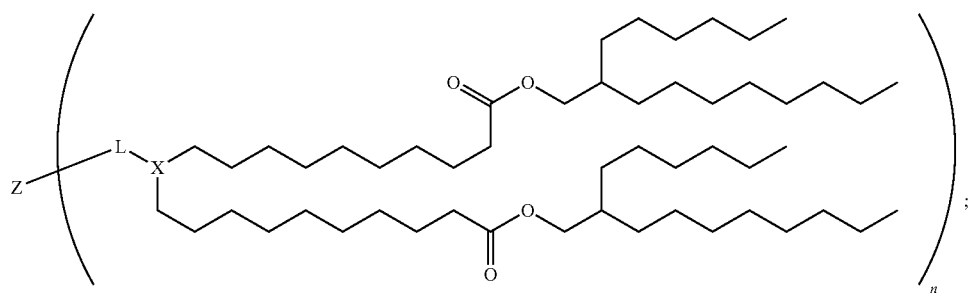
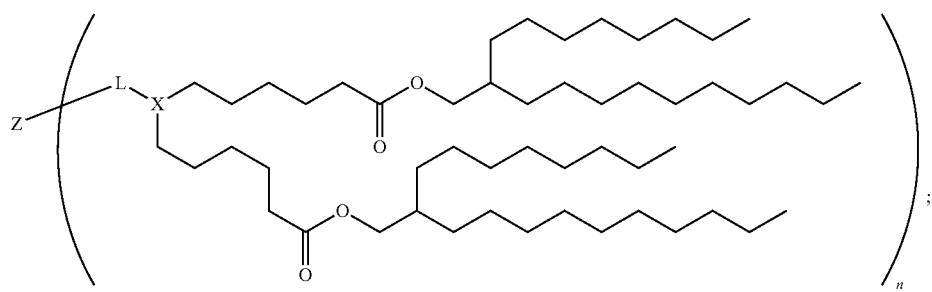

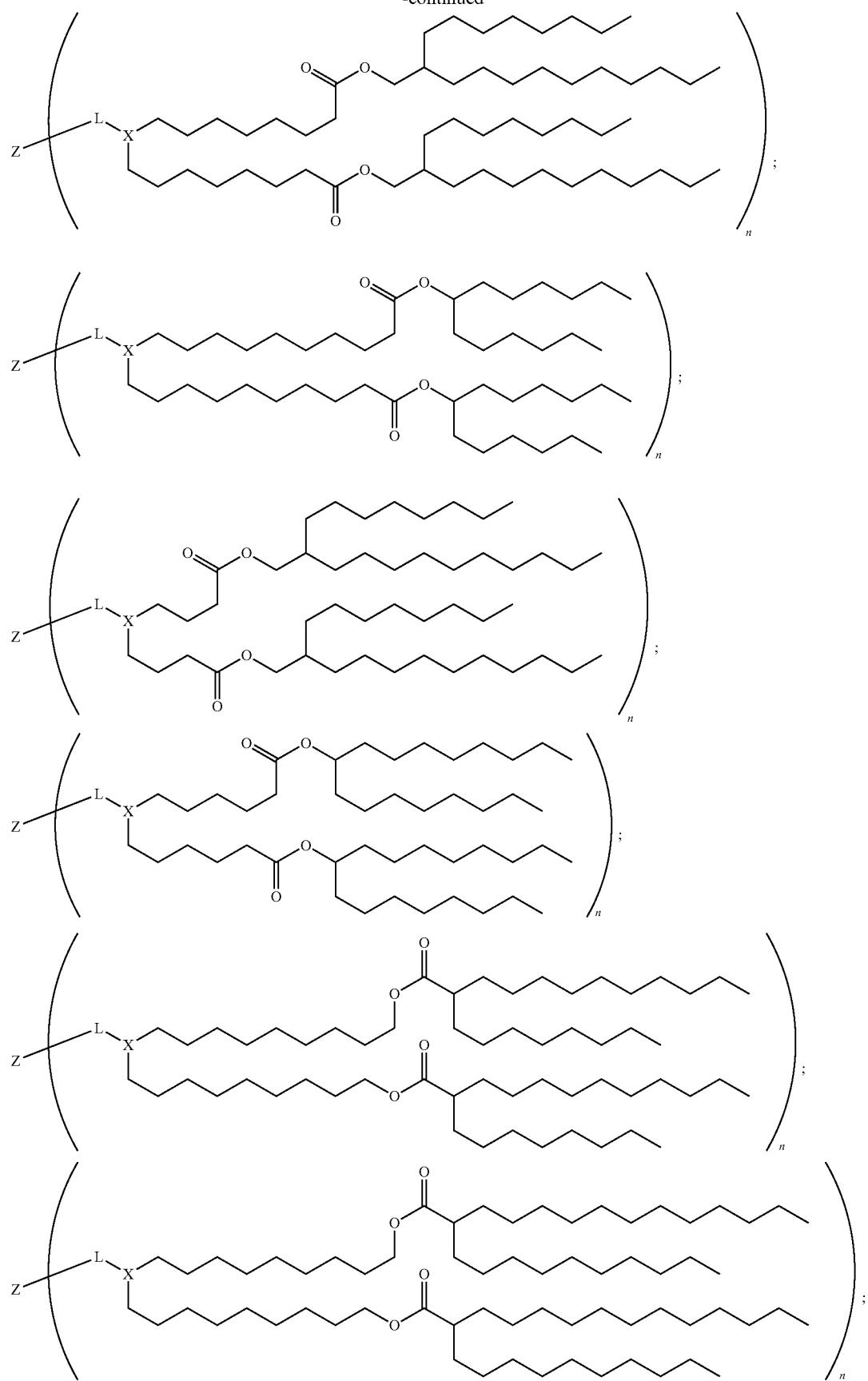

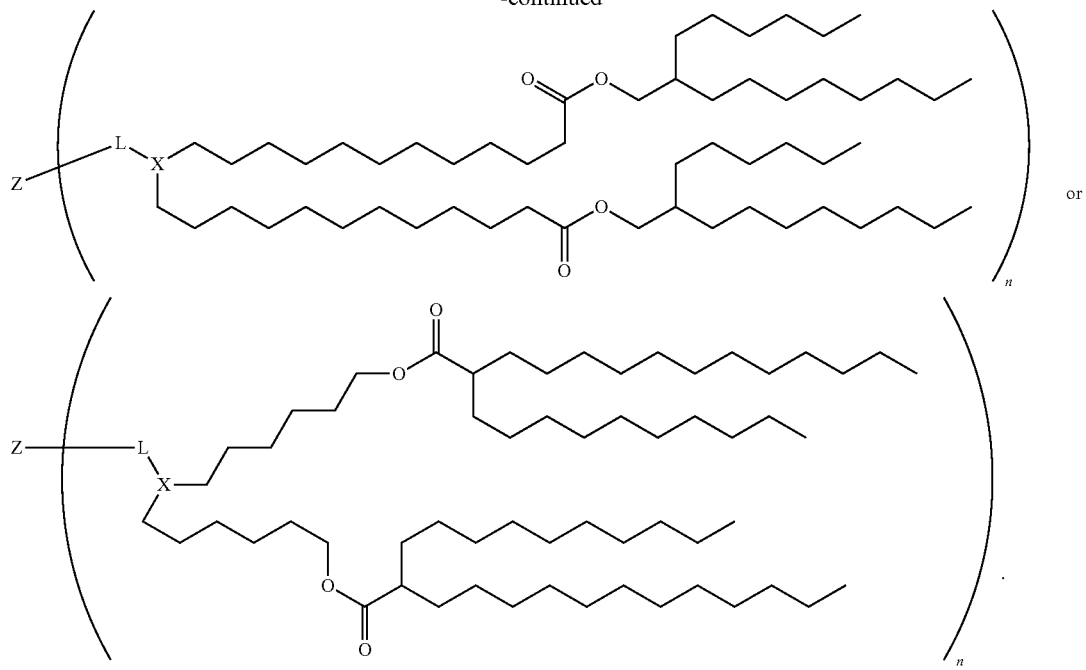

In still different embodiments a cationic lipid of Embodiments 1, 2 or 3 (e.g., the cationic lipid, the first cationic lipid, the second cationic lipid) has the structure of Formula (V):

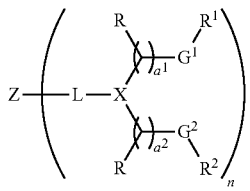

(V)

or a pharmaceutically acceptable salt, prodrug or stereoisomer thereof, wherein:

one of $G^1$ or $G^2$ is, at each occurrence, —O(C=O)—, —(C=O)O—, —C(=O)—, —O—, —S(O)$_y$—, —S—S—, —C(=O)S—, SC(=O)—, —N(R$^a$)C(=O)—, —C(=O)N(R$^a$)—, —N(R$^a$)C(=O)N(R$^a$)—, —OC(=O)N(R$^a$)— or —N(R$^a$)C(=O)O—, and the other of $G^1$ or $G^2$ is, at each occurrence, —O(C=O)—, —(C=O)O—, —C(=O)—, —O—, —S(O)$_y$—, —S—S—, —C(=O)S—, —SC(=O)—, —N(R$^a$)C(=O)—, —C(=O)N(R$^a$)—, —N(R$^a$)C(=O)N(R$^a$)—, —OC(=O)N(R$^a$)— or —N(R$^a$)C(=O)O— or a direct bond;

L is, at each occurrence, ~O(C=O)—, wherein ~ represents a covalent bond to X;

X is $CR^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

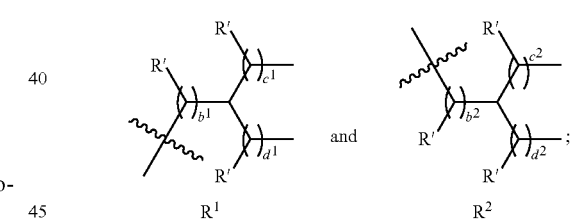

R' is, at each occurrence, independently H or $C_1$-$C_{12}$ alkyl;

$a^1$ and $a^2$ are, at each occurrence, independently an integer from 3 to 12;

$b^1$ and $b^2$ are, at each occurrence, independently 0 or 1;

$c^1$ and $c^2$ are, at each occurrence, independently an integer from 2 to 12;

$d^1$ and $d^2$ are, at each occurrence, independently an integer from 2 to 12;

y is, at each occurrence, independently an integer from 0 to 2; and n is an integer from 1 to 6, wherein $a^1$, $a^2$, $c^1$, $c^2$, $d^1$ and $d^2$ are selected such that the sum of $a^1+c^1+d^1$ is an integer from 18 to 30, and the sum of $a^2+c^2+d^2$ is an integer from 18 to 30, and wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In certain embodiments of Formula (V), $G^1$ and $G^2$ are each independently —O(C=O)— or —(C=O)O—.

In other embodiments of Formula (V), X is CH.

In some embodiments of Formula (V), the sum of $a^1+c^1+d^1$ is an integer from 20 to 30, and the sum of $a^2+c^2+d^2$ is an integer from 18 to 30. In other embodiments, the sum of $a^1+c^1+d^1$ is an integer from 20 to 30, and the sum of $a^2+c^2+d^2$ is an integer from 20 to 30. In more embodiments of Formula (V), the sum of $a^1+b^1+c^1$ or the sum of $a^2+b^2+c^2$ is an integer from 12 to 26. In other embodiments, $a^1$, $a^2$, $c^1$, $c^2$, $d^1$ and $d^2$ are selected such that the sum of $a^1+c^1+d^1$ is an integer from 18 to 28, and the sum of $a^2+c^2+d^2$ is an integer from 18 to 28, In still other embodiments of Formula (V), $a^1$ and $a^2$ are independently an integer from 3 to 10, for example an integer from 4 to 9.

In yet other embodiments of Formula (V), $b^1$ and $b^2$ are 0. In different embodiments $b^1$ and $b^2$ are 1.

In certain other embodiments of Formula (V), $c^1$, $c^2$, $d^1$ and $d^2$ are independently an integer from 6 to 8.

In different other embodiments of Formula (V), Z is alkyl or a monovalent moiety comprising at least one polar functional group when n is 1; or Z is alkylene or a polyvalent moiety comprising at least one polar functional group when n is greater than 1.

In more embodiments of Formula (V), Z is alkyl, cycloalkyl or a monovalent moiety comprising at least one polar functional group when n is 1. In other embodiments, Z is alkyl.

In other different embodiments of Formula (V), R is, at each occurrence, independently either: (a) H or methyl; or (b) R together with the carbon atom to which it is bound is taken together with an adjacent R and the carbon atom to which it is bound to form a carbon-carbon double bond. For example in some embodiments each R is H. In other embodiments at least one R together with the carbon atom to which it is bound is taken together with an adjacent R and the carbon atom to which it is bound to form a carbon-carbon double bond.

In more embodiments, each R' is H.

In certain embodiments of Formula (V), the sum of $a^1+c^1+d^1$ is an integer from 20 to 25, and the sum of $a^2+c^2+d^2$ is an integer from 20 to 25.

In other embodiments of Formula (V), $R^1$ and $R^2$ independently have one of the following structures:

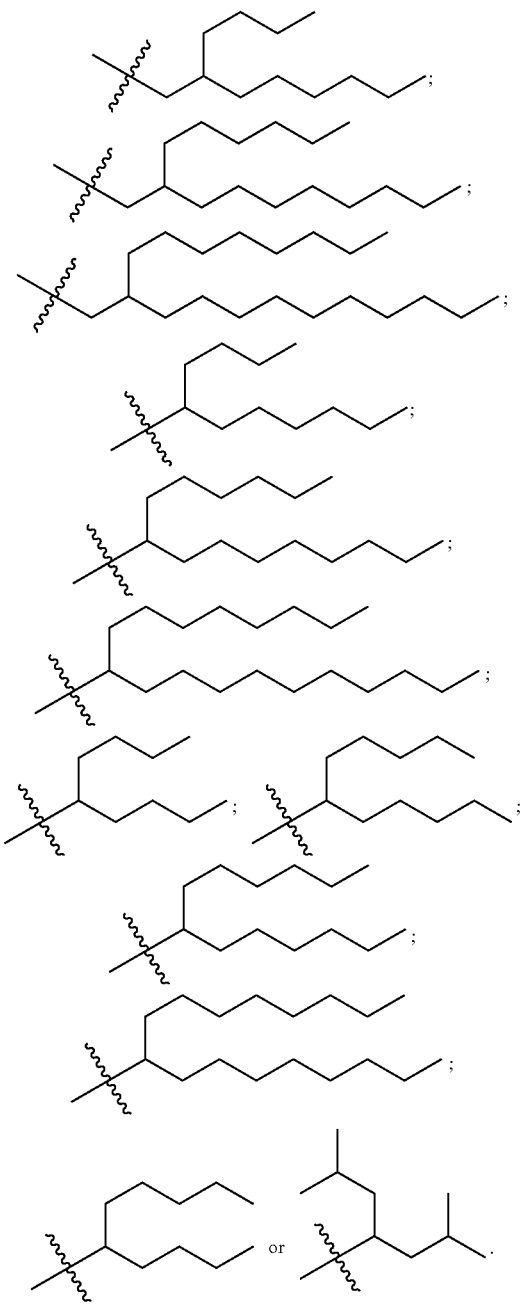

In more embodiments of Formula (V), the compound has one of the following structures:

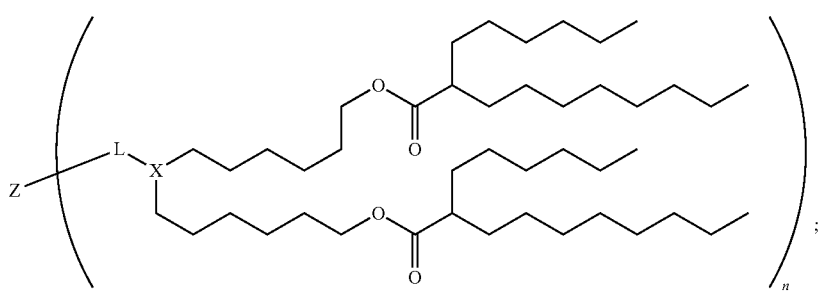

-continued
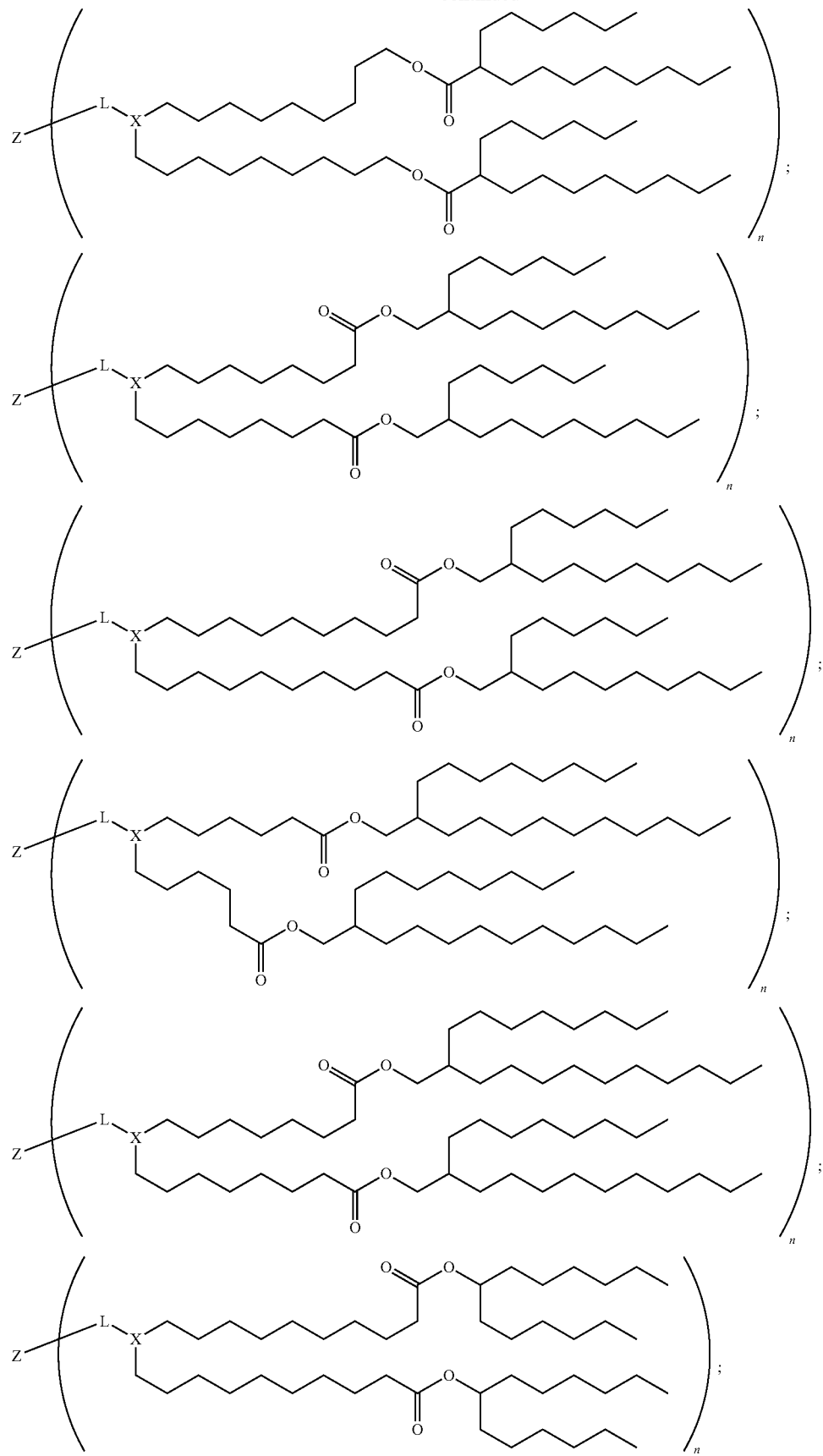

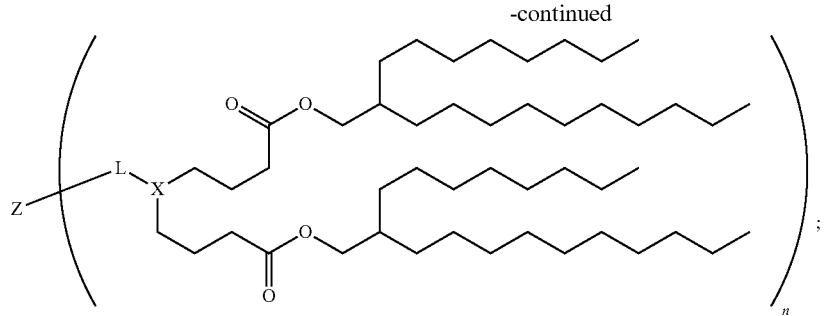;
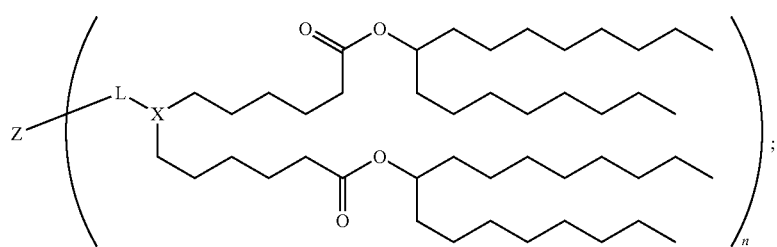;
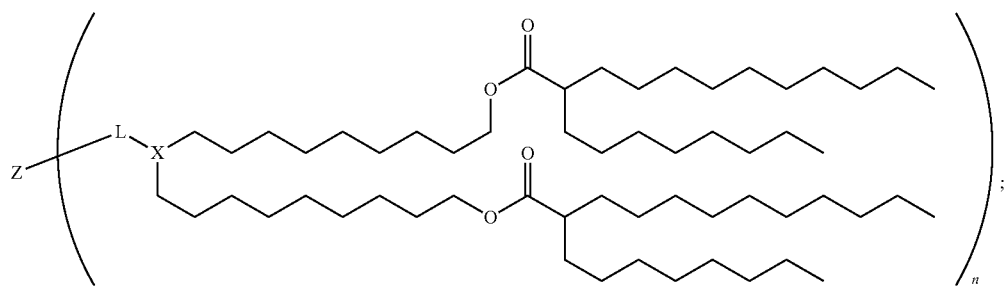;
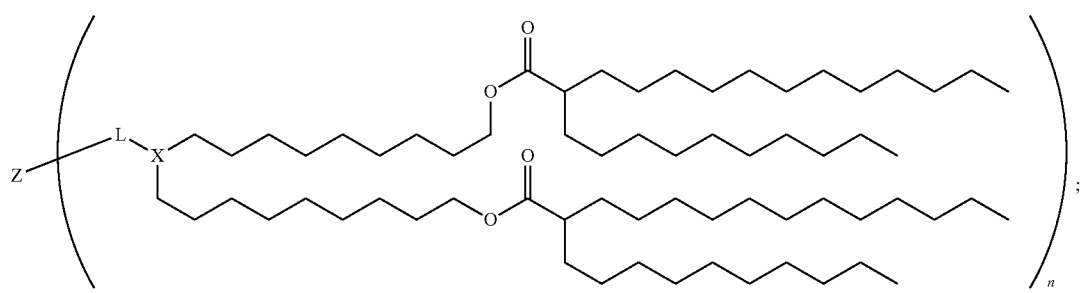;
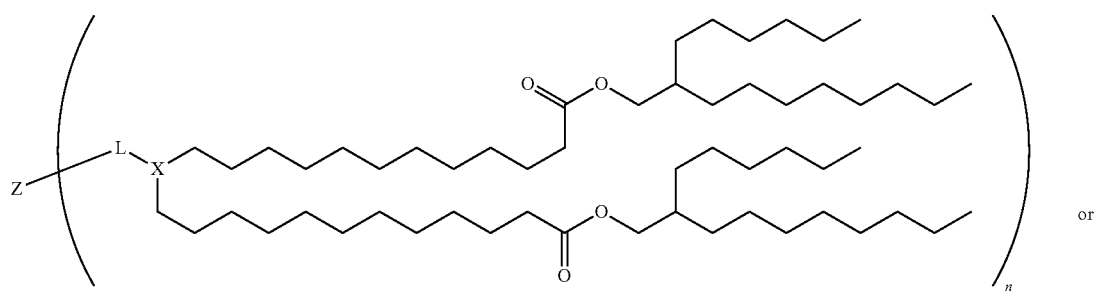 or

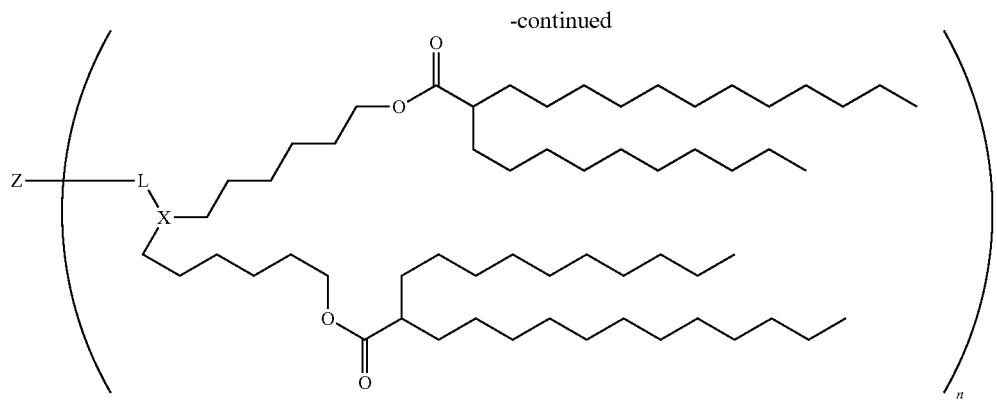

In any of the foregoing embodiments of Formula (IV) or (V), n is 1. In other of the foregoing embodiments of Formula (IV) or (V), n is greater than 1.

In more of any of the foregoing embodiments of Formula (IV) or (V), Z is a mono- or polyvalent moiety comprising at least one polar functional group. In some embodiments, Z is a monovalent moiety comprising at least one polar functional group. In other embodiments, Z is a polyvalent moiety comprising at least one polar functional group.

In more of any of the foregoing embodiments of Formula (IV) or (V), the polar functional group is a hydroxyl, alkoxy, ester, cyano, amide, amino, alkylaminyl, heterocyclyl or heteroaryl functional group.

In any of the foregoing embodiments of Formula (IV) or (V), Z is hydroxyl, hydroxylalkyl, alkoxyalkyl, amino, aminoalkyl, alkylaminyl, alkylaminylalkyl, heterocyclyl or heterocyclylalkyl.

In some other embodiments of Formula (IV) or (V), Z has the following structure:

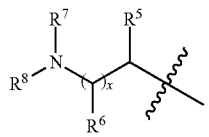

wherein:
$R^5$ and $R^6$ are independently H or $C_1$-$C_6$ alkyl;
$R^7$ and $R^8$ are independently H or $C_1$-$C_6$ alkyl or $R^7$ and $R^8$, together with the nitrogen atom to which they are attached, join to form a 3-7 membered heterocyclic ring; and
x is an integer from 0 to 6.

In still different embodiments of Formula (IV) or (V), Z has the following structure:

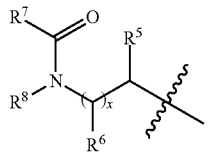

wherein:
$R^5$ and $R^6$ are independently H or $C_1$-$C_6$ alkyl;
$R^7$ and $R^8$ are independently H or $C_1$-$C_6$ alkyl or $R^7$ and $R^8$, together with the nitrogen atom to which they are attached, join to form a 3-7 membered heterocyclic ring; and
x is an integer from 0 to 6.

In still different embodiments of formula (IV) or (V), Z has the following structure:

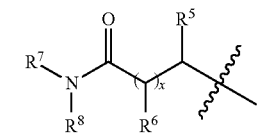

wherein:
$R^5$ and $R^6$ are independently H or $C_1$-$C_6$ alkyl;
$R^7$ and $R^8$ are independently H or $C_1$-$C_6$ alkyl or $R^7$ and $R^8$, together with the nitrogen atom to which they are attached, join to form a 3-7 membered heterocyclic ring; and
x is an integer from 0 to 6.

In some other embodiments of Formula (IV) or (V), Z is hydroxylalkyl, cyanoalkyl or an alkyl substituted with one or more ester or amide groups.

For example, in any of the foregoing embodiments of Formula (IV) or (V), Z has one of the following structures:

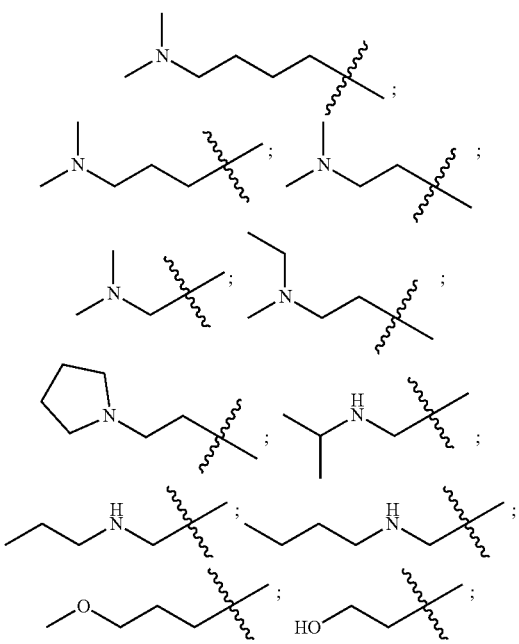

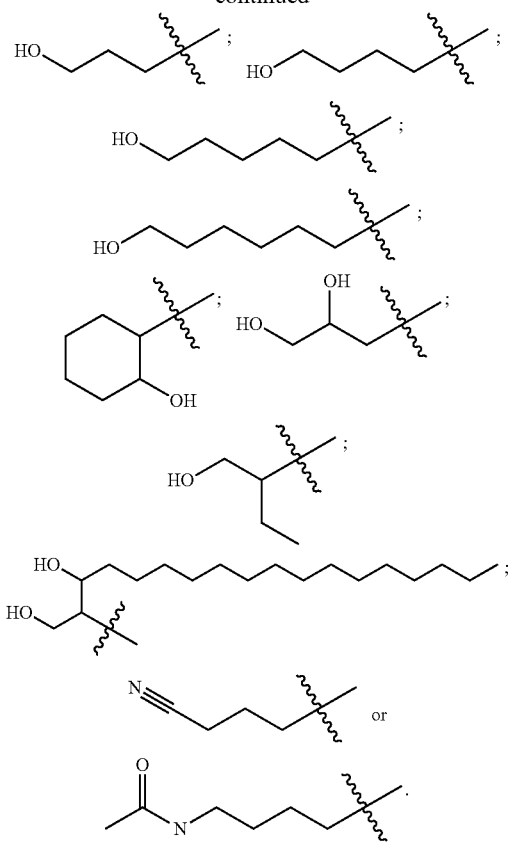
In other embodiments of Formula (IV) or (V), Z-L has one of the following structures:
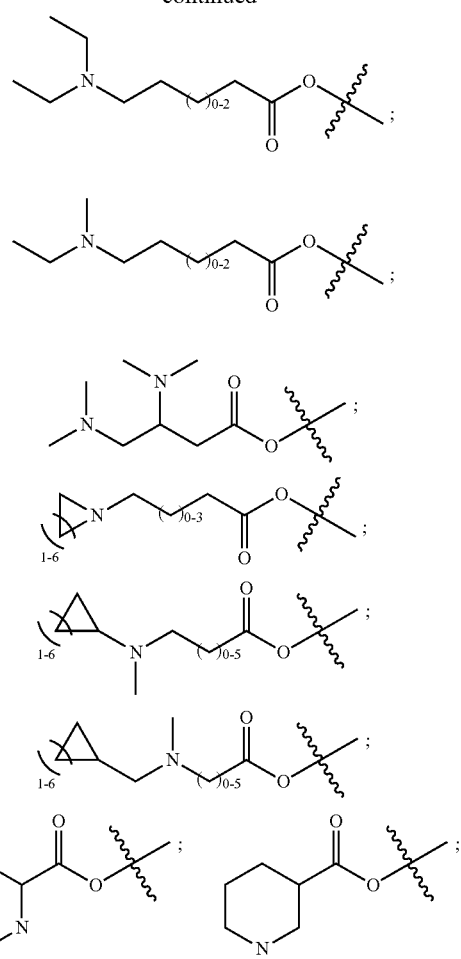
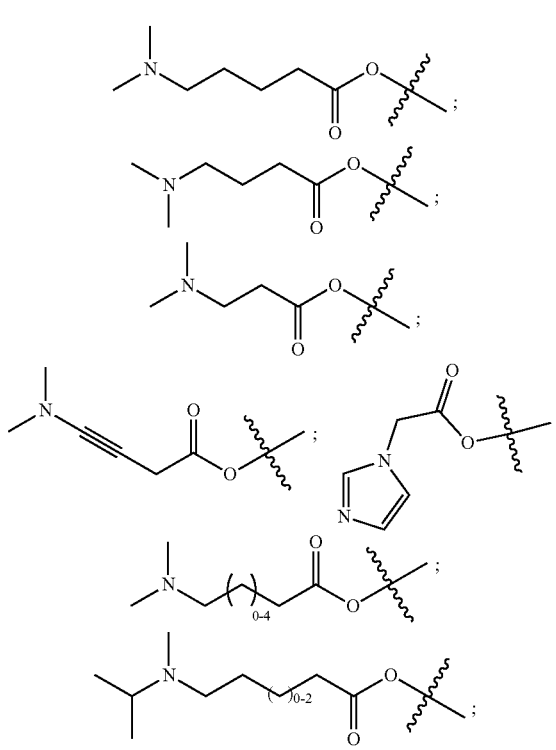

-continued
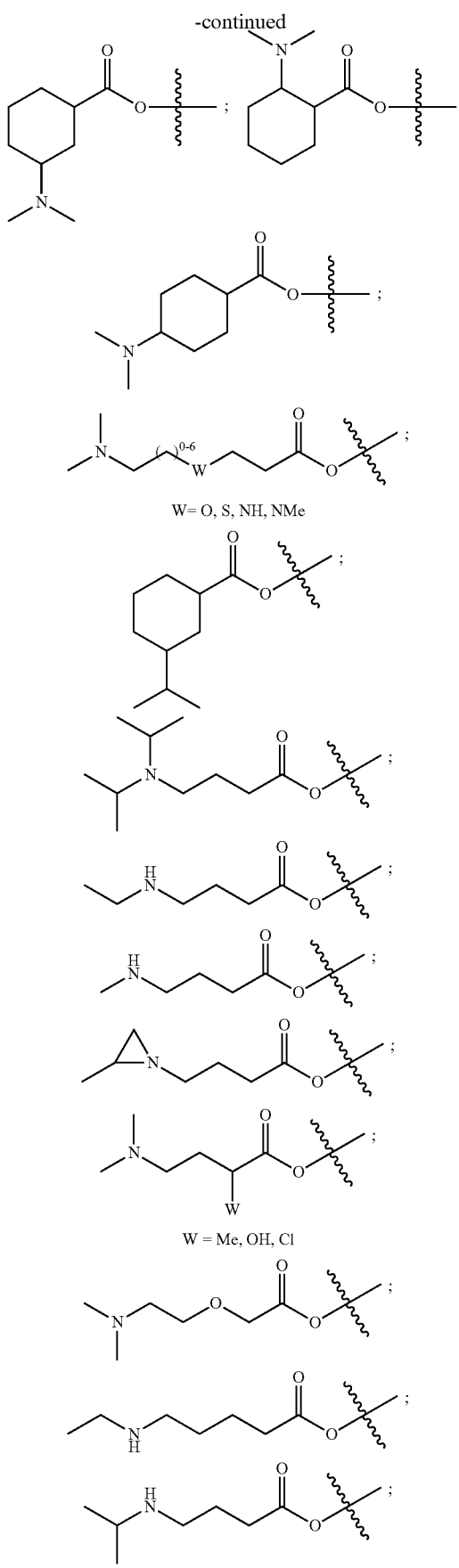
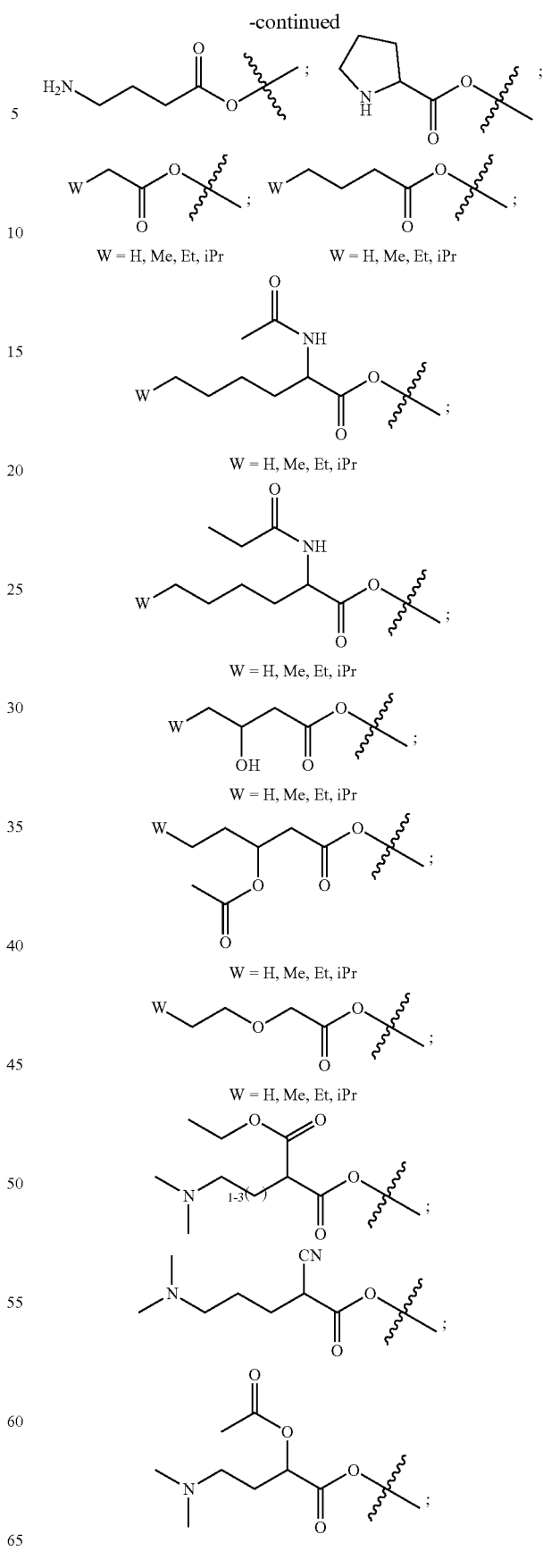

| 121 | 122 |
|---|---|

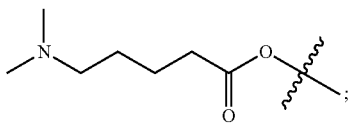

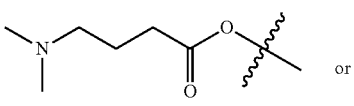

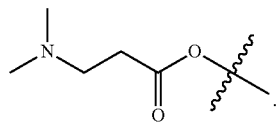

In still other embodiments, X is CH and Z-L has one of the following structures:

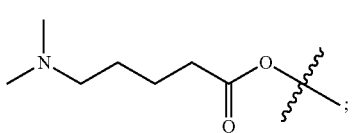

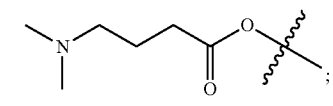

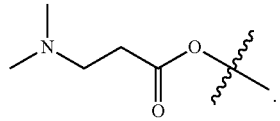

In some specific embodiments of Embodiment 3, the first and second cationic lipids are each, independently selected from a lipid of Formula IV. In some embodiments of Embodiment 3, the first and second cationic lipids are each, independently selected from a lipid of Formula V.

In various different embodiments, a cationic lipid of any one of the disclosed embodiments (e.g., the cationic lipid, the first cationic lipid, the second cationic lipid) has one of the structures set forth in Table 4 below.

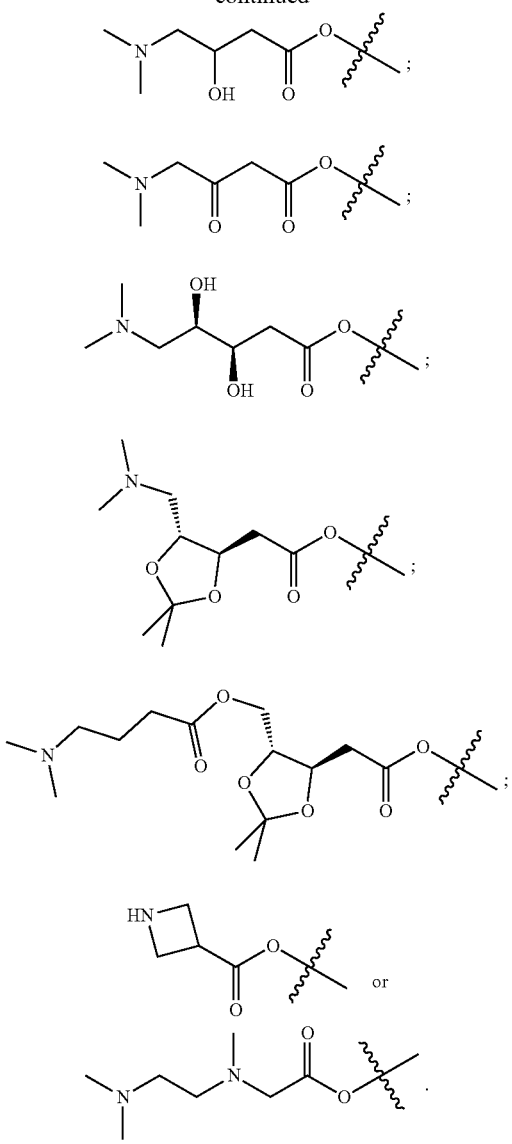

In other embodiments, Z-L has one of the following structures:

TABLE 4

Representative Compounds of Formula (IV) or (V)

| No. | Structure |
|---|---|
| IV-1 | 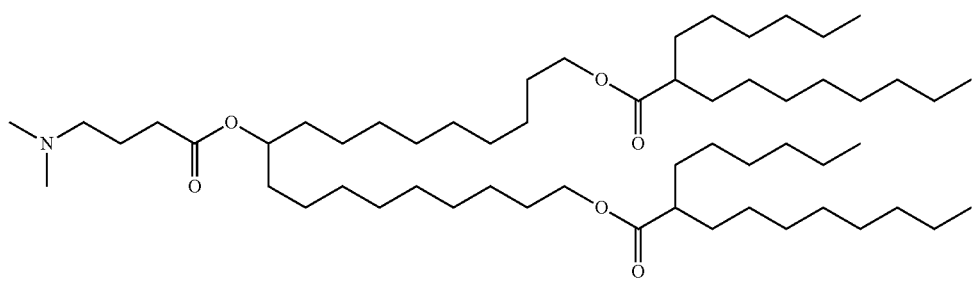 [SMILES: CCCCCCCCC(CCCCCC)C(=O)OCCCCCCCCCC(CCCCCCCCCOC(=O)C(CCCCCC)CCCCCCCC)OC(=O)CCCN(C)C] |

TABLE 4-continued

Representative Compounds of Formula (IV) or (V)

| No. | Structure |
|---|---|
| IV-2 | 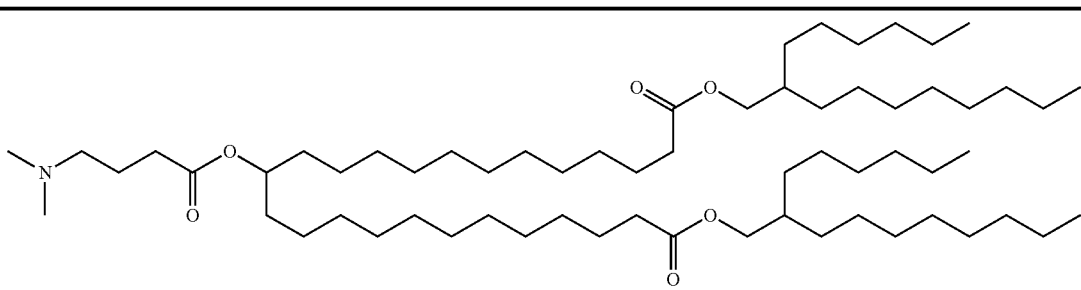 |
| IV-3 | 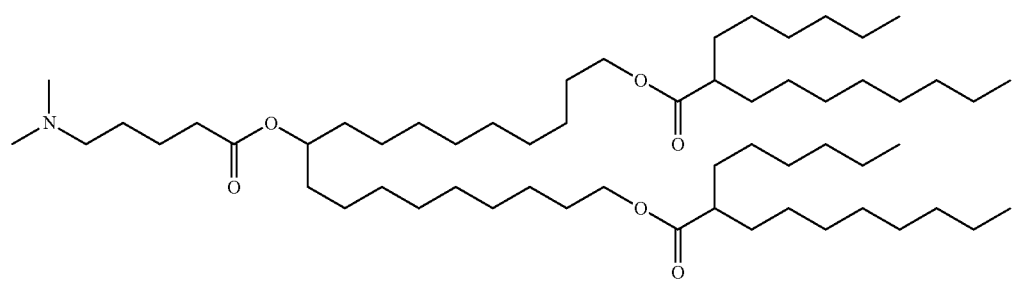 [SMILES: CCCCCCCCC(CCCCCC)C(=O)OCCCCCCCCCC(CCCCCCCCCOC(=O)C(CCCCCC)CCCCCCCC)OC(=O)CCCCN(C)C] |

In certain embodiments, the neutral lipid is present in any of the foregoing LNPs in a concentration ranging from 5 to 10 mol percent, from 5 to 15 mol percent, 7 to 13 mol percent, or 9 to 11 mol percent. In certain specific embodiments, the neutral lipid is present in a concentration of about 9.5, 10 or 10.5 mol percent. In some embodiments, the molar ratio of cationic lipid to the neutral lipid ranges from about 4.1:1.0 to about 4.9:1.0, from about 4.5:1.0 to about 4.8:1.0, or from about 4.7:1.0 to 4.8:1.0. In some embodiments, the molar ratio of total cationic lipid to the neutral lipid ranges from about 4.1:1.0 to about 4.9:1.0, from about 4.5:1.0 to about 4.8:1.0, or from about 4.7:1.0 to 4.8:1.0.

In some embodiments, a cationic lipid of Embodiments 1, 2 or 3 (e.g., the cationic lipid, the first cationic lipid, the second cationic lipid) has one of the following structures:

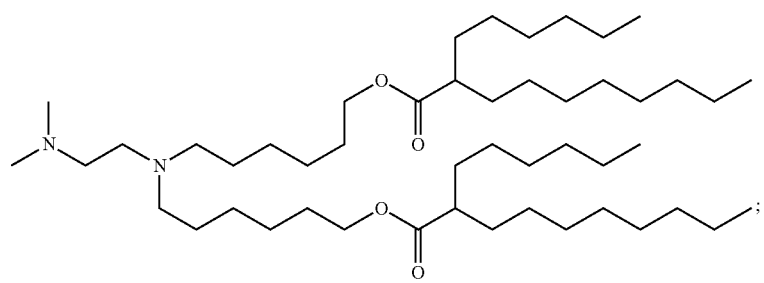

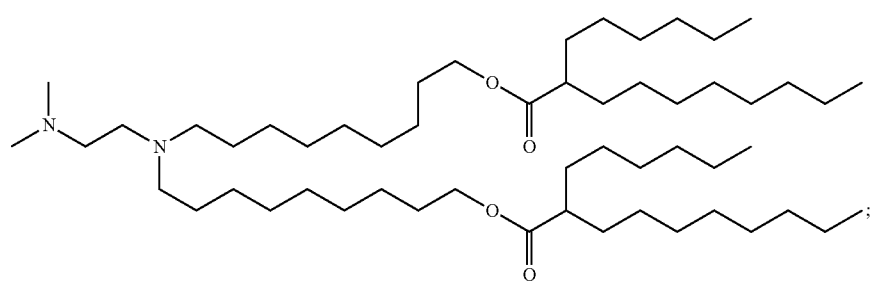

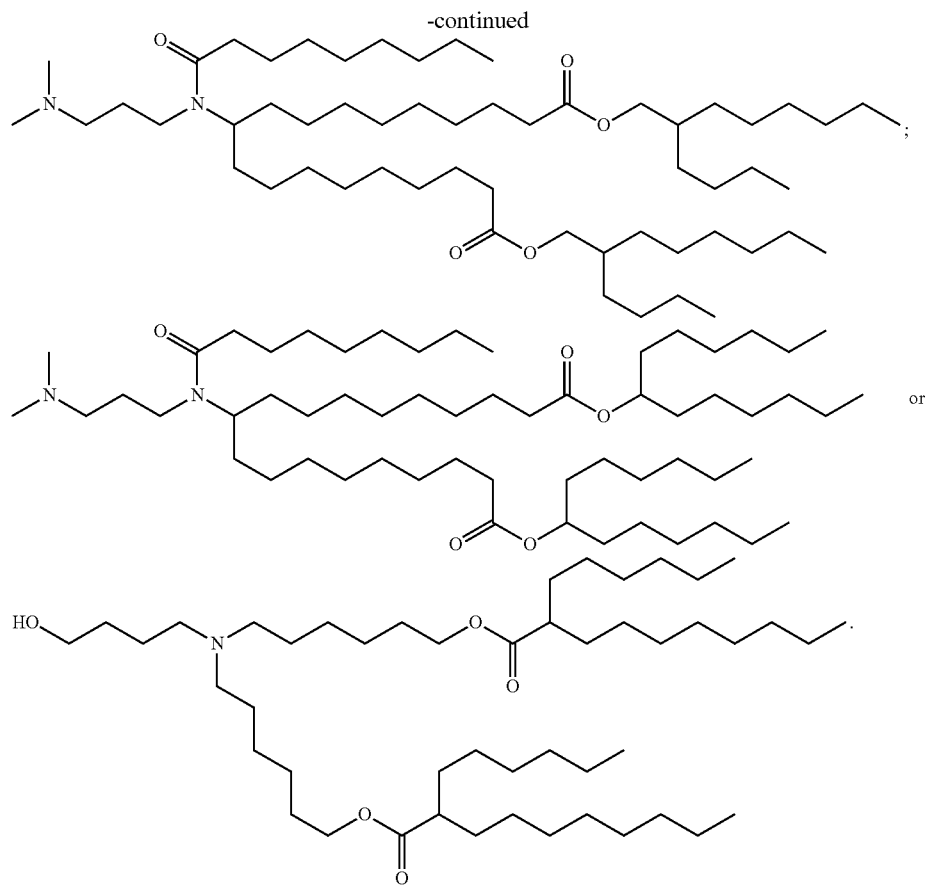

In some embodiments of Embodiments 1, 2 or 3, the cationic lipid has the following structure:

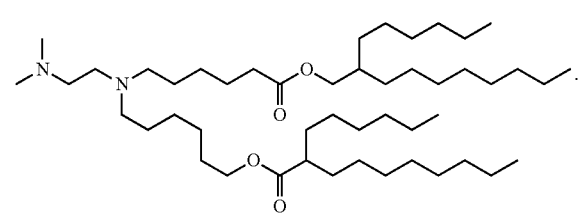 [SMILES: CCCCCCCCC(CCCCCC)COC(=O)CCCCCN(CCCCCCOC(=O)C(CCCCCC)CCCCCCCC)CCN(C)C]

In other embodiments of Embodiment 3, the first and second cationic lipids have the following structures, respectively:

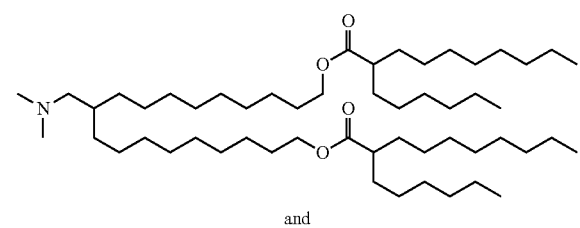

and

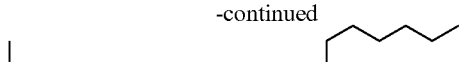

Exemplary neutral lipids for use in any of Embodiments 1, 2 or 3 include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE), and 1,2-dielaidoyl-sn-glycero-3-phosphoethanolamine (transDOPE). In one embodiment, the neutral lipid is 1,2-distearoyl-sn-glycero-3phosphocholine (DSPC). In some embodiments, the neutral lipid is selected from DSPC, DPPC, DMPC, DOPC, POPC, DOPE and SM. In some embodiments, the neutral lipid is DSPC.

In various embodiments, any of the disclosed lipid nanoparticles comprise a steroid or steroid analogue. In certain embodiments, the steroid or steroid analogue is cholesterol. In some embodiments, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In certain specific embodiments, the steroid is present in a concentration of 40, 41, 42, 43, 44, 45, or 46 molar percent.

In certain embodiments, the molar ratio of cationic lipid to the steroid ranges from 1.0:0.9 to 1.0:1.2, or from 1.0:1.0 to 1.0:1.2. In some of these embodiments, the molar ratio of cationic lipid to cholesterol ranges from about 5:1 to 1:1. In certain embodiments, the steroid is present in a concentration ranging from 32 to 40 mol percent of the steroid.

In certain embodiments, the molar ratio of total cationic lipid (i.e., the sum of the first and second cationic lipid) to the steroid ranges from 1.0:0.9 to 1.0:1.2, or from 1.0:1.0 to 1.0:1.2. In some of these embodiments, the molar ratio of total cationic lipid to cholesterol ranges from about 5:1 to 1:1. In certain embodiments, the steroid is present in a concentration ranging from 32 to 40 mol percent of the steroid.

In various other embodiments of Embodiments 1, 2 or 3, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate.

In various embodiments, the polymer conjugated lipid is present in a concentration ranging from 1.0 to 2.5 molar percent. In certain specific embodiments, the polymer conjugated lipid is present in a concentration of about 1.7 molar percent. In some embodiments, the polymer conjugated lipid is present in a concentration of about 1.5 molar percent.

In certain embodiments, the molar ratio of cationic lipid to the polymer conjugated lipid ranges from about 35:1 to about 25:1. In some embodiments, the molar ratio of cationic lipid to polymer conjugated lipid ranges from about 100:1 to about 20:1.

In certain embodiments, the molar ratio of total cationic lipid (i.e., the sum of the first and second cationic lipid) to the polymer conjugated lipid ranges from about 35:1 to about 25:1. In some embodiments, the molar ratio of total cationic lipid to polymer conjugated lipid ranges from about 100:1 to about 20:1.

In some embodiments of Embodiments 1, 2 or 3, the pegylated lipid has the following Formula (VI):

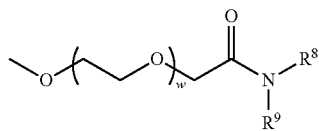

(VI)

or a pharmaceutically acceptable salt, tautomer or stereoisomer thereof, wherein:

$R^{12}$ and $R^{13}$ are each independently a straight or branched, saturated or unsaturated alkyl chain containing from 10 to 30 carbon atoms, wherein the alkyl chain is optionally interrupted by one or more ester bonds; and w has a mean value ranging from 30 to 60.

In some embodiments, $R^{12}$ and $R^{13}$ are each independently straight, saturated alkyl chains containing from 12 to 16 carbon atoms. In other embodiments, the average w ranges from 42 to 55, for example, the average w is 42, 43, 44, 45, 46, 47, 48, 49, 50, 51, 52, 53, 54 or 55. In some specific embodiments, the average w is about 49.

In some embodiments, the pegylated lipid has the following Formula (VIa):

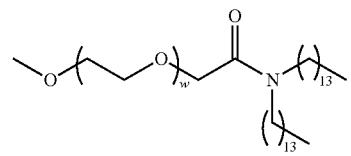

(VIa)

wherein the average w is about 49.

In some embodiments of Embodiments 1, 2 or 3, the therapeutic agent comprises a nucleic acid. For example, in some embodiments, the nucleic acid is selected from antisense and messenger RNA. For example, messenger RNA may be used to induce an immune response (e.g., as a vaccine), for example by translation of immunogenic proteins.

In some embodiments, a plurality of the lipid nanoparticles has a polydispersity of less than 0.12, or less than 0.08. In some embodiments, the lipid nanoparticle has a mean diameter ranging from 50 nm to 100 nm, or from 60 nm to 85 nm.

In other different embodiments, the invention is directed to a method for administering a therapeutic agent to a patient in need thereof, the method comprising preparing or providing any of the foregoing LNPs and/or administering a composition comprising the same to the patient. In some embodiments, the therapeutic agent is effective to treat the disease.

For the purposes of administration, the lipid nanoparticles of embodiments of the present invention may be administered alone or may be formulated as pharmaceutical compositions. Pharmaceutical compositions of certain embodiments comprise a lipid nanoparticle according to any of the foregoing embodiments and one or more pharmaceutically acceptable carrier, diluent or excipient. The lipid nanoparticle may be present in an amount which is effective to deliver the therapeutic agent, e.g., for treating a particular disease or condition of interest. Appropriate concentrations and dosages can be readily determined by one skilled in the art.

Administration of the lipid nanoparticles of some embodiments can be carried out via any of the accepted modes of administration of agents for serving similar utilities. The pharmaceutical compositions of some embodiments may be formulated into preparations in solid, semi-solid, liquid or gaseous forms, such as tablets, capsules, powders, granules, ointments, solutions, suspensions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intradermal, intrasternal injection or infusion techniques. Pharmaceutical compositions of some embodiments are formulated so as to allow the active ingredients contained therein to be bioavailable upon administration of the composition to a patient. Compositions that may be administered to a subject or patient may take the form of one or more dosage units, where for example, a tablet may be a single dosage unit, and a container comprising LNPs in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will typically contain a therapeutically effective amount of a lipid nanoparticle of any of the embodiments disclosed herein, comprising a therapeutic agent, or a pharmaceutically acceptable salt thereof, for treatment of a disease or condition of interest.

A pharmaceutical composition of some embodiments may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of some embodiments, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose; agents to act as cryoprotectants such as sucrose or trehalose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of certain embodiments intended for either parenteral or oral administration should contain an amount of a lipid nanoparticle of the invention such that a suitable dosage will be obtained.

The pharmaceutical composition of embodiments of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of some embodiments may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of other embodiments may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of embodiments in solid or liquid form may include an agent that binds to the LNP or therapeutic agent, and thereby assists in the delivery of the LNP or therapeutic agent. Suitable agents that may act in this capacity include a monoclonal or polyclonal antibody, or a protein.

In other embodiments, the pharmaceutical composition may comprise or consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

In some embodiments, the pharmaceutical compositions may be prepared by methodology well known in the pharmaceutical art. For example, a pharmaceutical composition intended to be administered by injection can be prepared by combining the lipid nanoparticles of the invention with sterile, distilled water or other carrier so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The pharmaceutical compositions of some embodiments are administered in a therapeutically effective amount, which will vary depending upon a variety of factors including the activity of the specific therapeutic agent employed; the metabolic stability and length of action of the therapeutic agent; the age, body weight, general health, sex, and diet of the patient; the mode and time of administration; the rate of excretion; the drug combination; the severity of the particular disorder or condition; and the subject undergoing therapy.

The pharmaceutical compositions of various embodiments may also be administered simultaneously with, prior to, or after administration of one or more other therapeutic agents. Such combination therapy includes administration of a single pharmaceutical dosage formulation of a composition of the invention and one or more additional active agents, as well as administration of the composition of the invention and each active agent in its own separate pharmaceutical dosage formulation. For example, a pharmaceutical composition of one embodiments and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation methods for the above lipids, lipid nanoparticles and compositions are described herein below and/or known in the art.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all lipids which exist in free base or acid form can be converted to their pharmaceutically acceptable salts by treatment with the appropriate inorganic or organic base or acid by methods known to one skilled in the art. Salts of the lipids can be converted to their free base or acid form by standard techniques.

The following Reaction Schemes illustrate methods to make lipids of Formula (I), (II), (III), (IV) or (V).

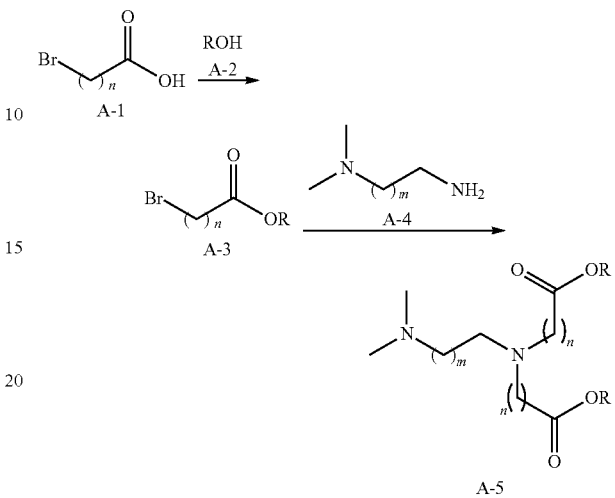

Embodiments of the lipid of Formula (I) (e.g., compound A-5) can be prepared according to General Reaction Scheme 1 ("Method A"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 1, compounds of structure A-1 can be purchased from commercial sources or prepared according to methods familiar to one of ordinary skill in the art. A mixture of A-1, A-2 and DMAP is treated with DCC to give the bromide A-3. A mixture of the bromide A-3, a base (e.g., N,N-diisopropylethylamine) and the N,N-dimethyldiamine A-4 is heated at a temperature and time sufficient to produce A-5 after any necessarily workup and or purification step.

GENERAL REACTION SCHEME 2

Other embodiments of the compound of Formula (I) (e.g., compound B-5) can be prepared according to General Reaction Scheme 2 ("Method B"), wherein R is a saturated or unsaturated $C_1$-$C_{24}$ alkyl or saturated or unsaturated cycloalkyl, m is 0 or 1 and n is an integer from 1 to 24. As shown in General Reaction Scheme 2, compounds of structure B-1 can be purchased from commercial sources or prepared according to methods familiar to one of ordinary skill in the art. A solution of B-1 (1 equivalent) is treated with acid chloride B-2 (1 equivalent) and a base (e.g., triethylamine). The crude product is treated with an oxidizing agent (e.g., pyridinium chlorochromate) and intermediate product B-3 is recovered. A solution of crude B-3, an acid (e.g., acetic acid), and N,N-dimethylaminoamine B-4 is then treated with a reducing agent (e.g., sodium triacetoxyborohydride) to obtain B-5 after any necessary work up and/or purification.

It should be noted that although starting materials A-1 and B-1 are depicted above as including only saturated methylene carbons, starting materials which include carbon-carbon double bonds may also be employed for preparation of compounds which include carbon-carbon double bonds.

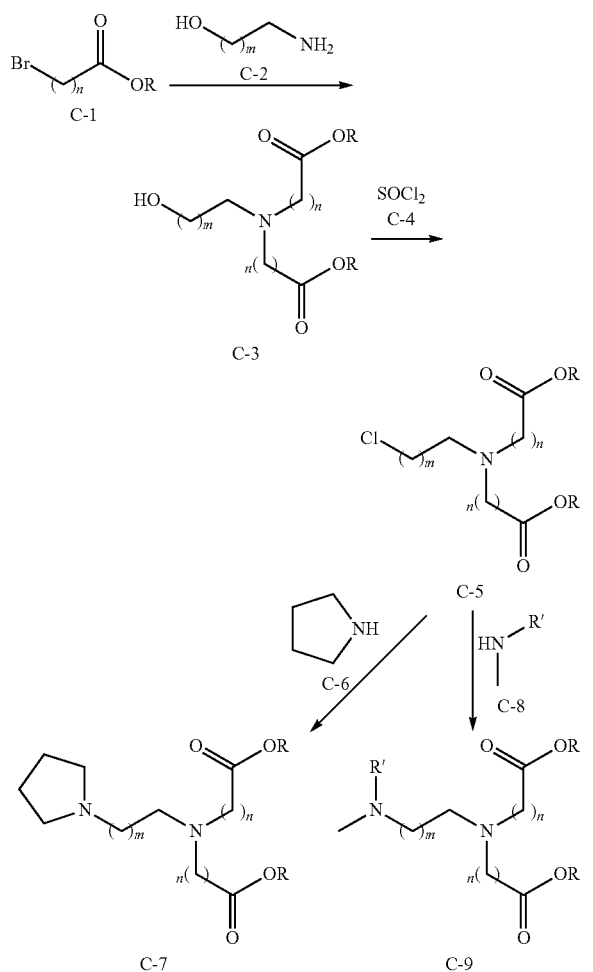

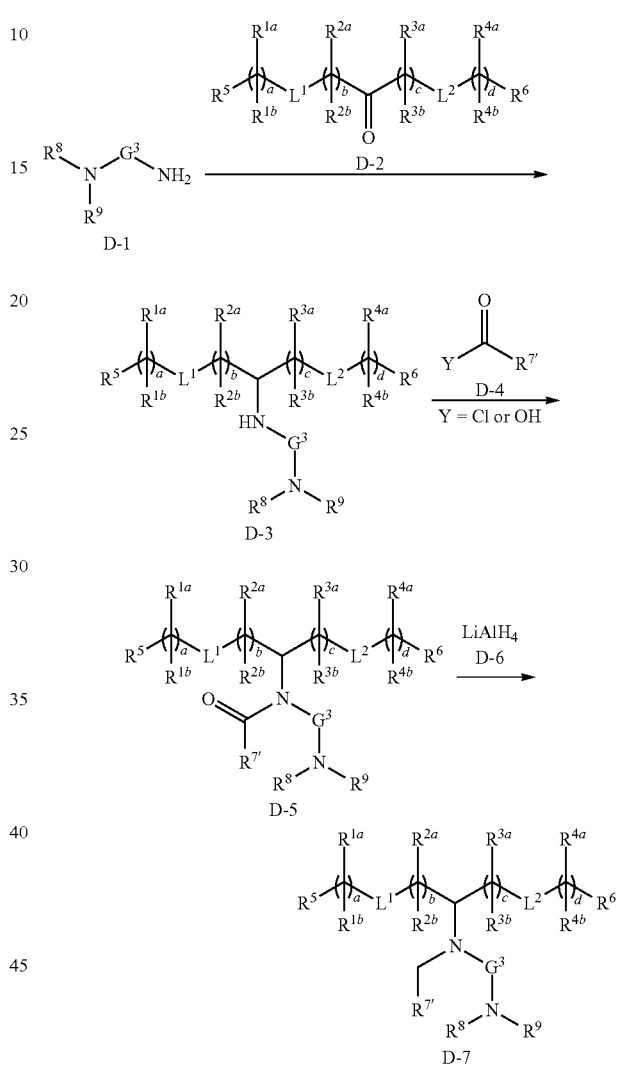

Different embodiments of the lipid of Formula (I) (e.g., compound C-7 or C9) can be prepared according to General Reaction Scheme 3 ("Method C"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 3, compounds of structure C-1 can be purchased from commercial sources or prepared according to methods familiar to one of ordinary skill in the art.

Embodiments of the compound of Formula (II) (e.g., compounds D-5 and D-7) can be prepared according to General Reaction Scheme 4 ("Method D"), wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^8$, $R^9$, $L^1$, $L^2$, $G^1$, $G^2$, $G^3$, a, b, c and d are as defined herein, and $R^{7'}$ represents $R^7$ or a $C_3$-$C_{19}$ alkyl. Referring to General Reaction Scheme 1, compounds of structure D-1 and D-2 can be purchased from commercial sources or prepared according to methods familiar to one of ordinary skill in the art. A solution of D-1 and D-2 is treated with a reducing agent (e.g., sodium triacetoxyborohydride) to obtain D-3 after any necessary work up. A solution of D-3 and a base (e.g., trimethylamine, DMAP) is treated with acyl chloride D-4 (or carboxylic acid and DCC) to obtain D-5 after any necessary work up and/or purification. D-5 can be reduced with LiAlH4 D-6 to give D-7 after any necessary work up and/or purification.

GENERAL REACTION SCHEME 5

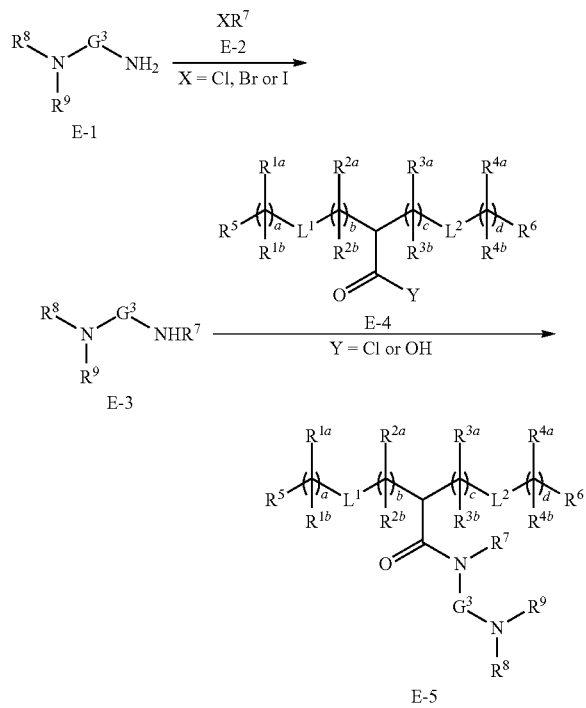

Embodiments of the lipid of Formula (II) (e.g., compound E-5) can be prepared according to General Reaction Scheme 5 ("Method E"), wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^7$, $R^8$, $R^9$, $L^1$, $L^2$, $G^3$, a, b, c and d are as defined herein. Referring to General Reaction Scheme 2, compounds of structure E-1 and E-2 can be purchased from commercial sources or prepared according to methods familiar to one of ordinary skill in the art. A mixture of E-1 (in excess), E-2 and a base (e.g., potassium carbonate) is heated to obtain E-3 after any necessary work up. A solution of E-3 and a base (e.g., trimethylamine, DMAP) is treated with acyl chloride E-4 (or carboxylic acid and DCC) to obtain E-5 after any necessary work up and/or purification.

GENERAL REACTION SCHEME 6

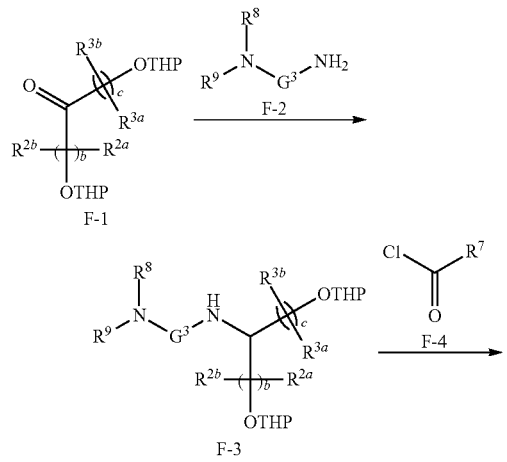

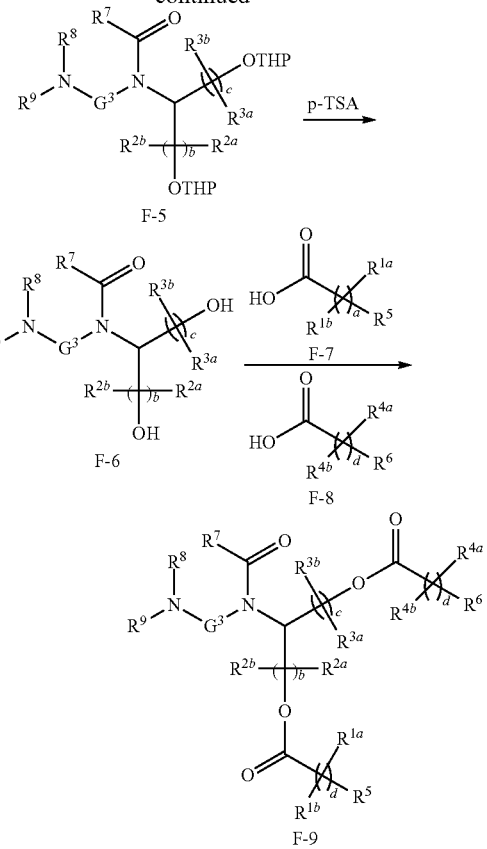

Other embodiments of the compound of Formula (II) (e.g., F-9) are prepared according to General Reaction Scheme 6. As illustrated in General Reaction Scheme 6, an appropriately protected ketone (F-1) is reacted under reductive amination conditions with amine F-2 to yield F-3. Acylation of F-3 with acid chloride F-4 yields acylated product F-5. Removal of the alcohol protecting group on F-5 followed by reaction with F-7 and/or F-8 and appropriate activating reagent (e.g., DCC) yields the desired compound F-9.

GENERAL REACTION SCHEME 7

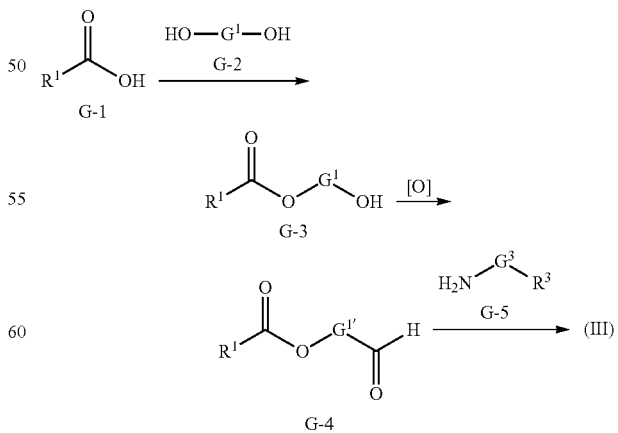

General Reaction Scheme 7 provides an exemplary method (Method G) for preparation of Lipids of Formula (III), wherein L¹ and L² are —(C=O)O—. G¹, G³, R¹ and R³ in General Reaction Scheme 7 are as defined herein for Formula (III), and G¹' refers to a one-carbon shorter homologue of G¹. Compounds of structure G-1 are purchased or prepared according to methods known in the art. Reaction of G-1 with diol G-2 under appropriate condensation conditions (e.g., DCC) yields ester/alcohol G-3, which can then be oxidized (e.g., PCC) to aldehyde G-4. Reaction of G-4 with amine G-5 under reductive amination conditions yields a lipid of Formula (III), wherein L¹ and L² are —(C=O)O—.

General Reaction Schemes 8-10 provide exemplary methods for preparation of compounds of Formula (IV) or (V).

GENERAL REACTION SCHEME 8

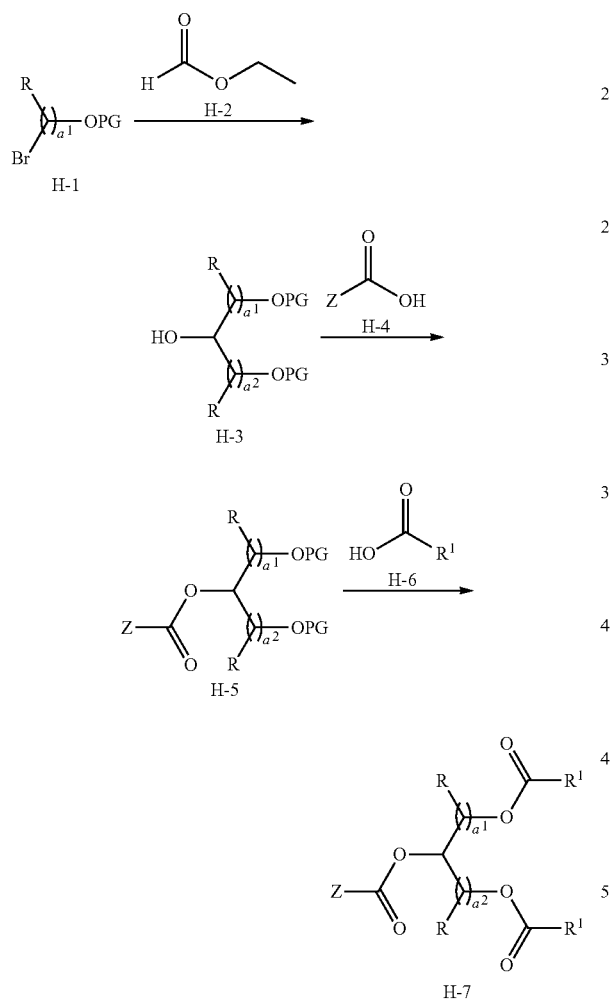

GENERAL REACTION SCHEME 9

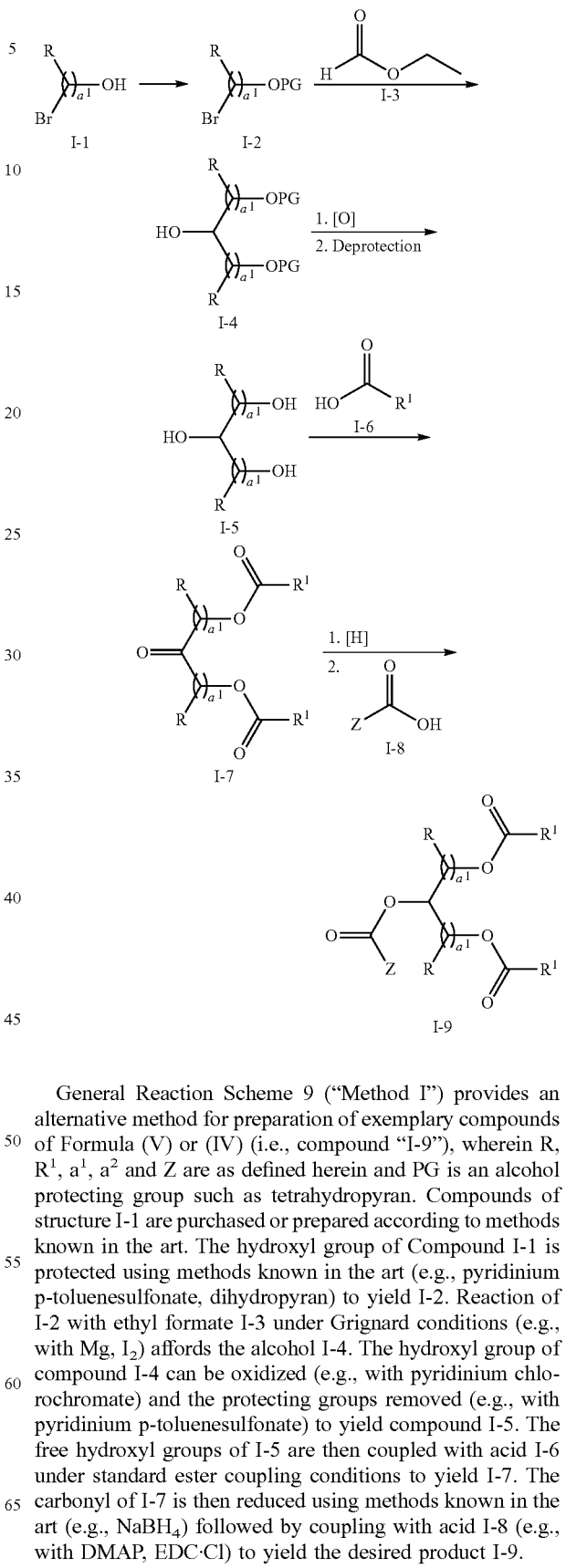

General Reaction Scheme 8 ("Method H") provides a method for preparation of exemplary compounds of Formula (V) or (IV) (i.e., compound "H-7"), wherein R, R¹, a¹, a² and Z are as defined herein, and PG is an alcohol protecting group such as tetrahydropyran. Compounds of structure H-1 are purchased or prepared according to methods known in the art. Reaction of H-1 with ethyl formate H-2 under Grignard conditions yields alcohol H-3, which can then be coupled with acid H-4 under standard conditions to yield H-5. Removal of the protecting group followed by coupling with acid H-6 yields H-7.

General Reaction Scheme 9 ("Method I") provides an alternative method for preparation of exemplary compounds of Formula (V) or (IV) (i.e., compound "I-9"), wherein R, R¹, a¹, a² and Z are as defined herein and PG is an alcohol protecting group such as tetrahydropyran. Compounds of structure I-1 are purchased or prepared according to methods known in the art. The hydroxyl group of Compound I-1 is protected using methods known in the art (e.g., pyridinium p-toluenesulfonate, dihydropyran) to yield I-2. Reaction of I-2 with ethyl formate I-3 under Grignard conditions (e.g., with Mg, I₂) affords the alcohol I-4. The hydroxyl group of compound I-4 can be oxidized (e.g., with pyridinium chlorochromate) and the protecting groups removed (e.g., with pyridinium p-toluenesulfonate) to yield compound I-5. The free hydroxyl groups of I-5 are then coupled with acid I-6 under standard ester coupling conditions to yield I-7. The carbonyl of I-7 is then reduced using methods known in the art (e.g., NaBH₄) followed by coupling with acid I-8 (e.g., with DMAP, EDC·Cl) to yield the desired product I-9.

GENERAL REACTION SCHEME 10

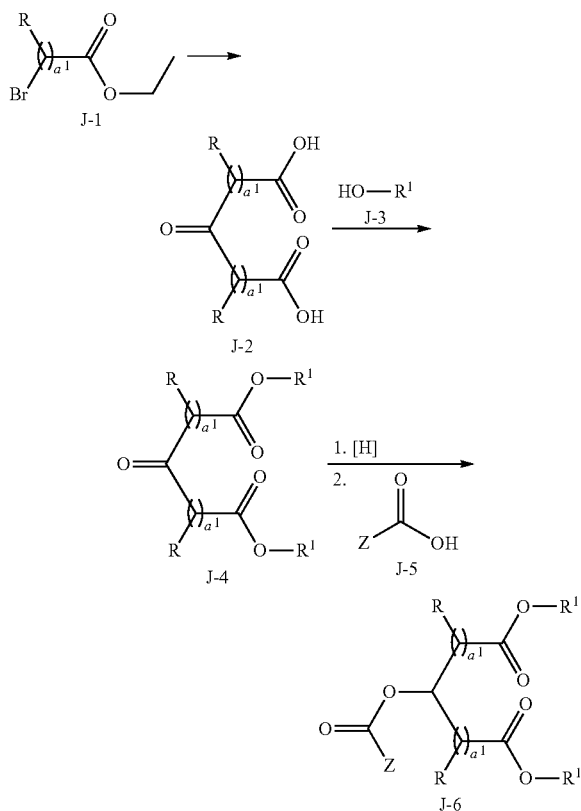

General Reaction Scheme 10 ("Method J") provides another alternative method for preparation of exemplary compounds of Formula (IV) or (V) (i.e., compound "J-6"), wherein R, $R^1$, $a^1$, $a^2$ and Z are as defined herein. Compounds of structure J-1 are purchased or prepared according to methods known in the art. Compound J-1 is used to form J-2 under appropriate conditions (e.g., diethyl acetone dicarboxylate, EtONa). Alcohol J-3 is then coupled to J-2 using standard conditions (e.g., DMAP, EDC·HCl) to yield J-4. The carbonyl of J-4 is reduced (e.g., with $NaBH_4$) followed by coupling with acid J-5 (e.g., with DMAP, EDC·HCl) to yield the desired product J-6.

It should be noted that various alternative strategies for preparation of compounds of Formula (IV) and (V) are available to those of ordinary skill in the art. For example, other compounds of Formula (IV) and (V) wherein $G^1$ and $G^2$ (as disclosed herein) are other than ester can be prepared according to analogous methods using the appropriate starting material. Further, the General Reaction Schemes above depict preparation of a compound of Formula (IV) and (V), wherein $R^1$ and $R^2$ as well as $a^1$ and $a^2$ are the same; however, this is not a required aspect of the invention and modifications to the above reaction scheme are possible to yield compounds wherein $R^1$ and $R^2$ as well as $a^1$ and $a^2$ are different (i.e., resulting in an asymmetric compound). The use of protecting groups as needed and other modification to the above General Reaction Schemes will be readily apparent to one of ordinary skill in the art.

The following examples are provided for purpose of illustration and not limitation.

EXAMPLES

Example 1

Preparation of Lipid Nanoparticle Compositions

Lipid nanoparticles, cationic lipids and polymer conjugated lipids (PEG-lipid) were prepared and tested according to the general procedures described in PCT Pub. Nos. WO 2015/199952, WO 2017/004143 and WO 2017/075531, the full disclosures of which are incorporated herein by reference, or were prepared as described herein.

Cationic lipid(s), DSPC, cholesterol and PEG-lipid were solubilized in ethanol at a desired molar ratio (e.g., 50:0 to 10:28.5 to 38.5:1.5 to 1.7 or 47.5:10:40.8:1.7). Lipid nanoparticles (LNP) were prepared at a total lipid to mRNA weight ratio of approximately 10:1 to 30:1. The mRNA was diluted to 0.2 mg/mL in 10 to 50 mM citrate buffer, pH 4. Syringe pumps were used to mix the lipid solution (i.e., LNP components solubilized in ethanol) with the mRNA aqueous solution at a ratio of about 1:5 to 1:3 (vol/vol) with total flow rates above 15 mL/min. The ethanol was then removed and the external buffer replaced with PBS by dialysis. Finally, the lipid nanoparticles were filtered through a 0.2 µm pore sterile filter. Lipid nanoparticle particle size was 55-95 nm diameter, and in some instances approximately 70-90 nm as determined by quasi-elastic light scattering using a Malvern Zetasizer Nano ZS (Malvern, UK).

Example 2

Luciferase mRNA In Vivo Evaluation Using the Lipid Nanoparticle Compositions

Luciferase mRNA in vivo evaluation studies were performed in 6-8 week old female C57BL/6 mice (Charles River) 8-10 week old CD-1 (Harlan) mice (Charles River) according to guidelines established by an institutional animal care committee (ACC) and the Canadian Council on Animal Care (CCAC). Varying doses of mRNA-lipid nanoparticle were systemically administered by tail vein injection and animals euthanized at a specific time point (e.g., 4 hours) post-administration. Liver and spleen were collected in pre-weighed tubes, weights determined, immediately snap frozen in liquid nitrogen and stored at −80° C. until processing for analysis.

For liver, approximately 50 mg was dissected for analyses in a 2 mL FastPrep tubes (MP Biomedicals, Solon Ohio). ¼" ceramic sphere (MP Biomedicals) was added to each tube and 500 µL of Glo Lysis Buffer—GLB (Promega, Madison Wis.) equilibrated to room temperature was added to liver tissue. Liver tissues were homogenized with the FastPrep24 instrument (MP Biomedicals) at 2×6.0 m/s for 15 seconds. Homogenate was incubated at room temperature for 5 minutes prior to a 1:4 dilution in GLB and assessed using SteadyGlo Luciferase assay system (Promega). Specifically, 50 µL of diluted tissue homogenate was reacted with 50 µL of SteadyGlo substrate, shaken for 10 seconds followed by 5 minute incubation and then quantitated using a CentroXS³ LB 960 luminometer (Berthold Technologies, Germany). The amount of protein assayed was determined by using the BCA protein assay kit (Pierce, Rockford Ill.). Relative luminescence units (RLU) were then normalized to total µg protein assayed. To convert RLU to ng luciferase a standard curve was generated with QuantiLum Recombinant Luciferase (Promega). For a representative formulation having a combination of two cationic lipids, a four-hour time point was chosen for an efficacy evaluation of the lipid formulation.

The FLuc mRNA (L-6107) from Trilink Biotechnologies will express a luciferase protein, originally isolated from the firefly, *Photinus pyralis*. FLuc is commonly used in mammalian cell culture to measure both gene expression and cell viability. It emits bioluminescence in the presence of the substrate, luciferin. This capped and polyadenylated mRNA is fully substituted with 5-methylcytidine and pseudouridine.

Example 3

Activity of Lipid Formulations Compared at Different Component Ratios

For a given set of lipid components, the interdependent effects on size, polydispersity, activity and encapsulation were determined by simultaneously varying all four components in controlled manner based on the principles of statistical design of experiments. This experimental design was generated and the resulting data was analyzed with DesignExpert 9 (StatEase Inc, MN) using the design ranges and constraints produced by I-Optimal. The mixture experimental design was built to resolve up to quadratic interaction terms. The design constraints used compound I-6 as the representative cationic lipid (ranging from 30 to 70 mol %), DSPC (ranging from 5 to 30 mol %), cholesterol (ranging from 5 to 50 mol %), PEG lipid (ranging from 0.5 to 3 mol %). When all parameters combine, the total is 100 mol %.

LNP's were formulated by an in-line mixing process as described in Example 1. These formulations were prepared such that the mRNA to cationic lipid ratio was held constant (N/P=6.3). The size and polydispersity index data were generated using Malvern Nanosizer ZS. The diameters given are intensity weighted means. Encapsulation was determined using a fluorescent intercalating dye based assay (Ribogreen). Activity data was generated using an in vivo murine model of mRNA expression based on *Photinus pyralis* (i.e., firefly) luciferase as described in Example 2.

Table 5 provides results of various design of experiment trials. The size and encapsulation results for these LNP's demonstrate that the particles are generally physically equivalent to each other for the majority of the experimental design space. It is apparent that very high cationic lipid formulations suffer from poor encapsulation and size characteristics regardless of the proportions of the other lipid components.

TABLE 5

Formulation proportions and resultant particle diameter, polydispersity, and encapsulation percentage.

| Trial No. | Lipid (I-6) % | DSPC % | Chol % | PEG (IVa) % | Mean diameter nm | PDI | Encap. % |
|---|---|---|---|---|---|---|---|
| 1 | 51.1 | 18.6 | 28.6 | 1.8 | 72.2 | 0.078 | 84.6 |
| 2 | 30.0 | 30.0 | 37.0 | 3.0 | 54.6 | 0.133 | 87.9 |
| 3 | 30.0 | 18.3 | 50.0 | 1.8 | 57.5 | 0.104 | 93.5 |
| 4 | 63.3 | 30.0 | 5.0 | 1.8 | 80.5 | 0.087 | 48.6 |
| 5 | 51.1 | 18.6 | 28.6 | 1.8 | 75.0 | 0.029 | 91.3 |
| 6 | 47.3 | 9.0 | 40.7 | 3.0 | 63.0 | 0.035 | 86.3 |
| 7 | 63.3 | 30.0 | 5.0 | 1.8 | 78.5 | 0.093 | 44.4 |
| 8 | 30.0 | 18.3 | 50.0 | 1.8 | 56.0 | 0.097 | 96.4 |
| 9 | 70.0 | 16.3 | 10.7 | 3.0 | 71.8 | 0.095 | 17.1 |
| 10 | 51.1 | 18.6 | 28.6 | 1.8 | 75.4 | 0.028 | 83.8 |
| 11 | 40.5 | 17.8 | 39.3 | 2.4 | 55.8 | 0.098 | 83.3 |
| 12 | 70.0 | 5.0 | 22.8 | 2.2 | 108.7 | 0.042 | 20.6 |
| 13 | 41.5 | 30.0 | 28.0 | 0.5 | 108.2 | 0.049 | 97.1 |
| 14 | 42.0 | 5.0 | 50.0 | 3.0 | 49.3 | 0.074 | 91.5 |
| 15 | 50.0 | 10.0 | 38.5 | 1.5 | 83.2 | 0.042 | 89.6 |
| 16 | 41.5 | 30.0 | 28.0 | 0.5 | 103.0 | 0.060 | 91.7 |
| 17 | 70.0 | 18.0 | 11.5 | 0.5 | 173.3 | 0.247 | 39.4 |
| 18 | 70.0 | 5.0 | 22.8 | 2.2 | 114.0 | 0.051 | 12.7 |
| 19 | 60.5 | 16.0 | 21.0 | 2.4 | 75.1 | 0.063 | 52.8 |
| 20 | 44.5 | 5.0 | 50.0 | 0.5 | 123.9 | 0.035 | 95.2 |
| 21 | 51.3 | 30.0 | 15.7 | 3.0 | 56.3 | 0.131 | 49.1 |

The data from the design of experiments was used to design further experiments to determine the optimal percentage of the various LNP components across a relevant range, i.e., that allows for equivalent desirable physical characteristics. Table 6 provides size, polydispersity, encapsulation % and activity for various LNP formulations comprising cationic lipid II-10. Table 7 provides size, polydispersity, encapsulation % and activity for various LNP formulations comprising cationic lipid II-9. Table 8 provides size, polydispersity, encapsulation % and activity for various LNP formulations comprising cationic lipid I-5. The activity data in Table 8 is reported as relative to the formulations comprising 50 mol % cationic lipid to address variability in activity for different batches of nominally the same mRNA. The data collectively show that LNPs comprising between 40 and 50 mol % of cationic lipid surprisingly have better activity relative to LNPs with cationic lipid outside this range even though polydispersity and/or encapsulation are generally equivalent across the given range.

TABLE 6

Cationic Lipid Titration for Compound II-10

| Cationic lipid/ DSPC/ Chol/ PEGA | size (nm) | PDI | Encapsulation (%) | Mean Activity at 1 mg/kg (ng/g) |
|---|---|---|---|---|
| 42.5/10/46/1.5 | 57 | 0.087 | 96 | 8602 |
| 45/10/43.5/1.5 | 61 | 0.029 | 97 | 11975 |
| 47.5/10/41/1.5 | 64 | 0.042 | 98 | 15869 |
| 50/10/38.5/1.5 | 71 | 0.043 | 97 | 12613 |

TABLE 7

Cationic Lipid Titration for Compound II-9

| Cationic lipid/ DSPC/ Chol/ PEGA | size (nm) | PDI | Encapsulation (%) | Mean Activity at 0.3 mg/kg (ng/g) |
|---|---|---|---|---|
| 42.5/10/46/1.5 | 60 | 0.070 | 95% | 2955 |
| 45/10/43.5/1.5 | 62 | 0.023 | 97% | 2686 |
| 47.5/10/41/1.5 | 64 | 0.002 | 97% | 3424 |
| 50/10/38.5/1.5 | 70 | 0.041 | 97% | 2997 |
| 55/10/33.5/1.5 | 78 | 0.002 | 95% | 1557 |

TABLE 8

Cationic Lipid Titration for Compound I-5

| Cat lipid/ DSPC/ Chol/ PEGA | size (nm) | PDI | Encaps | Mean Activity at 1 mg/kg | Relative to benchmark |
|---|---|---|---|---|---|
| 42.5/10/46/1.5 (mRNA batch A) | 71 | 0.002 | 96% | 4760 | 0.74 |
| 45/10/43.5/1.5 (mRNA batch A) | 71 | 0.019 | 98% | 6984 | 1.08 |
| 47.5/10/41/1.5 (mRNA batch A) | 68 | 0.042 | 97% | 7057 | 1.10 |
| 50/10/38.5/1.5 (mRNA batch A) | 71 | 0.040 | 97% | 6444 | 1 |
| 50/10/38.5/1.5 (mRNA batch B) | 77 | 0.033 | 93% | 15260 | 1 |
| 55/9/34.5/1.5 (mRNA batch B) | 84 | 0.007 | 91% | 13555 | 0.89 |
| 60/7.9/30.6/1.5 (mRNA batch B) | 90 | 0.015 | 90% | 12063 | 0.79 |
| 65/6.9/26.6/1.5 (mRNA batch B) | 102 | 0.013 | 85% | 4640 | 0.30 |

TABLE 9

Formulation Proportions and Experimental Results

| Trial No. | Cationic Lipid (I-5) % | Chol % | DSPC % | PEG (IVa) % | Activity ng/g | Mean Diameter nm | PDI | Encaps. % |
|---|---|---|---|---|---|---|---|---|
| 1 | 47.5 | 41 | 10 | 1.5 | 4103 | 73.9 | 0.047 | 96.5 |
| 2 | 53 | 35 | 10 | 2 | 3243 | 74.8 | 0.052 | 92.7 |
| 3 | 53 | 41 | 5 | 1 | 3813 | 85.4 | 0.054 | 95.4 |
| 4 | 46.5 | 47 | 5 | 1.5 | 2095 | 63.1 | 0.040 | 97.5 |
| 5 | 47.5 | 41 | 10 | 1.5 | 3742 | 74.5 | 0.023 | 96.1 |
| 6 | 42 | 47 | 10 | 1 | 1911 | 105.7 | 0.045 | 97.9 |
| 7 | 54 | 35 | 10 | 1 | 2627 | 98.6 | 0.026 | 91.3 |
| 8 | 36 | 47 | 15 | 2 | 1982 | 63.0 | 0.069 | 96.7 |
| 9 | 48.5 | 35 | 15 | 1.5 | 2770 | 77.1 | 0.035 | 94.9 |
| 10 | 52 | 41 | 5 | 2 | 3279 | 71.2 | 0.050 | 94.9 |
| 11 | 37 | 47 | 15 | 1 | 636 | 110.4 | 0.054 | 97.9 |
| 12 | 47.5 | 41 | 10 | 1.5 | 3132 | 72.9 | 0.036 | 97.3 |
| 13 | 58.5 | 35 | 5 | 1.5 | 2741 | 96.8 | 0.020 | 91.3 |
| 14 | 47.25 | 44 | 7.5 | 1.25 | 4385 | 74.1 | 0.008 | 97.5 |
| 15 | 42 | 41 | 15 | 2 | 3230 | 65.4 | 0.044 | 95.9 |

Example 4

Variable Formulation Component Proportions and Results

Similar to Example 3, the interdependent effects of all lipid components on activity as well as size and encapsulation can be determined by simultaneously varying all four components in controlled manner based on the principles of statistical design of experiments. The following experimental design was generated and the resulting data was analyzed with DesignExpert 9 (StatEase Inc, MN) using the design ranges and constraints given below. The I-Optimal mixture experimental design was built to resolve up to quadratic interaction terms.

The design constraints used compound II-5 as the cationic lipid (ranging from 36 to 59 mol %), DSPC (ranging from 5 to 15 mol %), cholersterol (ranging from 35 to 48 mol %), PEG lipid (ranging from 1 to 2 mol %). When all parameters combine, the total is 100 mol %.

LNP's were formulated by an in-line mixing process as described in Example 1. These formulations were prepared such that the mRNA to cationic lipid ratio was held constant (N/P=6.3). The size and polydispersity index data were generated using Malvern Nanosizer ZS. The diameters given are intensity weighted means. Encapsulation was determined using a fluorescent intercalating dye based assay (Ribogreen). Activity data was generated using an in vivo murine model of mRNA expression based on *Photinus pyralis* (i.e., firefly) luciferase as described in Example 1.

The data in Table 9 again show that LNPs comprising between 40 and 50 mol % of cationic lipid have better activity, polydispersity and/or encapsulation relative to LNPs with cationic lipid outside this range, regardless of variations in the other LNP components within a reasonable range.

Example 5

Synthesis of Compound I-1

Compound I-1 was prepared according to method B as follows:

A solution of octan-1,8-diol (9.8 g) in methylene chloride (100 mL) and tetrahydrofuran (60 mL) was treated with 2-ethylhexanoyl chloride (10 g). Triethylamine (15 mL) was slowly added and the solution stirred for three days. The reaction mixture was filtered and the filtrate washed with brine (2×). The organic fraction was dried over anhydrous magnesium sulfate, filtered and the solvent removed. The crude product was filtered through silica gel (20 g) using methylene chloride, yielding 15.8 g of crude product. The resultant oil was dissolved in methylene chloride (100 mL) and treated with pyridinium chlorochromate (13 g) for two hours. Diethyl ether (400 mL) as added and the supernatant filtered through a silica gel bed. The solvent was removed from the filtrate and resultant oil passed down a silica gel (77 g) column using a ethyl acetate/hexane (0-6%) gradient. 8-O-(2'-ethylhexanoyloxy)octanal (6.7 g) was recovered as an oil.

A solution of 8-O-(2'-ethylhexanoyloxy)octanal (6.7 g), acetic acid (25 drops) and 2-N,N-dimethylaminoethylamine (0.54 g) in methylene chloride (40 mL) was treated with sodium triacetoxyborohydride (1.5 g) overnight. The solution was washed with aqueous sodium hydrogen carbonate, followed by brine. The organic phase was dried over anhydrous magnesium sulfate, filtered and the solvent removed. The residue was passed down a silica gel (75 g) column using a methanol/methylene chloride (0-10%) gradient, followed by a second column (20 g), to yield compound I-1 (1 g) as a colorless oil.

Example 6

Synthesis of Compound I-2

Compound I-2 was Prepared According to Method A as Follows:

Under an argon atmosphere, to a round-bottom flask charged with phytol (593 mg, 2 mmol), 6-bromohexanoic acid (780 mg, 4 mmol) and 4-(dimethylamino)pyridine (60 mg) in dichloromethane (20 mL) was added dicyclohexylcarbodiimide (908 mg, 4.4 mmol). The precipitate was discarded by filtration. The filtrate was concentrated and the resulting residue was purified by column chromatography on silica gel eluted with a gradient mixture (0% to 3%) of ethyl acetate in hexanes. This gave a colorless oil (0.79 g 1.67 mmol, 83%) of (E)-3,7,11,15-tetramethylhexadec-2-enyl 6-bromohexanoate.

A solution of (E)-3,7,11,15-tetramethylhexadec-2-enyl 6-bromohexanoate (0.42 g, 0.887 mmol), N,N-diisopropylethylamine (1.5 mol eq., 1.33 mmol, MW 129.25, 171 mg) and N,N-dimethylethylenediamine (39 mg, 0.44 mmol) in DMF (4 mL) was heated at 77 C for 18 h. The reaction mixture was then cooled and extracted with hexanes (3×20 mL). The hexane extracts were combined, dried over sodium sulfate, filtered and concentrated. This is combined with $2^{nd}$ reaction (total about 0.7 g). The crude was purified several times by column chromatography on silica gel eluted with a gradient mixture (0% to 5%) of methanol in DCM. This gave a slightly yellow oil (39 mg) of the desired product. $^1$H NMR (400 MHz, CDCl$_3$) δ: 5.33 (m, 2H), 4.59 (m, 4H), 2.85-2.25 (m, 18H).

Example 7

Synthesis of Compound I-3

Compound I-3 was prepared in a manner analogous to compound I-2 starting from bromoacetic acid, rather than 6-bromohexanoic acid, to yield 22 mg of thick colorless oil, 0.029 mmol, 6%. $^1$H NMR (400 MHz, CDCl$_3$) δ: 5.32 (m, 2H), 4.62 (m, 4H), 3.62 (s, 2H), 3.60 (s, 2H), 3.28-2.33 (m, 10H), 2.09-2.00 (m, 4H), 1.76 (s, 3H), 1.70 (s, 3H), 1.60-1.47 (m, 6H), 1.47-0.97 (32H), 0.89-0.84 (m, 24H).

Example 8

Synthesis of Compound I-4

Compound I-4 was Prepared According to Method B as Follows:

A solution of dodecan-1,12-diol (10 g) in methylene chloride (100 mL) and tetrahydrofuran (50 mL) was treated with 2-ethylhexanoic acid (7.2 g), DCC (10.5 g), DMAP (3.5 g) and triethylamine (10 mL). The solution was stirred for four days. The reaction mixture was filtered and the filtrate washed with dilute hydrochloric acid. The organic fraction was dried over anhydrous magnesium sulfate, filtered and the solvent removed. The residue was dissolved in methylene chloride (50 mL), allowed to stand overnight, and filtered. The solvent was removed to yield 12.1 g crude product.

The crude product dissolved in methylene chloride (100 mL) and treated with pyridinium chlorochromate (8 g) overnight. Diethyl ether (400 mL) as added and the supernatant filtered through a silica gel bed. The solvent was removed from the filtrate and resultant oil passed down a silica gel (75 g) column using a ethyl acetate/hexane (0-6%) gradient. Crude 12-O-(2'-ethylhexanoyloxy)dodecanal (3.5 g) was recovered as an oil.

A solution of the crude product (3.5 g), acetic acid (60 drops) and 2-N,N-dimethylaminoethylamine (0.30 g) in methylene chloride (20 mL) was treated with sodium triacetoxyborohydride (0.86 g) overnight. The solution was washed with aqueous sodium hydrogen carbonate, followed by brine. The organic phase was dried over anhydrous magnesium sulfate, filtered and the solvent removed. The residue was passed down a silica gel (20 g) column using a methanol/methylene chloride (0-8%) gradient, followed by a second column (20 g), to yield the desired product as a (0.6 g) as a colorless oil.

Example 9

Synthesis of Compound I-5

Compound I-5 was Prepared According to Method B as Follows:

A solution of hexan-1,6-diol (10 g) in methylene chloride (40 mL) and tetrahydrofuran (20 mL) was treated with 2-hexyldecanoyl chloride (10 g) and triethylamine (10 mL). The solution was stirred for an hour and the solvent removed. The reaction mixture was suspended in hexane, filtered and the filtrate washed with water. The solvent was removed and the residue passed down a silica gel (50 g) column using hexane, followed by methylene chloride, as the eluent, yielding 6-(2'hexyldecanoyloxy)hexan-1-ol as an oil (7.4 g).

The purified product (7.4 g) was dissolved in methylene chloride (50 mL) and treated with pyridinium chlorochromate (5.2 g) for two hours. Diethyl ether (200 mL) as added and the supernatant filtered through a silica gel bed. The solvent was removed from the filtrate and resultant oil passed down a silica gel (50 g) column using a ethyl acetate/hexane (0-5%) gradient. 6-(2'-hexyldecanoyloxy) dodecanal (5.4 g) was recovered as an oil.

A solution of the product (4.9 g), acetic acid (0.33 g) and 2-N,N-dimethylaminoethylamine (0.40 g) in methylene chloride (20 mL) was treated with sodium triacetoxyborohydride (2.1 g) for two hours. The solution was washed with aqueous sodium hydroxide. The organic phase was dried over anhydrous magnesium sulfate, filtered and the solvent removed. The residue was passed down a silica gel (50 g) column using a methanol/methylene chloride (0-8%) gradient to yield the desired product (1.4 g) as colorless oil.

Example 10

Synthesis of Compound I-6

Compound I-6 was Prepared According to Method B as Follows:

Compound I-6 was prepared according to method B as follows: A solution of nonan-1,9-diol (12.6 g) in methylene chloride (80 mL) was treated with 2-hexyldecanoic acid (10.0 g), DCC (8.7 g) and DMAP (5.7 g). The solution was stirred for two hours. The reaction mixture was filtered and the solvent removed. The residue was dissolved in warmed hexane (250 mL) and allowed to crystallize. The solution was filtered and the solvent removed. The residue was dissolved in methylene chloride and washed with dilute hydrochloric acid. The organic fraction was dried over anhydrous magnesium sulfate, filtered and the solvent removed. The residue was passed down a silica gel column (75 g) using 0-12% ethyl acetate/hexane as the eluent, yielding 9-(2'-hexyldecanoyloxy)nonan-1-ol (9.5 g) as an oil.

The product was dissolved in methylene chloride (60 mL) and treated with pyridinium chlorochromate (6.4 g) for two hours. Diethyl ether (200 mL) was added and the supernatant filtered through a silica gel bed. The solvent was removed from the filtrate and resultant oil passed down a silica gel (75 g) column using a ethyl acetate/hexane (0-12%) gradient, yielding 9-(2'-ethylhexanoyloxy)nonanal (6.1 g) as an oil.

A solution of the crude product (6.1 g), acetic acid (0.34 g) and 2-N,N-dimethylaminoethylamine (0.46 g) in methylene chloride (20 mL) was treated with sodium triacetoxyborohydride (2.9 g) for two hours. The solution was diluted with methylene chloride washed with aqueous sodium hydroxide, followed by water. The organic phase was dried over anhydrous magnesium sulfate, filtered and the solvent removed. The residue was passed down a silica gel (75 g) column using a methanol/methylene chloride (0-8%) gradient, followed by a second column (20 g) using a methylene chloride/acetic acid/methanol gradient. The purified fractions were dissolved in methylene chloride, washed with dilute aqueous sodium hydroxide solution, dried over anhydrous magnesium sulfate, filtered and the solvent removed, to yield the desired product (1.6 g) as colorless oil.

Example 11

Synthesis of Compound I-7

Compound I-7 was prepared from 3,5,5-trimethylhexyl 10-bromodecanoate and N,N-dimethylethane-1,2-diamine according to method A to yield 144 mg of slightly yellow oil, 0.21 mmol, 11%). $^1$H NMR (400 MHz, CDCl$_3$) δ: 4.09 (t-like, 6.6 Hz, 4H), 2.58-2.51 (m, 2H), 2.44-2.34 (m, 6H), 2.29 (t-like, 7.5 Hz, 4H), 2.25 (s, 6H), 1.67-1.57 (m, 8H), 1.52-1.39 (m, 6H), 1.36-1.21 (m, 24H), 0.95 (d, 6.6 Hz, 6H), 0.90 (s, 18H).

Example 12

Synthesis of Compound I-8

Compound I-8 was prepared by method A in 15% yield. $^1$H NMR (400 MHz, CDCl$_3$) δ: 5.11-5.04 (m, 2H), 2.60-2.54 (m, 2H), 2.47-2.36 (m, 6H), 2.27 (t-like, 7.4 Hz, 4H), 2.25 (s, 6H), 1.66-1.40 (m, 16H), 1.34-1.23 (m, 24H), 0.91 (d, 6.5 Hz, 24H).

Example 13

Synthesis of Compound I-9

Compound I-9 was Prepared According to Method B as Follows:

A solution of nonan-1,9-diol (10.0 g) in methylene chloride (100 mL) was treated with citroneloyl chloride (10.1 g, prepared from citronelic acid and oxalyl chloride) and triethylamine (10 mL), and stirred for three days. The reaction mixture was diluted with methylene chloride and washed with dilute hydrochloric acid. The organic fraction was dried over anhydrous magnesium sulfate, filtered and the solvent removed. The residue was taken up in hexane, filtered and the solvent removed. The residue was passed down a series of silica gel columns (60-70 g) using hexane followed by methylene chloride as the eluent, yielding 9-(citroneloyloxy)nonan-1-ol (7.6 g) as an oil.

The product was dissolved in methylene chloride (50 mL) and treated with pyridinium chlorochromate (6.4 g) for 90 minutes. Diethyl ether (200 mL) as added and the supernatant filtered through a silica gel bed. The residue was dissolved in hexane and passed through a silica gel (20 g) column using hexane as the eluent, yielding 9-(citroneloyloxy)nonanal (5 g) as an oil.

A solution of the crude product (5 g), acetic acid (0.33 g) and 2-N,N-dimethylaminoethylamine (0.48 g) in methylene chloride (40 mL) was treated with sodium triacetoxyborohydride (1.2 g) overnight. The solution was diluted with methylene chloride and washed with aqueous sodium hydroxide. The organic phase was dried over anhydrous magnesium sulfate, filtered and the solvent removed. The residue was passed down a silica gel (50 g) column using a 0-12% methanol/methylene chloride gradient, followed by a second silica gel column (20 g) using the same gradient, to yield the desired product (0.6 g) as colorless oil.

Example 14

Synthesis of Compound I-10

Compound I-10 was prepared according to method A to yield 147 mg of colorless oil, 0.23 mmol, 17%. $^1$H NMR (400 MHz, CDCl$_3$) δ: 4.11 (t, 6.9 Hz, 4H), 2.56-2.52 (m, 2H), 2.44-2.35 (m, 6H), 2.29 (t-like, 7.5 Hz, 4H), 2.24 (s, 6H), 1.75-1.66 (m, 8H), 1.66-1.57 (m, 4H), 1.52 (q-like, 6.9 Hz, 4H), 1.46-1.38 (m, 4H), 1.38-1.13 (m, 30H), 0.98-0.87 (m, 4H).

Example 15

Synthesis of Compound I-11

Compound I-11 was prepared according to method A to yield 154 mg of slightly yellow oil, 0.22 mmol, 14%). $^1$H NMR (400 MHz, CDCl$_3$) δ: 4.88 (quintet, 6.2 Hz, 2H), 3.20-2.40 (m, 8H), 2.39 (s, 6H), 2.29 (t, 7.5 Hz, 4H), 1.67-1.56 (m, 4H), 1.56-1.48 (m, 8H), 1.38-1.21 (m, 44H), 0.92-0.86 (m, 12H).

Example 16

Synthesis of Compound I-12

Compound I-12 was prepared according to method A to yield 169 mg of slightly yellow oil, 0.26 mmol, 17%). $^1$H NMR (400 MHz, CDCl$_3$) δ: 4.03-3.95 (ABX pattern, 4H), 2.54 (m, 2H), 2.44-2.35 (m, 6H), 2.30 (t-like, 7.5 Hz, 4H), 2.25 (s, 6H), 1.66-1.54 (m, 6H), 1.47-1.23 (m, 40H), 0.92-0.88 (m, 12H).

Example 17

Synthesis of Compound I-13

Compound I-13 was prepared according to method A to yield 152 mg of white paste, 0.23 mmol, 16%. $^1$H NMR (400 MHz, CDCl$_3$) δ: 4.03 (t, 6.7 Hz, 4H), 3.10-2.41 (very broad, 8H), 2.34 (s, 6H), 2.30 (t, 7.5 Hz, 4H), 1.66-1.46 (m, 12H), 1.39-1.21 (m, 40H), 0.89 (t-like, 6.9 Hz, 6H).

Example 18

Synthesis of Compound I-14

Compound I-14 was prepared according to method A to yield 111 mg of colorless oil, 0.16 mmol, 11%. $^1$H NMR (400 MHz, CDCl$_3$) δ: 5.09 (m, 2H), 4.16-4.05 (m, 4H), 3.10-2.40 (very broad, 8H), 2.31 (s, 6H), 2.29 (t, 7.5 Hz, 4H), 2.06-1.89 (m, 4H), 1.69 (d, 0.8 Hz, 6H), 1.61 (s, 6H), 1.73-1.13 (m, 50H), 0.92 (d, 6.6 Hz, 6H).

Example 19

Synthesis of Compound I-15

Compound I-15 was prepared according to method A to yield 116 mg of white paste, 0.16 mmol, 10%. $^1$H NMR (400

MHz, CDCl$_3$) δ: 4.06 (t, 6.7 Hz, 4H), 2.62-2.51 (broad, 2H), 2.48-2.33 (br., 6H), 2.29 (t, 7.5 Hz, 4H), 2.25 (s, 6H), 1.69 (quintet, 7.0 Hz, 8H), 1.48-1.38 (br., 4H), 1.38-1.21 (m, 52H), 0.89 (t-like, 6.8 Hz, 6H).

Example 20

Synthesis of Compound I-16

Compound I-16 was prepared according to method A to yield 118 mg of colorless oil 0.17 mmol, 12%. $^1$H NMR (400 MHz, CDCl$_3$) δ: 4.06 (t, 6.8 Hz, 4H), 2.57-2.52 (m, 2H), 2.44-2.34 (m, 6H), 2.29 (t, 7.6 Hz, 4H), 2.25 (s, 6H), 1.62 (quintet-like, 7.0 Hz, 8H), 1.47-1.39 (m, 4H), 1.37-1.22 (m, 44H), 0.89 (t-like, 6.8 Hz, 6H).

Example 21

Synthesis of Compound I-17

Compound I-17 was prepared according to method A to yield 145 mg of slightly yellow oil, 0.21 mmol, 13%. $^1$H NMR (400 MHz, CDCl$_3$) δ: 5.01 (m, 0.27H from cis-isomer), 4.63 (tt, 11.2 Hz, 4.5 Hz, 1.73H from trans-isomer), 2.61-2.24 (18H), 2.01 (m, 4H), 1.81 (m, 4H), 1.61 (quintet-like, 7.2 Hz, 4H), 1.44 (m, 4H), 1.36-1.21 (24H), 1.11 (m, 4H), 1.01 (m, 2H), 0.87 (s, 2.7H from cis-isomer), 0.86 (s, 15.3H from trans-isomer).

Example 22

Synthesis of Compound I-18

Compound I-18 was prepared according to method A to yield 111 mg of colorless oil, 0.17 mmol, 14%. $^1$H NMR (400 MHz, CDCl$_3$) δ: 4.88 (quintet, 6.2 Hz, 2H), 2.61-2.51 (br., 2H), 2.48-2.34 (br, 6H), 2.29 (t, 7.6 Hz, 4H), 2.25 (s, 6H), 1.62 (quintet-like, 7.3 Hz, 4H), 1.55-1.48 (m, 8H), 1.47-1.39 (m, 4H), 1.37-1.21 (m, 32H), 0.91-0.86 (m, 12H).

Example 23

Synthesis of Compound I-19

Compound I-19 was prepared according to method A to yield 76 mg of colorless oil, 0.11 mmol, 6%. $^1$H NMR (400 MHz, CDCl$_3$) δ: 5.77 (dt-like, 14.4 Hz, 6.6 Hz, 2H), 5.55 (dtt-like, 14.4 Hz, 6.5 Hz, 1.4 Hz, 2H), 4.51 (dd, 6.6 Hz, 0.6 Hz, 4H), 2.61-2.50 (br., 2H), 2.50-2.34 (br. 6H), 2.30 (t, 7.5 Hz, 4H), 2.25 (s, 6H), 2.04 (q, 7.1 Hz, 4H), 1.62 (quintet, 7.3 Hz, 4H), 1.48-1.21 (40H), 0.88 (t-like, 6.8 Hz, 6H).

Example 24

Synthesis of Compound I-20

Compound I-20 was prepared according to the general procedure A to yield 157 mg of colorless oil, 0.22 mmol, 14%. $^1$H NMR (400 MHz, CDCl$_3$) δ: 3.97 (d, 5.8 Hz, 4H), 2.57-2.51 (m, 2H), 2.44-2.33 (m, 6H), 2.30 (t, 7.5 Hz, 4H), 2.24 (s, 6H), 1.63 (quintet-like, 7.3 Hz, 6H), 1.43 (quintet-like, 7.3 Hz, 4H), 1.36-1.21 (44H), 0.93-0.86 (m, 12H).

Example 25

Synthesis of Compound I-21

Compound I-21 was prepared according to the general procedure A to yield 164 mg of colorless oil, 0.21 mmol, 14%. $^1$H NMR (400 MHz, CDCl$_3$) δ: 3.97 (d, 5.8 Hz, 4H), 2.57-2.51 (m, 2H), 2.44-2.34 (m, 6H), 2.30 (t, 7.5 Hz, 4H), 2.24 (s, 6H), 1.62 (quintet-like, 7.3 Hz, 6H), 1.43 (quintet-like, 7.3 Hz, 4H), 1.36-1.21 (52H), 0.93-0.86 (m, 12H).

Example 26

Synthesis of Compound I-22

Compound I-22 was Prepared According to Method A as Follows:

Step 1

To a solution of 6-bromohexanoic acid (20 mmol, 3.901 g), 2-hexyl-1-decanol (1.8 eq, 36 mmol, 8.72 g) and 4-dimethylaminopyridine (DMAP 0.5 eq, 10 mmol, 1.22 g) in DCM (80 mL) was added DCC (1.1 eq, 22 mmol, 4.54 g). The resulting mixture was stirred at room temperature for 16 hours. The precipitate was discarded by filtration. The filtrate was concentrated. The residue was purified by column chromatography on silica gel eluted with a gradient mixture of ethyl acetate in hexanes (0 to 2%). This gave the desired product as a colorless oil (7.88 g, 18.8 mmol, 94%)

Step 2

A mixture of the bromide from step 1 (1.34 equiv., 7.88 g, 18.8 mmol), N,N-diisopropylethylamine (1.96 eq, 27.48 mmol, 4.78 mL) and N,N-dimethylethylenediamine (1 eq, 14.02 mmol, 1.236 g, 1.531 mL) in acetonitrile (70 mL) in 250 mL flask equipped with a condenser was heated at 79° C. (oil bath) for 16 hours. The reaction mixture was cooled to room temperature and concentrated. The residue was taken in a mixture of ethyl acetate and hexanes (1:9) and water. The phases were separated, washed with water (100 mL) and brine. Dried over sodium sulfate and concentrated (8.7 g oil). The crude (8.7 g oil) was purified by column chromatography on silica gel (0 to 3% MeOH in chloroform). The fractions containing the desired product were combined and concentrated. The residue was dissolved in 1 mL of hexane and filtered through a layer of silica gel (3-4 mm, washed with 8 mL of hexane). The filtrate was blown to dry with a stream of argon and dried well in vacuo overnight (1.30 g, mmol, %, colorless oil, desired product). $^1$H NMR (400 MHz, CDCl$_3$) δ: 3.96 (d, 5.8 Hz, 4H), 2.55-2.50 (m, 2H), 2.43-2.39 (m, 4H), 3.37-3.32 (m, 2H), 2.30 (t, 7.5 Hz, 4H), 2.23 (s, 6H), 1.63 (quintet-like, 7.6 Hz, 6H), 1.48-1.40 (m, 4H), 1.34-1.20 (52H), 0.88 (t-like, 6.8 Hz, 12H).

Example 27

Synthesis of Compound I-23

Compound I-23 was prepared according to the general procedure A to yield 200 mg of colorless oil, 0.24 mmol, 16%. $^1$H NMR (400 MHz, CDCl$_3$) δ: 3.97 (d, 5.8 Hz, 4H), 2.57-2.51 (m, 2H), 2.44-2.34 (m, 6H), 2.30 (t, 7.5 Hz, 4H), 2.24 (s, 6H), 1.67-1.58 (m, 6H), 1.43 (quintet-like, 7.3 Hz, 4H), 1.36-1.21 (60H), 0.89 (t-like, 6.8 Hz, 12H).

Example 28

Synthesis of Compound I-24

Compound I-24 was prepared according to the general procedure A to yield 138 mg of colorless oil, 0.18 mmol, 12%. $^1$H NMR (400 MHz, CDCl$_3$) δ: 4.90 (sixlet-liked, 6.3 Hz, 2H), 2.63-2.33 (br. 8H), 2.27 (t, 7.5 Hz, 4H), 2.26 (s, 6H), 1.66-1.57 (m, 4H), 1.51-1.39 (m, 6H), 1.35-1.21 (54H), 1.20 (d, 6.2 Hz, 6H), 0.89 (t-like, 6.8 Hz, 6H).

Example 29

Synthesis of Compound I-25

Compound I-25 was prepared according to the general procedure A to yield 214 mg of colorless oil, 0.24 mmol, 17%. $^1$H NMR (400 MHz, CDCl$_3$) δ: 3.97 (d, 5.8 Hz, 4H), 2.58-2.52 (m, 2H), 2.45-2.35 (m, 6H), 2.30 (t, 7.5 Hz, 4H), 2.25 (s, 6H), 1.62 (quintet-like, 7.0 Hz, 6H), 1.43 (quintet-like, 7.0 Hz, 4H), 1.36-1.21 (68H), 0.89 (t-like, 6.7 Hz, 12H).

Example 30

Synthesis of Compound I-26

Compound I-26 was prepared according to the general procedure A to yield 170 mg of colorless oil, 0.21 mmol, 13%. $^1$H NMR (400 MHz, CDCl$_3$) δ: 5.42-5.29 (m, 8H), 4.05 (t, 6.8 Hz, 4H), 2.77 (t, 6.5 Hz, 4H), 2.55-2.50 (m, 2H), 2.43-2.39 (m, 4H), 2.37-2.32 (m, 2H), 2.29 (t, 7.6 Hz, 4H), 2.23 (s, 6H), 2.05 (q, 6.8 Hz, 8H), 1.63 (quintet-like, 7.5 Hz, 8H), 1.48-1.40 (m, 4H), 1.39-1.23 (36H), 0.90 (t-like, 6.8 Hz, 6H).

Example 31

Synthesis of Compound I-27

Compound I-27 was prepared according to the general procedure A to yield 255 mg of colorless oil, 0.29 mmol, 18%. $^1$H NMR (400 MHz, CDCl$_3$) δ: 3.96 (d, 5.8 Hz, 4H), 2.55-2.50 (m, 2H), 2.43-2.39 (m, 4H), 3.37-3.32 (m, 2H), 2.30 (t, 7.5 Hz, 4H), 2.23 (s, 6H), 1.63 (quintet-like, 7.6 Hz, 6H), 1.48-1.40 (m, 4H), 1.34-1.20 (68H), 0.88 (t-like, 6.8 Hz, 12H).

Example 32

Synthesis of Compound I-28

Compound I-28 was prepared according to the general procedure A to yield 248 mg of colorless oil, 0.27 mmol, 19%. $^1$H NMR (400 MHz, CDCl$_3$) δ: 3.97 (d, 5.8 Hz, 4H), 2.57-2.52 (m, 2H), 2.44-2.34 (m, 6H), 2.30 (t, 7.5 Hz, 4H), 2.24 (s, 6H), 1.67-1.58 (m, 6H), 1.43 (quintet-like, 7.3 Hz, 4H), 1.36-1.21 (76H), 0.89 (t-like, 6.8 Hz, 12H).

Example 33

Synthesis of Compound I-29

Compound I-29 was prepared according to the general procedure A to yield 181 mg of colorless oil, 0.23 mmol, 17%. $^1$H NMR (400 MHz, CDCl$_3$) δ: 4.87 (quintet, 6.3 Hz, 4H), 2.56-2.51 (m, 2H), 2.43-2.34 (m, 6H), 2.27 (t, 7.5 Hz, 4H), 2.24 (s, 6H), 1.61 (quintet-like, 7.3 Hz, 4H), 1.55-1.46 (m, 8H), 1.46-1.37 (m, 4H), 1.36-1.08 (52H), 0.88 (t-like, 6.8 Hz, 12H).

Example 34

Synthesis of Compound I-30

Compound I-30 was prepared according to the general procedure A to yield 88 mg of colorless oil, 0.11 mmol, 3%. $^1$H NMR (400 MHz, CDCl$_3$) δ: 3.97 (d, 5.5 Hz, 4H), 2.58-2.51 (m, 2H), 2.49-2.44 (m, 4H), 2.38-2.30 (m, 6H), 2.24 (s, 6H), 1.75 (quintet-like, 7.3 Hz, 4H), 1.66-1.54 (m, 2H), 1.35-1.06 (64H), 0.89 (t-like, 6.4 Hz, 12H).

Example 35

Synthesis of Compound I-31

Compound I-31 was prepared according to the general procedure C to yield 275 mg of slightly yellow oil, 0.30 mmol, total yield 35% for three steps. $^1$H NMR (400 MHz, CDCl$_3$) δ: 3.97 (d, 5.8 Hz, 4H), 2.63-2.47 (m, 8H), 2.45-2.41 (m, 4H), 2.31 (t, 7.5 Hz, 4H), 1.82-1.74 (m, 4H), 1.64 (quintet-like, 7.6 Hz, 6H), 1.46 (quintet-like, 7.6 Hz, 4H), 1.36-1.18 (68H), 0.89 (t-like, 6.8 Hz, 12H).

Example 36

Synthesis of Compound I-32

Compound I-32 was Prepared According to Method C as Follows:

Step 1

To a solution of 2-aminoethanol (116 mg, 1.9 mmol, 115 µL, MW 61.08, d 1.012) in 15 mL of anhydrous THF, 2-hexyldecyl 6-bromohexanoate (1.9 eq, 1.52 g, 3.62 mmol), potassium carbonate (1.9 eq, 3.62 mmol, 500 mg), cesium carbonate (0.3 eq, 0.57 mmol, 186 mg,) and sodium iodide (10 mg) were added and was heated to reflux for 6 days under argon atmosphere. The solvent was evaporated under reduced pressure and the residue was taken up in hexanes and washed with water and brine. The organic layer was separated, dried over anhydrous sodium sulfate, filtered and evaporated under reduced to obtain a colorless oil. The crude product was purified by flash column chromatography on silica gel (230-400 mesh silica gel, MeOH in chloroform, 0 to 4%) to yield 936 mg of colorless oil (1.27 mmol, 70%).

Step 2

To a magnetically stirred and ice-cooled solution of 936 mg (1.27 mmol) of the product from step 1 in 2 mL of CHCl$_3$, was added thionyl chloride (2.9 eq, 3.70 mmol, 440 mg, 270 µL,) in 15 mL of chloroform dropwise under an Ar atmosphere. After the completion of addition of SOCl$_2$, the ice bath was removed and the reaction mixture was stirred for 16 hours at room temperature under an argon atmosphere. Removal of CHCl$_3$, and SOCl$_2$ under reduced pressure gave a thick yellow oil.

Step 3

The crude from step 2 was dissolved in THF (20 mL). To the THF solution was added pyrrolidine (1.6 mL, 1.36 g, 19 mmol). The sealed mixture was heated at 64° C. overnight. The reaction mixture was concentrated (dark brown oil). The residue was purified by flash dry column chromatography on silica gel (MeOH in chloroform, 0 to 4%). This gave the desired product as a slightly yellow oil (419 mg, 0.53 mmol, 83%). $^1$H NMR (400 MHz, CDCl$_3$) δ: 3.97 (d, 5.8 Hz, 4H), 2.65-2.47 (m, 8H), 2.45-2.41 (m, 4H), 2.31 (t, 7.5 Hz, 4H), 1.81-1.74 (m, 4H), 1.64 (quintet-like, 7.6 Hz, 6H), 1.46 (quintet-like, 7.6 Hz, 4H), 1.36-1.21 (52H), 0.89 (t-like, 6.8 Hz, 12H).

Example 37

Synthesis of Compound I-33

Compound I-33 was prepared according to the general procedure C to yield 419 mg of slightly yellow oil, 0.54 mmol, total yield 60% for three steps. $^1$H NMR (400 MHz, CDCl$_3$) δ: 3.97 (d, 5.8 Hz, 4H), 2.57-2.53 (m, 2H), 2.46-2.40 (m, 8H), 2.31 (t, 7.5 Hz, 4H), 2.23 (s, 3H), 1.64 (quintet-like, 7.6 Hz, 6H), 1.46 (quintet-like, 7.6 Hz, 4H), 1.36-1.20 (52H), 1.06 (t, 7.2 Hz, 3H), 0.89 (t-like, 6.8 Hz, 12H).

Example 38

Synthesis of Compound I-34

Compound I-34 was Prepared According to Method B as Follows:
A solution of nonan-1,9-diol (10 g) in methylene chloride (250 mL) was treated with 2-ethylhexanoic acid (4.5 g), DCC (7.7 g) and DMAP (4.2 g). The solution was stirred for three days. The reaction mixture was filtered and hexane (200 mL) added to the filtrate. The mixture was stirred and the precipitates allowed to settle out. The supernatant was decanted and the solvent removed. The residue was suspended in hexane (70 mL) and allowed to settle. The supernatant was decanted and the solvent removed. The residue was dissolved in hexane, allowed to stand at room temperature and then filtered. The solvent was removed and the residue passed down a silica gel column (50 g) using a 0-10% ethyl acetate/hexane gradient, followed by a 0-8% methanol/methylene chloride gradient, yielding 5.6 g of 9-(2'ethylhexanoyloxy)nonan-1-ol as a colorless oil.

The product dissolved in methylene chloride (70 mL) and treated with pyridinium chlorochromate (5 g) for two hours. Diethyl ether (250 mL) was added and the supernatant filtered through a silica gel bed. The solvent was removed from the filtrate and resultant oil dissolved in hexane. The suspension was filtered through a silica gel plug and the solvent removed, yielding crude 9-(2'ethylhexanoyloxy) nonanal (3.4 g) as an oil.

A solution of the crude product (3.4 g), acetic acid (0.52 g) and 2-N,N-dimethylaminoethylamine (0.33 g) in methylene chloride (50 mL) was treated with sodium triacetoxyborohydride (1.86 g) overnight. The solution was washed with aqueous sodium hydroxide solution. The organic phase was dried over anhydrous magnesium sulfate, filtered and the solvent removed. The residue was passed down a silica gel (50 g) column using an acetic acid/methanol/methylene chloride (2-0%/0-12%/98-88%) gradient. The purified fractions were washed with aqueous sodium hydrogen carbonate, dried over magnesium sulfate, filtered and the solvent removed, yielding compound I-34 as an oil (0.86 g).

Example 39

Synthesis of Compound I-35

Compound I-35 was Prepared According to Method B as Follows:
A solution of dodecan-1,12-diol (18.1 g) in methylene chloride (90 mL) was treated with citronelic acid (7.5 g), DCC (10.0 g) and DMAP (9.5 g). The solution was stirred overnight. The reaction mixture was filtered and the filtrate washed with dilute hydrochloric acid. The organic fraction was dried over anhydrous magnesium sulfate, filtered and the solvent removed to yield 12.2 g of crude 12-citroneloyloxydodecan-1-ol.

The crude product dissolved in methylene chloride (60 mL) and treated with pyridinium chlorochromate (6.8 g) for three hours. Diethyl ether (200 mL) as added and the supernatant filtered through a silica gel bed. The solvent was removed from the filtrate and resultant oil passed down a silica gel (75 g) column using a ethyl acetate/hexane (0-12%) gradient. Crude 12-citroneloyloxydodecanal (6.2 g) was recovered as an oil.

A solution of the crude product (6.2 g), acetic acid (0.44 g) and 2-N,N-dimethylaminoethylamine (0.50 g) in methylene chloride (40 mL) was treated with sodium triacetoxyborohydride (2.9 g) overnight. The solution was washed with aqueous sodium hydrogen carbonate, followed by brine. The organic phase was dried over anhydrous magnesium sulfate, filtered and the solvent removed. The residue was passed down a silica gel (75 g) column using an acetic acid/methanol/methylene chloride (2-0%/0-12%/98-88%) gradient. The purified fractions were washed with aqueous sodium hydrogen carbonate, dried over magnesium sulfate, filtered and the solvent removed, yielding compound I-35 (1.68 g) as an oil.

Example 40

Synthesis of Compound I-36

Compound I-36 was prepared according to the general procedure C to yield 108 mg of colorless oil (0.14 mmol). $^1$H NMR (400 MHz, CDCl$_3$) δ: 4.87 (quintet, 6.3 Hz, 2H), 2.56-2.51 (m, 2H), 2.45-2.40 (m, 4H), 2.38-2.33 (m, 2H), 2.29 (t, 7.5 Hz, 4H), 2.24 (s, 6H), 1.64 (quintet-like, 7.7 Hz, 4H), 1.55-1.41 (m, 12H), 1.35-1.18 (m, 52H), 0.89 (t-like, 6.8 Hz, 12H).

Example 41

Synthesis of Compound I-37

Compound I-37 was prepared according to the general procedure C to yield 330 mg of colorless oil (0.40 mmol, total yield 80% for three steps). $^1$H NMR (400 MHz, CDCl$_3$) δ: 4.87 (quintet, 6.5 Hz, 2H), 2.64-2.47 (m, 8H), 2.45-2.40 (m, 4H), 2.29 (t, 7.5 Hz, 4H), 1.81-1.74 (m, 4H), 1.64 (quintet-like, 7.6 Hz, 4H), 1.55-1.41 (m, 12H), 1.35-1.18 (m, 50H), 0.89 (t-like, 6.8 Hz, 12H).

Example 42

Synthesis of Compound I-38

Compound I-38 was Prepared According to Method B as Follows:
A solution of nonan-1,9-diol (16 g) in methylene chloride (100 mL) was treated with 2-butyloctanoic acid (10 g), DCC (10.3 g) and DMAP (6.7 g). The solution was stirred for three days. The reaction mixture was filtered and hexane (250 mL) added to the filtrate. The mixture was stirred and the precipitates allowed to settle out. The supernatant was decanted and the solvent removed. The residue was suspended in hexane and allowed to settle. The supernatant was decanted and the solvent removed (repeated twice). The residue was dissolved in hexane, allowed to stand at room temperature and then filtered. The solvent was removed and the residue passed down a silica gel column (18 g) using methylene chloride, yielding crude 9-(2'-butyloctanoyloxy) nonan-1-ol (17.7 g) as an oil.

The crude product was dissolved in methylene chloride (250 mL) and treated with pyridinium chlorochromate (11.2 g) overnight. Diethyl ether (750 mL) was added and the supernatant filtered through a silica gel bed. The solvent was removed from the filtrate and resultant oil dissolved in hexane (150 mL). The suspension was filtered through a silica gel plug and the solvent removed. The crude product was passed down a silica gel (80 g) column using a 0-6% ethyl acetate/hexane gradient, yielding 9-(2'-butyloctanoyloxy)nonanal (5.3 g) as an oil.

A solution of the product (5.3 g), acetic acid (0.37 g) and 2-N,N-dimethylaminoethylamine (0.47 g) in methylene chloride (50 mL) was treated with sodium triacetoxyborohydride (3.35 g) overnight. The solution was washed with aqueous sodium hydroxide solution. The organic phase was dried over anhydrous magnesium sulfate, filtered and the solvent removed. The residue was passed down a silica gel (60 g) column using an acetic acid/methanol/methylene chloride (2-0%/0-12%/98-88%) gradient. The purified fractions were washed with aqueous sodium hydrogen carbonate, dried over magnesium sulfate, filtered and the solvent removed, yielding compound I-38 as an oil (2.3 g).

Example 43

Synthesis of Compound I-39

Compound I-39 was Prepared According to Method B as Follows:

A solution of hexan-1,6-diol (12 g) in methylene chloride (250 mL) was treated with 2-decyltetradecanoic acid (17.5 g), DCC (11.3 g) and DMAP (6.8 g). The solution was stirred for overnight. The reaction mixture was filtered and hexane added to the filtrate. The mixture was stirred and the precipitates allowed to settle out. The supernatant was decanted and the solvent removed. The residue was passed down a silica gel column (80 g) using hexane followed by 0-1% methanol/methylene chloride, yielding crude 6-(2'-decyltetradecanoyloxy)hexan-1-ol (5.8 g) as an oil. The crude product was dissolved in methylene chloride (70 mL) and treated with pyridinium chlorochromate (2.9 g) for two hours. Diethyl ether (250 mL) was added and the supernatant filtered through a silica gel bed. The solvent was removed from the filtrate and resultant oil dissolved in hexane. The suspension was filtered through a silica gel plug and the solvent removed. The crude product was passed down a silica gel (10 g) column using a 0-5% ethyl acetate/hexane gradient, yielding 6-(2'-decyltetradecanoyloxy)hexanal (3.2 g) as an oil.

A solution of the product (3.2 g), acetic acid (0.28 g) and 2-N,N-dimethylaminoethylamine (0.15 g) in methylene chloride (20 mL) was treated with sodium triacetoxyborohydride (0.98 g) overnight. The solution was washed with aqueous sodium hydroxide solution. The organic phase was dried over anhydrous magnesium sulfate, filtered and the solvent removed. The residue was passed down a silica gel (50 g) column using an acetic acid/methanol/methylene chloride (2-0%/0-12%/98-88%) gradient. The purified fractions were washed with aqueous sodium hydrogen carbonate, dried over magnesium sulfate, filtered and the solvent removed, yielding compound I-39 as an oil (1.2 g).

Example 44

Synthesis of Compound I-40

Compound I-40 was Prepared According to Method B as Follows:

A solution of nonan-1,9-diol (10.1 g) in methylene chloride (200 mL) was treated with 2-octyldodecanoic acid (10.0 g), DCC (8.3 g) and DMAP (5.0 g). The solution was stirred for overnight. The reaction mixture was filtered and hexane (200 mL) added to the filtrate. The mixture was stirred and the precipitates allowed to settle out. The supernatant was decanted and the solvent removed. This process was repeated twice. The residue was passed down a silica gel column (75 g) using hexane followed by 4-10% methanol/methylene chloride, yielding crude 9-(2'-octyldodecanoyloxy)nonan-1-ol (~11 g) as an oil.

The crude product was dissolved in methylene chloride (70 mL) and treated with pyridinium chlorochromate (8 g) for two hours. Diethyl ether (400 mL) was added and the supernatant filtered through a silica gel bed. The solvent was removed from the filtrate and resultant oil dissolved in hexane. The suspension was filtered through a silica gel plug and the solvent removed, to yield the crude product, 9-(2'-octyldodecanoyloxy)nonanal (8.4 g), as an oil.

A solution of the product (8.4 g), acetic acid (0.84 g) and 2-N,N-dimethylaminoethylamine (0.55 g) in methylene chloride (60 mL) was treated with sodium triacetoxyborohydride (2.9 g) for two hours. The solution was washed with aqueous sodium hydroxide solution. The organic phase was dried over anhydrous magnesium sulfate, filtered and the solvent removed. The residue was passed down a silica gel (75 g) column using an acetic acid/methanol/methylene chloride (2-0%/0-12%/98-88%) gradient. The purified fractions were washed with aqueous sodium hydrogen carbonate, dried over magnesium sulfate, filtered and the solvent removed, yielding compound I-40 as an oil (3.2 g).

Example 45

Synthesis of Compound I-41

Compound I-41 was Prepared According to Method B as Follows:

A solution of nonan-1,9-diol (9.6 g) in methylene chloride (200 mL) was treated with 2-decyltetradecanoic acid (8.4 g), DCC (8.6 g) and DMAP (5.0 g). The solution was stirred for overnight. The reaction mixture was filtered and hexane (200 mL) added to the filtrate. The mixture was stirred and the precipitates allowed to settle out. The supernatant was decanted and the solvent removed. This process was repeated twice. The residue was passed down a silica gel column (75 g) using hexane followed by 4-10% methanol/methylene chloride, yielding crude 9-(2'-decyltetradecanoyloxy)nonan-1-ol (6.4 g) as an oil.

The crude product was dissolved in methylene chloride (50 mL) and treated with pyridinium chlorochromate (5.7 g) for two hours. Diethyl ether (200 mL) was added and the supernatant filtered through a silica gel bed. The solvent was removed from the filtrate and resultant oil dissolved in hexane. The suspension was filtered through a silica gel plug and the solvent removed, yielding crude 9-(2'-decyltetradecanoyloxy)nonanal (5 g) as an oil.

A solution of the product (5 g), acetic acid (0.45 g) and 2-N,N-dimethylaminoethylamine (0.32 g) in methylene chloride (20 mL) was treated with sodium triacetoxyborohydride (1.6 g) for two hours. The solution was washed with aqueous sodium hydroxide solution. The organic phase was dried over anhydrous magnesium sulfate, filtered and the solvent removed. The residue was passed down a silica gel (50 g) column using an acetic acid/methanol/methylene chloride (2-0%/0-12%/98-88%) gradient. The purified fractions were washed with aqueous sodium hydrogen carbonate, dried over magnesium sulfate, filtered and the solvent removed, yielding compound I-41 as oil (2.2 g).

Example 46

Synthesis of Compound II-1

Compound II-1 was prepared according to method A from compound II-5 to yield 240 mg of colorless oil, 0.32 mmol, 61%). $^1$H NMR (400 MHz, CDCl$_3$) δ: 5.43-5.30 (m, 8H), 2.78 (t, 6.5 Hz, 4H), 2.39-2.25 (m, 7H), 2.22 (s, 6H), 2.06 (q, 6.8 Hz, 8H), 1.53 (quintet, 7.3 Hz, 2H), 1.41-1.11 (54H), 0.92-0.87 (m, 9H).

Example 47

Synthesis of Compound II-2

Compound II-2 was Prepared According to Method A as Follows:

Compound II-7 (0.84 g, 0.96 mmol) was dissolved in THF (15 mL) and LAH (2 eq. 1.92 mmol, 73 mg, MW37.95) was added in portions at RT. After the reaction mixture was heated at 60° C. overnight, sodium sulfate hydrate was added. The mixture was stirred for 2 hours, filtered through a layer of silica gel. The filtrate was concentrated to give a slightly yellow oil (0.86 g). The crude product was purified by gravity column chromatography on silica gel (0 to 4% MeOH in chloroform). This gave the desired product as a colorless oil (420 mg, 0.49 mmol, 51%). $^1$H NMR (400 MHz, CDCl$_3$) δ: 5.43-5.30 (m, 12H), 2.78 (t, 6.4 Hz, 6H), 2.40-2.25 (m, 7H), 2.22 (s, 6H), 2.06 (q, 6.8 Hz, 12H), 1.53 (quintet, 7.3 Hz, 2H), 1.41-1.10 (58H), 0.90 (t, 6.8 Hz, 9H).

Example 48

Synthesis of Compound II-3

Compound II-3 was prepared according to method A from compound II-8 to yield 123 mg of colorless oil, 0.15 mmol, 41%). $^1$H NMR (400 MHz, CDCl$_3$) δ: 5.43-5.30 (m, 8H), 2.78 (t, 6.5 Hz, 4H), 2.35-2.24 (m, 5H), 2.22 (s, 6H), 2.15 (d, 5.5 Hz, 2H), 2.06 (q, 6.8 Hz, 8H), 1.52 (quintet, 7.3 Hz, 2H), 1.40-1.09 (65H), 0.92-0.87 (m, 12H).

Example 49

Synthesis of Compound II-5

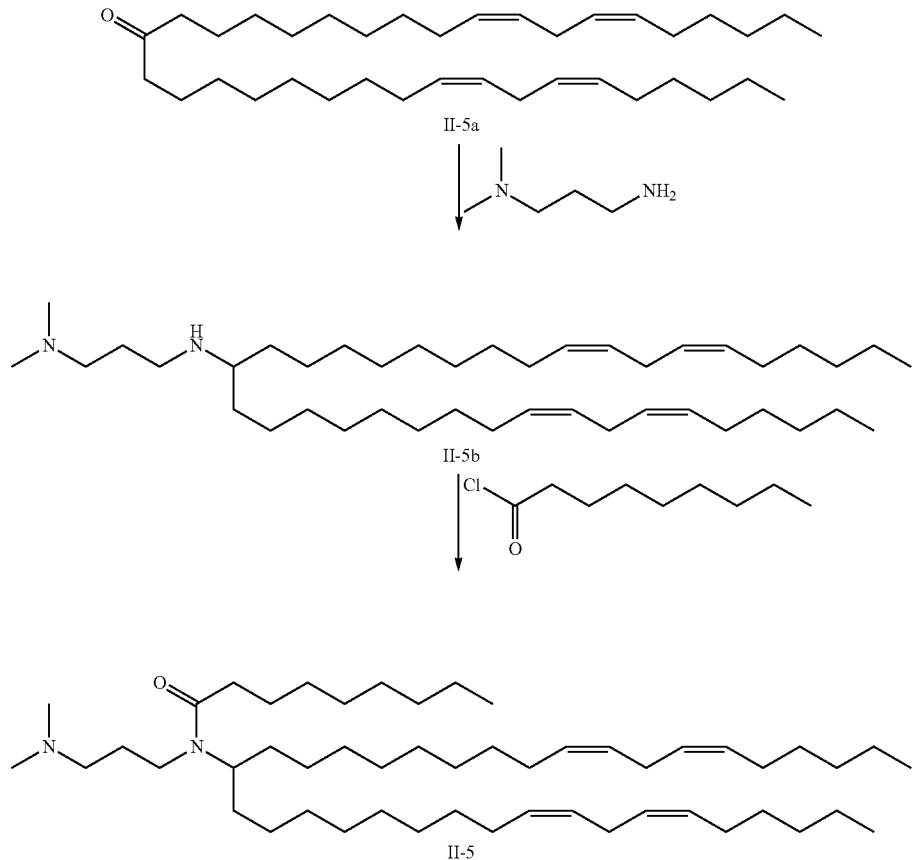

Compound II-5 was Prepared According to Method A as Follows:

Step 1

3-dimethylamine-1-propylamine (6 mmol, 612 mg) and the ketone II-5a (3.16 g, 6 mmol) were mixed in dichloroethane (25 mL) and then treated with sodium triacetoxyborohydride (8.49 mmol, 1.8 g) and AcOH (6 mmol, 0.36 g, 0.340 mL). The mixture was stirred at room temperature under an argon atmosphere for 2 days. The reaction mixture was quenched by adding 1 N NaOH (ca 20 mL), and the product was extracted with a mixture of hexane and ethyl acetate (ca 5%). The organic extract was washed with water/brine (1:1), brine, dried over $Na_2SO_4$ and concentrated to give the desired product II-5b as yellow oil (3.55 g). The crude product was used for the next step without any further purification.

Step 2

A solution of nonanoyl chloride (212 mg, 1.2 mmol) in benzene (10 mL) was added via syringe to a solution of compound II-5b (600 mg, 0.978 mmol) and triethylamine (5 mmol, 0.7 mL, 5 eq) and DMAP (20 mg) in benzene (10 mL) at RT in 10 min. After addition, the mixture was then diluted with a mixture of hexane and ethyl acetate (ca 5%), washed with water, washed with brine, dried over sodium sulfate, filtered and concentrated. The crude product (0.77 g) was purified by gravity column chromatography on silica gel (230-400 mesh silica gel, 40 g, MeOH in chloroform, 0 to 4%). This gave the desired product 5 as a colorless oil (563 mg, 0.75 mmol, 76%). $^1$H NMR (400 MHz, $CDCl_3$) δ: 5.43-5.30 (m, 8H), 4.56-4.36 (br., 0.3H, due to slow isomerization about amide bond), 3.64 (quintet, 7 Hz, 0.7H), 3.12-3.09 (m, 2H), 2.78 (t, 6.4 Hz, 4H), 2.33-2.25 (m, 4H), 2.23, 2.22 (two sets of singlet, 6H), 2.06 (q-like, 6.8 Hz, 8H), 1.76-1.66 (m, 4H), 1.50-1.40 (m, 4H), 1.40-1.15 (46H), 0.90 (t, 6.7 Hz, 6H), 0.88 (t, 6.8 Hz, 3H).

Example 50

Synthesis of Compound II-6

Compound II-6 was prepared according to the general procedure A to yield 0.98 g of slightly yellow oil, 1.13 mmol, 58%. $^1$H NMR (400 MHz, $CDCl_3$) δ: 5.43-5.30 (m, 12H), 4.55-4.32 (br., 0.3H, due to slow isomerization about amide bond), 3.63 (quintet-like, 7 Hz, 0.7H), 3.15-3.09 (m, 2H), 2.78 (t, 6.4 Hz, 6H), 2.33-2.25 (m, 4H), 2.22, 2.23 (two sets of singlet, 6H), 2.06 (q-like, 6.8 Hz, 12H), 1.76-1.60 (m, 4H), 1.49-1.16 (54H), 0.90 (t-like, 6.8 Hz, 9H).

Example 51

Synthesis of Compound II-7

Compound II-7 was Prepared According to Method A as Follows:

To a solution of 2-ethylheptanoic acid (1.5 eq. 0.83 mmol, 130 mg) in benzene (6 mL) and DMF (5-10 μL) was added oxalyl chloride (5 eq, 2.8 mmol, 349 mg, 0.24 mL) at room temperature. The mixture was stirred at room temperature for 30 min and then heated at 60° C. for 2 h under argon atmosphere. The mixture was concentrated. The residue was taken up in benzene (6 mL) and concentrated again to remove any oxalyl chloride. The residual oil (light yellow) was taken in 4 mL of benzene and added via syringe to a solution of compound II-5b (1 eq., 0.55 mmol, 337 mg) and triethylamine (5 eq, 2.8 mmol, 283 mg, 390 uL) and DMAP (10 mg) in benzene (6 mL) at room temperature in 10 min. After addition, the resulting mixture was stirred at room temperature overnight. TLC showed that there was not much reaction. The reaction was concentrated and dried well and used in the following. The residue was taken up in DCM (20 mL). DMAP (200 mg, 1.64 mmol) was added, followed by addition of DCC (1.64 mmol, 338 mg). The mixture was stirred for 11 days and filtered. The filtrate was washed with 5% NaOH (100 mL). The organic phase was washed with brine, dried over sodium sulfate. Filtration and concentration gave light brown oil (0.89 g). The crude product (0.89 g) was purified by column chromatography on silica gel (0 to 4% MeOH in chloroform). This gave the desired product as a colorless oil (122 mg, 0.16 mmol, 29%). $^1$H NMR (400 MHz, $CDCl_3$) δ: 5.43-5.30 (m, 8H), 4.69-4.51 (very br., estimated 0.4H, due to slow isomerization about amide bond), 3.72 (quintet-like, 6.9 Hz, 0.6H), 3.19-3.09 (m, 2H), 2.78 (t, 6.4 Hz, 4H), 2.55 (quintet-like, 6.5 Hz, 0.5H), 2.42 (quintet-like, 6.5 Hz, 0.5H), 2.29 (q-like, but could be two overlap triplets, 6.9 Hz, 2H), 2.24, 2.23 (two sets of singlet, integration ratio is about 1:1, 6H), 2.09-2.02 (m, 8H), 1.77-1.58 (m, 4H), 1.55-1.15 (48H), 0.93-0.85 (m, 12H).

Example 52

Synthesis of Compound II-8

Compound II-8 was prepared according to the general procedure A to yield 0.39 g of colorless oil, 0.46 mmol, 56%. $^1$H NMR (400 MHz, $CDCl_3$) δ: 5.43-5.30 (m, 8H), 4.55-4.32 (very br., estimated 0.3H, due to slow isomerization about amide bond), 3.71 (quintet-like, 7 Hz, 0.7H), 3.17-3.08 (m, 2H), 2.78 (t, 6.4 Hz, 4H), 2.59 (quintet-like, 6.5 Hz, 0.5H), 2.46 (quintet-like, 6.5 Hz, 0.5H), 2.40 (t, 7 Hz, 1H), 2.31 (t, 7 Hz, 1H), 2.28, 2.25 (two sets of singlet, integration ratio is about 1:1, 6H), 2.09-2.02 (m, 8H), 1.79-1.69 (m, 2H), 1.66-1.57 (m, 2H), 1.55-1.16 (62H), 0.92-0.86 (m, 12H).

Example 53

Synthesis of Compound II-9

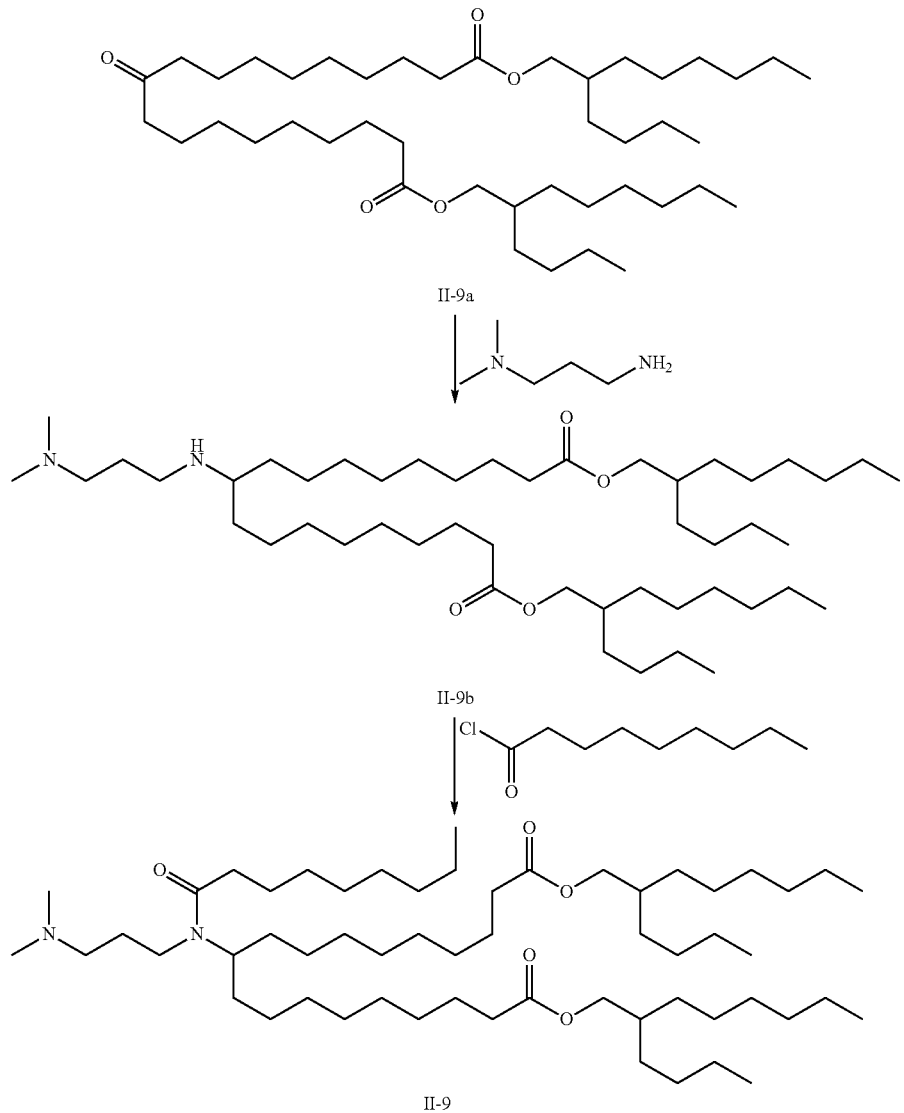

Compound II-9 was Prepared According to Method D as Follows:

Step 1

3-dimethylamine-1-propylamine (1 eq. 1.3 mmol, 133 mg, 163 µL; MW102.18, d 0.812) and the ketone II-9a (1 eq, 0.885 g, 1.3 mmol) were mixed in dichloroethane (8 mL) and then treated with sodium triacetoxyborohydride (1.4 eq, 1.82 mmol, 386 mg; MW 211.94) and AcOH (1 eq., 1.3 mmol, 78 mg, 74 µL, MW 60.05, d 1.06). The mixture was stirred at RT under an Ar atmosphere for 2 days. The reaction mixture was diluted with hexanes-EtOAc (9:1) and quenched by adding 0.1 N NaOH (20 mL). The organic phase was separated, washed with sat $NaHCO_3$, brine, dried over sodium sulfate, decanted and concentrated to give the desired product II-9b as a slightly yellow cloudy oil (1.07 g, 1.398 mmol).

Step 2

A solution of nonanoyl chloride (1.3 eq, 1.27 mmol, 225 mg) in benzene (10 mL) was added via syringe to a solution of the compound 9b from step 1 (0.75 g, 0.98 mmol) and triethylamine (5 eq, 4.90 mmol, 0.68 mL) and DMAP (20 mg) in benzene (10 mL) at RT in 10 min. After addition, the mixture was stirred at RT overnight. Methanol (5.5 mL) was added to remove excess acyl chloride. After 3 h, the mixture was filtered through a pad of silica gel (1.2 cm). Concentration gave a colorless oil (0.70 g). The crude product (0.70 g) was purified by flash dry column chromatography on silica gel (0 to 4% MeOH in chloroform). This yielded 457 mg of colorless oil, 0.50 mmol, 51%. $^1$H NMR (400 MHz, $CDCl_3$) δ: 4.54-4.36 (very br., estimated 0.3H, due to slow isomerization about amide bond), 3.977, 3.973 (two sets of doublets, 5.8 Hz, 4H), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 10H), 1.49-1.39 (m, 4H), 1.37-1.11 (62H), 0.92-0.86 (m, 15H).

Example 54

Synthesis of Compound II-10

Compound II-10 was prepared according to the general procedure D to yield 245 mg of colorless oil, 0.27 mmol, total yield 53% for 2 steps. $^1$H NMR (400 MHz, CDCl$_3$) δ: 4.87 (quintet-like, 6.3 Hz, 2H), 4.54-4.36 (very br., estimated 0.3H, due to slow isomerization about amide bond), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 8H), 1.55-1.39 (m, 12H), 1.37-1.11 (60H), 0.92-0.86 (m, 15H).

Example 55

Synthesis of Compound II-11

Compound II-11 was prepared according to the general procedure D to yield 239 mg of colorless oil, 0.26 mmol, total yield 52% for 2 steps. $^1$H NMR (400 MHz, CDCl$_3$) δ: 4.87 (quintet-like, 6.3 Hz, 2H), 4.54-4.36 (very br., estimated 0.3H, due to slow isomerization about amide bond), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 8H), 1.55-1.39 (m, 12H), 1.37-1.11 (62H), 0.92-0.86 (m, 15H).

Example 56

Synthesis of Compound II-12

Compound II-12 was prepared according to the general procedure D to yield 198 mg of colorless oil, 0.20 mmol, total yield 46% for 2 steps. $^1$H NMR (400 MHz, CDCl$_3$) δ: 4.54-4.36 (very br., estimated 0.3H, due to slow isomerization about amide bond), 3.974, 3.971 (two sets of doublets, 5.8 Hz, 4H), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 10H), 1.49-1.39 (m, 4H), 1.37-1.11 (76H), 0.92-0.86 (m, 15H).

Example 57

Synthesis of Compound II-13

Compound II-13 was prepared according to the general procedure A to yield 217 mg of colorless oil, 0.21 mmol, total yield 49% for 2 steps. $^1$H NMR (400 MHz, CDCl$_3$) δ: 4.54-4.36 (very br., estimated 0.3H, due to slow isomerization about amide bond), 3.973, 3.970 (two sets of doublets, 5.8 Hz, 4H), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 10H), 1.49-1.39 (m, 4H), 1.37-1.11 (78H), 0.92-0.86 (m, 15H).

Example 58

Synthesis of Compound II-14

Compound II-14 was prepared according to the general procedure A to yield 263 mg of colorless oil, 0.29 mmol, total yield 39% for 2 steps. $^1$H NMR (400 MHz, CDCl$_3$) δ: 4.54-4.36 (br., estimated 0.3H, due to slow isomerization about amide bond), 3.977, 3.973 (two sets of doublets, 5.8 Hz, 4H), 3.63 (quintet-like, 6.8 Hz, 0.7H), 3.17-3.10 (m, 2H), 2.53-2.43 (m, 6H), 2.34-2.26 (m, 6H), 1.83-1.71 (m, 6H), 1.70-1.57 (m, 8H), 1.49-1.38 (m, 4H), 1.37-1.11 (60H), 0.92-0.86 (m, 15H).

Example 59

Synthesis of Compound II-15

Compound II-15 was prepared according to the general procedure A to yield 234 mg of colorless oil, 0.25 mmol, total yield 34% for 2 steps. $^1$H NMR (400 MHz, CDCl$_3$) δ: 4.54-4.36 (br., estimated 0.3H, due to slow isomerization about amide bond), 3.977, 3.973 (two sets of doublets, 5.8 Hz, 4H), 3.63 (quintet-like, 6.8 Hz, 0.7H), 3.17-3.10 (m, 2H), 2.53-2.43 (m, 6H), 2.34-2.26 (m, 6H), 1.83-1.71 (m, 6H), 1.70-1.57 (m, 8H), 1.49-1.38 (m, 4H), 1.37-1.11 (62H), 0.92-0.86 (m, 15H).

Example 60

Synthesis of Compound II-16

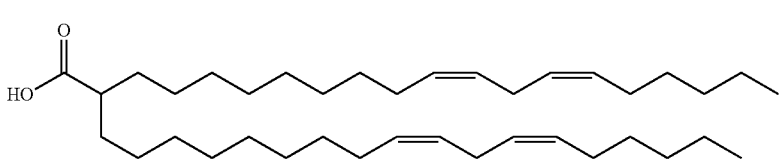

Chemical Formula: C$_{38}$H$_{68}$O$_2$
Molecular Weight: 556.95
018-19

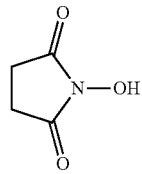

Chemical Formula: C$_4$H$_5$NO$_3$
Molecular Weight: 115.09
N-hydroxysuccinimide

DCC
DMAP
DCM

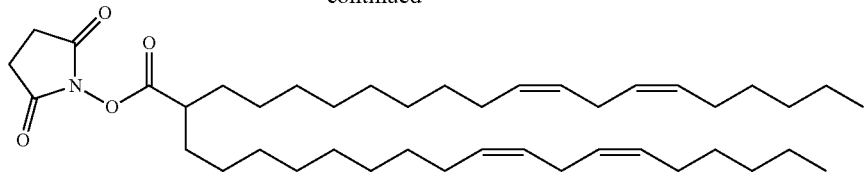

Chemical Formula: $C_{42}H_{71}NO_4$
Molecular Weight: 654.02
021-26A

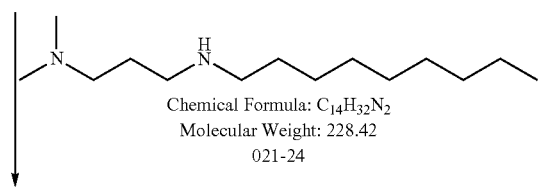

Chemical Formula: $C_{14}H_{32}N_2$
Molecular Weight: 228.42
021-24

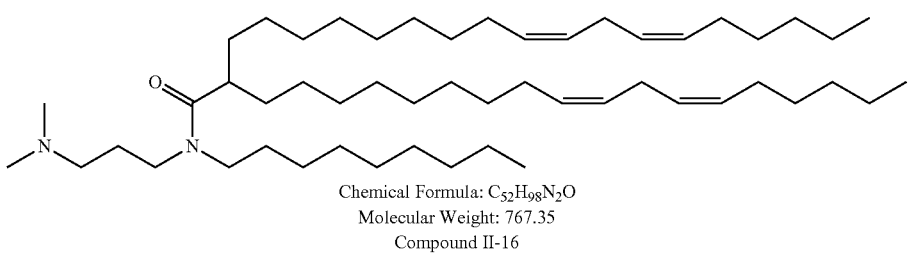

Chemical Formula: $C_{52}H_{98}N_2O$
Molecular Weight: 767.35
Compound II-16

Compound II-16 was Prepared According to Method B as Follows:

To a solution of the acid 018-19 (0.5 g, 0.90 mmol), N-hydroxysuccinimide (1.2 eq, 1.08 mmol, 124 mg) and DMAP (0.3 eq, 0.27 mmol, 33 mg) in DCM (20 mL) was added DCC (2 eq, 1.8 mmol, 371 mg). The resulting mixture was stirred at room temperature for 16 hours. The reaction mixture was then filtered and added into a solution of the amine 021-24 (1.26 mmol, 288 mg) in DCM (10 mL) and triethylamine (5 mmol, 696 μL). After 15 days, the mixture was concentrated. The residue was taken up in hexane/ethyl acetate/Et$_3$N (ca 9:1:0.3) and was filtered through a small pad of silica gel, washed with a mixture of hexane/ethyl acetate/Et$_3$N (ca 9:1:0.3). The filtrate was concentrated and a yellow oil was obtained (580 mg). The yellow oil was purified by column chromatography on silica gel (eluted with a gradient mixture of MeOH in Chloroform, 0 to 4.2%). This gave the desired product as a colorless oil (102 mg, 0.13 mmol, 14%). $^1$H NMR (400 MHz, CDCl$_3$) δ: 5.43-5.30 (m, 8H), 3.38-3.29 (m, 3H), 3.28-3.23 (m, 1H), 2.78 (t, 6.4 Hz, 4H), 2.56-2.47 (m, 1H), 2.30-2.24 (m, 2H), 2.23, 2.22 (two sets of singlet, 6H), 2.09-2.02 (m, 8H), 1.71 (quintet-like, 7.4 Hz, 2H), 1.66-1.48 (overlapped with water; estimated 4H), 1.47-1.18 (m, 50H), 0.92-0.86 (m, 9H).

Example 61

Synthesis of Compound II-24

Compound II-24 was prepared according to the general procedure A to yield 279 mg of slightly yellow oil, 0.29 mmol, total yield 44% for 2 steps. $^1$H NMR (400 MHz, CDCl$_3$) δ: 4.88 (quintet-like, 6.3 Hz, 3H), 3.62 (quintet-like, 6.8 Hz, 1H), 3.14-3.08 (m, 2H), 2.33-2.25 (m, 10H), 2.23, 2.22 (two sets of singlets, 6H), 1.76-1.58 (m, 10H), 1.52 (q-like, 6.7 Hz, 12H), 1.49-1.39 (m, 4H), 1.38-1.14 (50H), 0.89 (t-like, 18H).

Example 62

Synthesis of Compound II-35

Compound II-35 was prepared according to the general procedure A to yield 260 mg of slightly yellow oil, 0.29 mmol, total yield 33% for 2 steps. $^1$H NMR (400 MHz, CDCl$_3$) δ: 4.66-4.52 (very br., estimated 0.3H, due to slow isomerization about amide bond), 3.977, 3.973 (two sets of doublets, 5.8 Hz, 4H), 3.71 (quintet-like, 6.8 Hz, 0.7H), 3.19-3.09 (m, 2H), 2.54, 2.42 (two sets of quintet-like, 6.8 Hz, integration ratio is about 1:1.2, 1H), 2.33-2.25 (m, 6H), 2.24, 2.22 (two sets of singlet, 6H), 1.77-1.11 (74H), 0.93-0.85 (m, 18H).

Example 63

Synthesis of Compound II-17

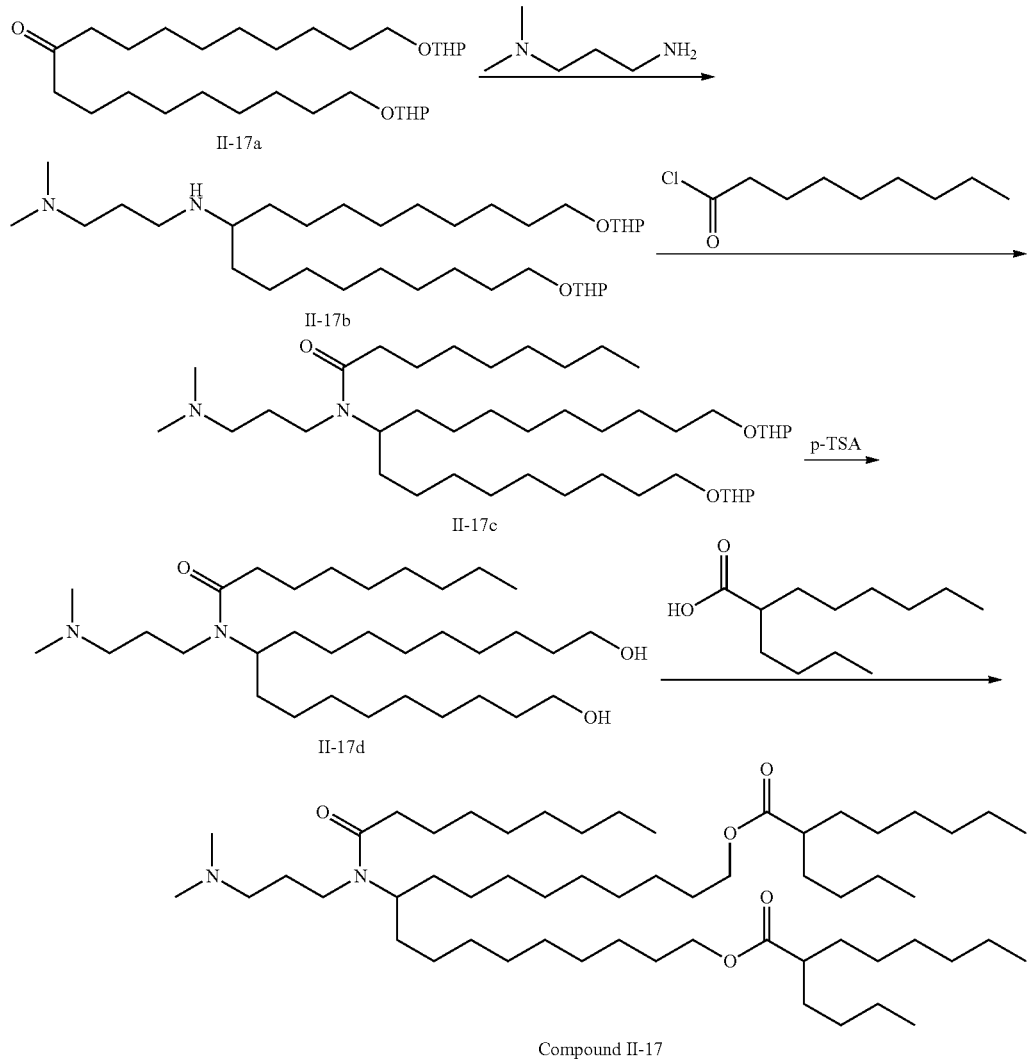

Compound II-17 was Prepared According to Method C as Follows:

Step 1

3-dimethylamino-1-propylamine (1 eq. 4.14 mmol, 423 mg, 521 µL) and ketone II-17a (1 eq., 2.0 g, 4.14 mmol) were mixed in DCE (30 mL) and then treated with sodium triacetoxyborohydride (1.4 eq., 5.80 mmol, 1.229 g) and AcOH (1 eq., 4.14 mmol, 249 mg, 235 The mixture was stirred at room temperature under argon atmosphere for 2 days.

The reaction mixture was diluted with a mixture of hexanes and ethyl acetate (9:1, 200 mL) and quenched by adding dilute NaOH solution (0.1 N, 270 mL). The two phases were separated. The organic phase was washed with sat NaHCO₃, brine, dried over sodium sulfate and filtered through a pad of silica gel. The pad was washed with 200 mL of a mixture of hexane and EtOAc (9:1). Then the pad was washed 200 mL of a mixture of DCM/MeOH/Et3N (85:15:1). The DCM/MeOH/Et3N washing was concentrated to give the desired product (II-17b) as a colorless oil (1.749 g, 3.07 mmol, 74%).

Step 2

A solution of nonanoyl chloride (0.333 mL) in benzene (10 mL) was added to a solution of compound II-17b (0.75 g) and triethylamine (0.92 mL) and DMAP (20 mg) in benzene (20 mL) at room temperature. The mixture was stirred at room temperature overnight. MeOH (1 mL) was added and the mixture continued to stir for 2 hours. The reaction mixture was filtered through a pad of silica gel. Concentration of the filtrate gave the desired product (II-17c) as a yellow oil (0.945 g).

Step 3

To a flask containing 17c (0.945 g, 1.33 mmol and EtOH (25 mL) was added p-toluenesulfonic acid hydrate (1.33 mmol, 253 mg) at room temperature. The resulting mixture was stirred overnight at RT. The reaction mixture was heated at 85° C. for 2 hours. More PTSA (160 mg) was added and the reaction mixture continued to heat at 75° C. overnight. The mixture was concentrated. The residue was taken up in DCM and washed with dilute NH₄OH solution. The organic phase was washed with a mixture of sat sodium bicarbonate and brine; dried over sodium sulfate. Concentration gave the desired product (II-17d) as a slightly yellow viscous oil (0.799 g, 1.47 mmol). The crude product was purified by silica gel column chromatography (0 to 15% methanol in DCM with trace of triethlyamine). This gave II-17d as a colorless oil (647 mg, 1.20 mmol, 90%).

Step 4

To a solution of II-17d (216 mg, 0.40 mmol), 2-butyloctanoic acid (5 eq, 2 mmol, 401 mg), and 4-dimethylaminopyridine (DMAP) (5.5 eq. 2.2 mmol, 269 mg) in dichloromethane (20 mL) was added DCC (5.5 eq, 2.2 mmol, 454 mg). After being stirred over for 4 days, 3 mL of MeOH was added. The mixture continued to stir for another 16 h. The mixture was filtered and the filtrate was concentrated to dryness. The crude product was purified by gravity column chromatography on silica gel (MeOH in DCM, 0 to 6%). This gave the desired compound II-17 as a slightly yellow oil (colorless oil, 175 mg, 0.19 mmol, 48%). $^1$H NMR (400 MHz, CDCl$_3$) δ: 4.07, 4.06 (two sets of triplets, 6.7 Hz, 4H), 3.64 (quintet-like, 6.8 Hz, 1H), 3.21-3.09 (two sets of multiplets, 2H), 3.00-2.37 (br. 6H), 2.36-2.20 (m, 6H), 2.05-1.85 (m, 2H), 1.79-1.53 (m, 10H), 1.52-1.39 (m, 8H), 1.37-1.03 (58H), 0.91-0.86 (m, 15H).

Example 64

Synthesis of Compound II-36

Compound II-36 was prepared according to the general procedure C to yield 156 mg of colorless oil, 0.15 mmol, 38% for the last step. $^1$H NMR (400 MHz, CDCl$_3$) δ: 4.07 (triplets, 6.7 Hz, 4H), 3.65 (quintet-like, 6.8 Hz, 1H), 3.21 (t-like, 6.8 Hz, 2H), 3.10-3.03 (br. 2H), 2.79, 2.78 (two sets of singlet, 6H), 2.35-2.28 (m, 4H), 2.09 (quintet-like, 7.5 Hz, 2H), 1.67-1.54 (m, 10H), 1.54-1.38 (m, 8H), 1.38-1.03 (74H), 0.91-0.86 (m, 15H).

Example 65

Synthesis of Compound II-37

Compound II-37 was prepared according to the general procedure A to yield 397 mg of colorless oil, 0.49 mmol, total yield 60% for 2 steps. $^1$H NMR (400 MHz, CDCl$_3$) δ: 5.43-5.30 (m, 8H), 4.13 (q, 7.1 Hz, 2H), 4.56-4.34 (br. 0.3H), 3.63 (quintet-like, 6.9 Hz, 0.7H), 3.15-3.08 (m, 2H), 2.78 (t-like, 6.4 Hz, 4H), 2.39-2.21 (m, 12H), 2.06 (q-like, 6.9 Hz, 8H), 1.79-1.55 (m, 6H), 1.50-1.40 (m, 4H), 1.40-1.15 (m, 45H), 0.90 (t-like, 6.8 Hz, 6H).

Example 66

Synthesis of Compound II-38

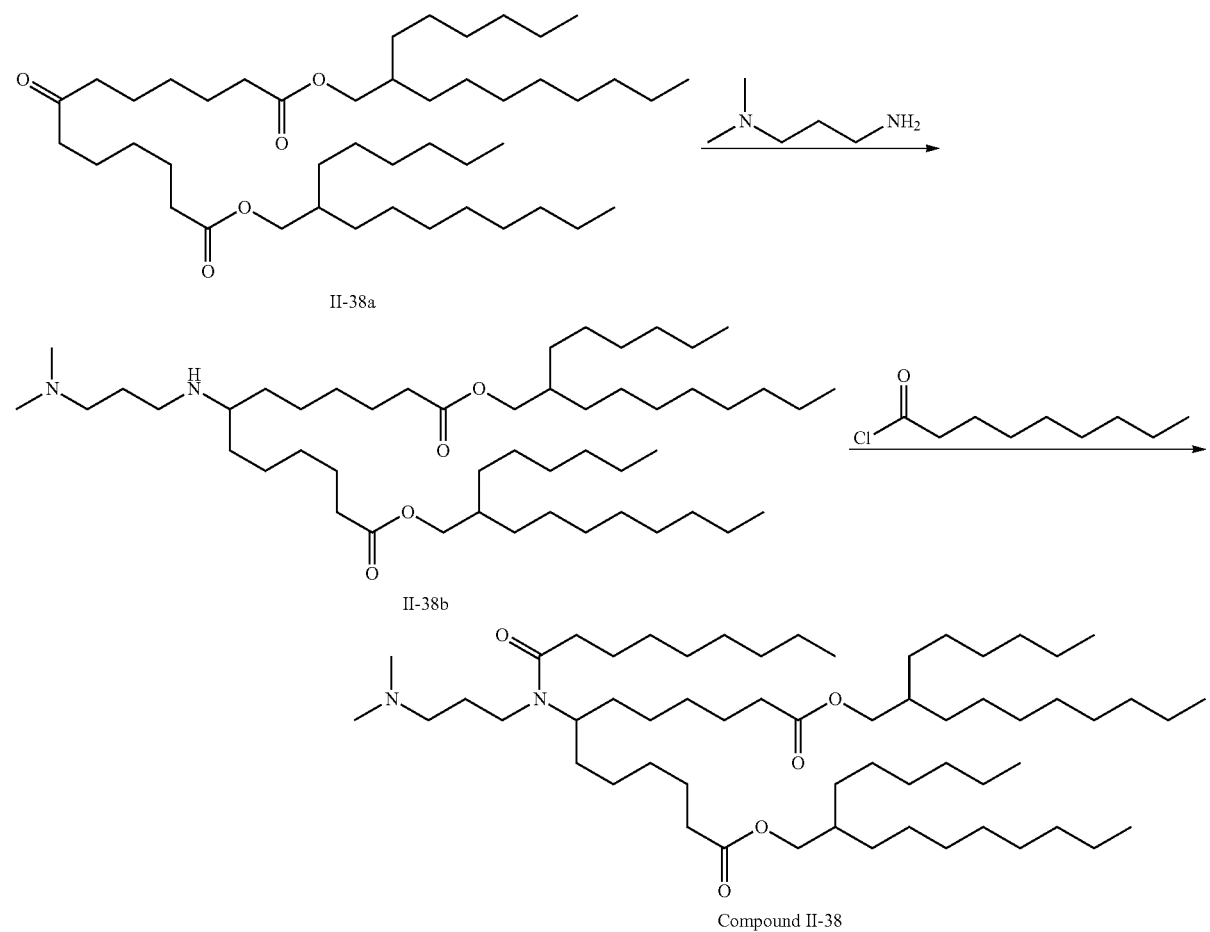

Compound II-38

Compound II-38 was Prepared According to Method A as Follows:

Step 1

To a solution of II-38a (1 eq., 1.266 g, 1.79 mmol) in DCE (15 mL) was added 3-dimethylamino-1-propylamine (1 eq. 1.79 mmol, 183 mg, 225 µL), followed by addition of sodium triacetoxyborohydride (1.4 eq., 2.51 mmol, 531 mg) and AcOH (1 eq., 1.79 mmol, 107 mg, 101 µL). The mixture was stirred at room temperature under argon atmosphere for 3 days.

The residue was diluted with hexanes-EtOAc (9:1, 150 mL) and washed with dilute NaOH solution (0.12 N, 100 mL), sat NaHCO$_3$, brine and dried over sodium sulfate. The organic phase was filtered through a pad of silica gel. The pad was washed with 200 mL of a mixture of hexane and EtOAc (9:1). Then the pad was washed with 200 mL of a mixture of DCM/MeOH/Et$_3$N (85:15:1). The DCM/MeOH/Et$_3$N washing was concentrated and dried on high vacuum line to give the desired product (II-38b) as a colorless oil (1.1 g, 1.38 mmol, 77%).

Step 2

A solution of nonanoyl chloride (1.5 eq., 0.68 mmol, 120 mg) in benzene (5 mL) was added to a solution of II-38b (0.45 mmol, 360 mg) and triethylamine (5 eq, 2.25 mmol, 228 mg, 314 µL) and DMAP (10 mg) in benzene (10 mL) at room temperature in 2 min under argon atmosphere. After addition, the mixture was stirred at room temperature overnight. MeOH (1 mL) was added and the mixture continued to stir 2 h. The crude was filtered through a pad of silica gel. The filtrate was concentrated. The residue (457 mg) was purified by flash column chromatography on silica gel (230-400 mesh silica gel, 40 g, MeOH in chloroform, 0 to 4.6%). This gave the desired product, compound II-38 as a colorless oil (410 mg, 0.44 mmol, 98%). $^1$H NMR (400 MHz, CDCl$_3$) δ: 4.61-4.35 (br., estimated 0.4H, due to slow isomerization about amide bond), 3.974, 3.964 (two sets of doublets, 5.7 Hz, 4H), 3.64 (quintet-like, 7.0 Hz, 0.6H), 3.14-3.08 (m, 2H), 2.34-2.25 (m, 8H), 2.23 (broad s, 6H), 1.77-1.58 (m, 10H), 1.53-1.39 (m, 4H), 1.37-1.15 (66H), 0.92-0.86 (m, 15H).

Example 67

Synthesis of Compound II-39

Compound II-39 was prepared according to the general procedure A to yield 370 mg of colorless oil, 0.40 mmol, total yield 69% for 2 steps. $^1$H NMR (400 MHz, CDCl$_3$) δ: 4.61-4.35 (br., estimated 0.4H, due to slow isomerization about amide bond), 3.974, 3.964 (two sets of doublets, 5.7 Hz, 4H), 3.64 (quintet-like, 7.0 Hz, 0.6H), 3.14-3.08 (m, 2H), 2.34-2.25 (m, 8H), 2.230, 2.221 (two sets of singlet, 6H), 1.75-1.58 (m, 10H), 1.51-1.39 (m, 4H), 1.37-1.15 (64H), 0.92-0.86 (m, 15H).

Example 68

Synthesis of Compound II-40

Compound II-40 was prepared according to the general procedure A to yield 382 mg of colorless oil, 0.39 mmol, total yield 68% for 2 steps. $^1$H NMR (400 MHz, CDCl$_3$) δ: 4.60-4.35 (br., estimated 0.3H, due to slow isomerization about amide bond), 4.13 (q, 7.2 Hz, 2H), 3.973, 3.964 (two sets of doublets, 5.7 Hz, 4H), 3.63 (quintet-like, 7.0 Hz, 0.7H), 3.14-3.08 (m, 2H), 2.34-2.25 (m, 10H), 2.229, 2.220 (two sets of singlet, 6H), 1.75-1.58 (m, 12H), 1.51-1.39 (m, 4H), 1.37-1.15 (64H), 0.89 (t-like, 7.8 Hz, 12H).

Example 68

Synthesis of Compound II-41

Compound II-41 was prepared according to the general procedure A to yield 309 mg of colorless oil, 0.30 mmol, total yield 73% for 2 steps. $^1$H NMR (400 MHz, CDCl$_3$) δ: 4.60-4.35 (br., estimated 0.3H, due to slow isomerization about amide bond), 3.972, 3.962 (two sets of doublets, 5.7 Hz, 4H), 3.64 (quintet-like, 7.1 Hz, 0.7H), 3.14-3.08 (m, 2H), 2.34-2.25 (m, 8H), 2.23, 2.22 (two sets of singlet, 6H), 1.75-1.58 (m, 10H), 1.51-1.39 (m, 4H), 1.35-1.21 (82H), 0.92-0.86 (m, 15H).

Example 70

Synthesis of Compound II-42

Compound II-42 was prepared according to the general procedure A to yield 235 mg of colorless oil, 0.23 mmol, total yield 56% for 2 steps. $^1$H NMR (400 MHz, CDCl$_3$) δ: 4.75-4.49 (br., estimated 0.4H, due to slow isomerization about amide bond), 3.97, 3.96 (two sets of doublets, 5.3 Hz, 4H), 3.72 (quintet-like, 7 Hz, 0.6H), 3.21-3.05 (m, 2H), 2.53, 2.42 (two sets of quintet-like, 6.6 Hz, integration ratio is about 1:1.7, 1H), 2.32-2.25 (m, 6H), 2.24, 2.22 (two sets of singlet, 6H), 1.78-1.56 (m, 10H), 1.53-1.39 (m, 6H), 1.38-1.17 (76H), 0.93-0.85 (m, 18H).

Example 71

Synthesis of Compound II-43

Compound II-43 was prepared according to the general procedure C to yield 187 mg of colorless oil, 0.23 mmol, 57% for the last step. $^1$H NMR (400 MHz, CDCl$_3$) δ: 4.077, 4.071 (two sets of triplets, 6.7 Hz, 4H), 4.56-4.34 (br. 0.3H), 3.64 (quintet-like, 6.9 Hz, 0.7H), 3.15-3.09 (m, 2H), 2.34-2.24 (m, 6H), 2.234-2.224 (two sets of singlet, 6H), 1.76-1.58 (m, 10H), 1.55-1.39 (m, 8H), 1.39-1.10 (48H), 0.92-0.86 (m, 15H).

Example 72

Synthesis of Compound II-44

Compound II-44 was prepared according to the general procedure A to yield 260 mg of colorless oil, 0.22 mmol, total yield 53% for 2 steps. $^1$H NMR (400 MHz, CDCl$_3$) δ: 4.59-4.35 (br., estimated 0.3H, due to slow isomerization about amide bond), 4.03-3.95 (m, 6H), 3.63 (quintet-like, 6.9 Hz, 0.7H), 3.14-3.08 (m, 2H), 2.33-2.24 (m, 10H), 2.229, 2.221 (two sets of singlet, 6H), 1.75-1.57 (m, 12H), 1.51-1.40 (m, 4H), 1.40-1.08 (87H), 0.92-0.86 (m, 18H).

Example 73

Synthesis of 6-(2'-hexyldecanoyloxy)hexan-1-al

A solution of hexan-1,6-diol (27.6 g) in methylene chloride (475 mL) was treated with 2-hexyldecanoic acid (19.8 g), DCC (18.2 g) and DMAP (11.3 g). The solution was stirred for three days. The reaction mixture was filtered and hexane (500 mL) added to the filtrate. The mixture was stirred and the precipitates allowed to settle out. The supernatant was decanted and washed with dilute hydrochloric acid. The organic phase was dried over anhydrous magnesium sulfate, filtered and the solvent removed, yielding 30 g of crude product.

The crude product dissolved in methylene chloride (200 mL) and treated with pyridinium chlorochromate (15 g) for two hours. Diethyl ether (600 mL) was added and the supernatant filtered through a silica gel bed. The solvent was removed from the filtrate and resultant oil dissolved in hexane. The suspension was filtered through a silica gel plug and the solvent removed. The residue was passed down a silica gel column (80 g) using hexane, followed by methylene chloride, as the eluent. 6-(2'-hexyldecanoyloxy)hexan-1-al (24 g) was obtained as a colorless oil.

Example 74

Synthesis of 4-(2'-hexyldecanoyloxy)butan-1-al

A solution of butan-1,4-diol (12.5 g) in methylene chloride (200 mL) was treated with 2-hexyldecanoic acid (9.2 g), DCC (8.8 g) and DMAP (4.9 g). The solution was stirred overnight. The reaction mixture was filtered and the solvent removed. The residue was dissolved in methylene chloride and washed with dilute hydrochloric acid. The organic phase was dried over anhydrous magnesium sulfate, filtered through a silica gel bed, and the solvent removed.

The crude product was dissolved in methylene chloride (150 mL) and treated with pyridinium chlorochromate (6 g) for one hour. Diethyl ether (450 mL) was added and the supernatant filtered through a silica gel bed. The solvent was removed from the filtrate and resultant oil dissolved in hexane. The suspension was filtered through a silica gel bed and the solvent removed, yielding 4-(2'-hexyldecanoyloxy)butan-1-al (11 g) was obtained as a colorless oil.

Example 75

Synthesis of Compound III-1

A solution of 6-(2'-hexyldecanoyloxy)hexan-1-al (3.0 g), acetic acid (0.21 g) and ethanolamine (0.14 g) in methylene chloride (50 mL) was treated with sodium triacetoxyborohydride (1.4 g) overnight. The solution was washed with dilute aqueous sodium hydroxide solution. The organic phase was dried over anhydrous magnesium sulfate, filtered and the solvent removed. The residue was passed down a silica gel column using a methanol/methylene chloride (0-8/100-92%) gradient, yielding compound III-1 as colorless oil (0.63 g).

Example 76

Synthesis of Compound III-2

A solution of 6-(2'-hexyldecanoyloxy)hexan-1-al (3.0 g), acetic acid (0.33 g) and 3-aminopropan-1-ol (0.17 g) in methylene chloride (20 mL) was treated with sodium triacetoxyborohydride (1.3 g) for one hour. The solution was washed with dilute aqueous sodium hydroxide solution. The organic phase was dried over anhydrous magnesium sulfate, filtered and the solvent removed. The residue was passed down a silica gel column using a methanol/methylene chloride (0-8/100-92%) gradient, yielding compound III-2 as colorless oil (1.1 g).

Example 77

Synthesis of Compound III-3

A solution of 6-(2'-hexyldecanoyloxy)hexan-1-al (2.4 g), acetic acid (0.33 g) and 4-aminobutan-1-ol (0.23 g) in methylene chloride (20 mL) was treated with sodium triacetoxyborohydride (1.3 g) for two hours. The solution was washed with aqueous sodium bicarbonate solution. The organic phase was dried over anhydrous magnesium sulfate, filtered and the solvent removed. The residue was passed down a silica gel column using a methanol/methylene chloride (0-8/100-92%) gradient, yielding compound III-3 as colorless oil (0.4 g).

Example 78

Synthesis of Compound III-4

A solution of 4-(2'-hexyldecanoyloxy)butan-1-al (2.4 g), acetic acid (0.30 g) and 4-aminobutan-1-ol (0.22 g) in methylene chloride (20 mL) was treated with sodium triacetoxyborohydride (1.3 g) for two hours. The solution was washed with dilute aqueous sodium hydroxide solution. The organic phase was dried over anhydrous magnesium sulfate, filtered and the solvent removed. The residue was passed down a silica gel column using a methanol/methylene chloride (0-8/100-92%) gradient. Partially purified fractions were passed down a second column using an acetic acid/methanol/methylene chloride (2-0/0-10/98-90%) gradient. Pure fractions were washed with aqueous sodium bicarbonate solution, yielding compound III-4 as colorless oil (0.9 g)

Example 79

Synthesis of Compound III-5

A solution of 4-(2'-hexyldecanoyloxy)butan-1-al (2.4 g), acetic acid (0.31 g) and 3-aminopropan-1-ol (0.17 g) in methylene chloride (20 mL) was treated with sodium triacetoxyborohydride (1.4 g) for one hour. The solution was washed with aqueous sodium bicarbonate solution. The organic phase was dried over anhydrous magnesium sulfate, filtered and the solvent removed. The residue was passed down a silica gel column using a methanol/methylene chloride (0-8/100-92%) gradient. Partially purified fractions were passed down a second column using an acetic acid/methanol/methylene chloride (2-0/0-8/98-92%) gradient. Pure fractions were washed with aqueous sodium bicarbonate solution, yielding compound III-5 as a colorless oil (0.57 g).

Example 80

Synthesis of Compound III-6

A solution of 4-(2'-hexyldecanoyloxy)butan-1-al (2.4 g), acetic acid (0.30 g) and ethanolamine (0.14 g) in methylene chloride (20 mL) was treated with sodium triacetoxyborohydride (1.3 g) for two hours. The solution was washed with aqueous sodium hydrogen carbonate solution. The organic phase was dried over anhydrous magnesium sulfate, filtered and the solvent removed. The residue was passed down a silica gel column using a methanol/methylene chloride (0-10/100-90%) gradient. Partially purified fractions were passed down a second column using an acetic acid/methanol/methylene chloride (2-0/0-9/98-92%) gradient. Pure fractions were washed with aqueous sodium bicarbonate solution, yielding compound III-6 as colorless oil (0.2 g).

Example 81

Synthesis of Compound III-7

A solution of 6-(2'-hexyldecanoyloxy)hexan-1-al (2.4 g), acetic acid (0.14 g) and 5-aminopentan-1-ol (0.24 g) in methylene chloride (20 mL) was treated with sodium triacetoxyborohydride (1.3 g) for two hours. The solution was washed with aqueous sodium hydrogen carbonate solution. The organic phase was dried over anhydrous magnesium sulfate, filtered and the solvent removed. The residue was passed down a silica gel column using a methanol/methylene chloride (0-8/100-92%) gradient, yielding compound III-7 as colorless oil (0.5 g).

Example 82

Synthesis of Compound III-8

A solution of 6-(2'-hexyldecanoyloxy)hexan-1-al (2.4 g), acetic acid (0.17 g) and 6-aminohexan-1-ol (0.26 g) in methylene chloride (20 mL) was treated with sodium triacetoxyborohydride (1.3 g) for two hours. The solution was washed with aqueous sodium hydrogen carbonate solution. The organic phase was dried over anhydrous magnesium sulfate, filtered and the solvent removed. The residue was passed down a silica gel column using a methanol/methylene chloride (0-8/100-92%) gradient, yielding compound III-8 as colorless oil (0.5 g).

Example 83

Synthesis of Compound III-9

A solution of 6-(2'-hexyldecanoyloxy)hexan-1-al (2.4 g) and trans-2-aminocyclohexanol hydrochloride (0.35 g) in methylene chloride (10 mL)/tetrahydrofuran (10 mL) was treated with sodium triacetoxyborohydride (1.3 g) for 1.5 hours. The solution was washed with aqueous sodium hydrogen carbonate solution. The organic phase was dried over anhydrous magnesium sulfate, filtered and the solvent removed. The residue was passed down a silica gel column using a methanol/methylene chloride (0-8/100-92%) gradient, yielding compound III-9 as colorless oil (0.6 g).

Example 84

Synthesis of Compound III-10

To a solution of 2-aminoethanol (106 mg, 1.75 mmol) in anhydrous THF (15 mL), 2-octyldodecyl 6-bromohexanoate (2 eq, 1.66 g, 3.5 mmol), potassium carbonate (2 eq, 3.5 mmol, 477 mg,) and cesium carbonate (0.3 eq, 0.525 mmol, 171 mg,) were added and was heated at 63° C. (oil bath) for 16 h. Trace of tetrabutylammonium iodide was added to the mixture and the mixture was heated to reflux for another 4 days. The solvent was evaporated under reduced pressure and the residue was taken in a mixture of hexanes and ethyl acetate (ca 9:1) and washed with water and brine. The organic layer was separated and dried over anhydrous sodium sulfate, filtered and evaporated under reduced to obtain an oil (1.6 g). The residue (1.6 g) was purified by column chromatography on silica gel (MeOH in chloroform, 0 to 4%). This gave compound III-10 as colorless oil (700 mg, 0.82 mmol, 47%).

Example 85

Synthesis of Compound III-11

To a solution of 2-aminoethanol (116 mg, 1.9 mmol, 115 µL) in 15 mL of anhydrous THF, 2-hexyldecyl 6-bromohexanoate (1.9 eq, 1.52 g, 3.62 mmol), potassium carbonate (1.9 eq, 3.62 mmol, 500 mg), cesium carbonate (0.3 eq, 0.57 mmol, 186 mg,) and sodium iodide (10 mg) were added and was heated to reflux for 6 days under argon. The solvent was evaporated under reduced pressure and the residue was taken up in hexanes and washed with water and brine. The organic layer was separated, dried over anhydrous sodium sulfate, filtered and evaporated under reduced pressure to obtain colorless oil. The crude product was purified by flash column chromatography on silica gel (MeOH in chloroform, 0 to 4%) to yield compound III-11 as colorless oil (936 mg, 1.27 mmol, 70%).

Example 86

Synthesis of Compound II-12

Compound III-12 was prepared in a manner analogous to the procedure for Compound III-11 to yield 538 mg of colorless oil, 0.86 mmol, 57%.

Example 87

Synthesis of Compound III-13

To a solution of 2-aminoethanol (171 mg, 2.81 mmol, 169 µL) in anhydrous THF (30 mL), 2-octyldodecyl 4-bromobutyrate (1.9 eq, 2.386 g, 5.33 mmol), potassium carbonate (1.9 eq, 5.33 mmol, 736 mg), cesium carbonate (0.3 eq, 0.84 mmol, 275 mg) and sodium iodide (10 mg) were added and was heated to reflux for 16 h under argon. TLC (Hexane/Ethyl acetate=9:1, CHCl$_3$/MeOH=19:1) showed that significant amount of 2-octyl-1-dodecanol was produced. The mixture was cooled and filtered. The filtrate was concentrated and the residue was dissolved in 2-octyl-1-dodecanol (2.1 g). A few beads of 4 Å molecular sieves and N,N-diisopropylethylamine (1.9 eq, 5.33 mmol, 683 mg, 0.92 mL) was added. The mixture was sealed and heated at 62° C. for another 4 days. The reaction mixture was cooled. Hexane was added. The hexane solution was decanted and concentrated to dryness. The residue was purified by column chromatography on silica gel (MeOH in chloroform, 0 to 4%) to yield compound III-13 as colorless oil (282 mg, 0.35 mmol, 13%).

Example 88

Synthesis of Compound III-14

To a solution of heptadecan-9-yl 6-bromohexanoate (2 eq, 1.13 g, 2.61 mmol) in anhydrous THF (15 mL), was added 2-aminoethanol (1 eq, 1.31 mmol, 79.7 mg), potassium carbonate (2 eq, 2.61 mmol, 361 mg,), cesium carbonate (0.3 eq, 0.39 mmol, 128 mg) and sodium iodide (6 mg). The mixture was heated to reflux for 7 days under Ar. The solvent was evaporated under reduced pressure and the residue was taken in hexanes/ethyl acetate (ca 10%) and washed with water and brine. The organic layer was separated and dried over anhydrous sodium sulfate, filtered and evaporated under reduced to obtain an oil (1 g). The residue (1 g) was purified by gravity column chromatography on silica gel (MeOH in DCM, 0 to 4%). This gave compound III-14 as colorless oil (757 mg 0.99 mmol, 76%).

Example 89

Synthesis of Compound III-15

To a solution of 2-hexyldecyl 5-bromopentanoate (2 eq, 1.22 g, 3 mmol) in 15 ml of anhydrous THF (opened for 2 month), was added 4-amino-1-butanol (1 eq, 1.5 mmol, 0.134 mg, 139 potassium carbonate (2 eq, 3 mmol, 415 mg), cesium carbonate (0.3 eq, 0.45 mmol, 146 mg) and sodium iodide (6 mg). The mixture was heated to reflux for 6 days under argon.

Example 90

Synthesis of a Representative PEG Lipid

Pegylated lipid 90-6 ("PEG-DMA") was prepared according to the above reaction scheme, wherein n approximates the center of the range of ethylene oxide repeating units in the pegylated lipid.

Synthesis of 90-1 and 90-2

To a solution of myristic acid (6 g, 26 mmol) in toluene (50 mL) was added oxalyl chloride (39 mmol, 1.5 eq, 5 g) at room temperature. After the resulting mixture was heated at 70° C. for 2 hours, the mixture was concentrated. The residue was taken up in toluene and concentrated again. The residual oil was added via a syringe to a concentrated ammonia solution (20 mL) at 10° C. The reaction mixture was filtered and washed with water. The white solid was dried in vacuo. The desired product was obtained as a white solid (3.47 g, 15 mmol, 58.7%).

Synthesis of 90-3

To suspension of 90-2 (3.47 g, 15 mmol) in THF (70 mL) was added in portions of lithium aluminum hydride (1.14 g,

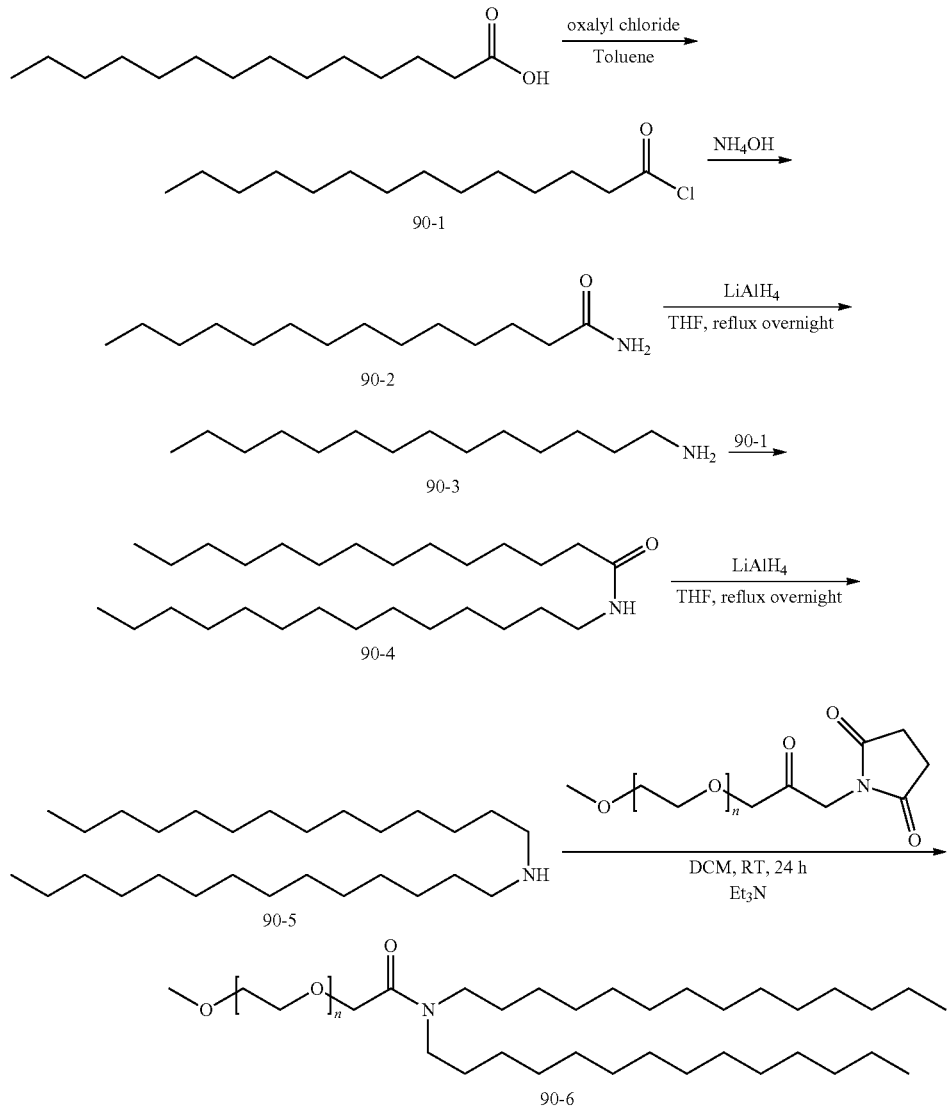

30 mmol) at room temperature during 30 min period of time. Then the mixture was heated to reflux gently (oil bath at 65° C.) overnight. The mixture was cooled to 5° C. and sodium sulfate 9 hydrate was added. The mixture was stirred for 2 hours, filtered through a layer of celite, washed with 15% of MeOH in DCM (200 mL). The filtrate and washings were combined and concentrated. The residual solid was dried in vacuo. The desired product was obtained as a white solid (2.86 13.4 mmol, 89.5%).

Synthesis of 90-4

To a solution of myristic acid (3.86 g, 16.9 mmol) in benzene (40 mL) and DMF (1 drop) was added oxalyl chloride (25.35 mmol, 1.5 eq. 3.22 g) at room temperature. The mixture was stirred at room temperature for 1.5 hours. Heated at 60° C. for 30 min. The mixture was concentrated. The residue was taken up in toluene and concentrated again. The residual oil (light yellow) was taken in 20 mL of benzene and added via syringe to a solution of 90-3 (2.86 13.4 mmol) and triethylamine (3.53 mL, 1.5 eq) in benzene (40 mL) at 10° C. After addition, the resulting mixture was stirred at room temperature overnight. The reaction mixture was diluted with water and was adjusted to pH 6-7 with 20% $H_2SO_4$. The mixture was filtered and washed with water. A pale solid was obtained. The crude product was recrystallized from methanol. This gave the desired product as an off-white solid (5.65 g, 13 mmol, 100%).

Synthesis of 90-5

To suspension of 90-4 (5.65 g, 13 mmol) in THF (60 mL) was added in portions lithium aluminum hydride (0.99 g, 26 mmol) at room temperature during 30 min period of time. Then the mixture was heated to reflux gently overnight. The mixture was cooled to 0° C. and sodium sulfate 9 hydrate. The mixture was stirred for 2 hours, then filtered through a pad of celite and silica gel and washed with ether first. The filtrate turned cloudy and precipitation formed. Filtration gave a white solid. The solid was recrystallized from MeOH and a colorless crystalline solid (2.43 g).
The pad of celite and silica gel was then washed 5% of MeOH in DCM (400 mL) and then 10% of MeOH in DCM with 1% of triethylamine (300 mL). The fractions containing the desired product were combined and concentrated. A white solid was obtained. The solid was re-crystalized from MeOH and a colorless crystalline solid (0.79 g). The above two solids (2.43 g and 0.79 g) were combined and dried in vacuo (3.20 g, 60%). $^1$H NMR (CDCl$_3$ at 7.27 ppm) δ: 2.58 (t-like, 7.2 Hz, 4H), 1.52-1.44 (m, 4H), 1.33-1.24 (m, 44H), 0.89 (t-like, 6.6 Hz, 6H), 2.1-1.3 (very broad, 1H).

Synthesis of 90-6

To a solution of 92-5 (7 mmol, 2.87 g) and triethylamine (30 mmol, 4.18 mL) in DCM (100 mL) was added a solution of mPEG-NHS (from NOF, 5.0 mmol, 9.97 g, PEG MW approx. 2,000, n=about 45) in DCM (120 mL,). After 24 h the reaction solution was washed with water (300 mL). The aqueous phase was extracted twice with DCM (100 mL×2). DCM extracts were combined, washed with brine (100 mL). The organic phase was dried over sodium sulfate, filtered, concentrated partially. The concentrated solution (ca 300 mL) was cooled at ca −15° C. Filtration gave a white solid (1.030 g, the unreacted starting amine). To the filtration was added Et$_3$N (1.6 mmol, 0.222 mL, 4 eq) and acetic anhydride (1.6 mmol, 164 mg). The mixture was stirred at room temperature for 3 hours and then concentrated to a solid. The residual solid was purified by column chromatography on silica gel (0-8% methanol in DCM). This gave the desired product as a white solid (9.211 g). $^1$H NMR (CDCl$_3$ at 7.27 ppm) δ: 4.19 (s, 2H), 3.83-3.45 (m, 180200H), 3.38 (s, 3H), 3.28 (t-like, 7.6 Hz, 2H, CH$_2$N), 3.18 (t-like, 7.8 Hz, 2H, CH2N), 1.89 (s, 6.6H, water), 1.58-1.48 (m, 4H), 1.36-1.21 (m, 48-50H), 0.88 (t-like, 6.6 Hz, 6H).

Example 91

Determination of pK$_a$ of Formulated Lipids

As described elsewhere, the pKa of formulated cationic lipids is correlated with the effectiveness of LNPs for delivery of nucleic acids (see Jayaraman et al, Angewandte Chemie, International Edition (2012), 51(34), 8529-8533; Semple et al, Nature Biotechnology 28, 172-176 (2010)). A representative preferred range of pKa is ~5 to ~7. The pK$_a$ of each cationic lipid was determined in lipid nanoparticles using an assay based on fluorescence of 2-(p-toluidino)-6-napthalene sulfonic acid (TNS). Lipid nanoparticles comprising of cationic lipid/DSPC/cholesterol/PEG-lipid (50/10/38.5/1.5 mol %) or a cationic lipid alone in PBS at a concentration of 0.4 mM total lipid are prepared using the in-line process as described in Example 1. TNS was prepared as a 100 µM stock solution in distilled water. Vesicles were diluted to 24 µM lipid in 2 mL of buffered solutions containing 10 mM HEPES, 10 mM MES, 10 mM ammonium acetate, 130 mM NaCl, where the pH ranged from 2.5 to 11. An aliquot of the TNS solution was added to give a final concentration of 1 µM and following vortex mixing fluorescence intensity was measured at room temperature in a SLM Aminco Series 2 Luminescence Spectrophotometer using excitation and emission wavelengths of 321 nm and 445 nm. A sigmoidal best fit analysis was applied to the fluorescence data and the pK$_a$ was measured as the pH giving rise to half-maximal fluorescence intensity.

Example 92

Preparation of LNPs Comprising First and Second Cationic Lipids

LNPs comprising two different cationic lipids were prepared using the general procedures set forth in Example 1. The LNPs included 0, 5, 10 or 15 mole percent of a first cationic lipid (i.e., Cationic Lipid 1), while the second cationic lipid (i.e., Cationic Lipid 2) was maintained at 10 mol percent in each LNP. Table 10 summarizes the ratio of components in each LNP and their properties.

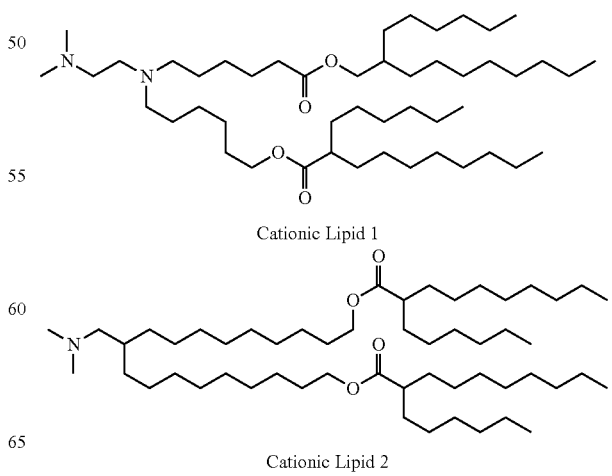

Cationic Lipid 1

Cationic Lipid 2

TABLE 10

Properties of LNPs

| Cat lipid 1/Cat lipid 2/DSPC/ Chol/PEGA* | pKa | size (nm) | PDI | Encaps | Mean Activity at 1 mg/kg | SD |
|---|---|---|---|---|---|---|
| 50/0/10/38.5/1.5 | 6.57 | 76 | 0.043 | 97 | 1628 | 680 |
| 45/5/10/38.5/1.5 | 6.42 | 73 | 0.053 | 97 | 2177 | 728 |
| 40/10/10/38.5/1.5 | 6.29 | 70 | 0.004 | 97 | 5645 | 2498 |
| 35/15/10/38.5/1.5 | 6.16 | 71 | 0.002 | 98 | 3198 | 327 |

The data in Table 10 show that LNPs comprising only lipid 1, which has a pKa outside the desirable range, have low activity, but activity of the LNPs can be surprisingly increased by combining cationic lipids 1 and 2.

Example 93

Synthesis of Compound IV-1

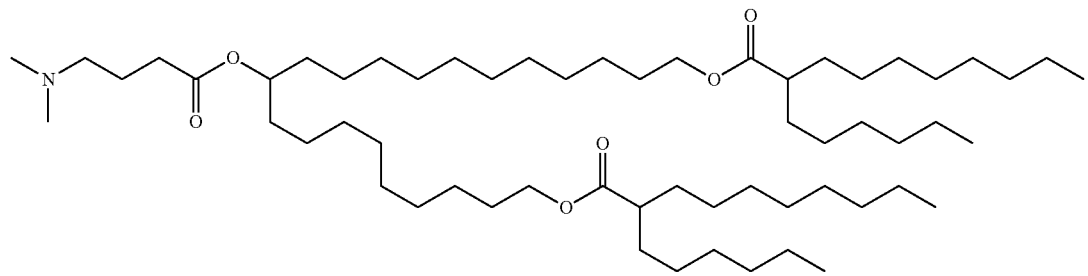 [SMILES: CCCCCCCCC(CCCCCC)C(=O)OCCCCCCCCCCCC(CCCCCCCCCOC(=O)C(CCCCCC)CCCCCCCC)OC(=O)CCCN(C)C]

10-{[4'-(dimethylamino)butanoyl]oxy}-19-[(2-hexyldecanoyl)oxy]nonadecyl 2-hexyldecanoate A solution of 10-[4'-(dimethylamino)butanoyl]oxynonadecan-1,19-diol (0.30 g), 2-hexyldecanoic acid (1.1 g), N-(3-dimethylaminopropyl)-N-ethylcarbodiimide hydrochloride (0.42 g) and 4-dimethylaminopyridine (0.27 g) in dichloromethane (20 mL) was stirred at room temperature overnight. The solution was washed with diluted hydrochloric acid, dried over anhydrous magnesium sulfate, filtered and the solvent removed. The residue was passed down a silica gel (20 g) column with 0-8% methanol/dichloromethane. The desired product was afforded (0.42 g).

Example 94

Synthesis of Compound IV-2

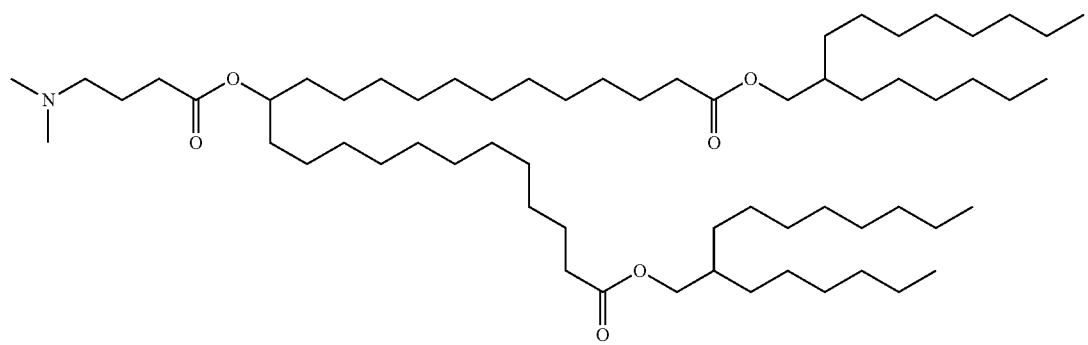 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

13-oxo-pentacosane-1,25-dioic acid

Sodium ethoxide (1.56 g) was dissolved in absolute ethanol (30 mL). Diethylacetone dicarboxylate (4.5 g) was added and the solution heated to reflux. Ethyl 11-bromododecanoate (6.8 g) was slowly added and the solution refluxed for an hour. Sodium ethoxide (1.53 g) was added, followed by ethyl 11-bromododecanoate (18 g). The solution was refluxed overnight. The reaction mixture was cooled, diluted with water, acidified with dilute hydrochloric acid, and extracted with methylene chloride. The organic fraction was washed with water and the solvent removed. The crude product was passed down a silica gel column (80 g) using methanol/methylene chloride to recover unreacted starting materials. The residue containing the product was treated with acetic acid (10 mL) and concentrated hydrochloric acid (20 mL), and then refluxed overnight. The solution was cooled, diluted with water and filtered. The collected precipitate was recrystallized from acetone, affording the desired product as a white powder (2.9 g).

1,25-di-(2'-hexyldecyl) 13-oxo-pentacosanedioate

A solution of 13-oxo-pentacosane-1,25-dioic acid (0.91 g), 4-dimethylaminopyridine (1.1 g), N-(3-dimethylaminopropyl)-N-ethylcarbodiimide hydrochloride (1.0 g) and 2-hexyldecan-1-ol (2.4 g) in dichloromethane (40 mL) was stirred at room temperature overnight. The solution was washed with diluted hydrochloric acid, dried over anhydrous magnesium sulfate, filtered and the solvent removed. The residue was passed down a silica gel (20 g) column using 0-4% ethyl acetate/hexane, affording the desired product (1 g).

1,25-di-(2'-hexyldecyl) 13-hydroxy-pentacosanedioate

A solution of 1,25-di-(2'-hexyldecyl) 13-oxo-pentacosanedioate (1 g) in tetrahydrofuran (10 mL) and methanol (10 mL) was treated with sodium borohydride (0.18 g). The reaction was stirred for 30 minutes and then diluted with water, acidified and extracted with dichloromethane. The organic fraction was dried over anhydrous magnesium sulfate, filtered, and the solvent removed to afford the crude product (0.95 g). The crude product was used in the next synthetic step without further purification.

1,25-di-(2'-hexyldecyl)13-{[4-(dimethylamino)butanoyl]oxy}pentacosanedioate (Compound IV-2)

A solution of crude 1,25-di-(2'-hexyldecyl) 13-hydroxy-pentacosanedioate (0.95 g), 4-dimethylaminopyridine (0.42 g), N-(3-dimethylaminopropyl)-N-ethylcarbodiimide hydrochloride (0.34 g) and N,N-dimethylaminobutyric acid hydrochloride (0.59 g) in dichloromethane (15 mL) was stirred at room temperature for one hour. The solution was washed with diluted hydrochloric acid followed by aqueous sodium bicarbonate. The organic phase was dried over anhydrous magnesium sulfate, filtered, and the solvent removed. The residue was passed down a silica gel (20 g) column using 0-6% methanol/dichloromethane to afford the desired product (0.81 g).

Example 95

Synthesis of Compound IV-3

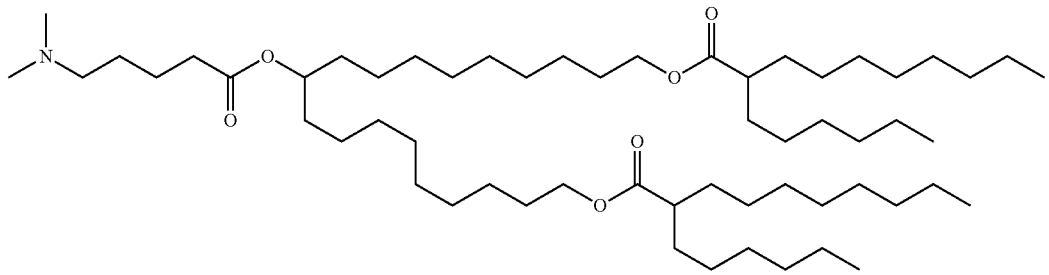 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

9-Tetrahydropyranyloxynonan-1-yl bromide

A solution of 9-bromononan-1-ol (25.6 g) and dihydropyran (10.5 g) in dichloromethane (100 mL) was treated with pyridine p-toluenesulfonate (2.8 g) overnight. The solution was diluted with water and extracted with dichloromethane. The organic fractions were dried over anhydrous magnesium sulfate, filtered, and the solvent removed to afford the desired crude product (35 g). The crude product was used in the next synthetic step without further purification.

1,19-Di(tetrahydropyranyloxy)nonadecan-10-ol

A solution of 9-tetrahydropyranyloxynonan-1-yl bromide (35 g) in diethyl ether (150 mL) was treated with magnesium (3.0 g). A crystal of iodine was added to initiate the reaction. The solution was refluxed for 4 days, then cooled to room temperature. Ethyl formate (4 mL) was slowly added and the solution refluxed for 2 hours. The solution was allowed to cool, then washed with dilute aqueous sulfuric acid. The organic phase was washed with water, dried over anhydrous magnesium sulfate, filtered, and the solvent removed to yield 25 g of crude product. The crude material was added to 5% sodium hydroxide in a 1:10 water/methanol solution (150 mL) and heated at 45° C. for one hour. The solution was cooled, diluted with water and extracted with hexane. The organic fractions were dried over anhydrous magnesium sulfate, filtered and the solvent removed. The residue was passed down a silica gel (200 g) column using 0-4% methanol/dichloromethane to afford the desired product (15 g).

1,19-Di(tetrahydropyranyloxy)nonadecan-10-one

A solution of 1,19-di(tetrahydropyranyloxy)nonadecan-10-ol (7.2 g) in dichloromethane (40 mL) was treated with pyridinium chlorochromate (4 g) and stirred overnight.

Diethyl ether (200 mL) was added and the solution filtered through a silica gel bed. The solvent was removed and the residue dissolved in hexane, then filtered through a silica gel bed. The solvent was removed and the residue passed down a silica gel (75 g) column using 0-3% methanol/dichloromethane to afford the desired product (3 g).

1,19-Dihydroxynonadecan-10-one

A solution of 1,19-di(tetrahydropyranyloxy)nonadecan-10-one (3 g) in methanol (100 mL)/water (10 mL) was treated with pyridinium p-toluenesulfonate (1 g) overnight. The solution was filtered to afford the desired product (0.8 g). Dilution of the filtrate with water, followed by extraction using dichloromethane afforded additional desired product (1.0 g).

1,19-Di(2'hexyldecanoyloxy)nonadecan-10-one

A solution of 1,19-dihydroxynonadecan-10-one (0.87 g), 2-hexyldecanoic acid (2.48 g), 4-dimethylaminopyridine (1.0 g) and N-(3-dimethylaminopropyl)-N-ethylcarbodiimide hydrochloride (1.68 g) in dichloromethane (40 mL) was stirred for three days. The solution was diluted with dichloromethane and washed with dilute hydrochloric acid. The organic fraction was dried over anhydrous magnesium sulfate, filtered, and the solvent removed. The residue was passed down a silica gel (50 g) column using dichloromethane to afford the desired product (2.8 g).

1,19-Di(2'hexyldecanoyloxy)nonadecan-10-ol

A solution of 1,19-di(2'hexyldecanoyloxy)nonadecan-10-one (1.06 g) in dichloromethane (10 mL) was treated with sodium borohydride (0.15 g). Methanol was added dropwise until the materials dissolved. The solution was stirred for 30 minutes and then partitioned between water and dichloromethane. The organic phase was dried over anhydrous magnesium sulfate, filtered and the solvent removed. The residue was passed down a silica gel (20 g) column using 0-12% ethyl acetate/hexane gradient to afford the desired product (0.40 g).

10-{[5-(dimethylamino)pentanoyl]oxy}-19-[(2-hexyldecanoyl)oxy]nonadecyl 2-hexyldecanoate (Compound IV-3)

A solution of 1,19-di(2'hexyldecanoyloxy)nonan-10-ol (0.40 g), 5-N,N-dimethylaminopentanoic acid (0.22 g), 4-dimethylaminopyridine (0.18 g) and N-(3-dimethylaminopropyl)-N-ethylcarbodiimide hydrochloride (0.18 g) in dichloromethane (20 mL) was stirred overnight. The solution was diluted with dichloromethane and washed with water. The organic fraction was dried over anhydrous magnesium sulfate, filtered and the solvent removed. The residue was passed down a silica gel (20 g) column using 0-3% methanol/dichloromethane to afford the desired product (0.24 g).

Example 96

Activity of Lipid Formulations Compared at Different Component Ratios

Phosphatidylglycerols carry a formal negative charge in their head-groups, i.e., they are permanently negatively charged across the relevant physiological pH range. The cationic lipid in this instance has a pKa of 6.57 which is higher than the expected ideal range which suggests it will produce an LNP that is more highly charged at neutral pH than would otherwise be wanted. Addition of small amounts of anionic charged lipid provides a competing negative charge that is thought to bring the overall surface charge closer to neutrality. Specific results for each respective anionic lipid are shown in Tables 11 and 12 below:

TABLE 11

Physical properties for LNPs formulated with DOPG.

| Cat lipid/DOPG/DSPC/Chol/PEGA | size (nm) | PDI | Encapsulation (%) | Mean Activity 1 mg/kg | SD |
|---|---|---|---|---|---|
| 50/0/10/38.5/1.5 | 72 | 0.043 | 97 | 6822 | 3387 |
| 50/0.5/9.5/38.5/1.5 | 69 | 0.015 | 96 | 5267 | 751 |
| 50/1/9/38.5/1.5 | 70 | 0.033 | 96 | 5051 | 160 |
| 50/2.5/7.5/38.5/1.5 | 67 | 0.028 | 96 | 7228 | 826 |
| 50/5/5/38.5/1.5 | 64 | 0.051 | 95 | 8417 | 400 |
| 50/10/0/38.5/1.5 | 69 | 0.047 | 95 | 5979 | 3873 |
| 50/1/10/37.5/1.5 | 70 | 0.030 | 96 | 8256 | 1229 |
| 50/5/10/33.5/1.5 | 63 | 0.077 | 94 | 7035 | 1735 |
| 50/10/10/28.5/1.5 | 59 | 0.042 | 91 | 4081 | 2463 |

Table 11 shows that addition of a negatively charged phosphatidylglycerol provides a benefit. It is also shown that the optimum for the addition of phosphatidylglycerol lipid moves to a lower range if the DSPC structural lipid is held constant.

TABLE 12

Physical properties for LNPs formulated with DSPG.

| Cat lipid/DSPG/DSPC/Chol/PEGA | size (nm) | PDI | Encaps (%) | Mean Activity 1 mg/kg | SD |
|---|---|---|---|---|---|
| 50/0/10/38.5/1.5 | 67 | 0.045 | 98 | 3627 | 1800 |
| 50/1/9/38.5/1.5 | 67 | 0.021 | 97 | 6252 | 3597 |
| 50/2.5/7.5/38.5/1.5 | 67 | 0.096 | 95 | 7500 | 5560 |
| 50/5/5/38.5/1.5 | 58 | 0.026 | 96 | 4033 | 2179 |

TABLE 12-continued

Physical properties for LNPs formulated with DSPG.

| Cat lipid/DSPG/DSPC/Chol/PEGA | size (nm) | PDI | Encaps (%) | Mean Activity 1 mg/kg | SD |
|---|---|---|---|---|---|
| 50/7.5/2.5/38.5/1.5 | 57 | 0.040 | 94 | 559 | 407 |
| 50/10/0/38.5/1.5 | 64 | 0.131 | 91 | 152 | 72 |
| 50/1/10/37.5/1.5 | 68 | 0.026 | 97 | 4594 | 1382 |
| 50/5/10/33.5/1.5 | 65 | 0.157 | 97 | 2243 | 1386 |
| 50/10/10/28.5/1.5 | 55 | 0.062 | 96 | 411 | 410 |

For comparison, a similar series described in Table 12 was generated using DSPG instead of DOPG, i.e., the same anionically charged headgroup but lipid tails that match DSPC. The results show a similar trend when DSPG is compared to DOPG. Specifically, there is a benefit to the addition of DSPG and that maximum benefit is achieved at lower levels if the DSPG is added in place of the steroid rather than the neutral lipid (e.g., DSPC). These results demonstrate the utility of phospatidylglycerols in general, the interplay of the other lipid components, and demonstrate the surprising benefit and utility of phosphatidylglycerols lipids.

Example 97

Variable mRNA to Lipid Ratios and Results

The effect of the proportion of mRNA to total lipid was investigated for a particular standard set of lipid proportions across three representative cationic lipids. LNP's were formulated by an in-line mixing process as described in Example 1. The lipid proportions were held constant at 47.5:10:40.7:1.8 for the cationic lipid, DSPC, Cholesterol and PEG-lipid respectively. The mRNA to lipid ratios are described in terms of the N/P ratio where N represents the moles of cationic lipid and P represents the moles of phosphate present as part of the nucleic acid backbone. Ratios described in this way are independent of the size of the nucleic acid. The size and polydispersity index data were generated using Malvern Nanosizer ZS. The diameters given are intensity weighted means. Encapsulation was determined using a fluorescent intercalating dye based assay (Ribogreen). Activity data was generated using an in vivo murine model of mRNA expression based on *Photinus pyralis* (i.e., firefly) luciferase as described in Example 2 using a dose of 1 mg/kg.

Figure 1B:
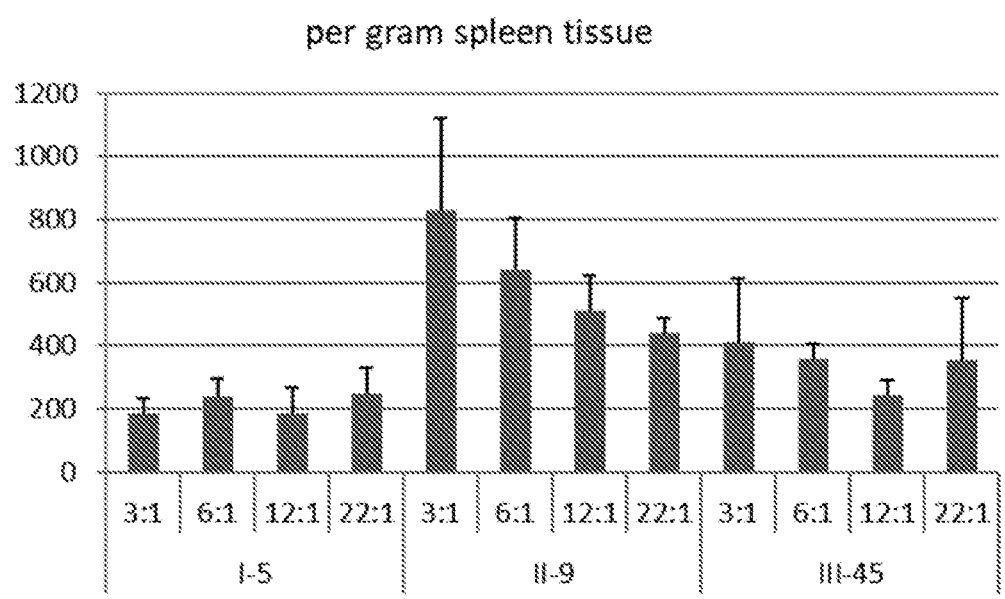

Table 13 summarizes results for each of three representative cationic lipids (compound I-5, II-9, III-45), and the luciferase activity data is plotted in FIGS. 1 and 2.

TABLE 13

Summary of Physical Characteristics and Luciferase Activity for representative LNP formulations with varying N/P ratio

| Cationic Lipid | N/P | Encapsulation (%) | Size (nm) | PDI | Liver Luc Activity ng/g | Spleen Luc Activity ng/g |
|---|---|---|---|---|---|---|
| I-5 | 3:1 | 94 | 86 | 0.072 | 7689 | 188 |
|  | 6:1 | 96 | 81 | 0.028 | 9509 | 236 |
|  | 12:1 | 98 | 75 | 0.026 | 12826 | 184 |
|  | 22:1 | 99 | 81 | 0.039 | 14538 | 247 |
| II-9 | 3:1 | 92 | 94 | 0.054 | 6727 | 831 |
|  | 6:1 | 95 | 88 | 0.033 | 12209 | 642 |
|  | 12:1 | 98 | 84 | 0.014 | 18330 | 514 |
|  | 22:1 | 98 | 84 | 0.017 | 12634 | 439 |

TABLE 13-continued

Summary of Physical Characteristics and Luciferase Activity for representative LNP formulations with varying N/P ratio

| Cationic Lipid | N/P | Encapsulation (%) | Size (nm) | PDI | Liver Luc Activity ng/g | Spleen Luc Activity ng/g |
|---|---|---|---|---|---|---|
| III-45 | 3:1 | 75 | 87 | 0.089 | 13308 | 410 |
|  | 6:1 | 86 | 74 | 0.068 | 15395 | 356 |
|  | 12:1 | 91 | 65 | 0.074 | 16596 | 243 |
|  | 22:1 | 94 | 57 | 0.083 | 16005 | 353 |

The invention claimed is:

1. A lipid nanoparticle comprising:
   i) from 47 to 48 mol percent of a cationic lipid;
   ii) a neutral lipid;
   iii) a steroid;
   iv) a polymer conjugated lipid; and
   v) a nucleic acid, or a pharmaceutically acceptable salt thereof, encapsulated within or associated with the lipid nanoparticle,
   wherein the cationic lipid has a structure of Formula II:

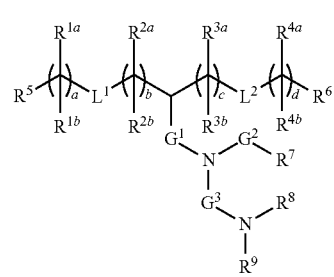

II or a pharmaceutically acceptable salt, tautomer or stereoisomer thereof, wherein:
one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O) NR$^a$— or —NR$^a$C(=O)O—, and the other of $L^1$ or $L^2$ is —O(C=O)—, —(C=O)O—, —C(=O)—, —O—, —S(O)—, —S—S—, —C(=O)S—, SC(=O)—, —NR$^a$C(=O)—, —C(=O)NR$^a$—, NR$^a$C(=O) NR$^a$—, —OC(=O)NR$^a$— or —NR$^a$C(=O)O— or a direct bond;
$G^1$ is $C_1$-$C_2$ alkylene, —(C=O)—, —O(C=O)—, —SC (=O)—, —NR$^a$C(=O)— or a direct bond;
$G^2$ is —C(=O)—, —(C=O)O—, —C(=O)S—, —C(=O)NR$^a$— or a direct bond;
$G^3$ is $C_1$-$C_6$ alkylene;
$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

2. The lipid nanoparticle of claim 1, comprising from 47.2 to 47.8 mol percent of the cationic lipid.

3. The lipid nanoparticle of claim 1, wherein the neutral lipid is present in a concentration ranging from 5 to 15 mol percent.

4. The lipid nanoparticle of claim 1, wherein the steroid is present in a concentration ranging from 32 to 40 mol percent.

5. The lipid nanoparticle of claim 1, wherein the molar ratio of the cationic lipid to the steroid ranges from 1.0:0.9 to 1.0:1.2.

6. The lipid nanoparticle of claim 1, wherein the cationic lipid has one of the following structures:

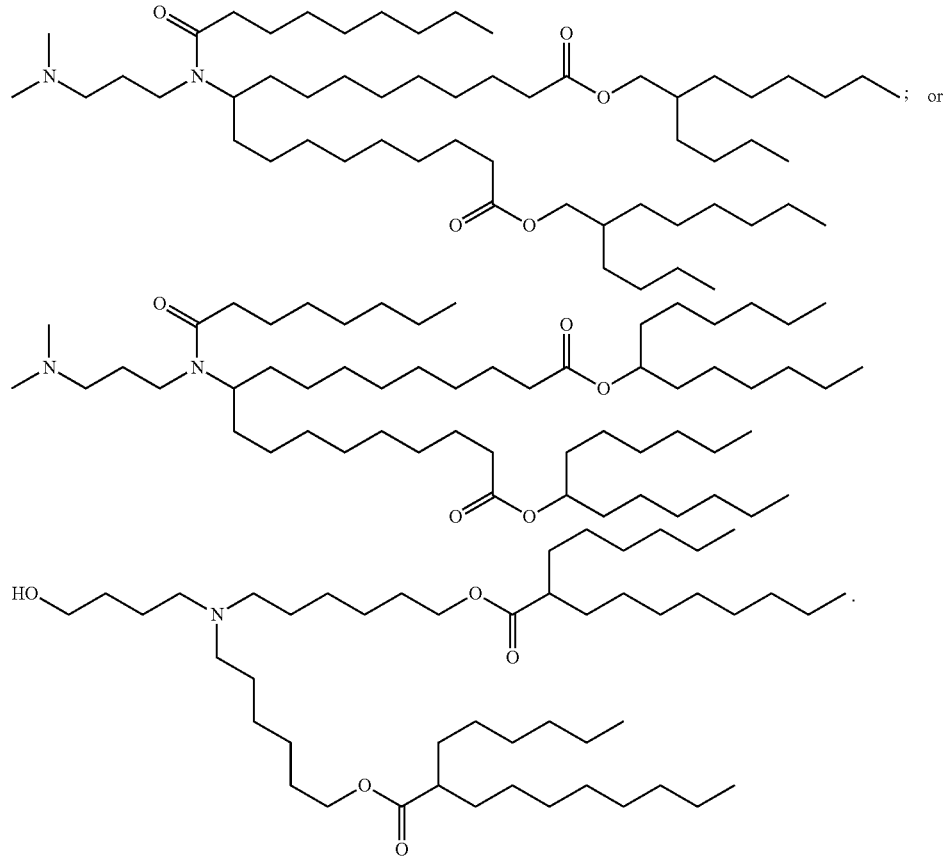

7. The lipid nanoparticle of claim 1, wherein the molar ratio of cationic lipid to the neutral lipid ranges from about 4.1:1.0 to about 4.9:1.0.

8. The lipid nanoparticle of claim 1, wherein the molar ratio of cationic lipid to steroid ranges from 5:1 to 1:1.

9. The lipid nanoparticle of claim 1, wherein the molar ratio of cationic lipid to polymer conjugated lipid ranges from about 100:1 to about 20:1.

10. The lipid nanoparticle of claim 1, wherein the neutral lipid is distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1 carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE) or 1,2-dielaidoyl-sn-glycero-3-phosphoethanolamine (transDOPE).

11. The lipid nanoparticle of claim 1, wherein the steroid is cholesterol.

12. The lipid nanoparticle of claim 1, wherein the polymer conjugated lipid is present in a concentration ranging from 1.0 to 2.5 molar percent.

13. The lipid nanoparticle of claim 1, wherein the polymer conjugated lipid is a pegylated lipid.

14. The lipid nanoparticle of claim 1, wherein the nucleic acid is selected from antisense and messenger RNA.

15. A pharmaceutical composition comprising a lipid nanoparticle of claim 1 and a pharmaceutically acceptable excipient.

16. A method for administering a therapeutic agent to a patient in need thereof, the method comprising administering the lipid nanoparticle of claim 1 to the patient.

17. A method for treating a disease in a patient in need thereof, the method comprising administering the lipid nanoparticle of claim 1 to the patient, wherein the therapeutic agent is effective to treat the disease.

18. The lipid nanoparticle of claim 1, wherein a plurality of the lipid nanoparticles has a polydispersity of less than 0.12.

19. A lipid nanoparticle comprising:
i) from 47 to 48 mol percent of a cationic lipid;
ii) a neutral lipid;
iii) a steroid;
iv) a polymer conjugated lipid; and
v) a nucleic acid, or a pharmaceutically acceptable salt thereof, encapsulated within or associated with the lipid nanoparticle,
wherein the cationic lipid has one of the following structures:

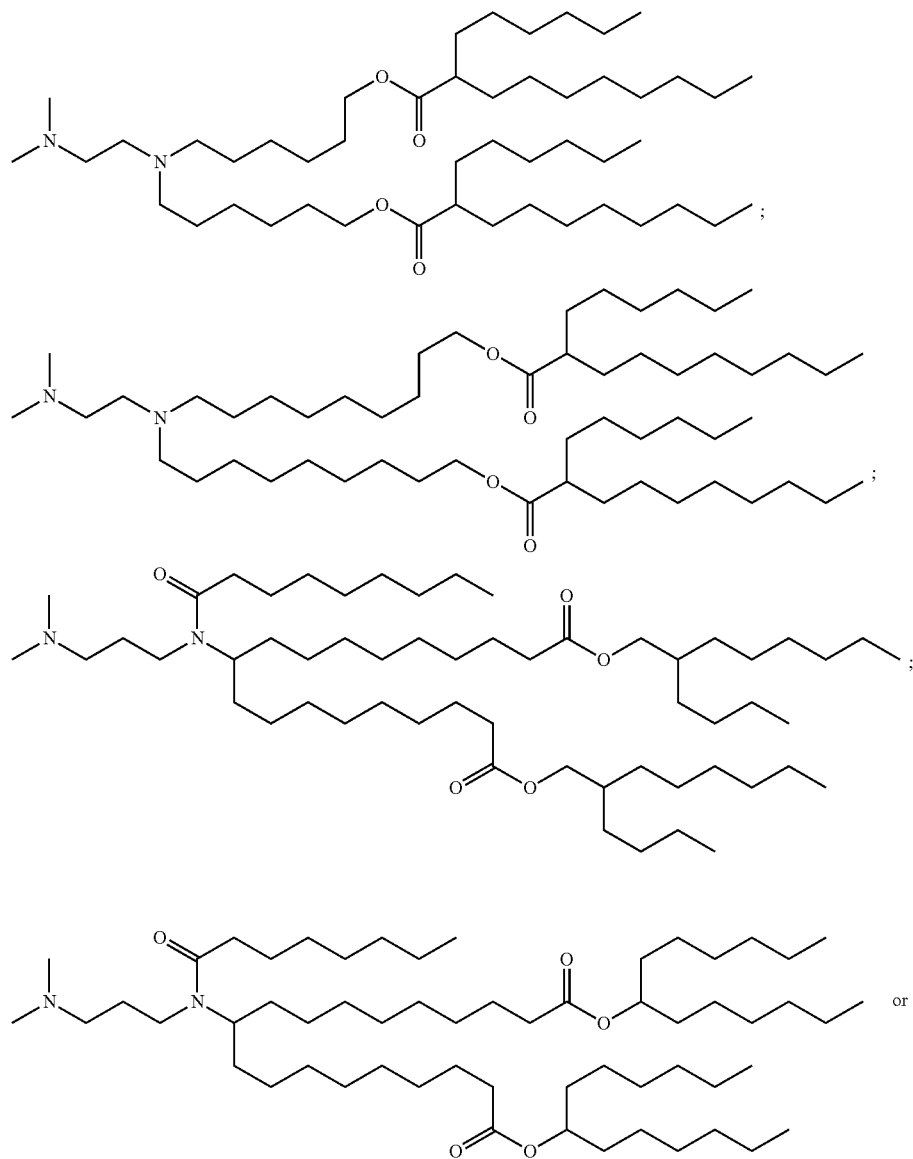

-continued

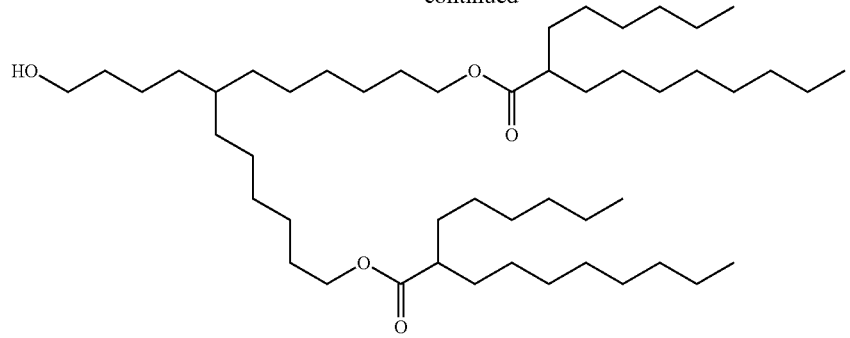

20. The lipid nanoparticle of claim 19, comprising from 47.2 to 47.8 mol percent of the cationic lipid.

21. The lipid nanoparticle of claim 19, wherein the neutral lipid is present in a concentration ranging from 5 to 15 mol percent.

22. The lipid nanoparticle of claim 19, wherein the steroid is present in a concentration ranging from 32 to 40 mol percent.

23. The lipid nanoparticle of claim 19, wherein the molar ratio of the cationic lipid to the steroid ranges from 1.0:0.9 to 1.0:1.2.

24. The lipid nanoparticle of claim 19, wherein the molar ratio of cationic lipid to the neutral lipid ranges from about 4.1:1.0 to about 4.9:1.0.

25. The lipid nanoparticle of claim 19, wherein the molar ratio of cationic lipid to steroid ranges from 5:1 to 1:1.

26. The lipid nanoparticle of claim 19, wherein the molar ratio of cationic lipid to polymer conjugated lipid ranges from about 100:1 to about 20:1.

27. The lipid nanoparticle of claim 19, wherein the neutral lipid is distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1 carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE) or 1,2-dielaidoyl-sn-glycero-3-phosphoethanolamine (transDOPE).

28. The lipid nanoparticle of claim 19, wherein the steroid is cholesterol.

29. The lipid nanoparticle of claim 19, wherein the polymer conjugated lipid is present in a concentration ranging from 1.0 to 2.5 molar percent.

30. The lipid nanoparticle of claim 19, wherein the polymer conjugated lipid is a pegylated lipid.

31. The lipid nanoparticle of claim 19, wherein the nucleic acid is selected from antisense and messenger RNA.

32. A pharmaceutical composition comprising a lipid nanoparticle of claim 19 and a pharmaceutically acceptable excipient.

33. A method for administering a therapeutic agent to a patient in need thereof, the method comprising administering the lipid nanoparticle of claim 19 to the patient.

34. A method for treating a disease in a patient in need thereof, the method comprising administering the lipid nanoparticle of claim 19 to the patient, wherein the therapeutic agent is effective to treat the disease.

35. The lipid nanoparticle of claim 19, wherein a plurality of the lipid nanoparticles has a polydispersity of less than 0.12.

* * * * *

UNITED STATES PATENT AND TRADEMARK OFFICE
CERTIFICATE OF CORRECTION

PATENT NO. : 11,712,481 B2  
APPLICATION NO. : 16/345592  
DATED : August 1, 2023  
INVENTOR(S) : Michael J. Hope et al.

Page 1 of 1

It is certified that error appears in the above-identified patent and that said Letters Patent is hereby corrected as shown below:

In the Claims

Column 189, Claim 1, Lines 14-15:
"independently either (a):" should read: --independently either: (a)--.

Columns 193 and 194, Line 1-15:
The following structure has an error:

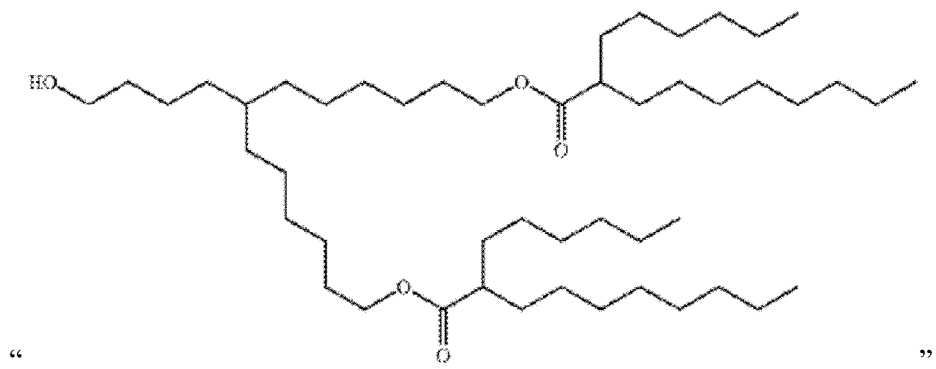

"

The correct structure should read:

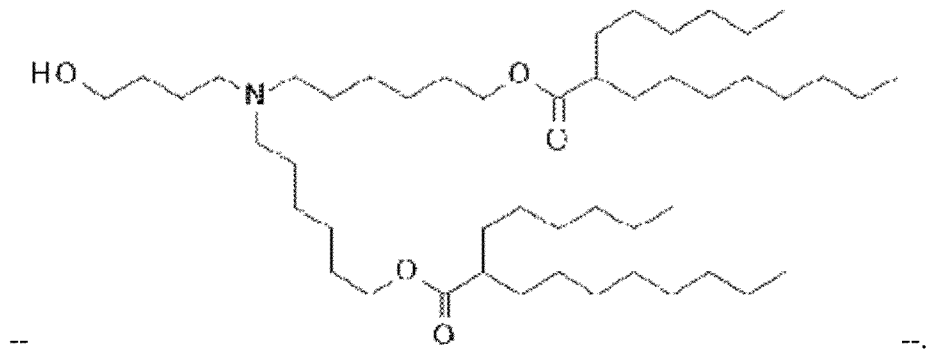

--.

Signed and Sealed this  
Thirtieth Day of December, 2025

John A. Squires  
*Director of the United States Patent and Trademark Office*